US012599316B2

(12) United States Patent
Ralston et al.

(10) Patent No.: US 12,599,316 B2
(45) Date of Patent: Apr. 14, 2026

(54) SYSTEMS AND METHODS FOR DETECTING AND TREATING NEUROPHYSIOLOGICAL IMPAIRMENT

(71) Applicant: Neursantys, Inc., Calgary (CA)

(72) Inventors: John D. Ralston, Portola Valley, CA (US); Ryan Michael Peters, Calgary (CA); Christopher J. Banman, Calgary (CA)

(73) Assignee: Neursantys, Inc., Calgary (CA)

( * ) Notice: Subject to any disclaimer, the term of this patent is extended or adjusted under 35 U.S.C. 154(b) by 1077 days.

(21) Appl. No.: 17/671,176

(22) Filed: Feb. 14, 2022

(65) Prior Publication Data

US 2022/0257149 A1 Aug. 18, 2022

Related U.S. Application Data

(60) Provisional application No. 63/302,094, filed on Jan. 23, 2022, provisional application No. 63/149,319, filed on Feb. 14, 2021.

(51) Int. Cl.
*A61B 5/11* (2006.01)
*A61B 5/00* (2006.01)
(Continued)

(52) U.S. Cl.
CPC ........... *A61B 5/1126* (2013.01); *A61B 5/1116* (2013.01); *A61B 5/4023* (2013.01);
(Continued)

(58) Field of Classification Search
None
See application file for complete search history.

(56) References Cited

U.S. PATENT DOCUMENTS

| | | | |
|---|---|---|---|
| 9,974,478 B1 * | 5/2018 | Brokaw | A61B 5/486 |
| 10,076,655 B2 * | 9/2018 | Paul | A61N 1/36542 |

(Continued)

OTHER PUBLICATIONS

Martinez-Mendez, R., Sekine, M., & Tamura, T. (2011). Detection of anticipatory postural adjustments prior to gait initiation using inertial wearable sensors. Journal of NeuroEngineering and Rehabilitation, 8(1), 17. https://doi.org/10.1186/1743-0003-8-17 (Year: 2011).*

(Continued)

*Primary Examiner* — Jacqueline Cheng
*Assistant Examiner* — Samuel C Kim
(74) *Attorney, Agent, or Firm* — COOLEY LLP

(57) ABSTRACT

A system includes a sensing assembly configured to be disposed on a mastoid of a user. The sensing assembly includes a housing, a first sensor disposed in the housing and configured to measure a first phybrata signal from the user, and a second sensor disposed in the housing and configured to measure a second phybrata signal from the user, the second phybrata signal different from the first phybrata signal. A controller is in communication with the sensing assembly. The controller is configured to: receive a first phybrata data from the sensing assembly, the first phybrata data including information obtained from the first phybrata signal and the second phybrata signal. The controller is configured to determine a phybrata parameter associated with the user based on the first phybrata data, and determine a phybrata signature associated with the user based on the phybrata parameter.

32 Claims, 66 Drawing Sheets

(51) Int. Cl.

| | |
|---|---|
| *A61N 1/36* | (2006.01) |
| *G16H 20/30* | (2018.01) |
| *G16H 40/63* | (2018.01) |
| *G16H 50/50* | (2018.01) |

(52) U.S. Cl.
CPC .......... *A61B 5/4842* (2013.01); *A61B 5/4848* (2013.01); *A61B 5/6814* (2013.01); *A61B 5/7264* (2013.01); *A61B 5/7275* (2013.01); *A61N 1/36025* (2013.01); *A61N 1/36031* (2017.08); *A61N 1/36046* (2013.01); *G16H 20/30* (2018.01); *G16H 40/63* (2018.01); *G16H 50/50* (2018.01); *A61B 2562/0219* (2013.01)

(56) References Cited

U.S. PATENT DOCUMENTS

| | | | | |
|---|---|---|---|---|
| 2006/0173509 | A1* | 8/2006 | Lee | A61B 5/4094 607/45 |
| 2007/0167985 | A1* | 7/2007 | Kirby | A61N 1/36036 607/55 |
| 2009/0198305 | A1* | 8/2009 | Naroditsky | A61B 5/4893 607/46 |
| 2009/0319004 | A1* | 12/2009 | Sabel | A61B 5/372 607/54 |
| 2010/0037694 | A1* | 2/2010 | Grossman | F16F 15/046 73/526 |
| 2011/0029045 | A1* | 2/2011 | Cevette | A61N 1/323 607/2 |
| 2013/0090704 | A1* | 4/2013 | Kolen | A61N 1/0476 607/45 |
| 2014/0336722 | A1* | 11/2014 | Rocon De Lima | A61N 1/36139 607/45 |
| 2015/0005841 | A1* | 1/2015 | Pal | A61N 1/0456 607/45 |
| 2015/0032186 | A1* | 1/2015 | Cushing | A61N 1/36038 607/57 |
| 2015/0282767 | A1 | 10/2015 | Stivoric et al. | |
| 2017/0197081 | A1* | 7/2017 | Charlesworth | A61N 1/36034 |
| 2017/0308671 | A1* | 10/2017 | Bahrami | G16H 10/60 |
| 2017/0333711 | A1* | 11/2017 | Tass | A61B 5/4082 |
| 2018/0055417 | A1 | 3/2018 | Munaretto | |
| 2018/0110466 | A1* | 4/2018 | Ralston | A61B 5/1114 |
| 2018/0193641 | A1* | 7/2018 | Black | A61N 1/36028 |
| 2018/0272118 | A1* | 9/2018 | Goldwasser | A61N 1/0492 |
| 2018/0361153 | A1* | 12/2018 | Heldman | A61N 1/36153 |
| 2019/0046787 | A1* | 2/2019 | Tyler | A61N 1/0492 |
| 2019/0167095 | A1* | 6/2019 | Krueger | A61B 3/113 |
| 2019/0371466 | A1* | 12/2019 | Nicolella | G16H 50/50 |
| 2020/0009383 | A1* | 1/2020 | Waclawik | A61N 1/0456 |
| 2020/0171307 | A1* | 6/2020 | Rockley | G02C 5/001 |
| 2022/0047196 | A1* | 2/2022 | Kuboi | A61B 5/4076 |
| 2022/0310196 | A1* | 9/2022 | Polykovskiy | G16B 20/00 |

OTHER PUBLICATIONS

Agrawal Y. et al. "Vestibular dysfunction: prevalence, impact and need for targeted treatment," J. Vestib. Res. 2013, 23(3):113-177.
Araujo C.G. et al. "Successful 10-second one-legged stance performance predicts survival in middle-aged and older individuals," Br. J. Sports Med., Sep. 2022, 56(17):975-980.
Bidargaddi N. et al. "Wavelet based approach for posture transition estimation using a waist worn accelerometer," In: Annual International Conference of the IEEE Engineering in Medicine and Biology—Proceedings. Annu Int Conf IEEE Eng Med Biol Soc, 2007, pp. 1884-1887.
Deveze A. et al. "Vestibular compensation and vestibular rehabilitation. Current Concepts and new trends," Neurophysiol. Clin., Jan. 2014, 44(1):49-57.

Fortino G. et al. "Enabling effective programming and flexible management of efficient body sensor network applications," IEEE Transactions on Human-Machine Systems, 2013, 43:115-133.
Godfrey A. et al. "Activity classification using a single chest mounted tri-axial accelerometer," Medical Engineering & Physics, 2011, 33:1127-1135.
Grafton S.T. et al., "Monitoring of postural sway with a head mounted wearable device: effects of gender, participant state, and concussion", Med Devices (Auckl), May 1, 2019, 12, pp. 151-164.
International Search Report and Written Opinion for International Application No. PCT/CA2022/050214 dated May 16, 2022, 18 pages.
King J, et al. "Electrical vestibular stimulation to improve static balance in older adults: a randomized control trial," Journal of NeuroEngineering and Rehabilitation, 2015, 29 pages.
Mariani B. et al "3D gait assessment in young and elderly subjects using foot-worn inertial sensors," Journal of Biomechanics, 2010, 43:2999-3006.
Nazarahari M. et al. "A novel instrumented shoulder functional test using wearable sensors in patients with brachial plexus injury," J. Shoulder Elbow Surg., 2021, 30, e493-e502.
Nazarahari M. et al. "Detection of daily postures and walking modalities using a single chest-mounted tri-axial accelerometer," Medical Engineering and Physics, 2018, 57:75-81.
[No Author Listed] Neursantys NEURVESTA, retrieved from the internet at https://cortex-design.com/work/neursantys/, on Jul. 29, 2025, 10 pages.
[No Author Listed] Vestibular, retrieved from the internet at https://sparxwellness.ca/services/vestibular/ on Jul. 29, 2025, 5 pages.
Palermo E. et al "Experimental evaluation of accuracy and repeatability of a novel body-to-sensor calibration procedure for inertial sensor-based gait analysis," Measurement, 2014, 52:145-155.
Paraschiv-Ionescu et al. "Ambulatory system for the quantitative and qualitative analysis of gait and posture in chronic pain patients treated with spinal cord stimulation," Gait and Posture, 2004, 20:113-125.
Paraschiv-Ionescu A. et al. "Barcoding human physical activity to assess chronic pain conditions," PLoS One, 2012, 7:e32239, 12 pages.
Rahmani M.H. et al. "Chest-Worn Inertial Sensors: A Survey of Applications and Methods," Sensors, 2021, 21:2875, 30 pages.
Ralston, J.D., et al., "Physiological Vibration Acceleration (Phybrata) Sensor Assessment of Multi-System Physiological Impairments and Sensory Reweighting Following Concussion", Med Devices (Auckl), Dec. 8, 2020, vol. 13, pp. 411-438.
Ralston JD et al. "Phybrata Digital Biomarkers of Age-Related Balance Impairments, Sensory Reweighting and Intrinsic Fall Risk." Medical Devices: Evidence and Research. Jun. 11, 2025, 18:319-336.
Ralston and Stanley, "Neursantys and Caring Hands Caregivers Partner to Pilot Bioelectronic Balance Restoration for Senior Living Communities," Mar. 12, 2025, retrieved from the internet at https://www.medtechdive.com/press-release/20250312-neursantys-and-caring-hands-caregivers-partner-to-pilot-bioelectronic-balan/, 6 pages.
Rast, F.M., et al., "Systematic review on the application of wearable inertial sensors to quantify everyday life motor activity in people with mobility impairments", Journal of Neuro Engineering and Rehabilitation, Nov. 4, 2020, No. 17, vol. 148, pp. 1-19.
Rivera, L.F., et al. "Towards continuous monitoring in personalized healthcare through digital twins", CASCON '19: Proceedings of the 29th Annual International Conference on Computer Science and Software Engineering, Nov. 2019, pp. 329-335.
Rueden, L.V., et al., "Combining Machine Learning and Simulation to a Hybrid Modelling Approach: Current and Future Directions", Berthold, M., Feelders, A., Krempl, G. ( eds) Advances in Intelligent Data Analysis XVIII, IDA Lecture Notes in Computer Science, 2020, vol. 12080. Springer, pp. 548-560.
Shumway-Cook A et al. "Predicting the Probability for Falls in Community-Dwelling Older Adults Using the Timed Up & Go Test," Physical Therapy, 2000, 80:896-903.

(56) References Cited

OTHER PUBLICATIONS

Sung P. and Rowland P. "Impact of sensory reweighting strategies on postural control using the sensory organization test in older adults with and without fall risks," Physiother Res. Int. Apr. 2014, 29(2):e2075, 10 pages.

* cited by examiner

FIG. 3

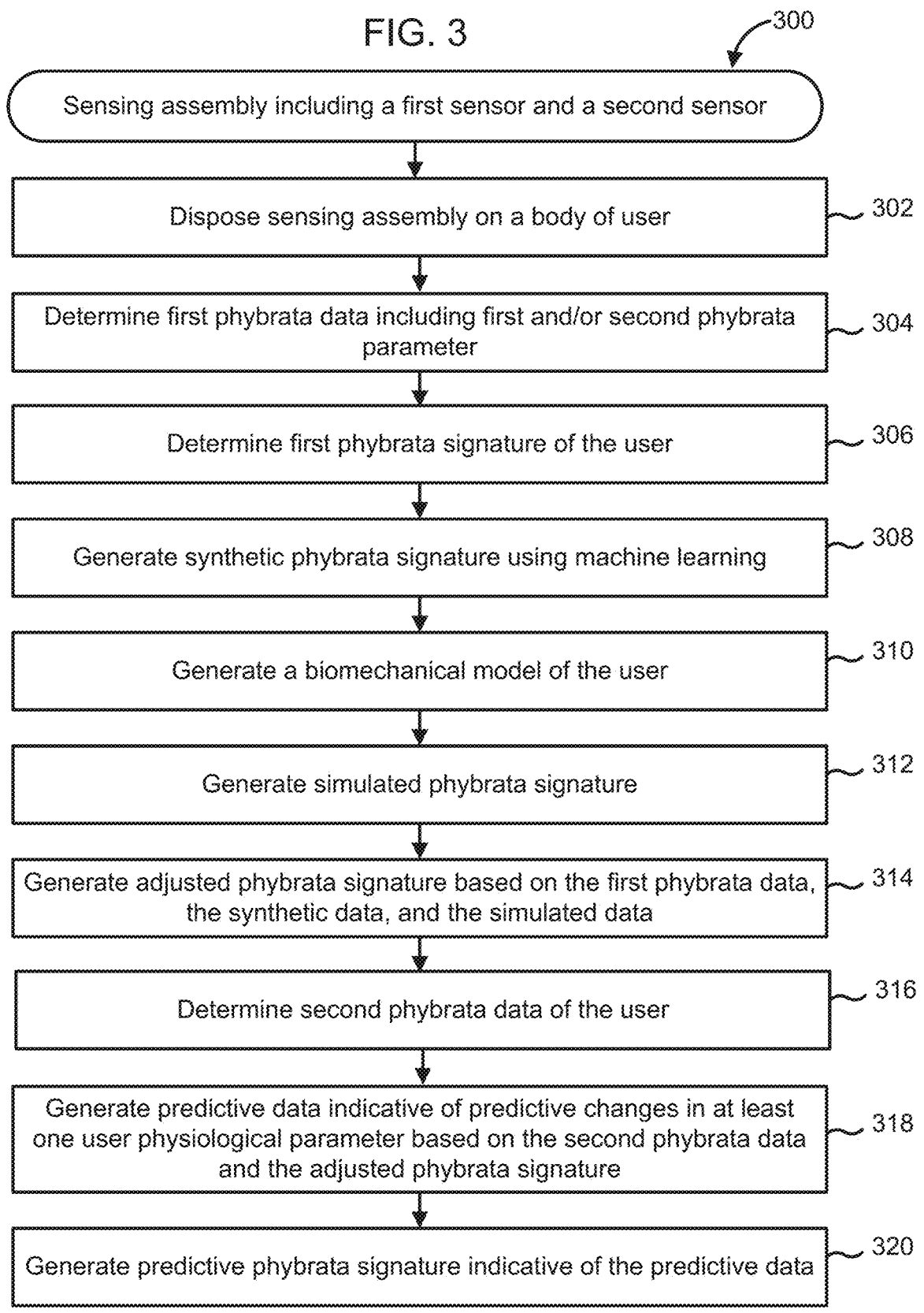

300

Sensing assembly including a first sensor and a second sensor

Dispose sensing assembly on a body of user — 302

Determine first phybrata data including first and/or second phybrata parameter — 304

Determine first phybrata signature of the user — 306

Generate synthetic phybrata signature using machine learning — 308

Generate a biomechanical model of the user — 310

Generate simulated phybrata signature — 312

Generate adjusted phybrata signature based on the first phybrata data, the synthetic data, and the simulated data — 314

Determine second phybrata data of the user — 316

Generate predictive data indicative of predictive changes in at least one user physiological parameter based on the second phybrata data and the adjusted phybrata signature — 318

Generate predictive phybrata signature indicative of the predictive data — 320

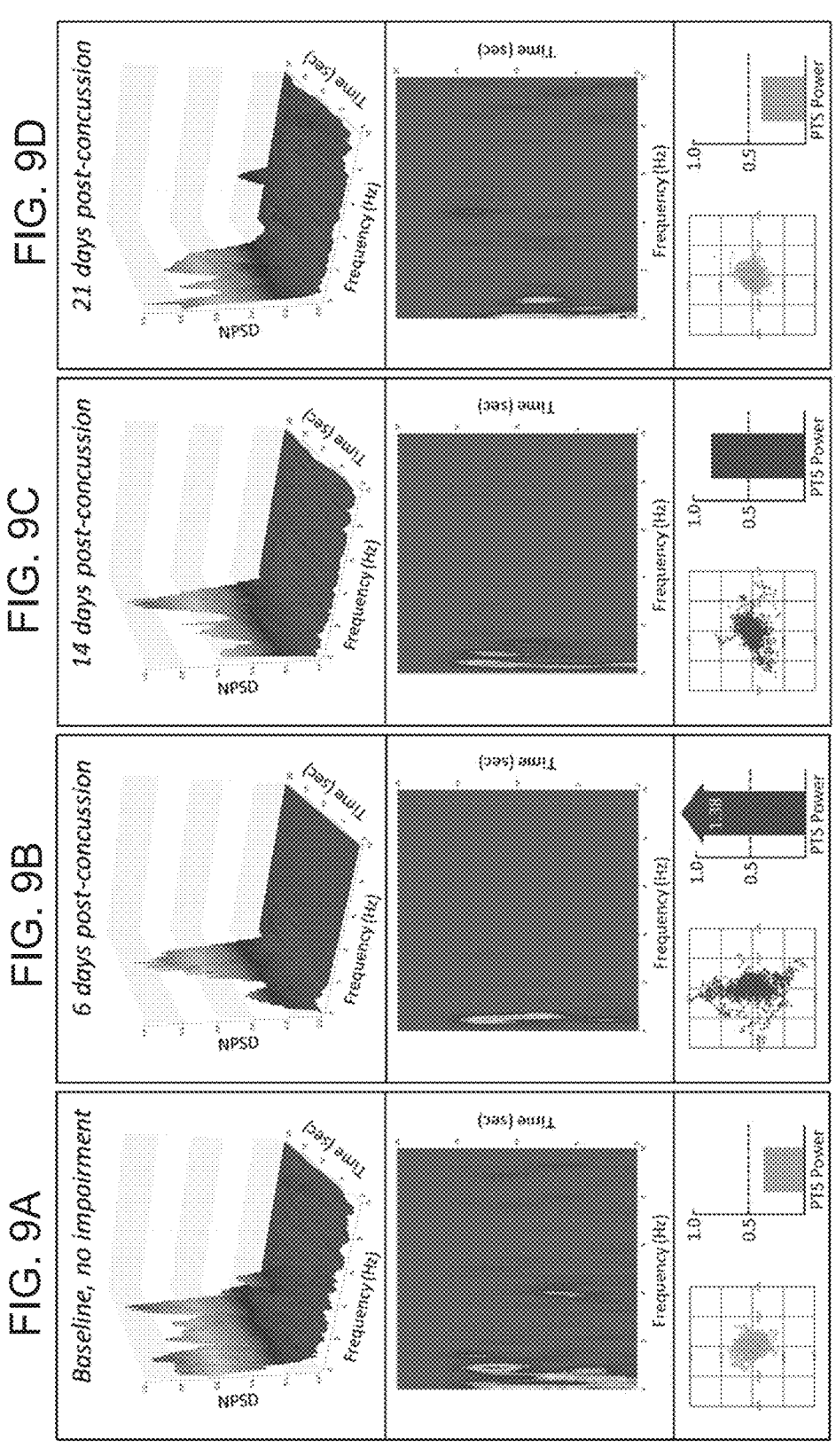

Dystonia (Eo, accel_x)

FIG. 21

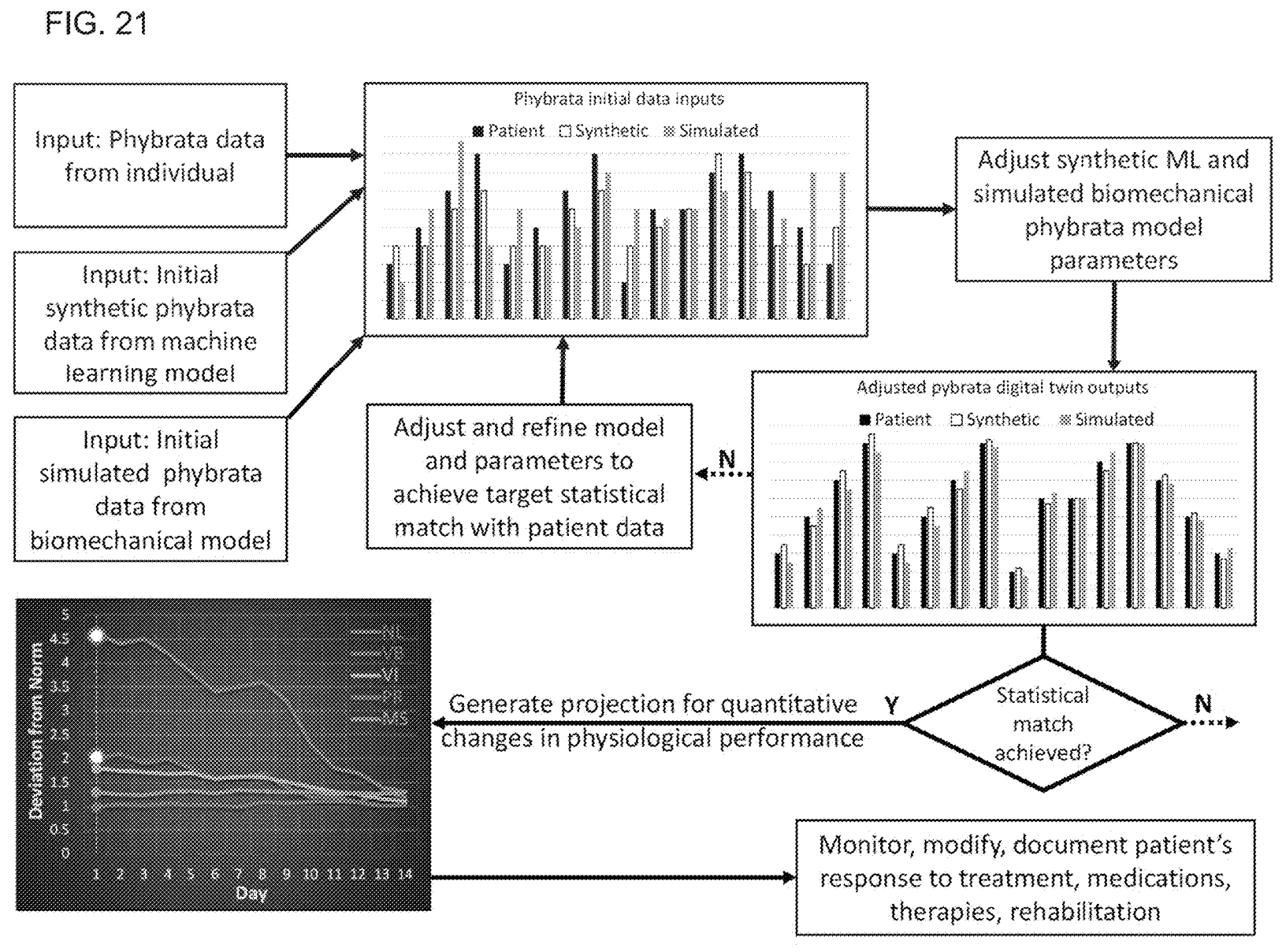

Input: Phybrata data from individual

Input: Initial synthetic phybrata data from machine learning model

Input: Initial simulated phybrata data from biomechanical model

Phybrata initial data inputs
■ Patient  □ Synthetic  ▨ Simulated

Adjust synthetic ML and simulated biomechanical phybrata model parameters

Adjusted phybrata digital twin outputs
■ Patient  □ Synthetic  ▨ Simulated

Adjust and refine model and parameters to achieve target statistical match with patient data

N

Statistical match achieved?

N

Y

Generate projection for quantitative changes in physiological performance

Monitor, modify, document patient's response to treatment, medications, therapies, rehabilitation Deviation from Norm Day

FIG. 22

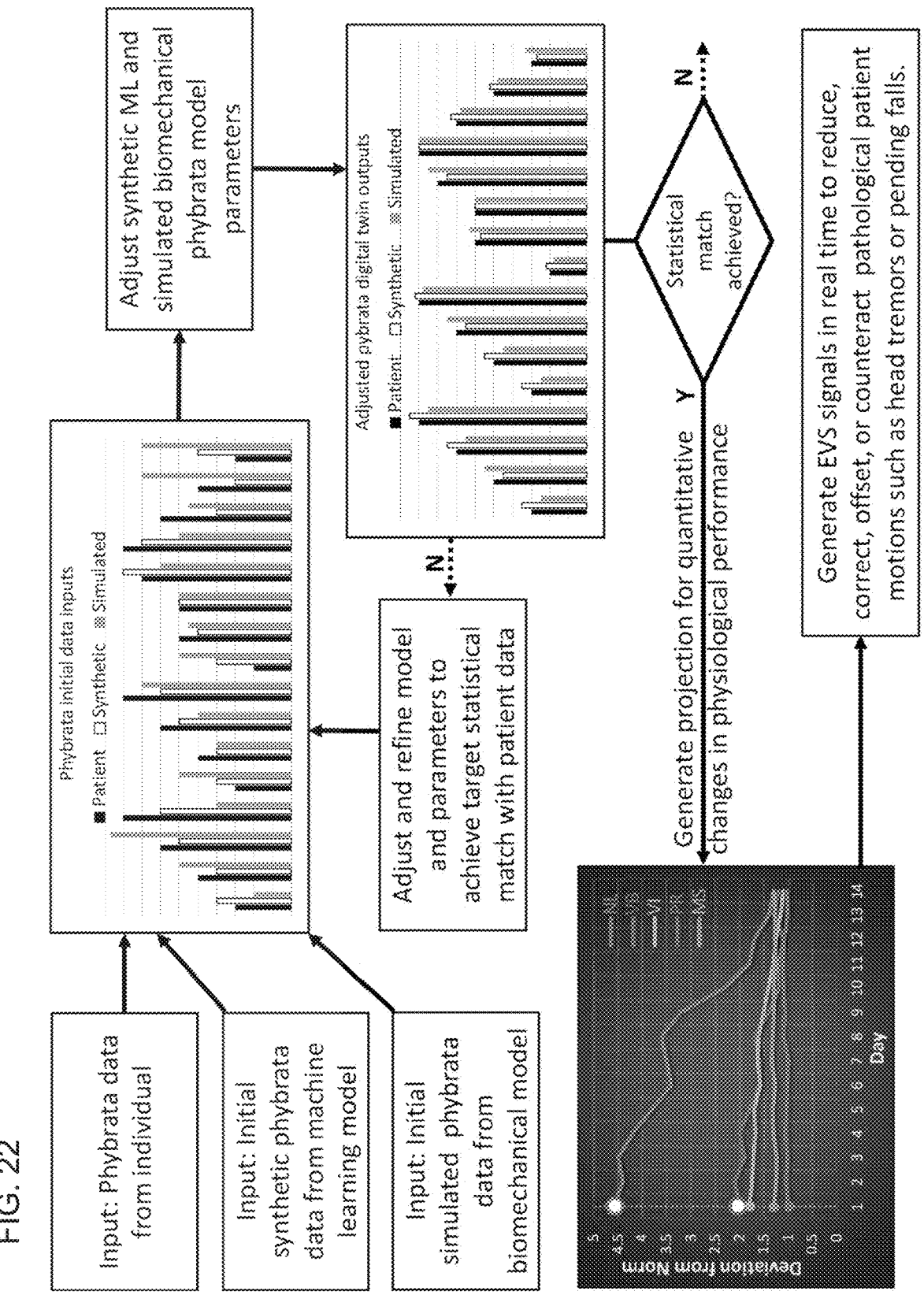

Input: Phybrata data from individual

Input: Initial synthetic phybrata data from machine learning model

Input: Initial simulated phybrata data from biomechanical model

Phybrata initial data inputs
■ Patient  □ Synthetic  ▨ Simulated

Adjust synthetic ML and simulated biomechanical phybrata model parameters

Adjusted phybrata digital twin outputs
■ Patient  □ Synthetic  ▨ Simulated

Adjust and refine model and parameters to achieve target statistical match with patient data Statistical match achieved?

Generate projection for quantitative changes in physiological performance

Generate EVS signals in real time to reduce, correct, offset, or counteract pathological patient motions such as head tremors or pending falls.

Deviation from Norm

Day

FIG. 35
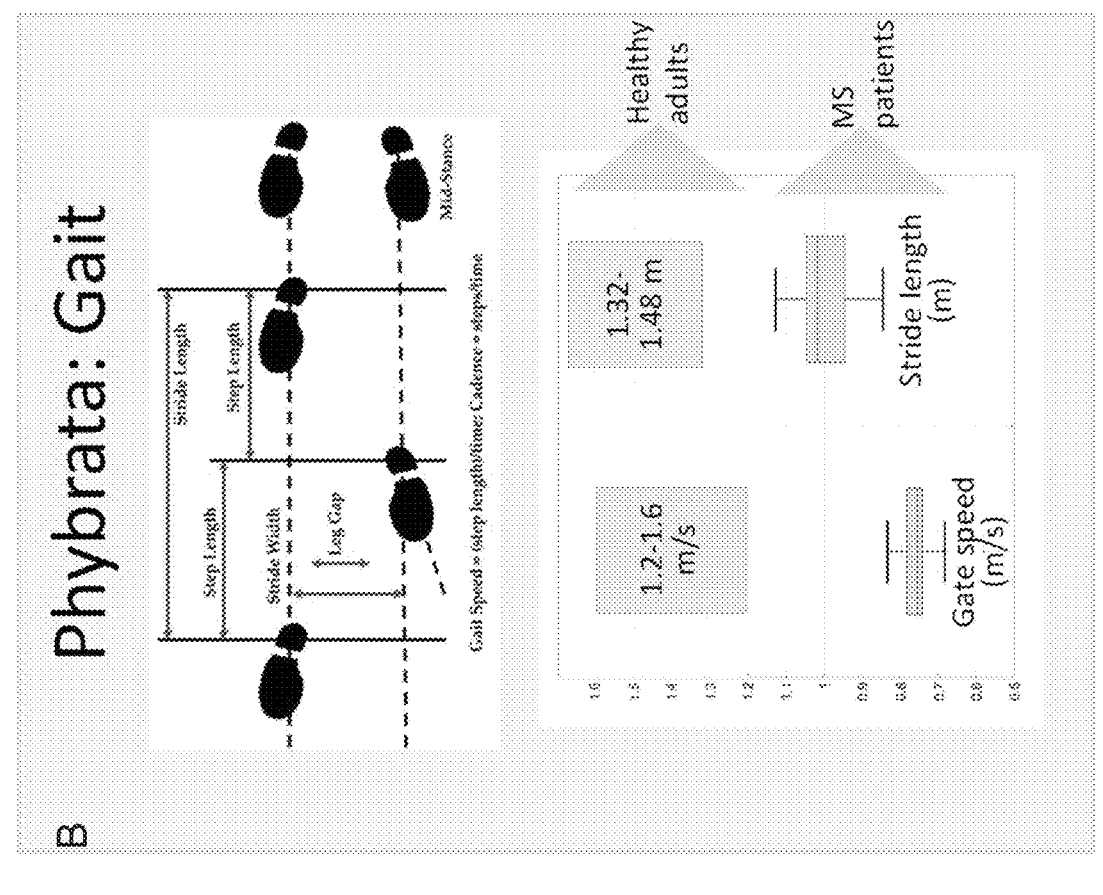
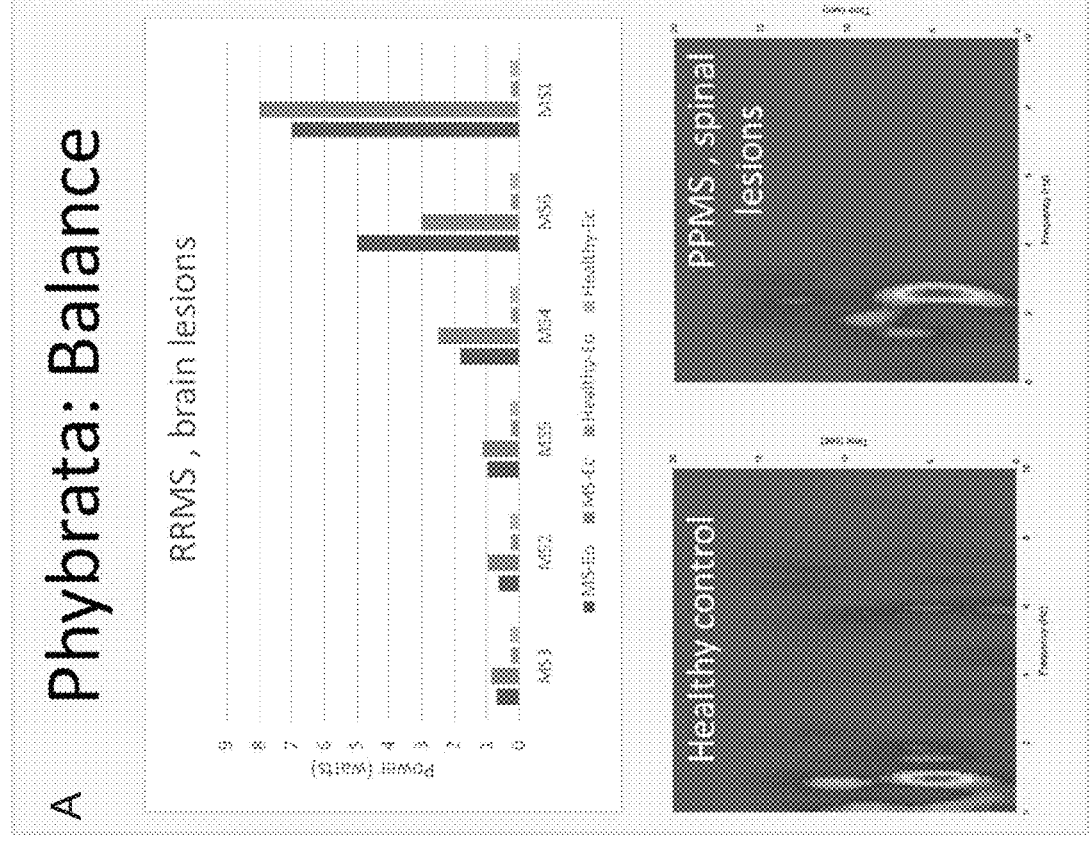

FIG. 38

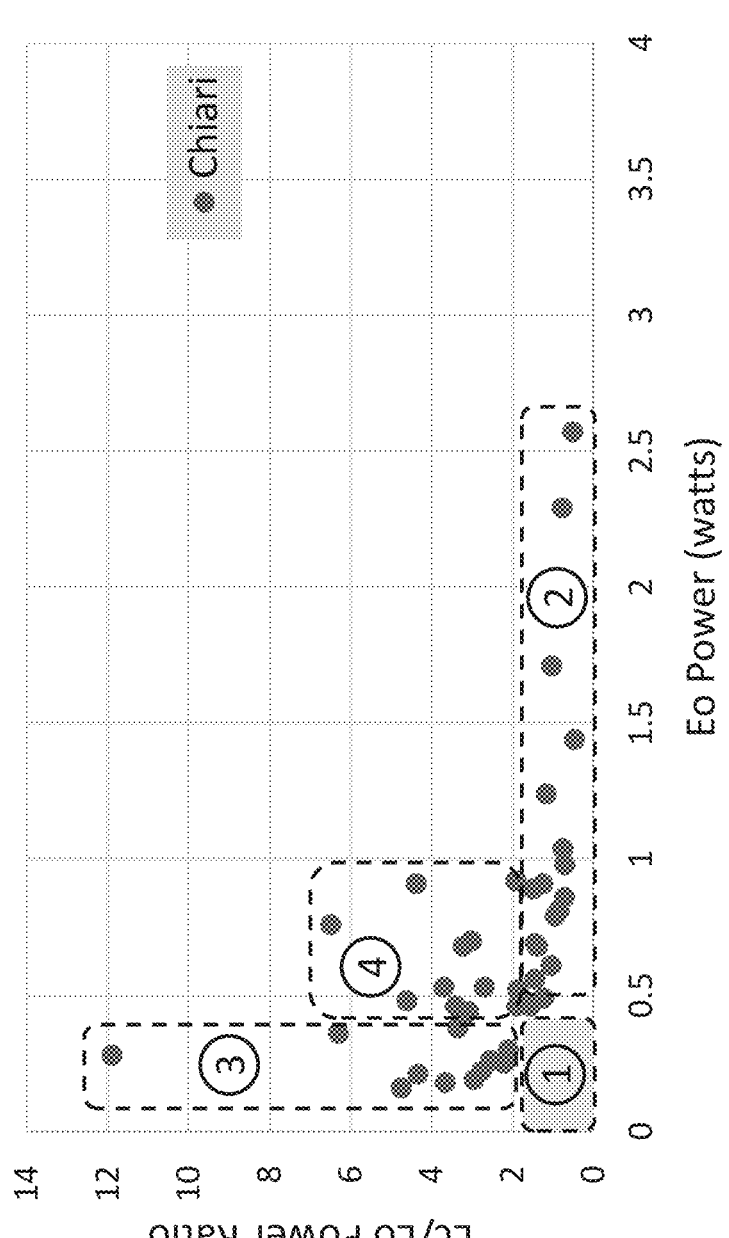

43 Chiari Malformation patients, pre-surgery

1. Unimpaired
2. Cerebellar herniation leading predominantly to impaired neural integration of motor afferents involved in postural stability
3. Cerebellar herniation leading predominantly to impaired vestibular control of postural stability
4. Cerebellar herniation leading to both impaired neural integration of motor afferents and vestibular control Neurosurgery – Vestibular Schwannoma

FIG. 41

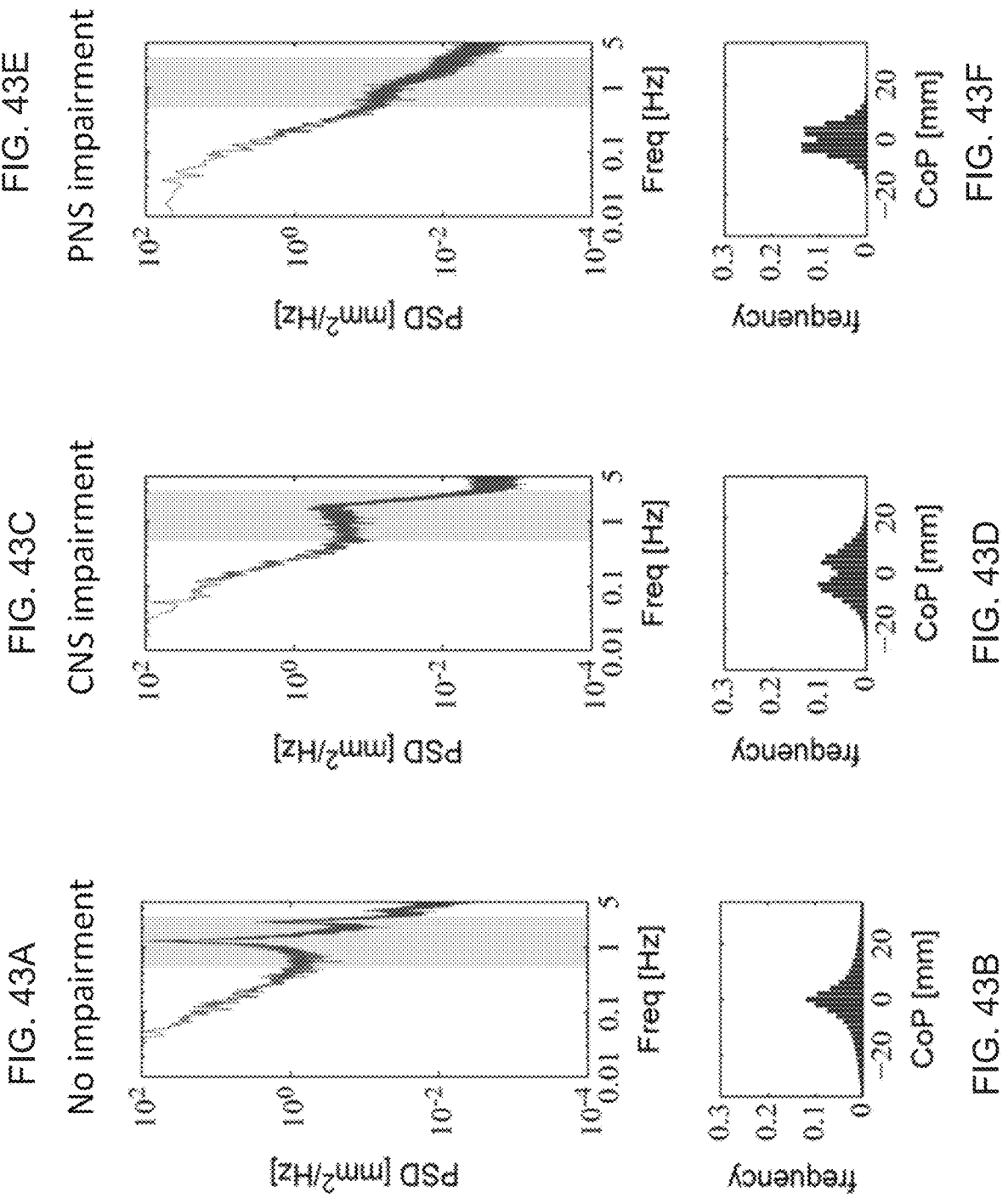

FIG. 45

Baseline: no EVS

A — Eyes Open

B — Eyes Closed

EVS: 0-25 Hz, 0.75 mA

C — Eyes Open

D — Eyes Closed

Baseline, no EVS

FIG. 56
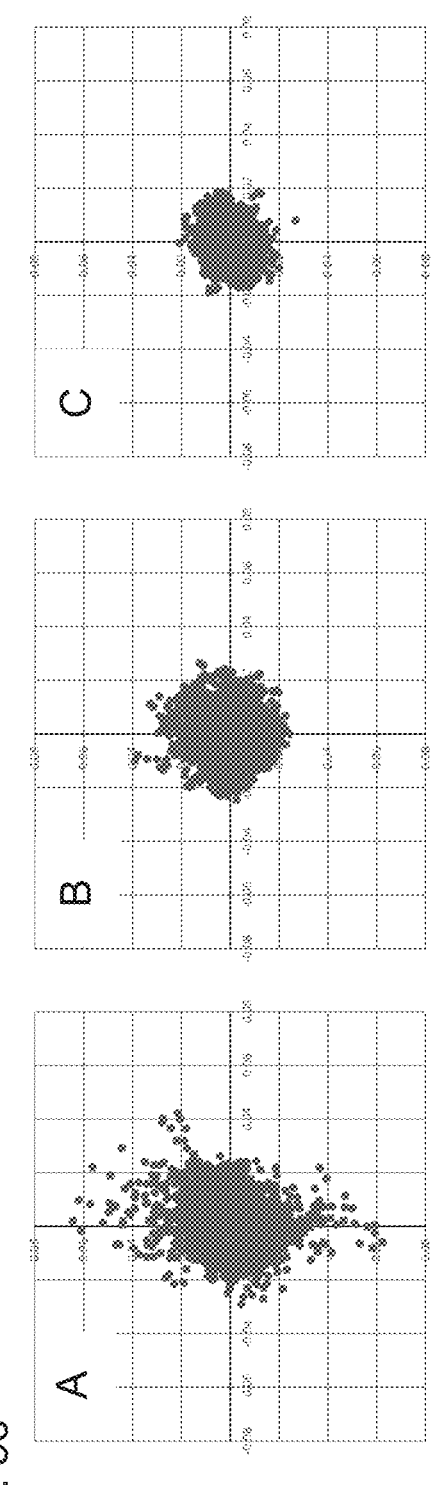
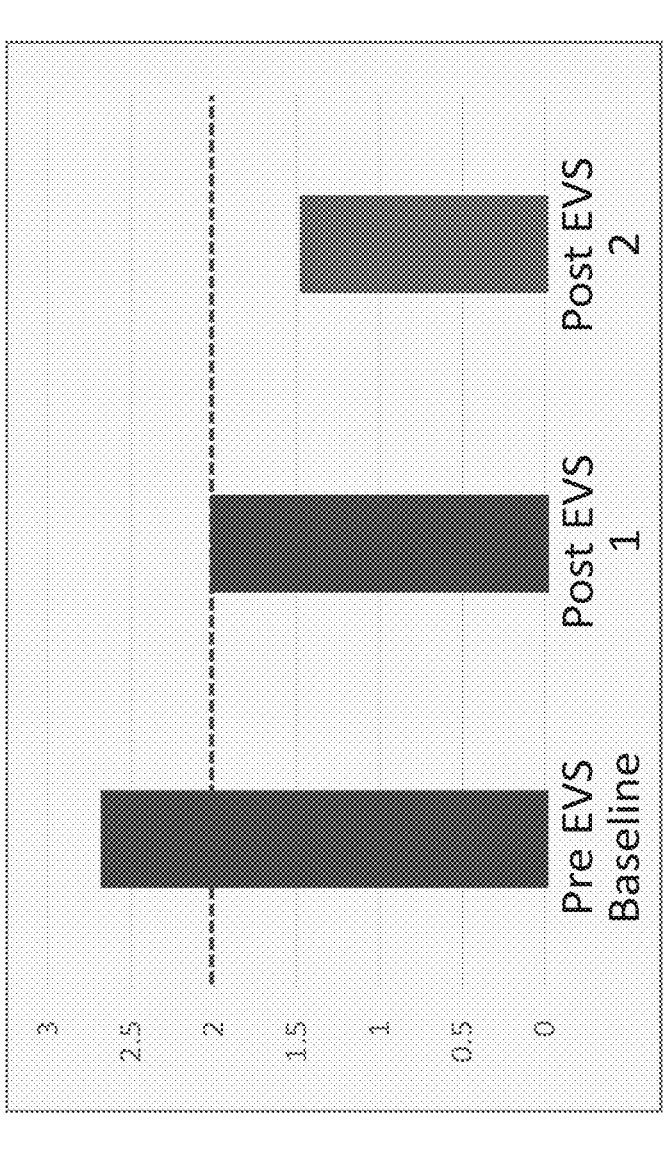

FIG. 58A

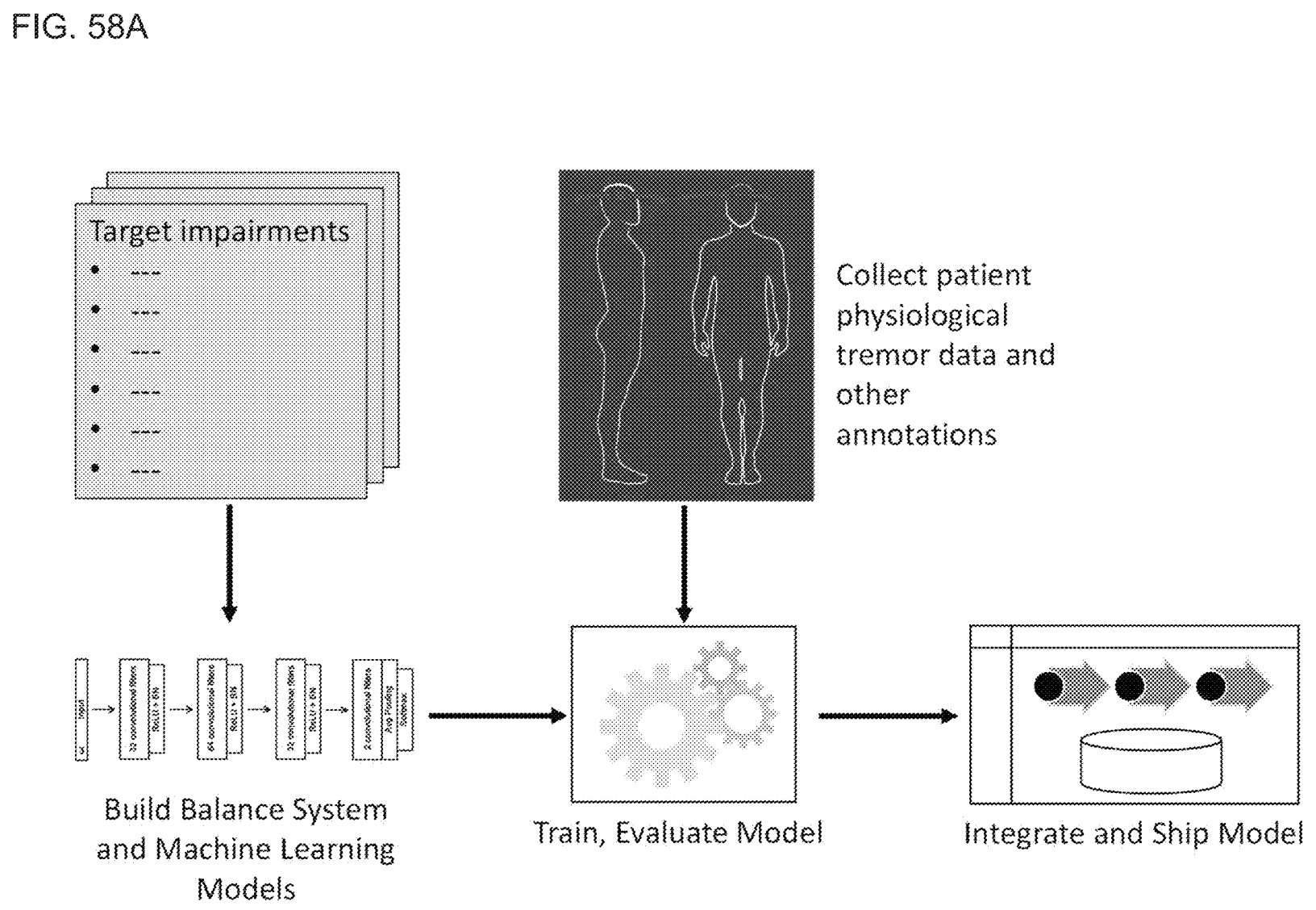

Collect patient physiological tremor data and other annotations

Train, Evaluate Model

Integrate and Ship Model

Target impairments

Build Balance System and Machine Learning Models

FIG. 58B

Collect patient phybrata data and other annotations

Identify predictive variables based on spatial, temporal, and frequency domain features. Construct univariate and multi-variate regression models and clinical prediction rules.

Train CNN model.

Assess diagnostic sensitivity, specificity.

Classify, quantify, and treat impairments

SYSTEMS AND METHODS FOR DETECTING AND TREATING NEUROPHYSIOLOGICAL IMPAIRMENT

CROSS-REFERENCE TO RELATED APPLICATIONS

This application claims priority to and the benefit of U.S. Provisional Application No. 63/149,319, entitled "SYSTEM AND METHOD FOR INTEGRATED NEUROPHYSI-OLOGICAL IMPAIRMENT DIAGNOSTICS AND THERAPEUTICS," and filed Feb. 14, 2021, and U.S. Provisional Application No. 63/302,094, entitled "ADAPTIVE ELECTRONIC BALANCE AID" and filed Jan. 23, 2022, the disclosures of which are hereby incorporated by reference in their entirety.

TECHNICAL FIELD

The present disclosure relates to systems and methods that provide neurophysiological sensing and/or neurophysiological stimulation to quantify and treat neurophysiological impairments.

BACKGROUND

Many different neurophysiological conditions, for example, neuro-disruptive and neurodegenerative medical conditions can seriously impact the lifestyle of patients. Such conditions can result from aging, disease, injuries, or genetic disorders. Diagnoses and treatment of such ailments is essential to improve the quality of life of such patients. However, diagnoses and treatments of these conditions are complicated by the fact that they can give rise to neurological damage or disruptions that are widely distributed through the brain and can thus affect all major structural and functionality components of the brain and connected physiological systems in the body.

Existing solutions for diagnosing these multiple impairments, and monitoring the effectiveness of treatments, medications, and rehabilitation either require scheduling patients for multiple complex tests carried out by multiple clinical specialists, using expensive lab equipment, or leverage clinical scoring tools that rely heavily on subjective clinical observation and patient self-reporting. Standard clinical scores and assessment tools that are widely used to both classify impairment severity and to measure patient changes for the above various medical conditions have varying utility for assessing the initial severity of patient impairments, and then final patient outcomes following treatment and rehabilitation for the corresponding medical conditions. For example, in the case of stroke patients, the modified Rankin Scale (mRS) is useful for assessing final patient outcomes but has little utility for assessing initial impairment severity. Due to their reliance on the combination of subjective clinician observations and patient self-reporting, all of these clinical scores can have systematic bias by the observer. Low sensitivity to change is another key problem with the above clinical scores—they may not discriminate improvement or decline very well, so they have limited utility during treatment and rehabilitation.

Existing solutions for treating many neurophysiological conditions rely on pharmacological medications with wide variations in patient response and significant adverse side effects, or high-risk surgical implants.

Limitations imposed by the above existing solutions on the efficiency and quality of care provided to patients include the following: the need to use multiple complex tests for definitive diagnoses delays the start of treatment, in some cases by years for patients in the early stages of multiple sclerosis and Parkinson's disease; highly individual impairment profiles and fluctuating symptoms complicate treatment; and sporadic and subjective monitoring of patient responses limit the ability to monitor, adjust, and maximize the effectiveness of treatments, medications, and rehabilitation therapies. These limitations lead to sub-optimal patient outcomes and generate large healthcare cost inefficiencies.

SUMMARY

Embodiments described herein relate to systems and methods for detecting and/or treating neurophysiological impairments, and in particular, to wearable devices that can detect physiological vibration acceleration ("phybrata") signatures associated with a user, develop a synthetic model of phybrata signatures, develop a biomechanical model or digital twin of the user to generate simulated phybrata signatures associated with the user, and/or generate stimulation signals to correct a balance, posture, or movement impairment of the user.

In some embodiments, a system includes a sensing assembly configured to be disposed on a mastoid of a user. The sensing assembly includes a housing, a first sensor disposed in the housing and configured to measure a first phybrata signal from the user, and a second sensor disposed in the housing and configured to measure a second phybrata signal from the user, which is different from the first phybrata signal. A controller is communicatively coupled to the sensing assembly. The controller is configured to: receive a first phybrata data from the sensing assembly, the first phybrata data including information obtained from the first phybrata signal and the second phybrata signal, determine a phybrata parameter associated with the user based on the first phybrata data, and determine a phybrata signature associated with the user based on the phybrata parameter.

In some embodiments, a system includes a stimulation assembly including a housing configured to be worn on a body of a user, and a set of electrodes coupled to the housing, at least a portion of the set of electrodes configured to be disposed on a mastoid of the user. A controller is in communication with the stimulation assembly. The controller is configured to: receive a phybrata signature associated with the user, determine stimulation signal parameters based on the phybrata signature, and selectively generate a signal based on the stimulation signal parameters, the signal configured to activate at least one of the set of electrodes to apply a stimulation signal to the user corresponding to the stimulation signal parameters.

In some embodiments, a system includes a sensing and stimulation assembly including a housing, a first sensor disposed in the housing and configured to measure a first phybrata signal from the user, and a second sensor disposed in the housing and configured to measure a second phybrata sign of the user different from the first phybrata parameter. A set of electrodes is coupled to the housing, at least a portion of the set of electrodes configured to be disposed on a mastoid of the user. A controller is communicatively coupled to the sensing and stimulation assembly. The controller is configured to: receive phybrata data from the sensing assembly, the phybrata data including information obtained from the first phybrata signal and the second phybrata signal, determine a phybrata parameter associated with the user based on the phybrata data, determine a phybrata signature associated with the user based on the phybrata parameter, determine stimulation signal parameters based on the phybrata signature, and selectively generate a signal based on the stimulation signal parameters, the signal configured to activate at least one pair of the set of electrodes to apply a stimulation signal to the user corresponding to the stimulation signal parameters.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE FIGURES

The foregoing and other features of the present disclosure will become more fully apparent from the following description and appended claims, taken in conjunction with the accompanying drawings. Understanding that these drawings depict only several implementations in accordance with the disclosure and are therefore, not to be considered limiting of its scope, the disclosure will be described with additional specificity and detail through use of the accompanying drawings.

FIG. 3 is a schematic flow chart of a method for generating a predictive phybrata signature indicative of predictive changes in at least one user physiological parameter based on phybrata signatures measured from a user, according to an embodiment.

FIGS. 9A-9D shows plots of normalized eyes-closed (Ec) anterior-posterior (AP) time-resolved phybrata power spectral density (NPSD) plots (top) and spectrograms (middle), along with phybrata spatial scatter plots (bottom, left), and phybrata power bar graphs (bottom, right) for an athlete tested healthy/baseline (FIG. 9A), 6 days post-concussion with neurological impairment (FIG. 9B), 14 days post-concussion (FIG. 9C), and 21 days post-concussion (FIG. 9D) a neurophysiological sensing system.

FIGS. 10A and 10B shows a sample phybrata data test report generated by a neurophysiological sensing system on day 1 (FIG. 10A) and day 10 (FIG. 10B), according to an embodiment.

FIG. 13 is a schematic block diagram of a biomechanical model of a user developed using a neurophysiological sensing system described herein, according to an embodiment.

FIG. 21 is a schematic block diagram of a method of generating predictive data indicative of predictive changes in at least one user physiological parameter based on phybrata signatures of a user determined using a sensing assembly, synthetic phybrata data generated using machine learning, and simulated phybrata data developed using a biomechanical model of a user via a neurophysiological sensing system, according to an embodiment.

FIG. 22 is a is a schematic block diagram of a method of generating predictive data indicative of predictive changes in at least one user physiological parameter based on phybrata signatures of a user determined using a sensing assembly, synthetic phybrata data generated using machine learning, and simulated phybrata data developed using a biomechanical model of a user via a neurophysiological sensing system, and generating stimulating signals to treat neurophysiological motion impairments in the user, according to an embodiment.

(FIG. 28, panel (a)) concussion (CN=0, 1); (FIG. 28, panel (b)) vestibular impairment (VI=0, 1); (FIG. 28, panel (c)) neurological impairment (NI=0, 1); and (FIG. 28, panel (d)) both vestibular and neurological impairments (VNI), for all possible cutoff values of the 4 phybrata metrics Eo, Ec, (Eo+Ec)/2, Ec/Eo; Eo=eyes open, Ec=eyes closed.

FIG. 35, panels A and pane; B shows examples of phybrata balance (FIG. 35, panel A) and gait parameters (FIG. 35, panel B) identified to derive multiple sclerosis (MS)-specific phybrata signatures and biomarkers that quantify disease progression and potentially classify lesion location.

FIG. 38 are scatter plots of Ec/Eo power ratio vs. Eo power for 43 pre-surgery Chiari malformation patients.

FIG. 41 are plots depicting a method of generating synthetic phybrata data, according to an embodiment.

FIGS. 43A-43F are plots of simulated phybrata data of a user having no impairment (FIGS. 43A-43B), having central nervous system (CNS) impairment (FIGS. 43C-43D), and peripheral nervous system (PNS) impairment (FIGS. 43E-43F), generated by a biomechanical model that serves as a digital twin of the user, according to an embodiment.

FIG. 45 are plots of calculated frequency-domain coherence between motion signals collected simultaneously from a mastoid-mounted phybrata sensor (PROTXX), electromyography electrodes attached to the calf muscle (RSOL), and a force plate (FP).

FIG. 56, panels A-C shows phybrata spatial scatter plots and FIG. 56, panel D shows Ec/Eo phybrata power ratio histograms from a sequence of pre-EVS therapy baseline tests and post-EVS therapy treatments for a user with a head-impact-induced vestibular balance impairment.

FIG. 58A is a schematic block diagram illustrating a design process for a catalog of health impairment models that can be used to classify specific medical conditions, according to an embodiment.

FIG. 58B is a schematic block diagram of a process of convolutional neural network (CNN) model training, performance testing, and balance signal synthesis, according to an embodiment.

Figure 1:
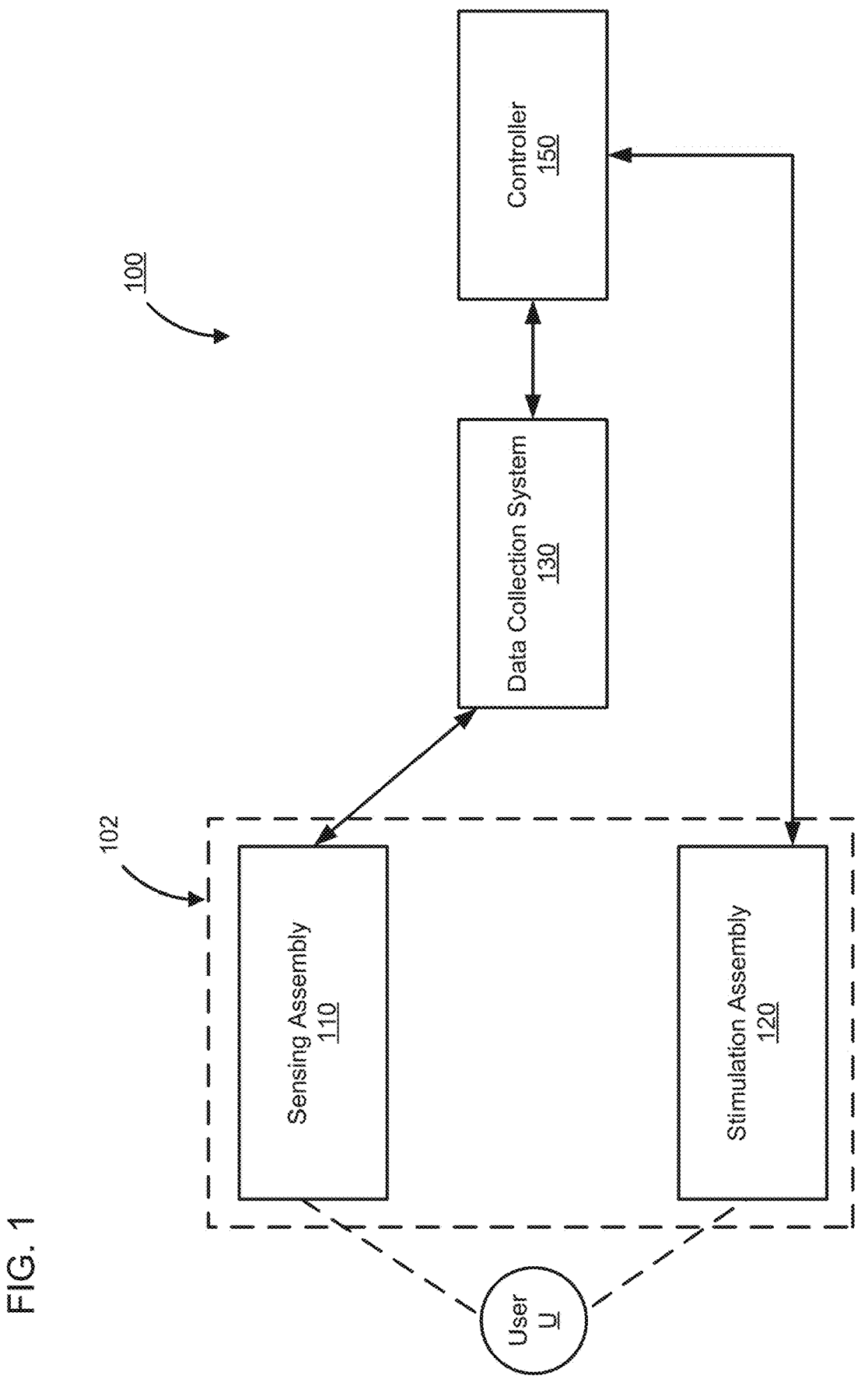
FIG. 1 is schematic block diagram of a system for generating phybrata signatures of a user, and applying neurophysiological stimulation to the user to treat neurophysiological impairments, according to an embodiment.

Taking each class together, the total mean SHAP value reflects each feature's global impact on model classification.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION

Embodiments described herein relate to systems and methods for detecting and/or treating neurophysiological impairments, and in particular, to wearable devices that can detect phybrata signatures associated with a user, develop a synthetic model of phybrata signatures, develop a biomechanical model or digital twin of the user to generate simulated phybrata signatures associated with the user, and/or generate stimulation signals to correct a balance, posture, or movement impairment of the user.

Patients with conditions such as age-related frailty, concussions, stroke, multiple sclerosis, Parkinson's disease, etc., can suffer from corresponding impairments to many different physiological systems in their bodies, including the central nervous system (CNS—brain and spinal cord), peripheral nervous system (PNS—somatic, autonomic), sensory systems (visual, vestibular, somatosensory), neurovascular system, and musculoskeletal system. For example, concussions and chronic sub-concussive head impact exposure are neuro-disruptive conditions that lead to a wide range of impact-induced damage locations (brain, vestibular system, visual system, cervical spine), volumes, topologies, and affected CNS, PNS, sensory, vascular, and musculoskeletal structures and functions. Stroke is a neuro-disruptive condition that leads to a wide range of occlusion/hemorrhage-induced lesion locations (brain, cerebral arteries), volumes, topologies, and affected CNS, PNS, sensory, vascular, and musculoskeletal structures and functions.

Multiple Sclerosis (MS) is a neuro-degenerative condition that leads to a wide range of autoimmune-induced inflammation, demyelination, and axonal damage lesion locations (brain, spinal cord, optic nerves), volumes, topologies, and affected CNS, PNS, sensory, vascular, and musculoskeletal structures and functions. Moreover, Parkinson's Disease (PD) is a neuro-degenerative condition that leads to degenerative loss of dopaminergic neurons in the midbrain (substantia nigra) that impairs the function of many other regions of the brain and related CNS, PNS, sensory, vascular, and musculoskeletal structures and functions.

Existing solutions for diagnosing these multiple impairments, and monitoring the effectiveness of treatments, medications, and rehabilitation either require scheduling patients for multiple complex tests carried out by multiple clinical specialists, using expensive lab equipment, or leverage clinical scoring tools that rely heavily on subjective clinical observation and patient self-reporting. Standard clinical scores and assessment tools that are widely used to both classify impairment severity and to measure patient changes for the above various medical conditions have varying utility for assessing the initial severity of patient impairments and then final patient outcomes following treatment and rehabilitation for the corresponding medical conditions. For example, in the case of stroke patients, the modified Rankin Scale (mRS) is useful for assessing final patient outcomes but has little utility for assessing initial impairment severity. Due to their reliance on the combination of subjective clinician observations and patient self-reporting, all of these clinical scores can have systematic bias by the observer. Low sensitivity to change is another key problem with the above clinical scores—they may not discriminate improvement or decline very well, so they have limited utility during treatment and rehab.

Many neuro-disruptive and neuro-degenerative conditions also present significant challenges in selecting, dosing, and monitoring patient response to pharmacological medications. For example, a majority of MS patients (approximately 85%) present with subacute relapses or attacks, with symptoms attributable CNS lesions. The relapse/attack is followed by a complete or partial remission/return to normal, only to be followed at a future date by another relapse usually in a different CNS location, thus presenting as relapsing and remitting MS (RRMS). Symptoms and signs depend upon the location of the MS lesions. Some symptoms may be very nonspecific, while others may be very suggestive of the diagnosis. As a result, the diagnosis of MS may be challenging in many patients.

The most common diagnostic tools used for accurate and early diagnosis of MS are those defined in the McDonald diagnostic criteria: blood tests to rule out other diseases with symptoms similar to MS; MRI imaging of lesions; electrophysiological tests of visual impairments (visual evoked potentials, VEP) and neuromotor impairments (somatosensory evoked potentials, SEP); and analysis of cerebrospinal fluid (CSF) immunologic biochemistry. In most patients with RRMS, the diagnosis is straightforward and based on a pattern of symptoms consistent with the disease and confirmed by MRI. Patients with PPMS or unusual symptoms typically require further testing, including CSF analysis, electrophysiological testing, and higher resolution MRI modalities. RRMS is characterized by recurrent attacks or relapses, which vary in frequency and severity, but there is a stable baseline between relapses. A relapse may however never completely revert to normal, and many patients are left with a residual disability.

Early recognition of an MS patient's first episode of neurologic symptoms, referred to as clinically isolated syndrome (CIS), enables earlier initiation of diseases-modifying therapies that can prolong the time to the next attack, reduce the amount of new disease seen on MRI scans, and slow the progression of physical disability and cognitive impairment. There is no cure for multiple sclerosis. Treatment typically focuses on speeding recovery from attacks, slowing the progression of the disease, and managing MS symptoms. Treatments for MS attacks include corticosteroids prescribed to reduce nerve inflammation, or blood plasma exchange (plasmapheresis) if symptoms are new, severe, and have not responded to steroids. For PPMS, there is currently only one FDA-approved disease-modifying therapy available, and it offers only a slight reduction in disease progression.

For RRMS, multiple disease-modifying therapies are available, but many carry significant health risks. Much of the immune response associated with MS occurs in the early stages of the disease. Aggressive treatment with these medications as early as possible can lower the relapse rate, slow the formation of new lesions, and potentially reduce risk of brain atrophy and disability accumulation. A significant gap in the above current care protocols is the inability to provide sufficiently frequent, quantitative, and financially accessible assessments of individual patient progression during treatment in order to better guide the selection, dosing, and efficacy monitoring of medications and physical therapy.

Similarly, the clinical presentation of Parkinson's disease (PD) is heterogeneous and overlaps with other conditions, including the Parkinsonian variant of multiple system atrophy (MSA-P), progressive supranuclear palsy (PSP) and essential tremor. Imaging of the brain in patients with Parkinsonism can increase the accuracy of differential diagnosis. Magnetic resonance imaging (MRI), single photon emission computed tomography (SPECT) and positron emission tomography (PET) allow brain imaging of structural, functional, and molecular changes in vivo in patients with PD. Clinical neurologists diagnose Parkinson's disease based on the patient's medical history, signs and symptoms, and a comprehensive neurological and physical examination. Definitive diagnosis of PD requires pathological confirmation of two invariant features: distinctive intraneuronal inclusions known as Lewy bodies in regions of predilection, and reduced numbers of dopamine neurons in the substantia nigra.

In addition to the above examinations, patient's may be given a Parkinson's disease medication such as levodopa, and significant improvement of symptoms with this medication will often confirm a diagnosis of Parkinson's disease. For many patients diagnosing Parkinson's disease can require multiple assessments carried out by neurologists trained in movement disorders, evaluating how the patient's condition and symptoms progress over time to confirm the diagnosis of Parkinson's disease. There are currently no proven neuroprotective therapies that slow or reverse disease progression in patients with PD, but medications can help control symptoms. People with Parkinson's disease have low brain dopamine concentrations. However, dopamine cannot be given directly, as it cannot enter the brain. Levodopa, the most effective Parkinson's disease medication, is a natural chemical that passes into your brain and is converted to dopamine. Dopamine agonists are an alternative class of PD medications that, unlike levodopa, do not change into dopamine, but instead mimic dopamine effects in the brain. Dopamine agonists are not as effective as levodopa in treating PD symptoms, but they last longer and may be used with levodopa to smooth the sometimes off-and-on effect of levodopa. A significant gap in the above current care protocols is the inability to provide sufficiently frequent, quantitative, and financially accessible assessments of individual patient response to therapeutic treatments to better guide the selection, dosing, and efficacy monitoring of medications and physical therapy.

Debilitating tremors in the head and limbs can also result from neurologic movement disorders such as essential tremor and dystonia. Essential tremor is the most common neurologic movement disorder and is characterized by rhythmic and regular oscillations that can lead to disabling action, postural, or rest tremors that significantly impair the ability to carry out their daily tasks. Dystonia is a severely debilitating movement disorder that involves involuntary sustained muscle contraction, causing focal motor impairments such as twitching of the eyes (blepharospasm), head and neck tremors (cervical dystonia), as well as repetitive twisting movement that result in abnormal posture. Head tremors often do not respond to drug treatment such as propranolol or primidone or to surgical treatment such as deep brain stimulation of the thalamic ventralis intermedius nucleus. As a result, botulinum toxin (Botox) is becoming widely used in the treatment of blepharospasm, cervical dystonia, and essential head tremor. Botox prevents the release of acetylcholine in synapses, leading to a reduction of pathological muscle movement. Local Botox injections are a safe approach for treating head tremors but determining the most effective injection location(s) can be a hit-or-miss process and the injections, which are expensive, and the therapy must be repeated every several months.

Many neuro-disruptive and neuro-degenerative conditions also significantly increase the risks of subsequent injuries, such as elevated orthopedic injury risk due to impaired balance in athletes and elevated fall risks due to impaired balance in elderly populations. A significant gap in the management of these risks is the inability to provide sufficiently frequent, quantitative, and financially accessible assessments of individual patient risks to better guide the selection, dosing, and efficacy monitoring of preventive interventions and medications.

Neuro-stimulation therapies include invasive and noninvasive approaches that involve the application of electrical stimulation to measure the response of various neural circuits and pathways for diagnostic purposes, as well as to induce therapeutic neuromodulation of dysfunctional neural circuitry. Examples of noninvasive approaches, in which external electrodes are utilized, include cranial electrical stimulation (CES), electrical stimulation of the eyes (ESE), and electrical vestibular stimulation (EVS).

CES includes a variety of transcranial pulsed-current stimulation devices that apply a particular amplitude, frequency, and waveform to patients. CES devices may include a box to control settings, connected via wires to a set of electrodes with variable placements on the head depending on the target application. Current amplitude and frequency are also variable, with most CES devices allowing up to 5 mA and operating over a frequency range of 0.5-500 Hz, typically with square or sinusoidal waveforms. CES can affect neurotransmitter and neurohormone concentrations, and treatment targets include insomnia, anxiety, depression, addiction, and ADHD. CES side-effects may include vertigo, skin irritation, and headache.

ESE is another therapy for either preserving or restoring vision in several retinal and optic nerve diseases, including glaucoma, age-related macular degeneration, diabetic retinopathy, and MS-related optical neuritis. Depending on the location of the electrodes, ESE may be referred to as transcorneal, transorbital, and transpalpebral. Various mechanisms are believed to underlie the effects of ESE, including increased production of neurotrophic agents, improved chorioretinal blood circulation, inhibition of proinflammatory cytokines, and remyelination of the optic nerve.

EVS is a safe and non-invasive procedure that can be used to diagnose and treat vestibular balance impairments, in which low-level electrical current is delivered to the vestibular system via electrodes applied to the mastoid. The vestibular system transduces linear and angular head motion and plays a role in stabilization of the eyes and head, standing balance control, and the perception of head motion. EVS has played an important role in understanding sensory signal processing in the vestibular system under normal and pathological conditions and has become an important noninvasive tool to probe neurosensory computations and to assist in the differentiation and treatment of vestibular syndromes.

EVS can be utilized both to diagnose vestibular impairments and to restore and enhance vestibular system function and neurological integration of vestibular sensory inputs. Proven clinical applications include diagnosis and rehabilitation of balance degradation due to aging, Parkinson's disease, stroke, traumatic brain injury (TBI), concussion, etc. EVS has also been utilized as a cost effective and safe way to simulate spatial disorientation and vestibular system response in pilots prior to aircraft operation and astronauts prior to spaceflight and exposure to microgravity.

Much like in other sensory systems, age-related deterioration of the human peripheral vestibular sensory apparatus is well documented. By age 70, anatomists report a 40% decline in the number of human motion sensing hair cell receptors in the vestibular organs. Older adults have an increased sensitivity to EVS, which likely represents a central gain enhancement mechanism that compensates for age-related hair cell receptor loss. Accelerated rates of vestibular hair cell receptor damage also potentially occur from repeated concussive blows to the head, for example, from physical impacts in many contact sports, heading the ball in soccer, punches in boxing, or explosive blast exposure in the military. As a result, EVS balance responses are also altered by both concussions and acute and chronic exposure to sub-concussive head impacts typical of many athletic, industrial, and other activities. EVS is a highly specific technique for probing the human vestibular system and is traditionally applied while recording electromyography (EMG) from lower leg muscles and/or ground reaction forces from a force plate. EVS can also be used to evoke whole-body postural responses, which is a useful tool for probing vestibular function.

Examples of invasive approaches, in which electrodes are surgically implanted within the brain or spinal cord, include deep brain stimulation, motor cortex stimulation, responsive neurostimulation, vagus neurostimulation, and spinal cord stimulation. These invasive approaches are used to treat neuromotor disorders caused by conditions such as Parkinson's disease, essential tremor, dystonia, epilepsy, obsessive-compulsive disorder, treatment-resistant depression, spinal cord injuries, neuropathic pain, and chronic pain. The need for invasive neurosurgeries and challenges in determining optimal locations for transplanted electrodes present many risks to the patient, leading to a preference for non-invasive techniques where possible. For example, for patients with incapacitating bilateral vestibular loss ("bilateral vestibulopathy), regular treatment options, such as medication, surgery, and/or vestibular rehabilitation, do not always suffice. Sensory substitution using EVS has been investigated as a possible solution for the development of a system capable of artificially restoring the vestibular function. Three approaches are currently being investigated: vestibular co-stimulation with a cochlear implant (CI), EVS with a vestibular implant (VI), and EVS using external stimulation via skin-attached electrodes over the mastoid.

However, conventional neurophysiological sensing and therapies include large sized equipment that can occupy large portion of a room, are expensive, and generally not amenable to allowing regular determination of phybrata signatures of a user, and to apply regular correction therapies, for example, stimulation signals (e.g., neurostimulation signals) to correct impairments in a patient or user's posture, gait, balance, etc. Thus, there is a clear unmet clinical need for easier to use and more quantitative impairment assessment tools that can provide: an adjuvant to clinical scores that is a precise and unbiased measure; a more sensitive and quantitative assessment of change during treatment, rehab, clinical trials; a reliable assessment of patient outcomes; and the ability to increase the frequency and duration of patient interactions via more effective, more personalized, and more efficient in-clinic and remote management of patients care, significantly lower healthcare costs, and most importantly, better patient outcomes. There is also a clear unmet clinical need for non-pharmacological and non-invasive alternatives to treat many neurophysiological conditions.

In contrast, embodiments of the systems and methods for neurophysiological sensing and stimulation described herein may provide one or more benefits including, for example: 1) provide a small wearable sensing assembly that can be worn on a mastoid of a user, enabling rapid and convenient determinant of phybrata data in various user positions; 2) using machine learning/artificial intelligence and/or a biomechanical model that represents a digital twin of the user to generate a predictive phybrata signature that is representative of the user's phybrata signature without requiring the user to wear the sensing assembly continuously, thereby reducing diagnostic cost and time for the user; 3) allowing diagnosis of neurophysiological impairment using phybrata signatures that result from a wide range of physiological and neurophysiological impairments that a user may suffer from; 4) allowing adjustment of a medicament regimen based on the phybrata signatures, thereby improving a therapeutic regimen being administered to the patient; 5) providing a wearable stimulation assembly that can easily and conveniently be used to treat neurophysiological impairments of a user based on determined phybrata signatures, allowing treatment in outpatient or remote setting and improving the therapeutic regimen; 6) allowing replacement of complex clinical equipment and time-consuming tests with easier-to-use, lower-cost, more widely accessible in-clinic and remote patient assessments; 7) integrating neuro-sensory and neuro-motor diagnostic capabilities with neuro-stimulation capabilities to further enhance diagnostic applications, to improve the administration of pharmacological treatments and rehabilitation therapies, and to provide non-pharmacological therapeutic treatment capabilities; and 8) integrating neuro-sensory and neuro-motor diagnostic capabilities with neuro-stimulation capabilities to further enhance diagnostic applications, to improve the administration of pharmacological treatments and rehabilitation therapies, and to provide non-pharmacological therapeutic treatment capabilities.

FIG. 1 is a schematic illustration of a system 100 for detecting neurophysiological biomarkers, and particularly, phybrata biomarkers of a user U, and/or for generating stimulating signals for treating neurophysiological impairments, according to an embodiment. As shown in FIG. 1 the system 100 includes a sensing assembly 110, and a controller 150. In some embodiments, the system 100 may additionally, or alternatively, include a stimulation assembly 120. For example, the sensing assembly 110 and the stimulation assembly 120 may be integrated into a sensing and stimulation assembly 102. In other embodiments, the sensing assembly 110 and the stimulation assembly 120 may be included in separate packages that are each in communication with the controller 150, or are otherwise part of separate systems. In some embodiments, the system 100 may also include a data collection system 130, for example a mobile phone (e.g., an iPHONE®, an ANDROID® phone, a WINDOWS® phone, a SYMBIAN® phone or the likes), a tablet computer, a personal computer (e.g., a desktop or a laptop), etc. The sensing assembly 110 and/or the stimulation assembly 120 may be configured to communicate with the controller 150 directly or via the data collection system 130.

The sensing assembly 110 may include a wearable sensing device configured to be worn on a mastoid of the user U. The sensing assembly 110 may include a housing that may be configured to be removably disposed on a mastoid of a user. The sensing assembly 110 may include a first sensor disposed in the housing and configured to measure a first phybrata signal from the user. The sensing assembly 110 may also include a second sensor disposed in the housing and configured to measure a second phybrata signal from the user different from the first phybrata signal, as described in further detail herein. At least a portion of the sensing assembly 110 may be configured to be attached behind one or both ears of the user U, for example, via an adhesive (e.g., a medical adhesive).

The sensing assembly 110 may be configured to detect microscopic involuntary physiological vibration acceleration (phybrata) motions of the user's U body and generate phybrata data corresponding to the motions of the user's U body. The involuntary motions of the user may be normal or pathological, and the sensing assembly 110 may be configured to detect such motions when the user U is standing still, with the user's U eyes open or eyes closed, or when the user U is in motion. The phybrata data may include complex features and feature ensembles in the spatial domain, time domain, and/or frequency domain, which may be indicative of disrupted balance (e.g., incorrect posture, imbalance while standing, change in movement, age related balance issues, etc.) and may also be indicative of neurophysiological impairment to distinguish between healthy and impaired users (e.g., indicative of a concussion, a stroke, Parkinson's diseases, multiple sclerosis, elderly frailty, peripheral neuropathy, peripheral arterial disease, spinal stenosis, chronic pain, invasive surgery, etc.).

The stimulation assembly 120 may also include a wearable device to house stimulation electronics and/or rechargeable battery modules, for example, configured to be worn around a neck of the user U. The stimulation assembly 120 may also include a housing (e.g., configured to be worn around the neck of the user U), and a set of electrodes disposed outside the housing, at least a portion of the set of electrodes configured to be disposed on a mastoid of the user (e.g., disposed behind the ear of the user U via an adhesive), and/or any other portion of the body of the user U, for example, to the back of a neck of the user U.

The stimulation assembly 120 may be configured to selectively apply a stimulation signal to the user U based on the user U's specific phybrata signatures that may have been determined by the controller 150 based on phybrata data acquired by the sensing assembly 110. The stimulation signals may include EVS, ESE, or CES signals that are configured to cause an increase in the ability of the user U's nervous system (e.g., vestibular nerve) to conduct signals from the peripheral vestibular organs to the brain, and the ability of the corresponding neurosensory and neuromotor structures in the brain itself to process these signal's to correct a disruption in user U's posture, balance while standing, or gait while walking, to reduce balance and movement disruptions caused by aging, concussions, stroke, Parkinson's disease, central neuro-degenerative disorders, cerebral palsy (e.g., in children) cybersickness due to exposure to virtual reality (VR), exposure to microgravity during spaceflight, etc., or to enhance rehabilitation of the user U.

As previously described, the neurophysiological sensing functions of the sensing assembly 110, and the neurophysiological stimulation functions of the stimulation assembly 120 may be integrated together into a sensing and stimulation assembly 102, for example, a wearable device configured to be worn on the user U (e.g., around a portion of the neck of the user U) and having sensors and electrodes configured to be removably coupled (e.g., via an adhesive) to at least the mastoid of the user U. In such embodiments, the sensing and stimulation assembly 102 is configured to selectively sense phybrata data from the user U, as well as selectively apply stimulating signals to the user U to correct any impairment in the user U determined from the user U's phybrata signature associated with the user U's phybrata data acquired by the sensing and stimulation assembly 102.

The sensing assembly 110 and/or the stimulation assembly 120 may be in communication with the controller 150 directly, or via the data collection system 130, as previously described. The data collection system 130 may be configured to receive phybrata data from the sensing assembly 110, display the raw data to user, communicate the data to the controller 150, at least partially process the data, display phybrata signatures and/or other relevant data to the user U or a caregiver, and may also be configured to communicate stimulation signal parameters to the stimulation assembly 120 to cause the stimulation assembly 120 to generate stimulation signals for correcting an imbalance, or impairment in balance or posture of a user. In some embodiments, the data collections system 130 (e.g., operations thereof) may be integrated into the controller 150.

The sensing assembly 110, and/or the stimulation assembly 120 may be in communication with the data collection system 130 and/or the controller 150 via a device-to-device communications link or a communication network, for example, any suitable Local Area Network (LAN) or Wide Area Network (WAN), which may be supported by Frequency Division Multiple Access (FDMA), Time Division Multiple Access (TDMA), Code Division Multiple Access (CDMA) (particularly, Evolution-Data Optimized (EVDO)), Universal Mobile Telecommunications Systems (UMTS) (particularly, Time Division Synchronous CDMA (TD-SCDMA or TDS) Wideband Code Division Multiple Access (WCDMA), Long Term Evolution (LTE), evolved Multimedia Broadcast Multicast Services (eMBMS), High-Speed Downlink Packet Access (HSDPA), and the like), Universal Terrestrial Radio Access (UTRA), Global System for Mobile Communications (GSM), Code Division Multiple Access 1x Radio Transmission Technology (1x), General Packet Radio Service (GPRS), Personal Communications Service (PCS), 802.11X, ZigBee, Bluetooth, Wi-Fi, any suitable wired network, combination thereof, and/or the like.

The controller 150 may include a local server, a remote server, a cloud network, etc., which may be continuously or selectively in communication with the sensing assembly 110 and/or the stimulation assembly 120. The controller 150 is configured to receive the phybrata data from the sensing assembly, which includes the first phybrata signal and the second phybrata signal measured by the sensing assembly 110, and process the phybrata data to determine a phybrata parameter(s), and/or a phybrata signature associated with the user based on the phybrata data measured from the user U. The controller 150 may also be configured to determine quantitative phybrata metrics and/or synthetic phybrata data associated with the user U using machine learning or artificial intelligence based on the phybrata signature. In some embodiments, the controller 150 may also be configured to generate a biomechanical model of the user U that represents a digital twin of the user, and generate simulated data associated with the user U using the biomechanical model.

The controller 150 may also be configured to determine stimulation signal parameters based on the phybrata signature, and selectively generate a signal based on the stimulation signal parameters, which is configured to activate at least one of the set of electrodes in the stimulation assembly 120 to apply a stimulation signal corresponding to the stimulation signal parameters to the user U. The controller 150 may be configured to communicate the stimulation signal to the stimulation assembly 120 directly or via the data collection system 130.

Figure 2:
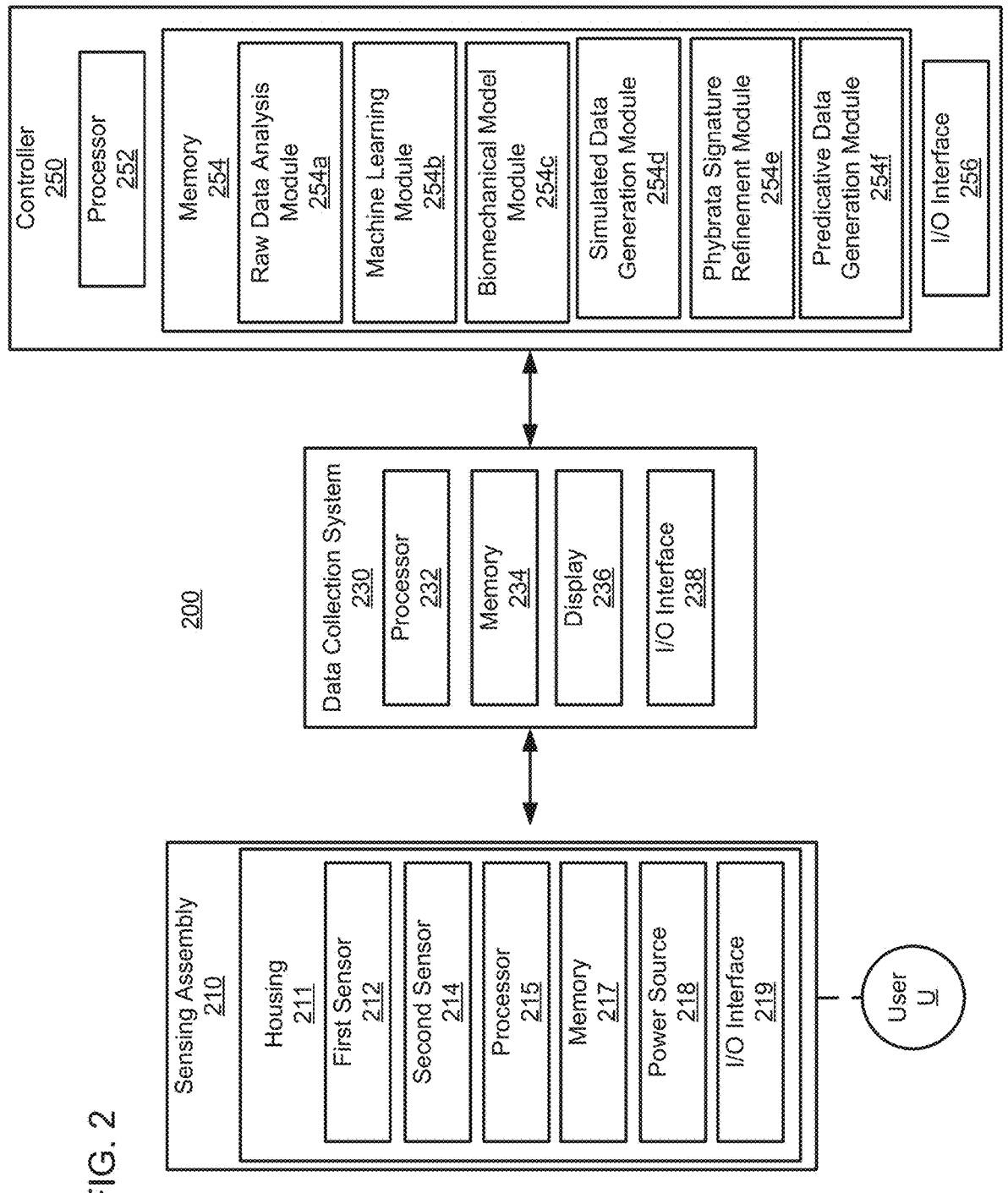
FIG. 2 is a schematic block diagram of a system including a sensing assembly, a controller, and optionally, a data collection system, for generating phybrata signatures of a user, according to an embodiment.

Expanding further, FIG. 2 is a schematic block diagram of a system 200 for sensing neurophysiological signals, i.e., phybrata signals from a user U. The system 200 includes a sensing assembly 210, and a controller 250, and in some embodiments, a data collection system 230. In some embodiments, the data collection system 230 may be integrated into the controller 250.

The sensing assembly 210 includes a housing 211 in which a first sensor 212 and a second sensor 214 are disposed. The housing 211 may have a small form factor such that the housing 211 is configured to be worn by the user U. For example, at least a portion of the housing 211 may be configured to be removably worn on a mastoid of the user U, for example, behind the ear of the user U. For example, the housing 211 may be configured to be removably disposed behind the ear of the user U via an adhesive (e.g., a medical adhesive). The housing 211 may be formed from any suitable material, for example, metals, plastics, polymers, or any other suitable lightweight material.

The first sensor 212 is disposed in the housing 211 and configured to measure a first phybrata signal from the user U. For example, the first sensor 212 may include a linear acceleration sensor (e.g., an accelerometer) configured to measure linear acceleration of the user U over a period of time. The second sensor 214 may also be disposed in the housing 211 and configured to measure a second phybrata signal from the user U that is different from the first phybrata signal. For example, the second sensor 214 may include a rotation velocity sensor (e.g., a gyroscope) configured to measure a rotational velocity of the user U over a period of time. As described herein, the term "phybrata signals" implies the signals that are actually measured by the first sensor 212 and/or the second sensor 214 attached to the user U's mastoid, including but not limited to accelerometer signals, gyroscope signals, or any other signals measured by any other sensor included in the sensing assembly 210.

The first sensor 212 and the second sensor 214 may be configured to detect microscopic voluntary and involuntary motions of the body of the user U, that may be both normal and pathological, for example, when the user U is sitting, standing, or walking and with the user U's eyes open, eyes closed, head stationary, head moving, standing, sitting, walking, etc. The first and second sensors 212 and 214, thus together generate phybrata data that includes the first phybrata signal and the second phybrata signal, i.e., phybrata data collected from the first phybrata signal and the second phybrata signal, for example, over a period of time. The phybrata data may include complex features and features ensembles in the spatial domain, time domain, and/or frequency domain, which are representative of a phybrata signature associated with the user U.

The sensing assembly 210 may also include a processor 215, a memory 217, a power source 218, and an input/output (I/O) interface 219. The processor 215 may be implemented as a general-purpose processor, an Application Specific Integrated Circuit (ASIC), one or more Field Programmable Gate Arrays (FPGAs), a Digital Signal Processor (DSP), a group of processing components, or other suitable electronic processing components. The memory 217 (e.g., Random Access Memory (RAM), Read-Only Memory (ROM), Non-volatile RAM (NVRAM), Flash Memory, hard disk storage, etc.) stores data (e.g., phybrata data) and/or computer code for facilitating at least some of the various processes described herein. The memory 217 may include tangible, non-transient volatile memory, or non-volatile memory. The memory 217 may include a non-transitory processor 215 readable medium that stores programming logic that, when executed by the processor 215, controls the operations of the sensing assembly 210. In some arrangements, the processor 215 and the memory 217 form various processing circuits described with respect to the sensing assembly 210.

The power source 218 may include a battery e.g., rechargeable battery (e.g., Li-ion, Li-polymer, NiCad, etc.) or a disposable battery (e.g., a coin cell), and configured to provide electrical power to the sensors 212, 214, and the processor 215. The I/O interface 219 is structured for sending and receiving data (e.g., over a communication network) from the data collection system 230 and/or the controller 250. Accordingly, the I/O interface 219 includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like.

The processor 215 may be configured to selectively activate the first sensor 212 and the second sensor 214, for example, based on a signal received from the controller 250 or the data collection system 230. The processor 215 may also be configured to receive and in some embodiments, process data received from the sensors 212, 214 (e.g., amplify data, filter to remove noise, etc.) and communicate phybrata data via the I/O interface 219 to the controller 250 (e.g., via the data collection system 230). As used herein, the term "phybrata data" is the phybrata information that is generated and transmitted by sensing assembly 210 to the data collection system 230 (e.g., mobile app used to configure and run tests), and/or the controller 250. The phybrata data may include some or all of the phybrata signals measured from the user U by the sensing assembly 210.

In some embodiments, the phybrata data may include at least one of temporal acceleration plots, spatial scatter plots, eyes open (Eo) phybrata powers, eyes closed (Ec) phybrata powers, receiver operating characteristic (ROC) curves, phybrata power spectral density (PSD) plots, time-resolved phybrata power spectral density (TRPSD) plots, or sensory reweighting responses. In some embodiments, the processor 215 may be configured to process the raw phybrata signal acquired by the sensors 212, 214 to generate the phybrata data. In some embodiments, the controller 250 may be configured to receive the raw phybrata data from the sensing assembly 210 and process the raw data to generate processed phybrata data, and the raw and/or processed phybrata data may be further processed to generate phybrata based digital biomarkers that may be used to identify, quantify, and/or monitor impairments to specific physiological systems in the body of the user U.

Because the sensing assembly 210 is small and wearable, the sensing assembly 210 advantageously allows monitoring of phybrata data of the user U over extended periods of time, and may be flexibly used to acquire such data while the user U is standing, sitting, or moving and enables remote monitoring of phybrata parameters of the user U (e.g., home based monitoring). In some embodiments, the sensing assembly 210 may be configured to measure the phybrata data within 0.5 mins to 2 mins, inclusive (e.g., 0.5, 0.6, 0.7, 0.8, 0.9, 1.0, 1.1, 1.2, 1.3, 1.4, 1.5, 1.6, 1.7, 1.8, 1.9, or 2.0 mins, inclusive) of the sensors 212 and 214 being activated after the user U has worn the sensing assembly 210 (e.g., on a mastoid of the user U). Thus, the sensing assembly 210 allows for non-invasive measurement of phybrata data that can identify, quantify, and monitor impairments in the user U's balance, posture, or gait using the unique phybrata signature of the user U.

The data collection system 230 may include, for example, a mobile phone (e.g., an iPHONE®, an ANDROID® phone, a WINDOWS® phone, a SYMBIAN® phone or the likes), a tablet computer, a personal computer (e.g., a desktop or a laptop), a smartwatch, or any other suitable data collection system. The data collections system 230 may include a processor 232, a memory 234, a display 236, and an I/O interface 238. The processor 232 may be implemented as a general-purpose processor, an Application Specific Integrated Circuit (ASIC), one or more Field Programmable Gate Arrays (FPGAs), a Digital Signal Processor (DSP), a group of processing components, or other suitable electronic processing components. The memory 234 (e.g., Random Access Memory (RAM), Read-Only Memory (ROM), Non-volatile RAM (NVRAM), Flash Memory, hard disk storage, etc.) stores data (e.g., phybrata data) and/or computer code for facilitating at least some of the various processes described herein. The memory 234 may include tangible, non-transient volatile memory, or non-volatile memory. The memory 234 may include a non-transitory processor 232 readable medium that stores programming logic that, when executed by the processor 232, controls the operations of the data collection system 230. In some arrangements, the processor 232 and the memory 234 form various processing circuits described with respect to the data collection system 230.

The I/O interface 238 may be structured for sending and receiving data (e.g., over a device-to-device communications link or a communication network) from the sensing assembly 210 and/or the controller 250. Accordingly, the I/O interface 238 includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like. The display 236 may include a light emitting diode (LED), a liquid crystal display (LCD), a plasma display, an e-ink display, or any other suitable display.

The data collection system 230 may be configured to receive the phybrata data from the sensing assembly 210 and may be configured to store the data on the memory 234, and/or display the raw phybrata data. In some embodiments, the processor 232 may be configured to process the data, for example, to generate spatial scatter plots, eyes open (Eo) phybrata powers, eyes closed (Ec) phybrata powers, receiver operating characteristic (ROC) curves, phybrata power spectral density (PSD) plots, time-resolved phybrata power spectral density (TRPSD) plots, or sensory reweighting response, which are displayed on the display 236. In some embodiments, the data collection system 230 may be configured to receive processed data from the controller 250, for example, synthetic data, simulated data, biomechanical model, predicted phybrata data, etc., as described herein, and display the data on the display 236. The data collections system 250 may also be configured to generate generic or custom reports for the user U, that may be representative of the user U's balance, posture, gait, or neurophysiological symptoms, etc. In some embodiments, the data collections system 230 may display on the display 236, or transmit via the I/O interface 238 the phybrata data, phybrata signature, or other relevant information in a simple and intuitive summary report format for clinicians and patients (e.g., the user U).

The controller 250 is communicatively coupled to the sensing assembly 210, for example, via the data collection system 230. The controller 250 may include a processor 252, a memory 254, and an I/O interface 256. In various embodiments, the controller 250 may include a remote server or a cloud computing network. The processor 252 may be implemented as a general-purpose processor, an Application Specific Integrated Circuit (ASIC), one or more Field Programmable Gate Arrays (FPGAs), a Digital Signal Processor (DSP), a group of processing components, or other suitable electronic processing components.

The memory 254 (e.g., Random Access Memory (RAM), Read-Only Memory (ROM), Non-volatile RAM (NVRAM), Flash Memory, hard disk storage, etc.) stores data (e.g., phybrata data) and/or computer code for facilitating at least some of the various processes described herein. The memory 254 may include tangible, non-transient volatile memory, or non-volatile memory. The memory 254 may include a non-transitory processor 252 readable medium that stores programming logic that, when executed by the processor 252, controls the operations of the controller 250. In some arrangements, the processor 252 and the memory 254 form various processing circuits described with respect to the controller 250.

The I/O interface 256 may be structured for sending and receiving data (e.g., over a communication network) from the sensing assembly 210 and/or the data collection system 230. Accordingly, the I/O interface 256 includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like.

The controller 250 may be configured to receive phybrata data from the sensing assembly 210, which includes information obtained from the first phybrata signal and the second phybrata signal, for example, phybrata related information extracted by the sensing assembly 210 or the data collection system 230. The controller 250 may be configured to determine a phybrata parameter associated with the user U based on the phybrata data. As used herein, the term "phybrata parameter" implies parameters that are "identified in" or "extracted from" the phybrata data using, for example, some combination of signal processing, statistical data analysis, and machine learning. These phybrata parameters may include features found in every users' phybrata data, which can be used to assess the performance of and impairments/disruptions of different physiological systems in the users' body.

In some embodiments, the phybrata parameter may include spatial-domain parameters, time-domain parameters, or frequency-domain parameters. Each of the spatial domain parameters, time-domain parameters, or frequency-domain parameters may include at least one of temporal acceleration plots, spatial scatter plots, eyes open (Eo) phybrata powers, eyes closed (Ec) phybrata powers, receiver operating characteristic (ROC) curves, phybrata power spectral density (PSD) plots, time-resolved phybrata power spectral density (TRPSD) plots, or sensory reweighting responses. The controller 250 may also be configured to determine a phybrata signature associated with the user U based on the first phybrata parameter. The phybrata signature may include at least one of spatial-domain phybrata features, time-domain phybrata features, and/or frequency-domain phybrata features, which are indicative of a phybrata behavior of the user U, and may be specific to the user U, for example, based upon a neurophysiological behavior of the user U. As used herein, the term "phybrata signature" implies a set of phybrata parameters, determined, calculated, or generated via additional statistical data analysis, machine learning, and/or artificial intelligence, that together present an overall performance assessment or impairment diagnosis that is unique to a specific user.

In some embodiments, the controller 250 may be configured to determine quantitative phybrata metrics based on the phybrata signature. The quantitative phybrata metric may be configured to independently classify, quantify, and/or track a magnitude and time evolution of at least one of a balance performance, a postural stability performance, a movement performance, a disruption or impairment to a specific physiological system, or a specific disease state, injury, or genetic disorder associated with the user U. As used herein, the term "quantitative phybrata metric" is meant to be synonymous with a "phybrata biomarker". Such a phybrata biomarker is a subset of all of the observed signatures, or a "special" signature which, when present, can be used universally for any user to independently classify, quantify, and/or track a magnitude and time evolution of at least one of a balance performance, a postural stability performance, a movement performance, a disruption or impairment to a specific physiological system, or a specific disease state, injury, or genetic disorder associated with the user U.

In some embodiments, the controller 250 may also be configured to generate synthetic phybrata data associated with the user U using machine learning or artificial intelligence based on the phybrata data, and may generate a signal indicative of the synthetic phybrata data. As used herein, the term "synthetic" when use with the term "phybrata data", implies data that is generated using only mathematical procedures. When properly constructed, synthetic phybrata data has the same statistical properties as measured phybrata data, and therefor yields compatible phybrata parameters, signatures, and metrics/biomarkers. In other words, synthetic phybrata data is artificially generated phybrata data and does not include real user data.

In some embodiments, the controller 250 may be configured to determine synthetic phybrata parameters associated with the user U based on the determined phybrata data, and also determine a synthetic phybrata signature associated with the user U based on the determined phybrata signature. In some embodiments, the controller 250 may be configured to determine a synthetic quantitative phybrata metric based on the synthetic phybrata signature. The synthetic quantitative phybrata metric may be configured to classify, quantify, and/or track a magnitude and time evolution of at least one of a balance performance, a postural stability performance, a movement performance, a disruption or impairment to a specific physiological system, or a specific disease state, injury, or genetic disorder associated with the user U.

The controller 250 may be configured to use the quantitative phybrata metric determined from the raw phybrata data, as well as the synthetic quantitative phybrata metric to independently classify, quantify, and/or track a magnitude and time evolution of at least one of a balance performance, a postural stability performance, a movement performance, a disruption or impairment to a specific physiological system, or a specific disease state, injury, or genetic disorder associated with the user U. The synthetic quantitative phybrata metric that is determined using statistical and machine learning data analysis by the controller 250, may leverage unique features and feature ensembles in phybrata signals to identify and analyze the different contributions made by each of the body's physiological systems to biomechanical stabilization of the head and eyes of the user U as the reference platform that the body uses to enable balance and movement.

In some embodiments, the controller 250 is also configured to generate a biomechanical model of the user U. The biomechanical model may represent a digital twin of the user U, and may be configured to include a range of neurosensory inputs and neuromotor outputs associated with the user U. The biomechanical model may include a full range of active vs. passive, open-loop vs. closed-loop, intermittent vs. continuous, and high-complexity vs. low-complexity control behaviors that are able to account for and replicate normal and impaired balance postural stability and sensory reweighting of the user U during balance and gait. Phybrata digital twin systems represented by the biomechanical model incorporate phybrata signatures, statistical data analytics models, machine learning models, and phybrata-based human biomechanical models to enable more rapid and quantitative diagnoses of complex medical conditions, enable earlier initiation of treatment, and provide more comprehensive monitoring and feedback to optimize individual patient responses to pharmacological medications, non-pharmacological treatments, and rehabilitation therapies.

The controller 250 may be configured to generate simulated phybrata data associated with the user U based on the determined phybrata data, and may generate a signal indicative of the simulated phybrata data. As used herein, the term "simulated" used with the term phybrata data implies data that is generated through simulations of the biomechanical model. The controller 250 may be configured to determine simulated phybrata parameters associated with the biomechanical model of the user U based on the determined phybrata parameters. The controller 250 may also be configured to determine a simulated phybrata signature associated with the biomechanical model of the user U based on the determined phybrata signature, and determine a simulated quantitative phybrata metric based on the simulated phybrata signature. The simulated quantitative phybrata metric may be configured to classify, quantify, and/or track a magnitude and time evolution of at least one of a balance performance, a postural stability performance, a movement performance, a disruption or impairment to a specific physiological system, or a specific disease state, injury, or genetic disorder associated with the user U.

In some embodiments, the controller 250 is further configured to generate adjusted phybrata data based on the determined phybrata data, the synthetic phybrata data, and the simulated phybrata data, and determine an adjusted phybrata signature indicative of the adjusted phybrata data for the user U. The adjusted phybrata data may be a statistical and mathematical match fit of the synthetic and simulated data with the raw phybrata data captured by the sensing assembly 210 from the user U, enabling the use of the synthetic and simulated phybrata data to further diagnose and/or correct neurophysiological impairment in the user U.

In some embodiments, the phybrata data initially captured from the user U may be a first phybrata data. The controller 250 may be further configured to receive a second phybrata data from the user U (e.g., captured from the user U by the sensing assembly 210 at a later time than the first phybrata data), and compare a second phybrata data associated with the user U measured by the sensing assembly 210 with the adjusted phybrata data. For example, the second phybrata data may be captured by the sensing assembly 210 once the first phybrata data has been captured and processed by the controller 250. The controller 250 may be configured to generate predictive data based on the comparison between the second phybrata data and the adjusted phybrata data, the predictive data indicative of projected physiological changes in the user, and generate a signal indicative of the predictive data. Thus, the adjusted phybrata data may represent a close fit to actual phybrata data expected to be captured from the user U, for example, using the biomechanical model. The controller 250 may also generate a predictive phybrata signature indicative of the predictive data.

In some embodiments, the projected physiological changes may include changes in at least a balance, a posture, or a movement performance of the user. In some embodiments, the projected physical changes may include changes in a disease or injury state of the user U. The disease or injury state may include at least one of a concussion, a stroke, Parkinson's diseases, multiple sclerosis, elderly frailty, peripheral neuropathy, peripheral arterial disease, spinal stenosis, chronic pain, or invasive surgery.

In some embodiments, projected physical changes include changes in response to a treatment, a medication, a therapy, or rehabilitation. For example, a caregiver may use the results of the projected physiological changes to monitor and document the user U's response to a course of treatment, medications, therapies, and/or rehabilitation. In some embodiments, the disease state is Parkinson's disease, and the medication is one or more of dopaminergic drugs such as Levodopa and carbidopa (Duopa, Rytary, Sinemet), dopaminergic add-on drugs such as Safinamide (Xadago), Amantadine (Gocovri), or Symmetrel, dopamine agonists such as pramipexole (Mirapex), rotigotine (Neupro), or ropinirole (Requip), Anticholinergics such as benztropine (Cogentin) and trihexyphenidyl (Artane), Mao-B inhibitors such as selegiline (Eldepryl, Zelapar)) and rasagiline, and/or COMT inhibitors such as entacapone (Comtan), opicapone (Ongentys), and Tolcapone (Tasmar).

In some embodiments, the disease state is multiple sclerosis, and the medication is one or more of the following: Alemtuzumab (Lemtrada), Cladribine (Mavenclad), Dimethyl fumarate (Tecfidera), Diroximel fumarate (Vumerity), Fingolimod (Gilenya), Glatiramer acetate (Copaxone, Glatopa), Interferon beta-1a (Avonex, Rebif), Interferon beta-1b (Betaseron), Mitoxantrone (Novantrone), Monomethyl fumarate (Bafiertam), Natalizumab (Tysabri), Ocrelizumab (Ocrevus), Ozanimod (Zeposia), Peginterferon beta-1a (Plegridy), Siponimod (Mayzent), or Teriflunomide (Aubagio), In some embodiments, the controller 250 may include various circuitries or modules configured to perform the operations of the controller 250. For example, as shown in FIG. 2, the controller 250 includes a raw data analysis module 254a, a machine learning module 254b, a biomechanical model module 254c, a simulated data generation module 254d, a phybrata signature refinement module 254e, and a predictive data generation module 254f. It should be understood that FIG. 2 shows only one embodiment of the controller 250, any other controller capable of performing the operations described herein can be used.

In one configuration, the raw data analysis module 254a, the machine learning module 254b, the biomechanical model module 254c, the simulated data generation module 254d, the phybrata signature refinement module 254e, and the predictive data generation module 254f are embodied as machine or computer-readable media (e.g., stored in the memory 254) that is executable by a processor, such as the processor 252. As described herein and amongst other uses, the machine-readable media (e.g., the memory 254) facilitates performance of certain operations of the raw data analysis module 254a, the machine learning module 254b, the biomechanical model module 254c, the simulated data generation module 254d, the phybrata signature refinement module 254e, and the predictive data generation module 254f to enable reception and transmission of data. For example, the machine-readable media may provide an instruction (e.g., command, etc.) to, e.g., acquire data. In this regard, the machine-readable media may include programmable logic that defines the frequency of acquisition of the data (or, transmission of the data). Thus, the computer readable media may include code, which may be written in any programming language including, but not limited to, Java or the like and any conventional procedural programming languages, such as the "C" programming language or similar programming languages. The computer readable program code may be executed on one processor or multiple remote processors. In the latter scenario, the remote processors may be connected to each other through any type of network (e.g., CAN bus, wireless network, etc.).

In another configuration, the raw data analysis module 254a, the machine learning module 254b, the biomechanical model module 254c, the simulated data generation module 254d, the phybrata signature refinement module 254e, and the predictive data generation module 254f may be embodied as one or more circuitry components including, but not limited to, processing circuitry, network interfaces, peripheral devices, input devices, output devices, sensors, etc.

In some embodiments, the raw data analysis module 254a, the machine learning module 254b, the biomechanical model module 254c, the simulated data generation module 254d, the phybrata signature refinement module 254e, and the predictive data generation module 254f may take the form of one or more analog circuits, electronic circuits (e.g., integrated circuits (IC), discrete circuits, system on a chip (SOCs) circuits, microcontrollers, etc.), telecommunication circuits, hybrid circuits, and any other type of "circuit." In this regard, the raw data analysis module 254a, the machine learning module 254b, the biomechanical model module 254c, the simulated data generation module 254d, the phybrata signature refinement module 254e, and the predictive data generation module 254f may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on.

Thus, the raw data analysis module 254a, the machine learning module 254b, the biomechanical model module 254c, the simulated data generation module 254d, the phybrata signature refinement module 254e, and the predictive data generation module 254f may also include programmable hardware devices such as field programmable gate arrays, programmable array logic, programmable logic devices or the like. In this regard, the raw data analysis module 254a, the machine learning module 254b, the biomechanical model module 254c, the simulated data generation module 254d, the phybrata signature refinement module 254e, and the predictive data generation module 254f may include one or more memory devices for storing instructions that are executable by the processor(s) of the raw data analysis module 254a, the machine learning module 254b, the biomechanical model module 254c, the simulated data generation module 254d, the phybrata signature refinement module 254e, and the predictive data generation module 254f. The one or more memory devices and processor(s)

may have the same definition as provided below with respect to the memory 254 and the processor 252.

In the example shown, the controller 250 includes the processor 252 and the memory 254. The processor 252 and the memory 254 may be structured or configured to execute or implement the instructions, commands, and/or control processes described herein with respect to the raw data analysis module 254a, the machine learning module 254b, the biomechanical model module 254c, the simulated data generation module 254d, the phybrata signature refinement module 254e, and the predictive data generation module 254f. Thus, the depicted configuration represents the afore-mentioned arrangement in which the raw data analysis module 254a, the machine learning module 254b, the bio-mechanical model module 254c, the simulated data genera-tion module 254d, the phybrata signature refinement module 254e, and the predictive data generation module 254f are embodied as machine or computer-readable media. How-ever, as mentioned above, this illustration is not meant to be limiting as the present disclosure contemplates other embodiments such as the aforementioned embodiment in which the raw data analysis module 254a, the machine learning module 254b, the biomechanical model module 254c, the simulated data generation module 254d, the phy-brata signature refinement module 254e, and the predictive data generation module 254f, or at least one circuit the raw data analysis module 254a, the machine learning module 254b, the biomechanical model module 254c, the simulated data generation module 254d, the phybrata signature refine-ment module 254e, and the predictive data generation mod-ule 254f are configured as a hardware unit. All such com-binations and variations are intended to fall within the scope of the present disclosure.

The processor 252 may be implemented as one or more general-purpose processors, an application specific inte-grated circuit (ASIC), one or more field programmable gate arrays (FPGAs), a digital signal processor (DSP), a group of processing components, or other suitable electronic process-ing components. In some embodiments, the one or more processors may be shared by multiple circuits (e.g., the raw data analysis module 254a, the machine learning module 254b, the biomechanical model module 254c, the simulated data generation module 254d, the phybrata signature refine-ment module 254e, and the predictive data generation mod-ule 254f) may comprise or otherwise share the same pro-cessor which, in some example embodiments, may execute instructions stored, or otherwise accessed, via different areas of memory 254.

The raw data analysis module 254a may be configured to receive the phybrata data from the sensing assembly 210, and may also be configured to process the phybrata data to determine the phybrata parameter and/or the phybrata sig-nature associated with the user U, as previously described. In some embodiments, the raw data analysis module 254a may be configured to determine quantitative phybrata met-rics based on the phybrata signature. In some embodiments, the phybrata data is indicative of real-time closed-loop feedback of phybrata signals and biomarkers, including postural stability, gait, or daily living activities, that may be utilized to detect and quantify unwanted pathological body movements, such as those caused by essential tremor or dystonia, or other neurophysiological impairments described herein.

The machine learning module 254b may be configured use machine learning or artificial intelligence to generate the synthetic phybrata data, the synthetic phybrata parameters, and/or the synthetic phybrata signature associated with the user U, and may also generate a signal indicative of the synthetic phybrata data, the synthetic phybrata parameters, and/or the synthetic phybrata signature, as previously described. In some embodiments, the machine learning module 254b may also be configured to generate synthetic quantitative phybrata metrics based on the synthetic phy-brata signature that may be configured to classify, quantify, and/or track a magnitude and time evolution of at least one of a balance performance, a postural stability performance, a movement performance, a disruption or impairment to a specific physiological system, or a specific disease state, injury, or genetic disorder associated with the user U.

The biomechanical model module 254c is configured to generate a biomechanical model of the user, for example, a skeletal or wireframe model of the user U that substantially mimics the user's posture, gait, and/or balance. The biome-chanical model may be configured to include a range of neurosensory inputs and neuromotor outputs associated with the user U.

The simulated data generation module 254d may be configured to generate the simulated phybrata data, the simulated phybrata parameter, and/or the simulated phybrata signature associated with the user U, and may also generate a signal indicative of the synthetic phybrata data, the simu-lated phybrata parameter, and/or the simulated phybrata signature, as previously described. In some embodiments, the simulated data generation module 254d may also be configured to generate a simulated quantitative phybrata metric based on the simulated phybrata signature, which is configured to classify, quantify, and/or track a magnitude and time evolution of at least one of a balance performance, a postural stability performance, a movement performance, a disruption or impairment to a specific physiological sys-tem, or a specific disease state, injury, or genetic disorder associated with the user U.

The phybrata signature refinement module 254e is con-figured to determine an adjusted phybrata data based on the phybrata data, the synthetic phybrata data, and/or the simu-lated phybrata data, determine an adjusted phybrata signa-ture indicative of the adjusted phybrata data, and may also generate a signal indicative of the adjusted phybrata data and/or adjusted phybrata signature. For example, the phy-brata signature refinement module 254e may iteratively fit the synthetic and/or simulated data to the raw phybrata data acquired from the user U to generate adjusted phybrata data, and the adjusted phybrata signature that may be a substan-tially accurate representation of the user U's raw phybrata signature, i.e., of the user U's neurophysiological behavior.

The predictive data generation module 254f may be also be configured to receive the second phybrata data from the sensing assembly 210 that is measured from the user U by the sensing assembly 210, and that may be received and processed by the raw data analysis module 254a. The predictive data generation module 254f may also be config-ured compare the second phybrata data that with the adjusted phybrata data, and generate predictive data based on the comparison between the second phybrata data and the adjusted phybrata data, and may generate a signal indicative of the predictive data. The predictive data may be indicative of projected physiological changes in the user U. The predictive data generation module 245f may also be config-ured to generate a predictive phybrata signature indicative of the predictive data. The projected physiological changes may include changes in a balance performance, a postural stability performance, a movement performance, a disruption or impairment to a specific physiological system, or a specific disease state, injury, or genetic disorder associated with the user U.

In some embodiments, the projected physiological changes may include a disease or injury state or a response to a treatment, a medication, a therapy, and/or rehabilitation of the user U. In some embodiments, the projected physiological changes determined based on real-time closed-loop feedback of phybrata signals and phybrata signature (e.g., corresponding to phybrata biomarkers), including postural stability, gait, or daily living activities may be utilized to detect a pending fall episode based on motion that deviates outside of a specified boundary, either in the mediolateral or anterolateral plane—such as those that become more common due to degraded balance in elderly populations, to determine the optimum EVS frequency, amplitude, and duration to induce an offsetting postural response, and to apply the corresponding EVS in order to induce a postural response back towards a neutral position (e.g., via the stimulation assembly 120, 420). In some embodiments, the sensitivity and specificity of the sensing assembly 210 for the classification and quantification of vestibular-specific impairments and disorders is further enhanced by integrating a stimulation assembly (e.g., the stimulation assembly 120, 420) into the sensing assembly 210 (e.g., in the sensing and stimulation assembly 102) in order to incorporate stimulation functionality (e.g., EVS functionality) therein.

Current methodologies use electromyography (EMG) or force plate data to measure EVS-evoked balance responses. In contrast, the sensing assembly 210 is wearable, and being situated on the head—the body segment where EVS-evoked postural responses are the largest—the sensing assembly 210 provides a more sensitive means of measuring EVS-evoked, whole-body balance responses. Integrating EVS technologies into the sensing assembly 210 may provide a novel, cost-effective means of measuring and enhancing vestibular balance function in a wearable form factor and provides a new tool for probing vestibular balance function in the clinic and in the field, as described herein.

FIG. 3 is a schematic flow chart of a method 300 for generating predictive data indicative of predictive changes in at least one user physiological parameter based on phybrata signatures measured from a user, according to an embodiment. While described with respect to the system 200, it should be appreciated that the operations of the method 300 are equally applicable to any system configured to detect and process phybrata signatures associated with a user for predictive diagnostics of a user's neurophysiological condition and any impairments thereof.

The method 300 includes disposing the sensing assembly 210 on a body of a user, at 302. For example, the housing 211 of the sensing assembly 210 may be removably disposed on a mastoid of the user (e.g., behind the ear of the user) and secured thereto via an adhesive. At 304, the sensing assembly 210 determines a first phybrata data from the user, for example, by measuring the first phybrata signal and the second phybrata signal from the user, as previously described. The phybrata signals may be measured while the user is sitting, standing, shaking the user's head, walking, etc.

At 306, the controller 250 receives the first phybrata data from the user, determines a first phybrata parameter, and determines the first phybrata signature of the user based on the first phybrata parameter, as previously described. At 308, the controller 250 generates the synthetic phybrata signature using machine learning or artificial intelligence, as previously described. For example, the controller 250 may generate synthetic phybrata data associated with the user based on the first phybrata data, determine the synthetic phybrata parameter associated with the user based on the determined phybrata parameter, and generate the synthetic phybrata signature associated with the user based on the determined phybrata signature, as previously described. In some embodiments, the controller 250 may also determine the synthetic quantitative phybrata metric based on the synthetic phybrata signature, the synthetic quantitative phybrata metric configured to classify, quantify, and/or track a magnitude and time evolution of at least one of a balance performance, a postural stability performance, a movement performance, a disruption or impairment to a specific physiological system, or a specific disease state, injury, or genetic disorder associated with the user U.

In some embodiments, the controller 250 may also generate a biomechanical model of the user, at 310. At 312, the controller 250 may use the biomechanical model to generate simulated phybrata data. For example, the controller 250 may generate simulated phybrata data associated with the biomechanical model of the user based on the first phybrata data. The controller 250 may also determine simulated phybrata parameters associated with the biomechanical model of the user based on the determined phybrata parameter, and determine a simulated phybrata signature associated with the biomechanical model of the user based on the determined phybrata signature. In some embodiments, the controller 250 may also determine a simulated quantitative phybrata metric based on the simulated phybrata signature, the simulated quantitative phybrata metric configured to classify, quantify, and/or track a magnitude and time evolution of at least one of a balance performance, a postural stability performance, a movement performance, a physiological disruption, or a physiological impairment associated with the user.

At 314, the controller 250 generates an adjusted phybrata signature based on the first phybrata data, and the synthetic data and/or the simulated data. For example, the controller 250 may generate adjusted phybrata data based on the first phybrata data, the synthetic phybrata data, and the simulated phybrata data, and determine an adjusted phybrata signature indicative of the adjusted phybrata data for the user.

At 316, the sensing assembly 210 may be used to determine second phybrata data from the user. At 318, the controller 250 generates predictive data indicative of predictive changes in at least one user physiological parameter (e.g., the user's balance, posture, or movement) based on the second phybrata data and the adjusted phybrata signature. For example, the controller 250 may compare the second phybrata data with the adjusted phybrata data, and generate predictive data based on the comparison between the second phybrata data and the adjusted phybrata data, the predictive data indicative of projected physiological changes in the user. At 320, the controller 250 generates a predictive phybrata signature indicative of the predictive data. The controller 250 may also generate a signal indicative of the predictive phybrata signature, for example, configured to be stored in a memory or displayed on a display (e.g., the display 236 of the data collection system 230).

Figure 4:
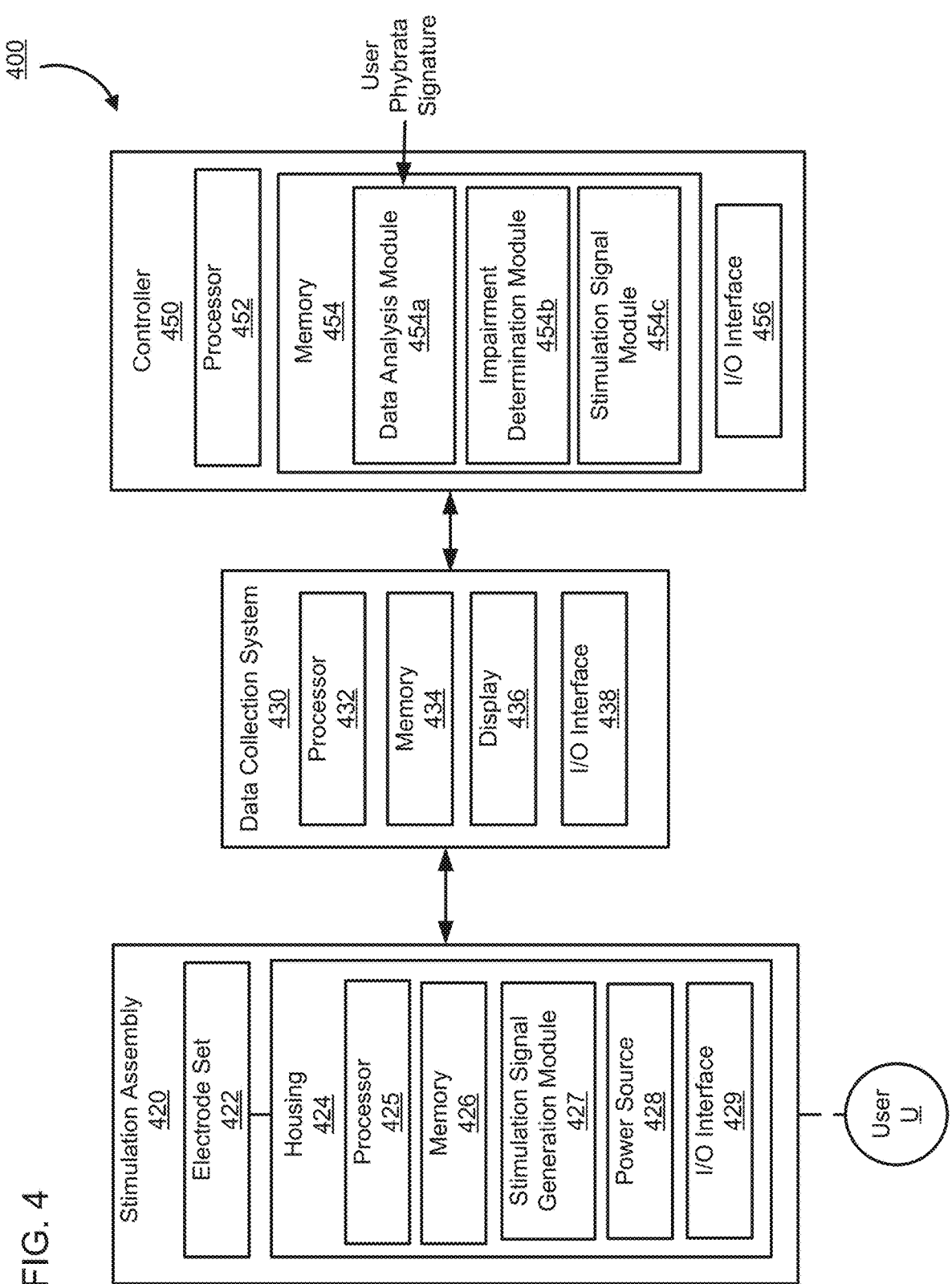
FIG. 4 is a schematic block diagram of a system including a stimulation assembly and a controller for generating stimulating signals for treating neurophysiological impairments in a user based on the user's phybrata signature, according to an embodiment.

FIG. 4 is a schematic block diagram of a system 400 including a stimulation assembly 420, a controller 450, and optionally, a data collection system 430, for generating stimulating signals for treating neurophysiological impairments in a user U based on the user U's phybrata signature, according to an embodiment.

The stimulation assembly 420 includes a set of electrodes 422, and a housing 424 within which a processor 425, a memory 426, a stimulation signal generation module 427, a power source 428, and an I/O interface 429 may be disposed. The set of electrodes 422 are coupled to the housing 424, for example, disposed outside the housing 424, such that at least a portion of the set of electrodes 422 are configured to be disposed on a mastoid of the user U. For example, a first portion of the set of electrodes 422 (e.g., one or a pair of electrodes 422) may be configured to be removably disposed behind one, or both ears of the user U and may be secured thereto by an adhesive (e.g., an electrically conductive adhesive). In some embodiments, a second portion of the set of electrodes 422 (e.g., one or two electrodes 422) different from the first portion may be disposed on a surface of, or outside housing 424 and configured to contact the back of the neck of the user U.

The housing 424 may be configured to have a form factor so that it is wearable on the user U's body. For example, the housing 424 may be structured as a collar configured to be worn around the at least a portion of the neck of the user U. In some embodiments, the first portion of the set of electrodes 422 are coupled via electrical leads to the stimulation signal generation module 427, and the second portion of the set of electrodes 422 may be disposed on the surface of the housing 424, or on flaps extending from the housing 424, such that second portion of the set of electrodes 422 are configured to be disposed on, and contact a back of the neck of the user U when the housing 424 is worn around at least a portion of the neck of the user U. In some embodiments, the stimulation assembly 420 may be integrated with a sensing assembly (e.g., the sensing assembly 110, 210) so as to form an integrated sensing and stimulation assembly (e.g., the sensing and stimulation assembly 102).

The processor 425 may be implemented as a general-purpose processor, an Application Specific Integrated Circuit (ASIC), one or more Field Programmable Gate Arrays (FPGAs), a Digital Signal Processor (DSP), a group of processing components, or other suitable electronic processing components. The memory 426 (e.g., Random Access Memory (RAM), Read-Only Memory (ROM), Non-volatile RAM (NVRAM), Flash Memory, hard disk storage, etc.) stores data (e.g., phybrata data) and/or computer code for facilitating at least some of the various processes described herein. The memory 426 may include tangible, non-transient volatile memory, or non-volatile memory. The memory 426 may include a non-transitory processor readable medium that stores programming logic that, when executed by the processor 425, controls the operations of the stimulation assembly 420. In some arrangements, the processor 425 and the memory 426 form various processing circuits described with respect to the stimulation assembly 420.

The power source 428 may include a battery e.g., rechargeable battery (e.g., Li-ion, Li-polymer, NiCad, etc.) or a disposable battery (e.g., a coin cell), and may be configured to selectively provide electrical power to at least a portion of the set of electrodes 422. The I/O interface 429 is structured for sending and receiving data (e.g., over a communication network) from the data collection system 430 and/or the controller 450. Accordingly, the I/O interface 429 includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like.

The stimulation signal generation module 427 may include hardware and/or software configured to selective generate stimulation signals that cause the set of electrodes 422 to apply stimulation signals to the user U. The signal generation module 427 may include a signal generation circuit, for example, a resistor-capacitor (RC) circuit, a quartz crystal, or any other signal generator to generate stimulation signals. The stimulation signals may include a radiofrequency signal, pulse signal, a waveform, an analog signal, a digital signal, or any other suitable stimulation signal.

In some embodiments, the stimulation signals may include EVS signals, CES signals, and/or CES signals. Aging causes loss of the motion sensing cells in the vestibular organs, both the otolith organs that detect linear motion and the semicircular canals that detect rotational motion. EVS is a specialized form of neuro-stimulation that can counteract the corresponding decreases in the signals generated by the vestibular organs, by increasing the ability of the vestibular nerve to conduct the signals to the brain, and the ability of the corresponding neurosensory and neuromotor structures in the brain itself to process these signals and stabilize balance and movement. EVS may enhance vestibular rehabilitation and reduction of balance and movement disruptions caused by aging, concussions, stroke, Parkinson's disease, central neuro-degenerative disorders, cerebral palsy in children, cybersickness during virtual reality (VR) exposure, and microgravity exposure during spaceflight.

In some embodiments, the stimulation assembly 420 may be communicatively coupled to the controller 450 via the data collection system 430. The data collection system 430 may include, for example, a mobile phone (e.g., an iPHONE®, an ANDROID® phone, a WINDOWS® phone, a SYMBIAN® phone or the likes), a tablet computer, a personal computer (e.g., a desktop or a laptop), a smartwatch, or any other suitable data collection system. The data collections system 430 may include a processor 432, a memory 434, a display 436, and an I/O interface 438, which may be substantially similar in structure to the processor 232, the memory 234, the display 236, and the I/O interface 238, as previously described.

The data collection system 430 may be configured to communicate stimulation signal parameters determined by the controller 450 to the stimulation assembly 420, and/or receive feedback from the stimulation assembly 420. In some embodiments, the data collection system 230 may be configured to receive phybrata data that may have been previously collected from the user U by a sensing assembly (e.g., the sensing assembly 110, 210), from the sensing assembly or the controller 450, and may be configured to display such data on the display 436. In some embodiments, the data collection system 430 may also be configured to generate real-time plots of the stimulation signal being applied to the user U via the stimulation assembly 420, and may generate reports displaying the phybrata data and/or the stimulation signals being applied to the user U.

The controller 450 is in communication with the sensing assembly 420, for example, via the data collection system 430. The controller 450 may include a processor 452, a memory 454, and an I/O interface 456. In various embodiments, the controller 450 may include a remote server or a cloud computing network. In some embodiments, the operations of the controller 250 and 450 may be integrated into a single controller configured to perform the operations of each of the controller 250 and 450, for example, to control operations of the sensing and stimulation assembly (e.g., the assembly 102) that integrates the structure and function of the sensing assembly (e.g., the sensing assembly 110, 210), and the stimulation assembly (e.g., the stimulation assembly 120, 420).

The processor 452 may be implemented as a general-purpose processor, an Application Specific Integrated Circuit (ASIC), one or more Field Programmable Gate Arrays (FPGAs), a Digital Signal Processor (DSP), a group of processing components, or other suitable electronic processing components. The memory 454 (e.g., Random Access Memory (RAM), Read-Only Memory (ROM), Non-volatile RAM (NVRAM), Flash Memory, hard disk storage, etc.) stores data (e.g., phybrata data) and/or computer code for facilitating at least some of the various processes described herein. The memory 454 may include tangible, non-transient volatile memory, or non-volatile memory. The memory 454 may include a non-transitory processor 452 readable medium that stores programming logic that, when executed by the processor 452, controls the operations of the controller 450. In some arrangements, the processor 452 and the memory 454 form various processing circuits described with respect to the controller 450.

The I/O interface 256 may be structured for sending and receiving data (e.g., over a communication network) from the sensing assembly 210 and/or the data collection system 230. Accordingly, the I/O interface 256 includes any of a cellular transceiver (for cellular standards), local wireless network transceiver (for 802.11X, ZigBee, Bluetooth, Wi-Fi, or the like), wired network interface, a combination thereof (e.g., both a cellular transceiver and a Bluetooth transceiver), and/or the like.

The controller 450 is configured to receive a phybrata signature associated with the user U, for example, (e.g., an adjusted phybrata signature, as previously described), and in some embodiments, predictive signature, as previously described. In some embodiments, the controller 450 may be configured to receive phybrata signatures and process the signature to generate a predictive signature indicative of neurophysiological behavior of the user U, as previously described.

The controller 450 may be configured to determine stimulation signal parameters based on the phybrata signature. For example, the controller 450 may be configured to determine if a neurophysiological impairment exists in the user U based on the phybrata signature, for example, the type of the neurophysiological impairment (e.g., the amount of imbalance in posture or balance due to age, frailty, neurodegenerative disease, and/or injury). The controller 450 may then determine stimulation signal parameters that are configured to treat or correct the neurophysiological impairment in the user U. In some embodiments, the phybrata signature is indicative of a vestibular imbalance in the user U due to age, injury, or disease, and the stimulation signal is configured to correct the vestibular imbalance.

The controller 450 may be configured to selectively generate a signal based on the stimulation signal parameters. The signal may be communicated to the stimulation assembly 420 directly from the controller 450, or via the data collection system 430. The signal may be configured to cause the stimulation signal generation module 427 to activate at least one pair of the set of electrodes 422 to apply a stimulation signal corresponding to the stimulation signal parameters to the user U.

In some embodiments, the set of electrodes 422 may include EVS electrodes. In such embodiments, the phybrata signature may be indicative of at least one of a vestibular impairment, an unwanted physical motion, a head tremor, or a fall associated with the user U, and the stimulation signal includes a therapeutic EVS signal or a corrective EVS signal. The therapeutic EVS signal may be configured to reduce or eliminate the vestibular impairment. The corrective EVS signal may be configured to reduce or eliminate an unwanted physical motion or a head tremor. The corrective EVS signal may also be configured to induce a postural response in the user back towards a neutral position to reduce the risk of a fall.

In some embodiments, the stimulation signal may be an EVS waveform. In such embodiments, the controller 450 may be configured to determine, based on the phybrata signature, relative timings for a postural reaction and anticipatory adjustment of the user U and calculate a predicted physiological signature associated with the user U. The predicted physiological signature may include at least one of a predicted magnitude, a predicted phase, and a predicted delay between motions of different segments of a body of the user U. The controller 450 may be configured to generate and selectively adjust parameters of the EVS waveform applied to the user U based on the predicted physiological signature so as to adjust the balance performance, postural stability performance, and/or movement performance of the user U.

In some embodiments, the phybrata signature is indicative of a vestibular impairment in the user U due to age, injury, or disease, and the therapeutic stimulation signal may be configured to reduce or eliminate the vestibular impairment. In some embodiments, the therapeutic EVS signal is configured to improve disrupted balance performance, postural stability performance, or movement performance of the user U. In some embodiments, the corrective EVS signal is configured to induce a postural response in the user U back towards a neutral position to reduce the risk of a fall. In some embodiments, the corrective EVS signal is configured to reduce or eliminate a head tremor in the user U.

Expanding further, in some embodiments, the phybrata signature, adjusted phybrata signature, and/or the predictive phybrata signature, may provide an "accelerated aging" model to study the development and correction of balance disruptions. If a vestibular impairment is identified, the controller 450 may enable a caregiver to identify the EVS stimulation parameters that optimize balance improvement. Optimal EVS current levels and frequencies may be different for each user U, based on the user U's specific phybrata signature, for example, based on one or more phybrata biomarkers that may be derived from spatial domain phybrata data, time domain phybrata data, frequency domain phybrata data, and phybrata sensory reweighting data.

In some embodiments, the EVS simulation may include a stochastic electrical signal with a noise-like spectrum that includes frequencies uniformly distributed across the range from 0 Hz to 25 Hz, inclusive (e.g., 0. 1. 2, 4, 6, 8, 10, 12, 14, 16, 18, 20, 22, 24, or 25 Hz, inclusive). In some embodiments, the EVS simulation may include a stochastic electrical signal with a noise-like spectrum that includes only the specific frequency ranges in which phybrata sensory reweighting data that indicate a significant change in the user U's vestibular performance.

In some embodiments, the EVS simulation may include a sub-threshold resonant stochastic electrical signal. "Sub-threshold" in this case implies that the EVS current amplitude is less than the user U's perceptual threshold, so that the user U has no tactile sensation as current is being applied from the EVS electrodes. In some embodiments, the EVS perceptual threshold may be in a range 0.5 mA to 1.0 mA, inclusive (e.g., 0.5, 0.6, 0.7, 0.8, 0.9, or 1.0 mA, inclusive).

In some embodiments, the controller 450 may be configured to determine the user U's EVS perceptual threshold by scanning the stimulation signal (e.g., a current or voltage) applied at the set of electrodes 422, for example, in steps of 0.05 mA beginning at 0.1 mA and asking the user U to indicate when the user U is first able perceive a sensation at the application site on their mastoid. "Resonant" in this case means that the EVS current amplitude is selected to maximize the user U's vestibular balance performance improvement via the stochastic resonance response. The EVS stochastic resonance current level may be in a range 15% to 85%, inclusive, of the perceptual threshold.

In some embodiments, the controller 450 may be configured to determine the maximum stochastic resonance by scanning the stimulation signal (e.g., current or voltage) applied at the set of electrodes 422, for example in steps of 0.05 mA beginning at a level equal to 10% of the user U's perceptual threshold, and monitoring the user U's vestibular balance performance improvement as indicated, for example, by spatial-domain phybrata acceleration data, time-domain phybrata acceleration and power data, and/or frequency-domain and time-resolved frequency domain phybrata data.

In some embodiments, the EVS frequency "buckets" that maximize the user U's vestibular balance performance improvement are determined by scanning the stochastic EVS current frequencies applied at the EVS electrodes 422, for example in buckets of width 0.2 Hz beginning at 0-0.2 Hz, inclusive, and ending at 24.8-25 Hz, inclusive, and monitoring the user U's vestibular balance performance improvement as indicated by one or more phybrata data sources selected from spatial-domain phybrata acceleration data, time-domain phybrata acceleration and power data, frequency-domain and time-resolved frequency domain phybrata data, and phybrata sensory reweighting data.

In some embodiments, clinicians can then prescribe the appropriate 6-12 weeks EVS therapy, with the patient typically wearing the stimulation assembly 420 1-5 times a week for 10-30 minutes, inclusive during each session, during which the optimized EVS signal determined by the controller 450 is applied. Single-session EVS therapeutic improvement can persist for 24-72 hours, inclusive. Multi-session (e.g., 12 weeks) therapeutic improvements can persist up to 6 months. The ability to monitor the user U's response as the EVS is being applied and progress over time enables adaptive therapeutic treatment that's personalized to each user's unique balance impairment and recovery trajectory.

Monitoring vestibular performance improvement over the length of the EVS therapy treatment allows the clinician to continuously assess the patient's response to the EVS therapy. In some embodiments, the caregiver may adjust the EVS stimulation parameters prior to or following each therapeutic session to achieve continuing improvement or to increase the level of improvement. In some embodiments, the target level of vestibular performance improvement to be achieved over the multi-week duration of the EVS therapy treatment is the level observed when the optimized EVS signal is applied in the initial diagnostic session. If and when no further vestibular performance improvement is observed, the EVS therapy treatment can be ended. In some embodiments, the use U may then undergo regular follow-up assessments, and the EVS therapy treatment can be repeated.

Thus, the system 400 enables therapeutic applications for stabilizing balance in a wearable and easy to use assembly. Two different approaches may be used: 1) sub-threshold noisy EVS (stochastic resonance effect); 2) supra-threshold EVS pulses that are triggered by excessive deviations in body motion and evoke balance responses that return the body back towards a neutral position. Stochastic resonance is a term used to define the use of undetectable (sub-threshold) noisy stimulation to enhance the performance of a sensory system of the user U. Sub-threshold noisy EVS has previously been used to stabilize balance performance, and the stimulation assembly 420 achieves a vestibular stochastic resonance effect.

In some embodiments, delivering supra-threshold EVS pulses triggered by excessive postural deviations (e.g., detected by the sensing assembly 110, 210), may make it possible to stabilize balance or correct other undesirable body motions by evoking corrective EVS-evoked reflexive balance responses. This vestibular enhancement system may have applications in suppressing unwanted pathological movements, such as those caused by essential tremor, Parkinson's disease, or dystonia, and in preventing falls, such as those that become more common due to degraded balance in elderly populations. Vestibular standing balance function can be assessed by delivering noisy EVS stimulation during standing balance trials, while electromyography and ground reaction forces (for example, center of pressure, or COP, from a force plate) are recorded. In this case, the EVS stimulation may be strong enough that the participant can detect the stimulation (supra-threshold).

In some embodiments, the stimulation signal may include sub-threshold noisy EVS that may have a balance stabilizing effect owing to the phenomenon of stochastic resonance. For example, sub-threshold noisy EVS stimulation (in a range of 0 Hz to 25 Hz, inclusive, at a current level below the perceptual threshold of the user U, may be applied continuously or intermittently while the user U stands relaxed. Vestibular psychophysical procedures may be used to determine noisy EVS detection thresholds for each user U. Once the user U's detection threshold is determined, EVS may be applied at 75% of the user U's detection threshold to exert a significant stabilizing effect on standing balance of the user U.

In some embodiments, the stimulation signal may include supra-threshold EVS pulses that evoke corrective movements of the user's body, integrated with the phybrata sensor data in a real-time closed-loop control system to enhance sensory feedback for users with vestibular impairment (e.g., from aging or head trauma). Measuring the effect of sinusoidal pulses of various amplitudes and frequencies on phybrata signal enables the controller 450 to determine the optimum supra-threshold EVS frequency, amplitude, and duration to correct a variety of movement impairments and to prevent falls in different users. Supra-threshold sinusoidal EVS pulses are triggered based on movements of the user U's body detected by the phybrata sensor. When the user U's motion deviates outside of a specified boundary (either in the mediolateral or anterolateral plane), EVS pulses are delivered causing postural response back towards a neutral position or towards an otherwise desired position.

In some embodiment, the set of electrodes 422 include CES electrodes. In such embodiments, the stimulation signal may be a CES waveform, and the controller 450 may be configured to determine, based on the phybrata signature, relative timings for a postural reaction and anticipatory adjustment of the user U. The controller 450 may be configured to calculate a predicted neurological signature associated with the user U, which includes at least one of a predicted magnitude, a predicted phase, and a prediction delay between motions of different segments of a body of the user U. The controller 450 may be configured to generate and selectively adjust parameters of the CES waveform applied to the user U based on the predicted neurological signature to adjust neuromotor, neurosensory, neurocognitive, or neuropsychological impairment of the user U.

In some embodiments, the set of electrodes 422 include ESE electrodes. In such embodiments, the stimulation signal may include an ESE waveform, and the controller 450 may be configured to determine, based on the phybrata signature, relative timings for a postural reaction and anticipatory adjustment of the user U. The controller 450 may be configured to calculate a predicted neurological signature associated with the user U, which may include at least one of a predicted magnitude, a predicted phase, and a prediction delay between motions of different segments of a body of the user U. Moreover, the controller 450 may be configured to generate and selectively adjust parameters of the ESE waveform applied to the user U based on the predicted neurological signature to adjust a neuromotor or neurosensory impairment of the user U. In some embodiments, the neurosensory impairment may include optical neuritis caused by one or more multiple sclerosis lesions on the optic nerve.

In some embodiments, the controller 450 may include various circuitries or modules configured to perform the operations of the controller 450. For example, as shown in FIG. 4, the controller 450 includes a data analysis module 454a, an impairment determination module 454b, and stimulation signal module 454c. It should be understood that FIG. 4 shows only one embodiment of the controller 450, any other controller capable of performing the operations described herein can be used. Each of the data analysis module 454a, the impairment determination module 454b, and the stimulation signal module 454c may have similar structure as described with respect to the modules 254a-254f included in the controller 250, as previously described, and therefore, the structure of modules 454a-454c is not described in further detail.

The data analysis module 454a may be configured to receive the phybrata signature, the adjusted phybrata signature, and/or the predictive phybrata signature, for example, from the sensing assembly 120, 220, or from the controller 150, 250, and in some embodiments, may process the data, for example, to identify specific signatures that may be used to generate the stimulation signal.

The impairment determination module 454b may be configured to determine the type and/or quantity of the impairment being experienced by the user U based on the phybrata signature, the adjusted phybrata signature, and/or the predictive phybrata signature.

The stimulation signal module 454c may be configured to determine stimulation signal parameters for treating or correcting the user U's impairment based on the type and/or quantity of impairment being experienced by the user U, and generate a signal configured to cause the stimulation signal generation module 427 of the stimulation assembly 420 to activate at least one pair of the set of electrodes 422, as previously described.

Figure 5:
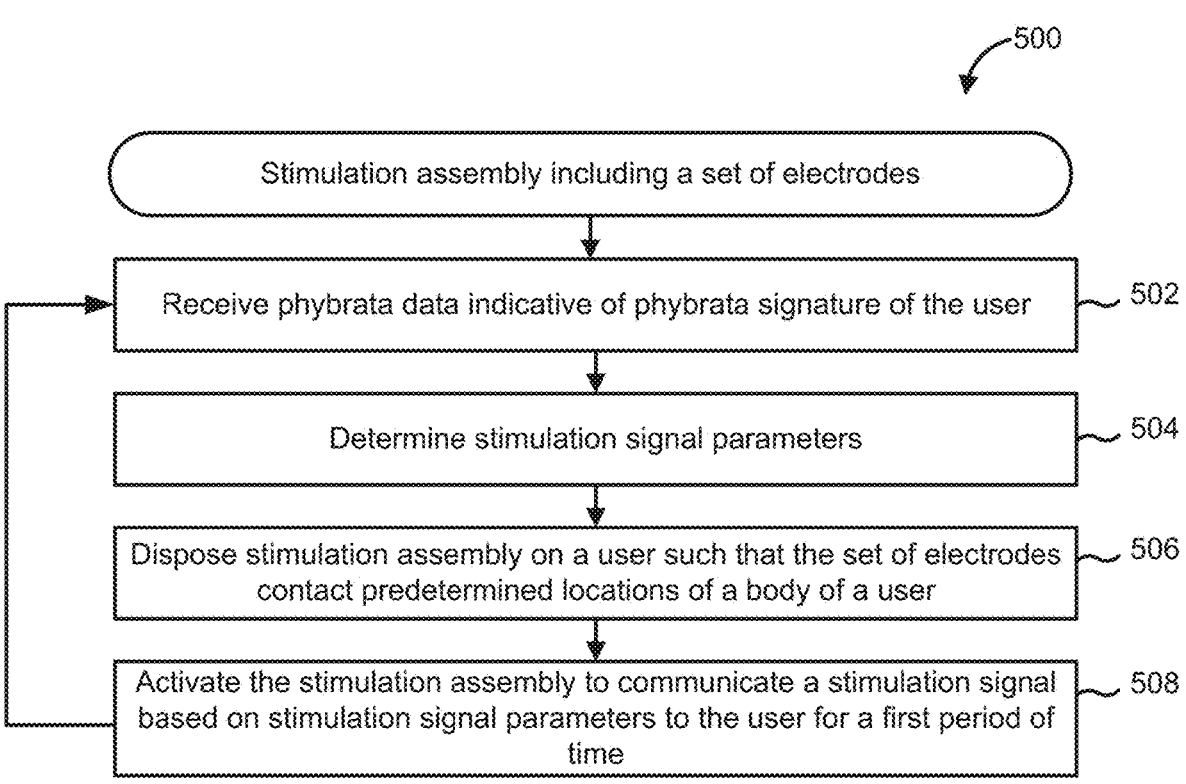
FIG. 5 is a schematic flow chart of a method for treating neurophysiological impairment in a user by applying stimulation signals using a wearable stimulation assembly, according to an embodiment.

FIG. 5 is a schematic flow chart of a method 500 for treating neurophysiological impairment in a user by applying stimulation signals using a wearable stimulation assembly, for example, the stimulation assembly 120, 420 included in the system 100, 400, according to an embodiment. While described with respect to the stimulation assembly 420 and the controller 450 included in the system 400, it should be appreciated that the operations of the method 500 are applicable to any system configured to generate stimulation signal parameters and generate a signal configured to cause a stimulation assembly to apply stimulating signals to a user U.

The method 500 includes receiving, by the controller 450, phybrata data indicative of a phybrata signature of a user, at 502. In some embodiments, the controller 450 may also receive the adjusted phybrata signature, and/or the predictive phybrata signature. The controller 450 may receive the data from the sensing assembly 110 or 210, that may be a separate assembly, or integrated into the sensing and stimulation assembly 102, as previously described, or may receive the data from the data collection system 230, 430, or the controller 250 included in the system 200.

At 504, the controller 450 determines stimulation signal parameters based on the phybrata signature of the user, as previously described. At 506, the stimulation assembly 220 is disposed on the user such that set of electrodes 422 contact predetermined location of the body of the user. For example, at least a first portion of the set of electrodes 422 may be disposed on the mastoid of the user, for example, behind the ear of the user. In some embodiments, a second portion of the set of electrodes 422 may be disposed on the back of the neck of the user.

At 508, the stimulation assembly is activated, based on a signal received from the controller 450, to communicate a stimulation signal based on the stimulation signal parameters to the user for a first period of time. For example, the controller 450 may generate a signal based on the stimulation signal parameters and communicate the signal to the stimulation assembly 420 (e.g., via the data collection system 430). The signal is configured to cause the stimulation signal generation module 427 to activate at least a pair of the set of electrodes 422 to apply a stimulation signal to the user to treat or correct the impairment in the user, as previously described.

Figure 6A:
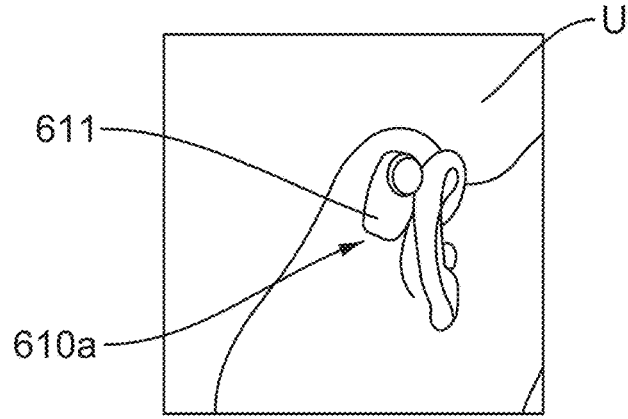
FIG. 6A is a perspective view of a sensing assembly disposed on a mastoid of a user, according to an embodiment.

FIG. 6A is a perspective view of a sensing assembly 610a disposed on a mastoid of a user U, according to an embodiment. The sensing assembly 610a has a small form factor and is configured removably disposed on a mastoid of the user, i.e., behind the ear of the user U as shown in FIG. 6A. The sensing assembly 610a may be removably secured behind the ear of the user via an adhesive. The sensing assembly 610a includes a housing 611 in which one or more phybrata sensors, for example, the first sensor 212 and the second sensor 214 may be disposed, which are configured to measure phybrata signals from the user U, as previously described. The sensing assembly 610a may include other components, for example, the processor 215, the memory 217, the power source 218, and/or the I/O interface 219, as previously described. The phybrata sensor 610a may enable a one-minute (e.g., 30 seconds Eo and 30 seconds Ec), non-invasive phybrata monitoring and data collection system that can identify, quantify, and monitor impairments using the unique biomechanical vibrational signature of each physiological system.

Figure 6B:
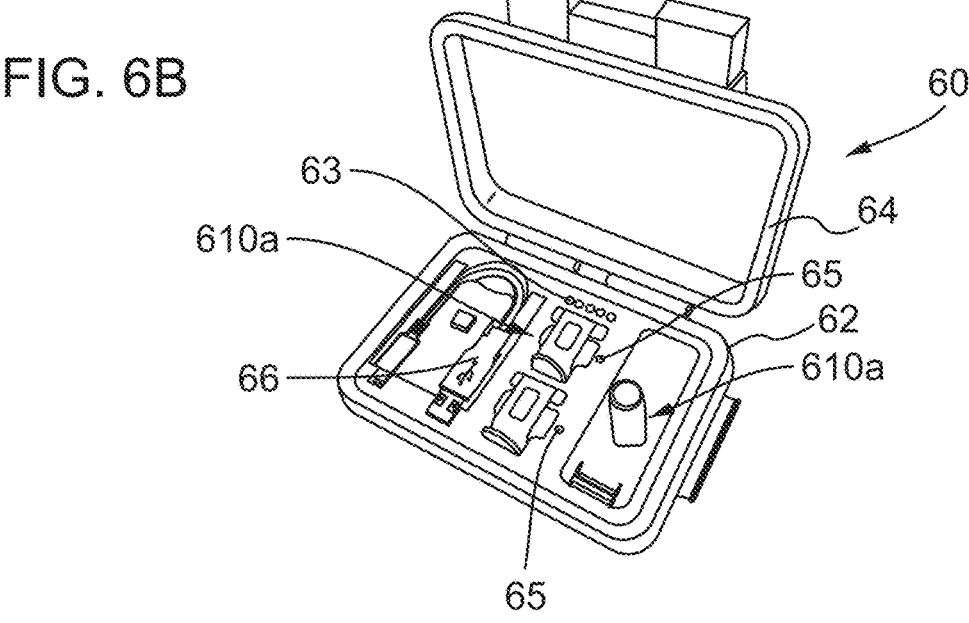
FIG. 6B is a perspective view of a kit including the sensing assembly of FIG. 6A, according to an embodiment.

FIG. 6B is a perspective view of a kit 66 including the sensing assembly 610a of FIG. 6A, according to an embodiment. The kit 66 includes a casing 62 within which a pair of sensing assemblies 610a are disposed. A lid 64 is coupled to the casing 62 and is configured to be selectively opened or closed to access the various components disposed in the casing 62. The casing 62 may include a power source that may be rechargeable so as to provide a portable charging source for charging the sensing assemblies 610. The casing 62 may also include wireless charging components (e.g., induction coils) to wirelessly charge a power source (e.g., the power source 218) included in each of the sensing assemblies 610a disposed in the casing 62.

A first set of visual indicators 63 (e.g., LED lights) may be provided in the casing 62 and may be configured to indicate an amount of power remaining in the power source included in the casing 62. In some embodiments, a second set of visual indicators 65 (e.g., one or more LED lights)

may also be provided in the casing 62 and configured to indicate whether the sensing assemblies 610a are properly disposed in the casing 62 and are being charged. An electrical lead (e.g., a USB cable) may also be provided in the kit 60. The electrical lead 66 may be configured to allow electrical coupling of the casing 62 to an external power source to allow charging of the power source included in the casing 62, and/or to be removably coupled to the sensing assemblies 610a, for example, to allow charging of the sensing assemblies 610a, communication of information thereto (e.g., firmware updates), and/or acquire data therefrom.

Figure 6C:
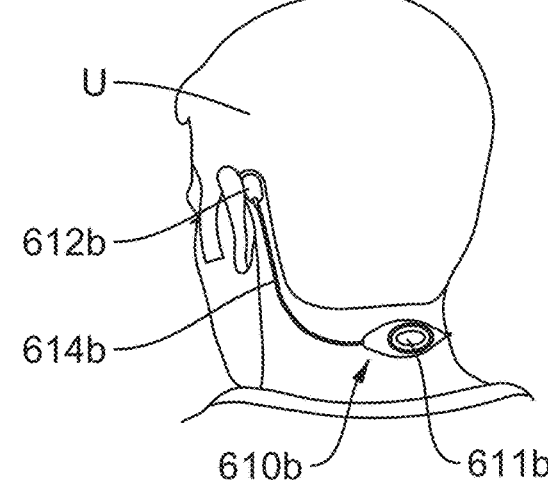
FIG. 6C is perspective view of a sensing assembly configured to be worn on a neck of a user and having sensors thereof disposed on a mastoid of a user, and which can also include a stimulation assembly, according to an embodiment.

FIG. 6C is a perspective view of a sensing assembly 610b, according an embodiment. Different from the sensing assembly 610a, the sensing assembly 610b includes a housing 611b configured to be disposed or worn on a neck of a user U. The sensing assembly 610b includes one or more sensors 612b removably disposed on a mastoid of the user U, for example, via an adhesive. A lead 614b electrically couples the one or more sensors 612b to electronic components that may be disposed in the housing 611b. The sensing assembly 610b may allow a larger power source to be included in the housing 611b, may house additional physiological sensors, and may be easier to wear on the body of the user U.

In some embodiments, the sensing assembly 610b may also include stimulation electronics and stimulation electrodes integrated therein such that the assembly 610b is a sensing and stimulation assembly 610b. As previously described, EVS is an effective method for isolating vestibular balance function without stimulating other sensory systems contributing to balance and motor control (vision, proprioception). Vestibular evoked myogenic potentials (VEMPs), short latency, vestibular-dependent reflexes that are evoked by short bursts of sound delivered through headphones or vibration applied to the skull, have been shown to preferentially activate the otolith organs rather than the semicircular canals and are used clinically to measure otolith function.

EVS involves applying electrical current through electrodes placed over the mastoid processes of the skull, which is the same anatomical location as the where the sensing and simulation assembly 610b is disposed, making the integration of sensing and stimulation features (e.g., EVS functionality) into a single device highly desirable. With EVS, electrical current is used to directly stimulate (i.e., alter the cellular membrane potential) of both the vestibular hair cell receptors within the otoliths and semicircular canals and the vestibular afferent neurons that innervate them, with a greater effect on the irregularly firing than the regularly firing afferent nerve fibers. EVS can be applied with many different types of stimulus waveforms to probe vestibular-specific balance control mechanisms and impairments or, in conjunction with eye-tracking, to probe vestibulo-ocular reflex function similar to commonly used clinical vestibular-ocular motor screening (VOMS) testing. In addition to assessing vestibular balance control, EVS can also be utilized to evoke compensatory whole-body balance responses, both tilt and rotation.

As illustrated in FIG. 6C, the sensing and stimulation assembly 610b integrates EVS functionality with the phybrata sensor's precision motion detection into a vestibular prosthesis that can monitor an individual's postural stability and provide real-time feedback for calculating corrective or offsetting electrical vestibular stimuli to significantly reduce, counteract, or compensate for degraded posture or movement in arbitrary directions, reduce or eliminate pathological movement such as head tremors, or reduce fall risks in elderly and other balance-impaired populations. The many demonstrated applications of EVS, together with the ability of the sensing and stimulation assembly 610b to classify and quantify a vestibular-specific signature in the postural control of a sub-group of concussed patients, demonstrate the significant utility of the EVS-enabled phybrata wearable device disclosed herein to assess, monitor, and enhance balance an movement performance both in clinical settings and remotely, and for many different clinical, athletic, industrial, and military populations suffering from balance or movement impairments caused by concussions and other injury, disease, or age-related disorders.

Figures 7A, 7B, 7C:
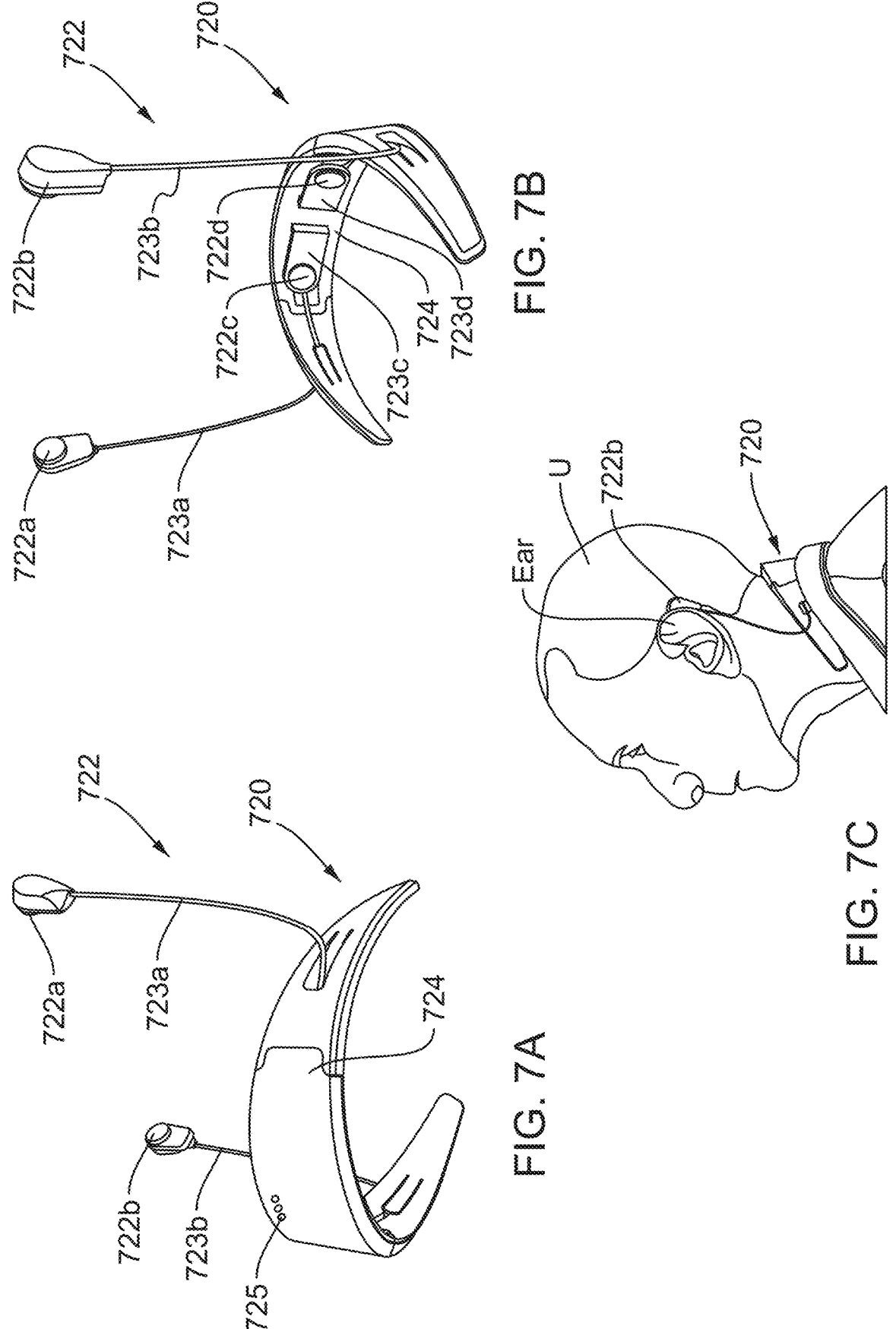
FIGS. 7A-7B are back and front perspective views of a wearable stimulation assembly for treating neurophysiological impairments, according to an embodiment.
FIG. 7C is a side view of the stimulation assembly of FIGS. 7A-7B worn on a neck of a user.

FIGS. 7A-7B are back and front perspective views of a wearable stimulation assembly 720 for treating neurophysiological impairments, according to an embodiment. FIG. 7C is an isometric view of the stimulation assembly 720 of FIGS. 7A-7B worn on a neck of a user U. The stimulation assembly 720 includes a housing 724 structured as a collar such that that housing 724 can be worn around a portion of a neck of the user U, for example, define a curvature such that housing 724 can be disposed around a back of the neck of the user U, as shown in FIG. 7C. The housing 724 may be formed from a durable and lightweight material, for example, aluminum, plastics, etc. Various components of the stimulation assembly 720 (e.g., the processor 425, the memory 426, the stimulation signal generation module 427, the power source 428, and/or the I/O interface 429) may be disposed in the housing 724. A set of visual indicators 725 (e.g., LED lights) may be provided on the housing 724 and may be configured to indicate a charge status of a power source included in the stimulation assembly 720, a connectivity status (e.g., a wireless connectivity status), and/or other information corresponding to the operation of the stimulation assembly 720.

The stimulation assembly 720 includes a set of electrodes 722 that include a first electrode 722a, a second electrode 722b, a third electrode 722c, and a fourth electrode 722d. The first and second electrodes 722a, 722b are coupled to the housing 724 (e.g., electronic components disposed in the housing 724) via a first electrical lead 723a and a second electrical lead 723b. The first and second electrodes 723a, 723b are configured to be removably disposed on a mastoid of the user U, for example, via a medical adhesive. The third and fourth electrodes 723c and 723b are coupled to a portion of the housing 724 that is configured to be disposed proximate to the neck of the user U when the stimulation assembly 720 is worn on the neck of the user U. The third and fourth sensors 723c and 723b are coupled to the housing 724 via flaps 723c and 723d, respectively, as shown in FIG. 7B, but in some embodiments, may be disposed on a surface of the housing 724. At least a pair of the set of electrodes 722 may be activated to apply a stimulation signal to the user U to correct an impairment of the user U, as previously described, for example, based on a signal received from the controller 150 or 450, as previously described. In some embodiments, phybrata sensors may also be integrated into the first electrode 722a and/or the second electrode 722b, such that the assembly 720 is a sensing and stimulation assembly.

Figure 8A:
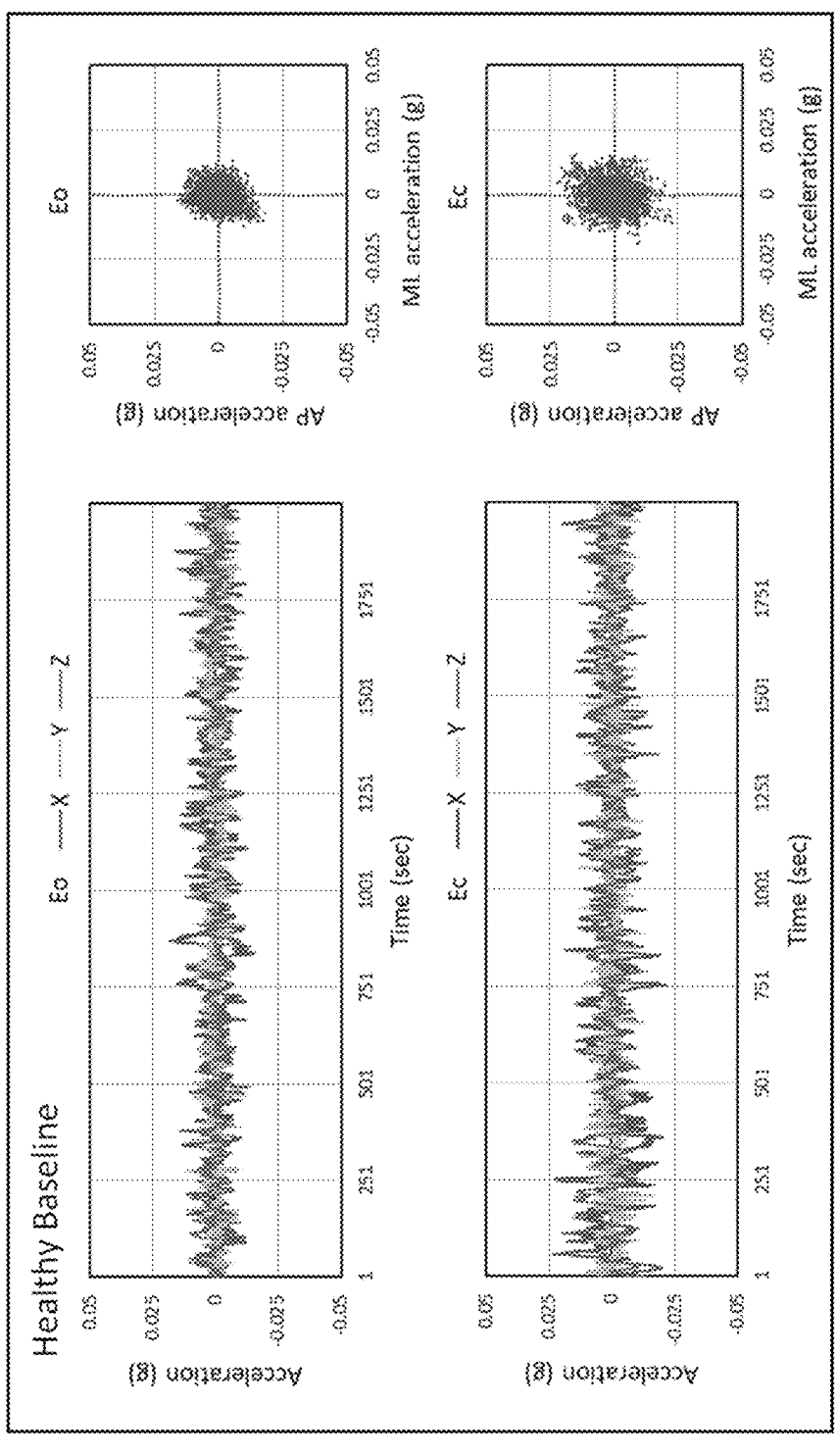
FIG. 8A shows plots of sample eyes open (Eo) and eyes closed (Ec) x (anterior-posterior, AP), y (vertical), z (medial-lateral, ML) acceleration time series data and AP/ML acceleration spatial scatter plots for age/gender-matched healthy baseline participants generated using a neurophysiological sensing system.
Figure 8B:
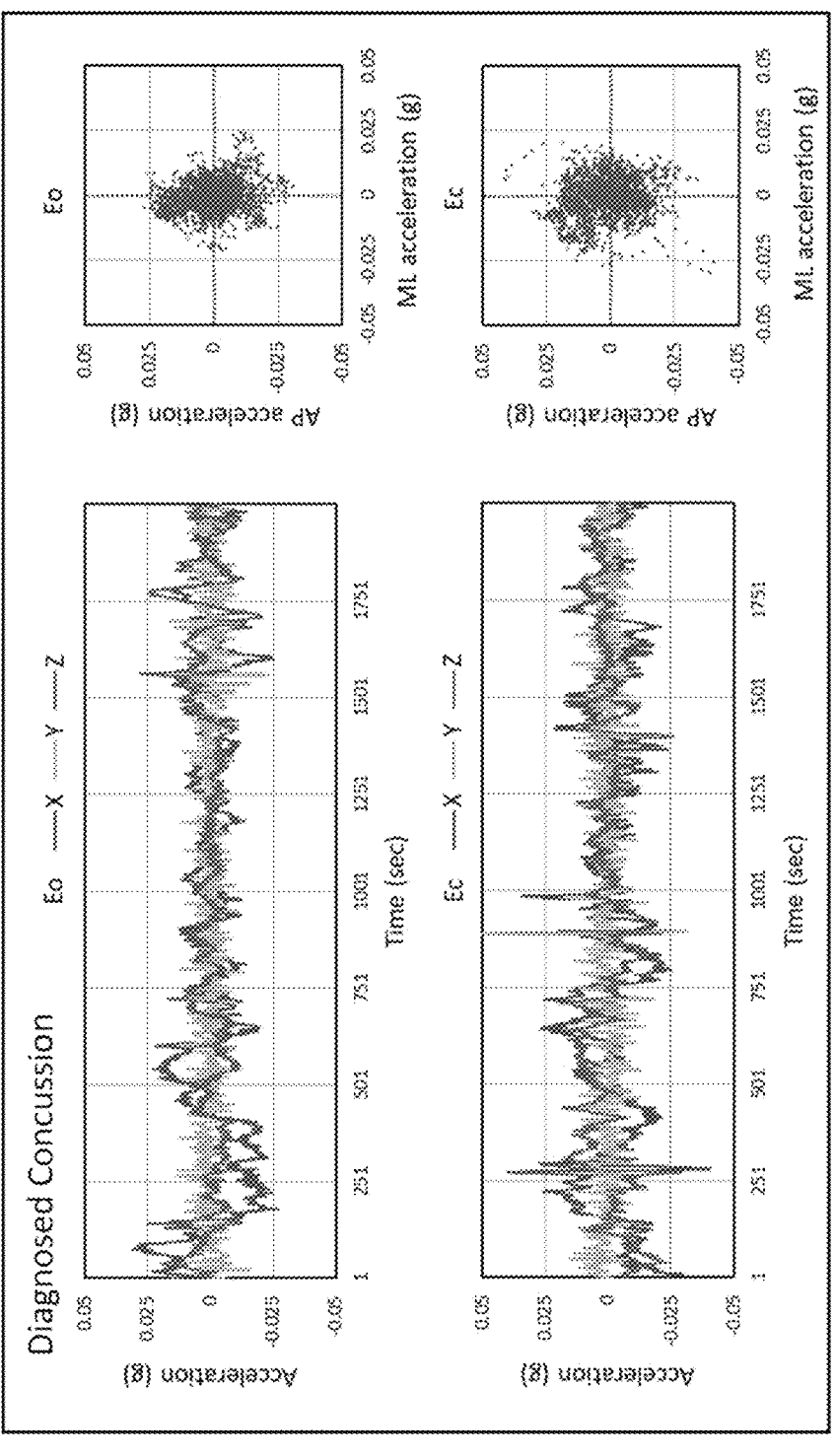
FIG. 8B shows plots of sample eyes open (Eo) and eyes closed (Ec) x (anterior-posterior, AP), y (vertical), z (medial-lateral, ML) acceleration time series data and AP/ML acceleration spatial scatter plots for age/gender-matched patient with diagnosed concussion generated using a neurophysiological sensing system.

FIG. 8A shows plots of sample eyes open (Eo) and eyes closed (Ec) x (anterior-posterior, AP), y (vertical), z (medial-lateral, ML) acceleration time series data and AP/ML acceleration spatial scatter plots for age/gender-matched healthy baseline participants generated using a neurophysiological sensing system, for example, the system 100, 200. FIG. 8B shows plots of sample eyes open (Eo) and eyes closed (Ec)

x (anterior-posterior, AP), y (vertical), z (medial-lateral, ML) acceleration time series data and AP/IL acceleration spatial scatter plots for age/gender-matched patient with diagnosed concussion generated using a neurophysiological sensing system, for example, the system 100, 200.

FIGS. 9A-9D shows plots of normalized eyes-closed (Ec) anterior-posterior (AP) time-resolved phybrata power spectral density (NPSD) plots (top) and spectrograms (middle), along with phybrata spatial scatter plots (bottom, left), and phybrata power bar graphs (bottom, right) for an athlete tested healthy/baseline (FIG. 9A), 6 days post-concussion with neurological impairment (FIG. 9B), 14 days post-concussion (FIG. 9C), and 21 days post-concussion (FIG. 9D) a neurophysiological sensing system. The phybrata signals shown in FIGS. 8A-9D include complex features and feature ensembles in the spatial domain, time domain, and frequency domain. Table 1 provides examples of spatial-domain, time-domain, frequency-domain, and sensory reweighting metrics that may be used as components of the phybrata signature.

TABLE 1

Examples of various phybrata metrics

| Example Spatial Domain Metrics | Example Time Domain Metrics | Example Frequency Domain Metrics |
| --- | --- | --- |
| Area | Eo(total, x, y, z), Abs, % Norm | $f_{VT}$, $f_{VS}$, $f_{CN}$, $f_{PN}$, $f_{PR}$, $f_{MS}$ (Eo, Ec, Ec – Eo) |
| Path length | min, max, median, mean, variance, stnd dev | P, PSD, NPSD |
| L/R, F/B, U/D, Abs, % Norm | Ec(total, x, y, z), Abs, % Norm | Abs, % Total, % Norm |
| | min, max, median, mean, variance, stnd dev (Eo + Ec)/2, Abs, % Norm | Sensory reweighting (system change rank) |
| | Ec/Eo, Abs, % Norm | |

Table 2 lists examples of phybrata biomarkers that may be indicative of various neurophysiological diseases used to identify, quantify, and/or monitor impairments to specific physiological systems in the body of the user.

TABLE 2

Example biomarkers that are indicative of various neurophysiological diseases.

| Impairment | Example Biomarker |
| --- | --- |
| Neurological impairment | Eo(total): % Norm |
| Vestibular impairment | Ec/Eo: % Norm/$f_{VT}$: NPSD, % Total, % Norm |
| Proprioceptive impairment | L/R, F/B: Abs, % Norm/$f_{PR}$ |
| Brain demyelination | $f_{CN}$: NPSD, % Total, % Norm |
| Optic nerve demyelination | $f_{VT}$: NPSD, % Total, % Norm |
| Spinal cord demyelination | $f_{PN}$: NPSD, % Total, % Norm |
| Dopaminergic deficit | $f_{CN} + f_{MS}$: NPSD, % Total, % Norm |

Figures 10A, 10B:
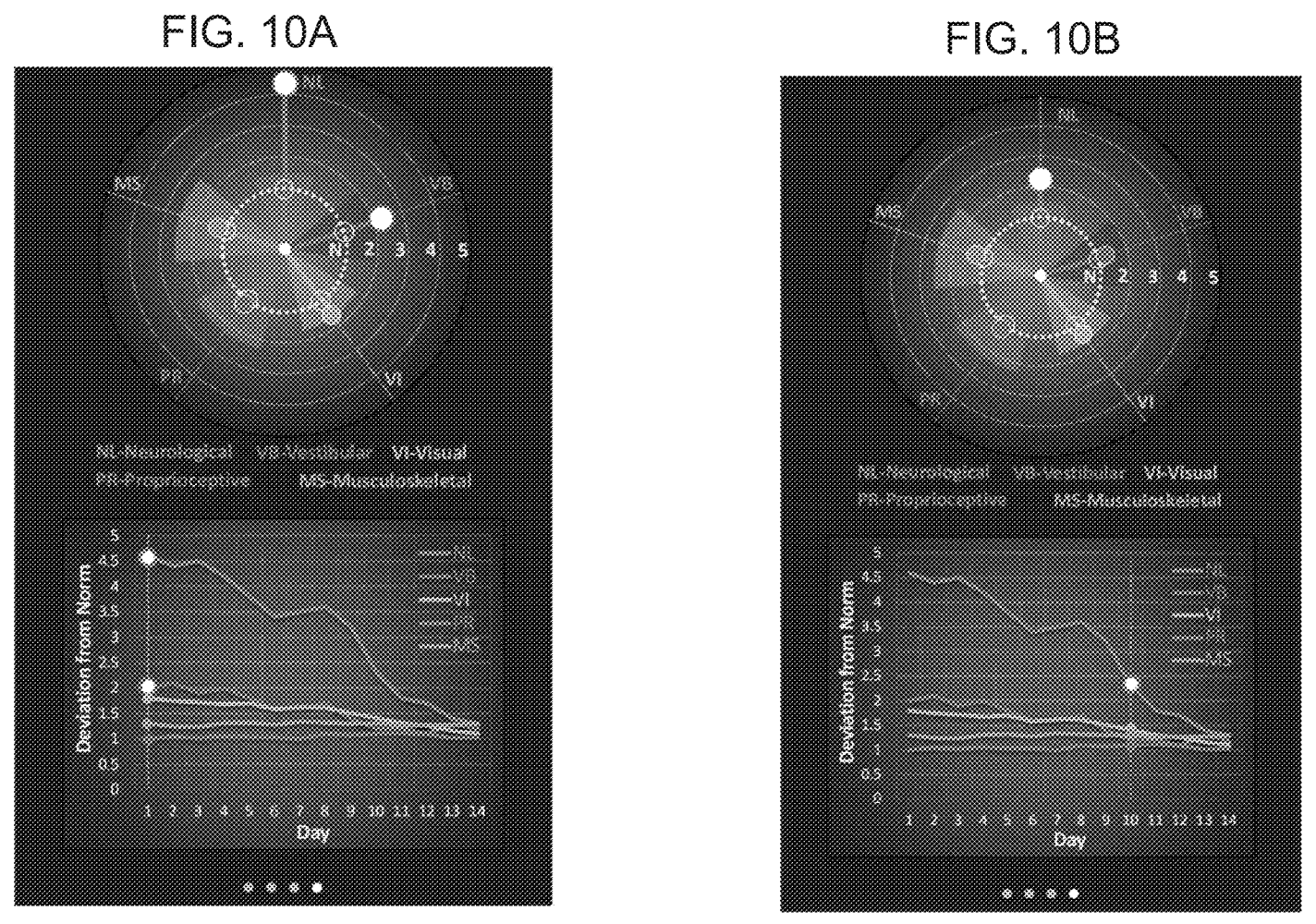

FIGS. 10A and 10B shows a sample phybrata data test report generated by a neurophysiological sensing system on day 1 (FIG. 10A) and day 10 (FIG. 10B), according to an embodiment. For example, the phybrata data may be acquired by a sensing assembly (e.g., the sensing assembly 110, 210), and communicated to a data collection system (e.g., the data collection system 130, 230, 430) that may generate and display the reports shown in FIGS. 10A-10B, that may be used by clinicians or users (e.g., patients).

Figure 11B:
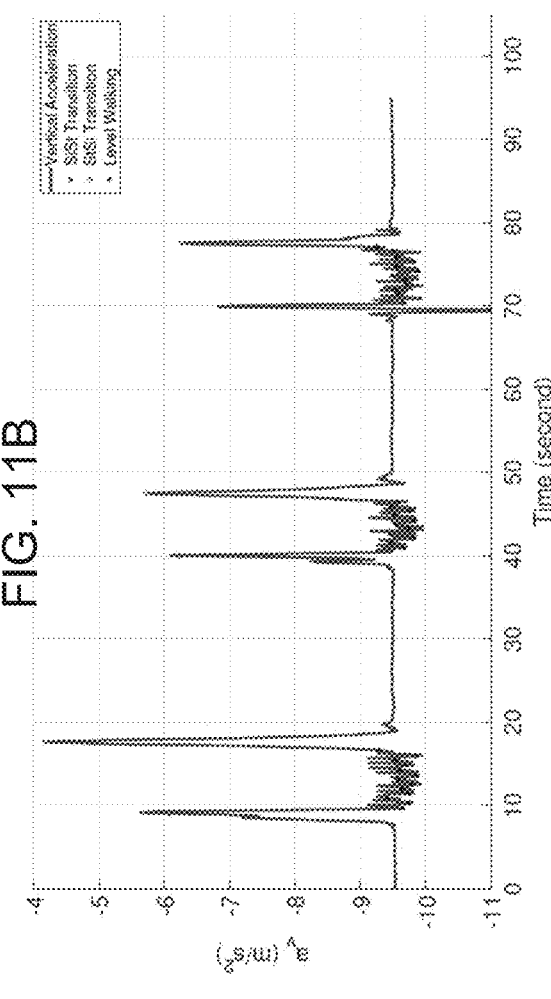
FIG. 11B shows a plot of the vertical acceleration of the user measured using a neurophysiological sensing system.
Figure 11A:
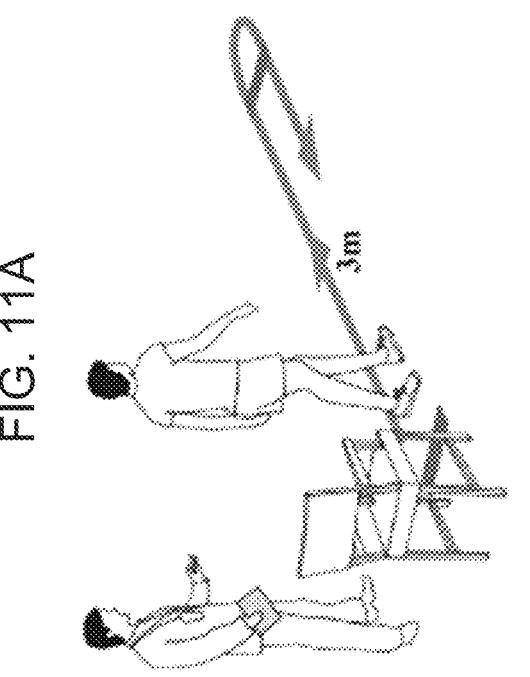
FIG. 11A illustrates a gait analysis test being performed on a patient or user.
Figure 12:
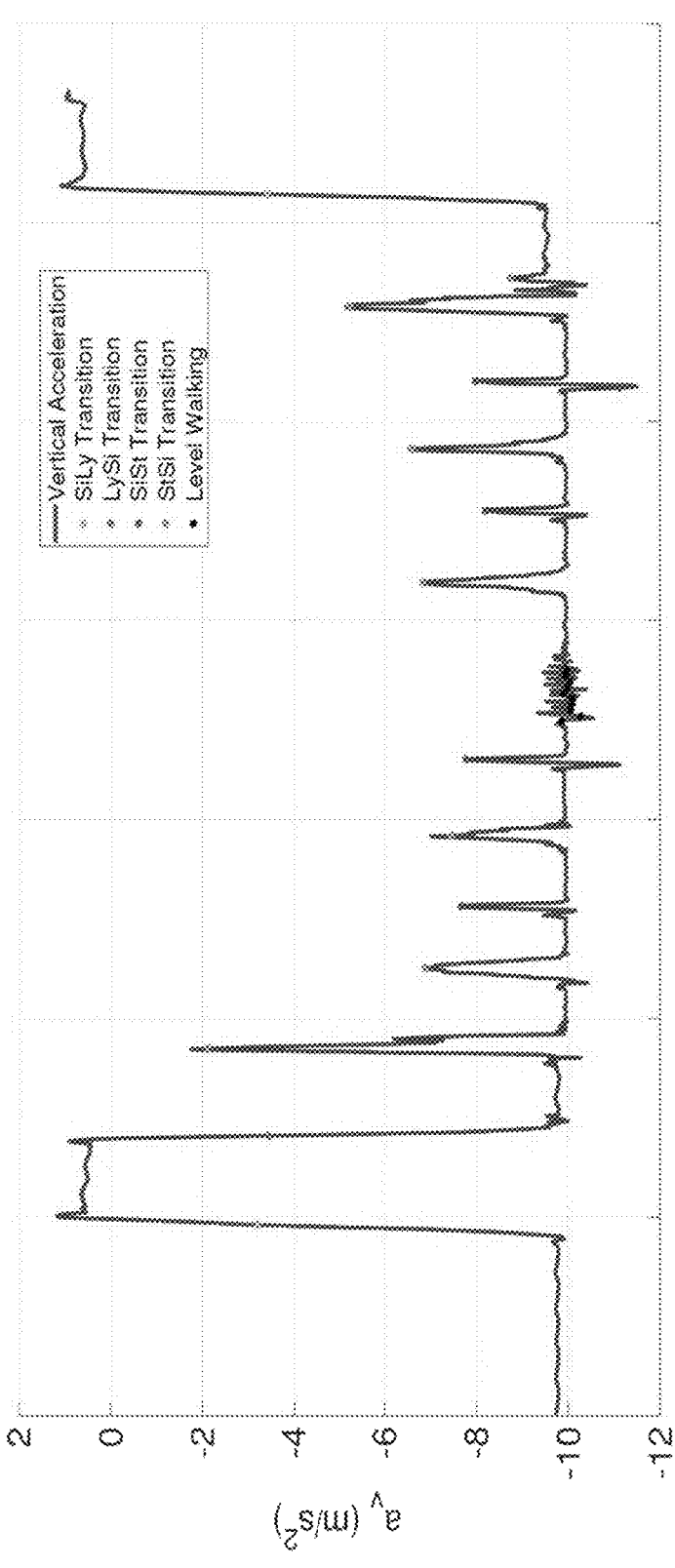
FIG. 12 is a plot of vertical acceleration and various gait analysis variables that may be included in a phybrata signature using extended monitoring of a patient using a neurophysiological sensing system.
Figures 14A, 14B, 14C, 14D:
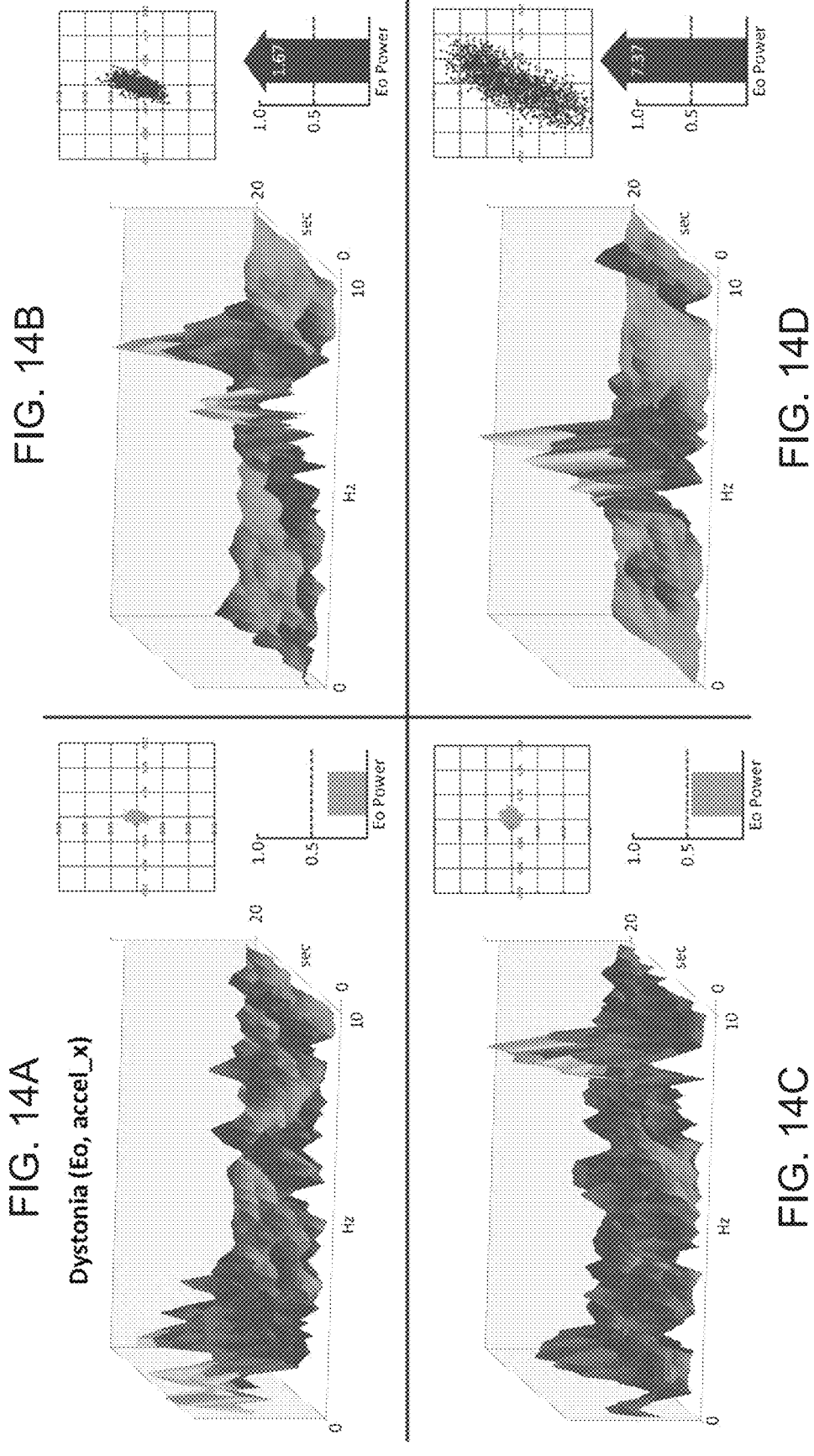
FIGS. 14A-14D are plots of phybrata signatures of a user including normalized eyes-open (Eo) and eyes-closed (Ec) anterior-posterior (AP, x) time-resolved phybrata power spectral density (NPSD) plots, along with AP/IL acceleration spatial scatter plots and bar graphs of phybrata power, for four dystonia patients with progressively greater head tremor severity, generated using a neurophysiological sensing system.

FIG. 11A illustrates a balance and gait analysis test being performed on a patient or user, and FIG. 11B shows a plot of the vertical acceleration of the user measured using a neurophysiological sensing system, for example, the system 100 or 200. The vertical acceleration plot shown in FIG. 11B is indicative of normal or impaired gait performance when the user wearing the sensing assembly, for example, the sensing assembly 110, 210, walks over a period of time. Similarly, FIG. 12 is a plot of vertical acceleration and various gait analysis variables that may be included in a phybrata signature using extended monitoring of a patient using a neurophysiological sensing system, and indicate pathological patterns in activities of daily living of the patient during extended remote patient monitoring. Table 3 lists various balance and gait analysis test variables that may be obtained using the neurophysiological sensing systems described herein during a gait test.

TABLE 3

Balance and gait test variables measured using a sensing assembly.

| TUG Variable | Description |
| --- | --- |
| turn2_maximum_yaw_velocity | Maximum angular velocity around the vertical-axis during the second turn |
| turn1_maximum_yaw_velocity | Maximum angular velocity around the vertical-axis during the first turn |
| stsi_maximum_flexion_angular_velocity | Maximum flexion angular velocity of the trunk during the stand to sit transition |
| stsi_flexion_range | Total flexion range of the trunk during the stand to sit transition |
| stsi_extension_range | Total extension range of the trunk during the stand to sit transition |
| sist_maximum_flexion_angular_velocity | Maximum flexion angular velocity of the trunk during the sit to stand transition |
| sist_maximum_extension_angular_velocity | Maximum extension angular velocity of the trunk during the sit to stand transition |
| sist_flexion_range | Total flexion range of the trunk during the sit to stand transition |
| sist_extension_range | Total extension range of the trunk during the sit to stand transition |
| walk2_duration | Duration of the walking phase starting after the first turn till the start of the second turn |
| walk1_duration | Duration of the walking phase starting after sit to stand till the first turn |
| turn2_duration | Duration to perform the second turn |
| turn1_duration | Duration to perform the first turn |

TABLE 3-continued

Balance and gait test variables measured using a sensing assembly.

| TUG Variable | Description |
| --- | --- |
| total_duration | Total duration to perform the TUG |
| stsi_total_duration | Total duration of the stand to sit transition |
| stsi_flexion_duration | Flexion duration of the stand to sit transition |
| stsi_extension_duration | Extension duration of the stand to sit transition |
| sist_total_duration | Total duration of the sit to stand transition |
| sist_flexion_duration | Flexion duration of the sit to stand transition |
| sist_extension_duration | Extension duration of the sit to stand transition |

Figure 13:
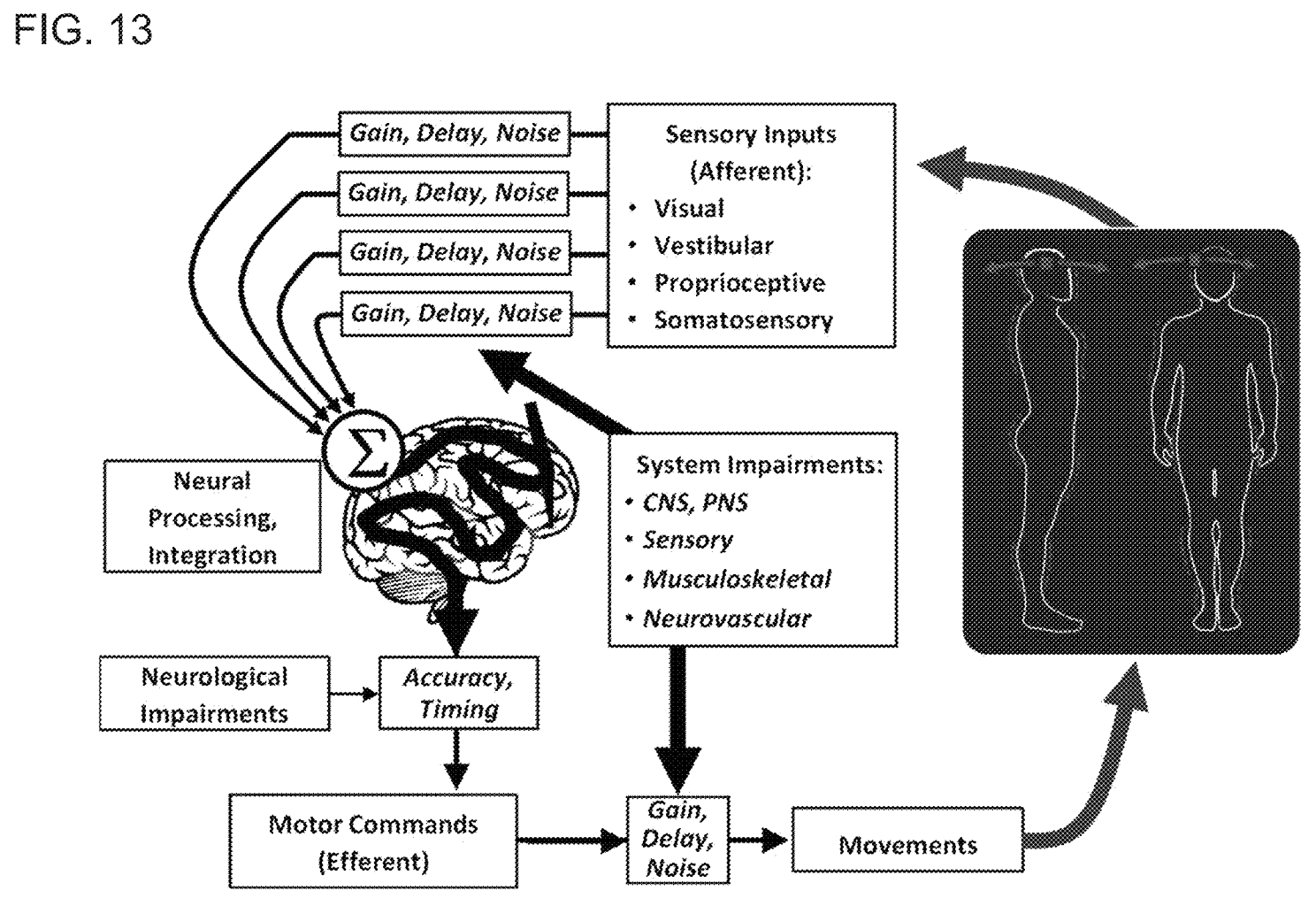

FIG. 13 is a schematic block diagram of a biomechanical model of a user developed using a neurophysiological sensing system described herein, according to an embodiment. As depicted in FIG. 13, the phybrata-based human biomechanical mode includes the full range of active vs. passive, open-loop vs. closed-loop, intermittent vs. continuous, and high-complexity vs. low-complexity control behaviors that are able to account for and replicate normal and impaired balance and gait stability and sensory reweighting. The biomechanical model serves as a phybrata digital twin system that incorporates phybrata sensors, statistical data analytics models, machine learning models, and phybrata-based human biomechanical models to enable more rapid and quantitative diagnoses of complex medical conditions, enable earlier initiation of treatment, and provide more comprehensive monitoring and feedback to optimize individual patient responses to pharmacological medications, non-pharmacological treatments, and rehabilitation therapies.

FIGS. 14A-14D are plots of phybrata signatures of a user including normalized eyes-open (Eo) and eyes-closed (Ec) anterior-posterior (AP, x) time-resolved phybrata power spectral density (NPSD) plots, along with AP/IL acceleration spatial scatter plots and bar graphs of phybrata power, for four dystonia patients with progressively greater head tremor severity, generated using a neurophysiological sensing system (e.g., the system 100, 200). FIGS. 14A-14D depict real-time phybrata signals utilized to detect and quantify unwanted pathological movements, such as those caused by essential tremor or dystonia, which can then be used to determine an appropriate stimulation signal to reduce impairment, for example, the optimum EVS frequency, amplitude, and duration to induce offsetting motion, and to apply the corresponding EVS in real-time closed-loop feedback in order to reduce the severity of the tremor.

Figure 15A:
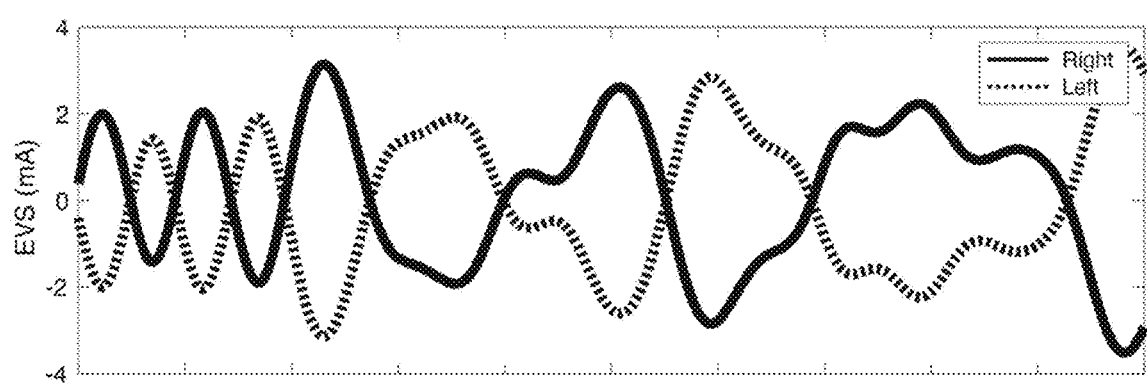
FIGS. 15A-15C show plots of postural stability data collected simultaneously from a mastoid-mounted sensing assembly (FIG. 15C) and a force plate (FIG. 15B) during the application of a suprathreshold EVS signal (FIG. 15A).
Figure 15B:
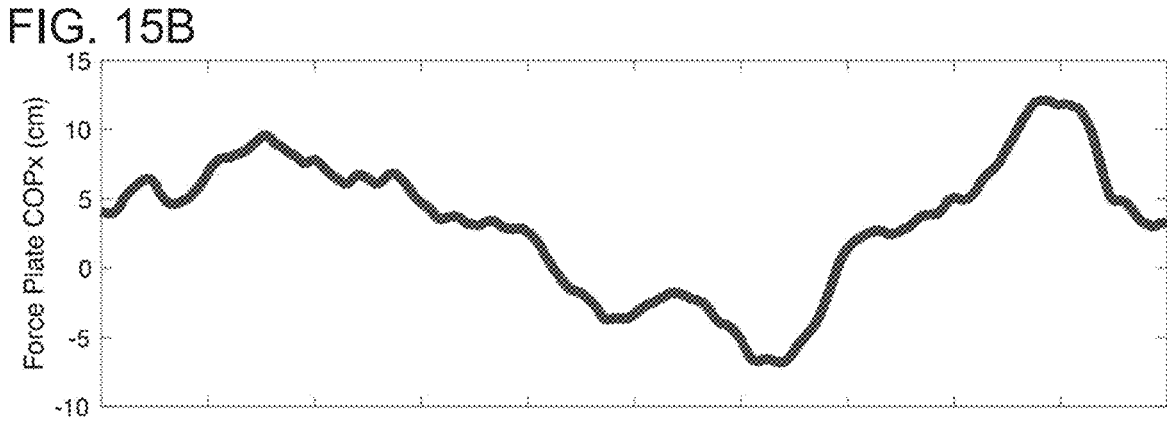
Figure 15C:
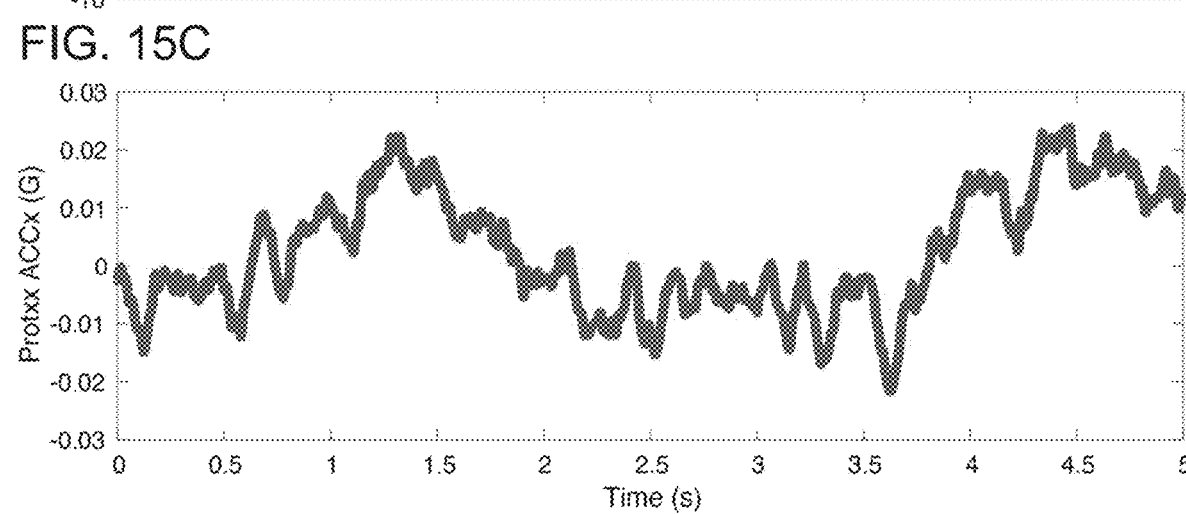

FIGS. 15A-15C show plots of postural stability data collected simultaneously from a mastoid-mounted sensing assembly (FIG. 15C) and a force plate (FIG. 15B) during the application of a suprathreshold EVS signal (FIG. 15A). Specifically, the generation of corrective movements can be assessed by delivering noisy EVS stimulation during standing balance trials, while electromyography and ground reaction forces (for example, center of pressure, or COP, from a force plate) are recorded. In this case, the EVS stimulation is strong enough that the participant can detect the stimulation (supra-threshold). Surface EMG is recorded from gastrocnemius, soleus, and tibialis anterior bilaterally. The phybrata sensing assembly is attached to the participant's upper mastoid process. Testing is conducted with the head left, with the head right, and with the head forward to obtain the phybrata data corresponding to corrective movements that are shown in FIG. 15C.

Figure 16:
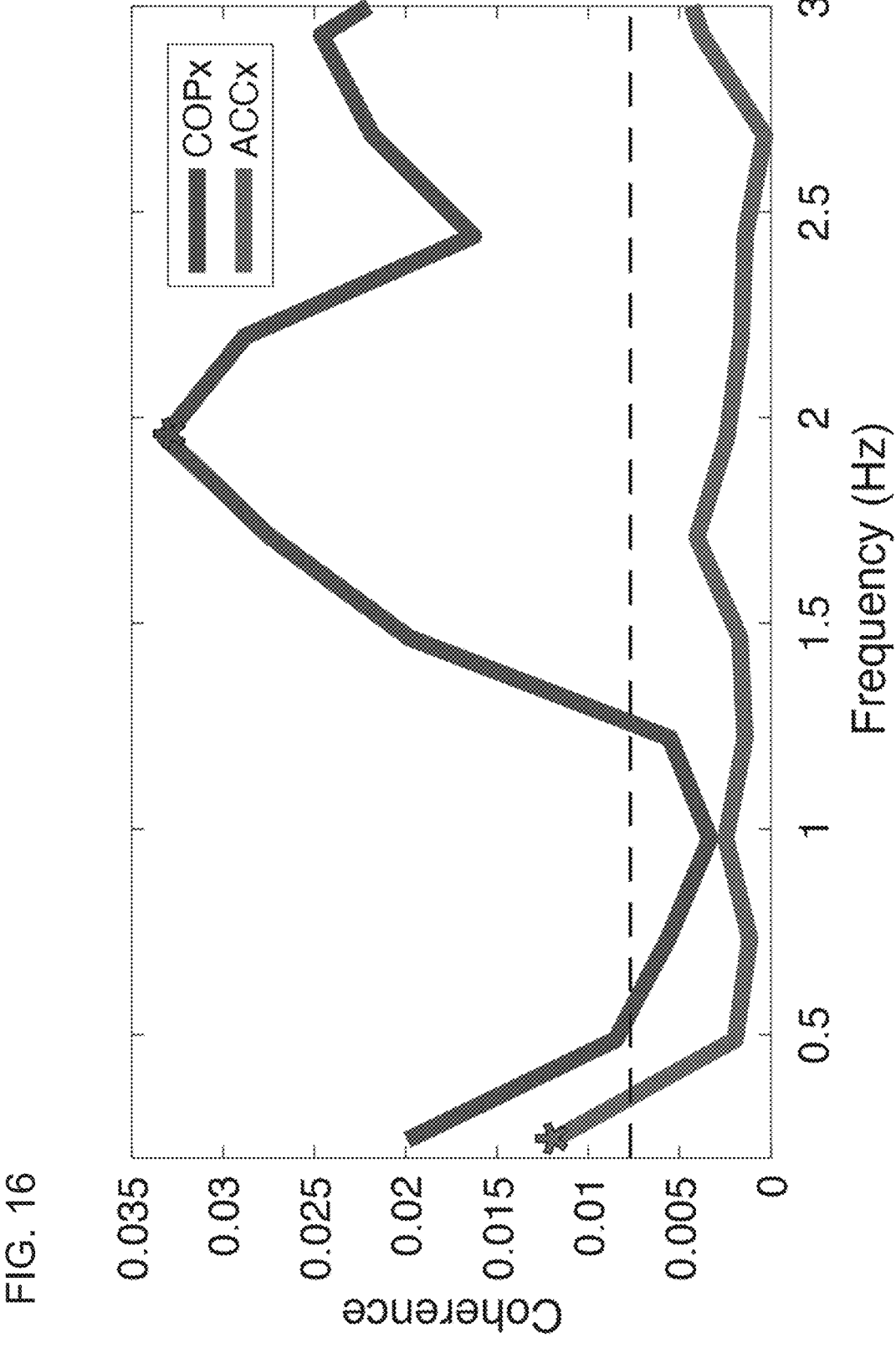
FIG. 16 is a plot of calculations of the frequency-domain coherence between motion signals measured simultaneously using a mastoid-mounted assembly (ACCx) and a force plate (COPx).
Figure 17:
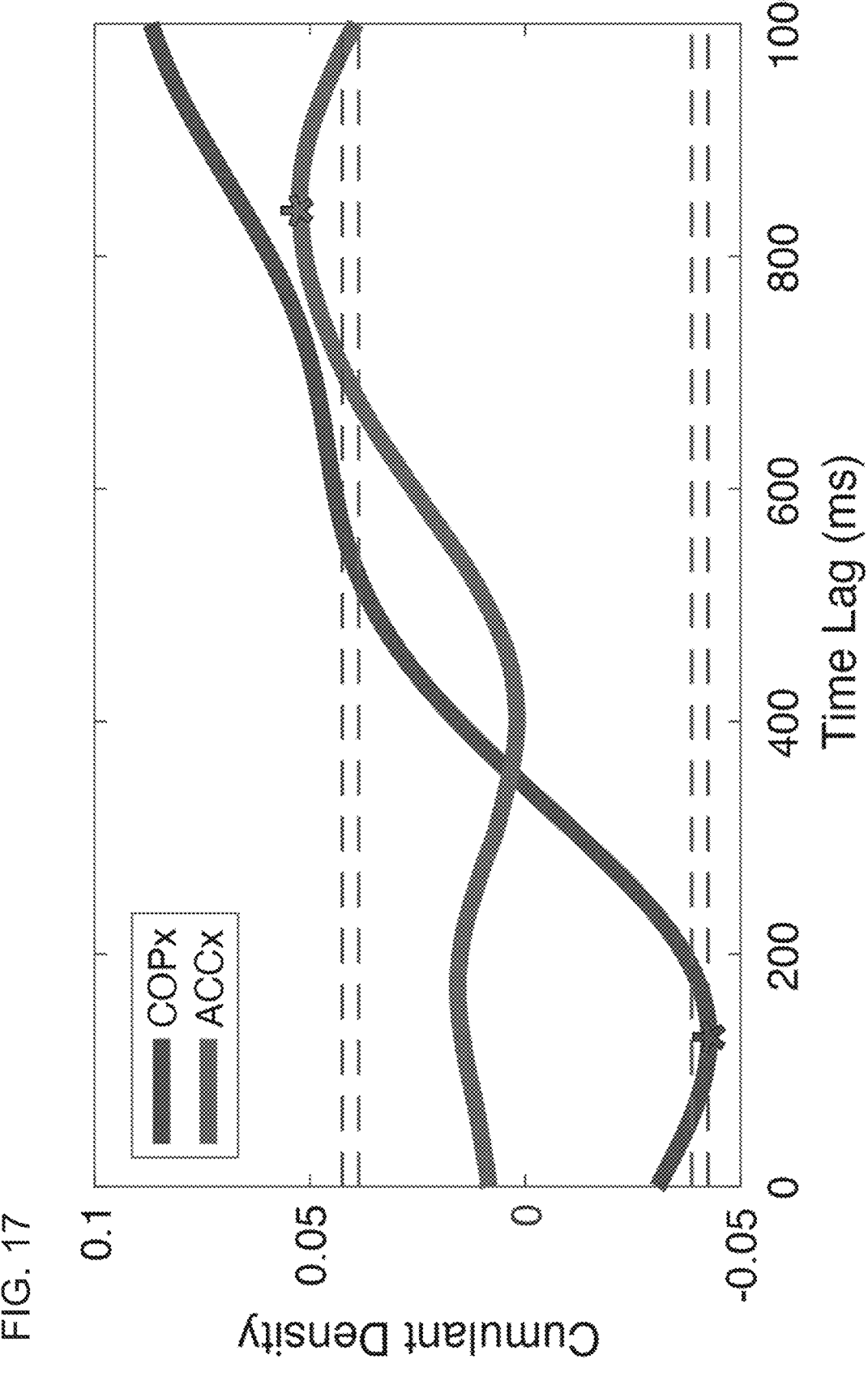
FIG. 17 is a plot of calculations of the time-domain cumulant density between motion signals measured simultaneously using a mastoid-mounted assembly (ACCx) and a force plate (COPx).

FIG. 16 is a plot of calculations of the frequency-domain coherence between motion signals measured simultaneously from using a mastoid-mounted assembly (ACCx) and a force plate (COPx). Phybrata and force plate recordings are time-synced for each head position for cross-correlation analysis. Outcome measures from these analyses are correlations in frequency content (coherence) as shown in FIG. 16. FIG. 17 is a plot of calculations of the time-domain cumulant density between motion signals measured simultaneously from using a mastoid-mounted assembly (ACCx) and a force plate (COPx), and shows correlations in the time-domain (cumulant density), as well as the gain and phase calculated between the input (EVS waveform) and outputs (COP and phybrata recordings). As illustrated in FIG. 15C, the subtle, whole-body balance responses evoked by supra-threshold noisy EVS can be detected by the phybrata sensor, and this approach provides superior detection and assessment of vestibular-evoked balance responses to those obtained using traditional EMG and force plate measures.

The utility of EVS diagnostics disclosed here was demonstrated by examining the effects of repetitive head impact (RHI) events in combat sports athletes were examined. Lower-limb muscle responses evoked with EVS between fighters (boxing/Muay Thai) and non-fighter controls were compared. Each participant received suprathreshold stochastic vestibular stimulation (SVS) (0-25 Hz, ±3 mA) over their mastoid processes while they stood relaxed with their head to the left or right. Surface electromyography was recorded from the medial gastrocnemius and soleus muscles bilaterally. SLR and MLR peaks were significantly delayed in the fighter group compared to the controls. SLR and MLR peak amplitudes were also significantly lower in the fighters. Fighter-estimated cumulative repetitive head impact (RHI) events demonstrated strong positive correlations with the timing of SLR and MLR peaks. Cumulative RHI events also negatively correlated with peak MLR amplitude and response gain at frequencies above 5 Hz.

Figures 18A, 18B, 18C, 18D:
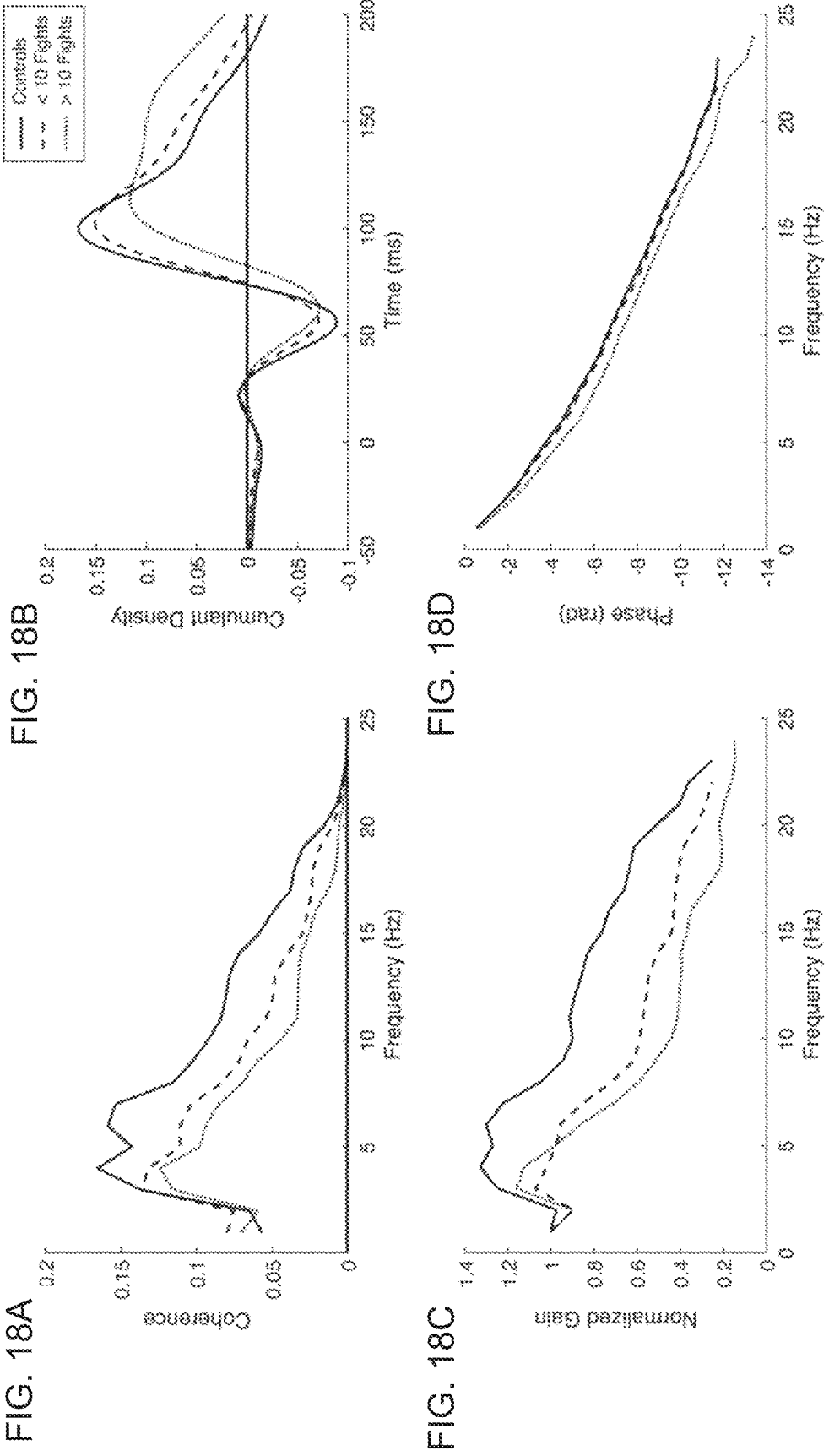
FIGS. 18A-18D are plots of coherence (FIG. 18A) depicting the frequency domain correlations between the SVS and left medial gastrocnemius (head right condition), cumulant density (FIG. 18B) depicting the time domain representation of the same correlations shown in panel FIG. 18A, bode plots for gain spectra (FIG. 18C), and phase spectra for the input-output relationship (FIG. 18D), for three different groups of test subjects.
Figures 19A, 19B, 19C, 19D:
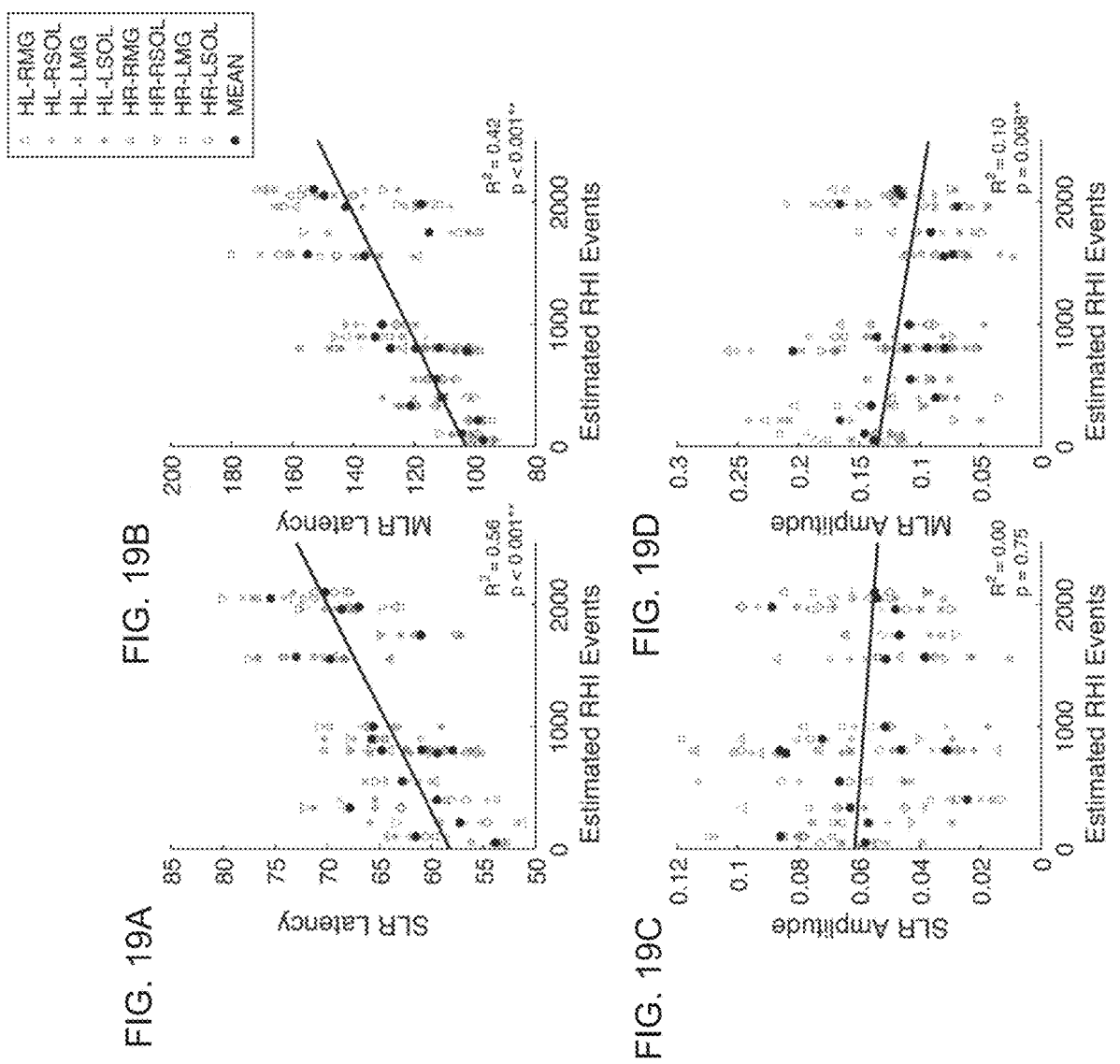
FIGS. 19A-19D are plots of correlations for the timing of peak short and medium latency responses (SLR and MLR) (FIGS. 19A and 19B) and amplitude (FIGS. 19C and 19D.

FIGS. 18A-18D are plots of coherence (FIG. 18A) depicting the frequency domain correlations between the EVS and left medial gastrocnemius (head right condition), cumulant density (FIG. 18B) depicting the time domain representation of the same correlations shown in FIG. 18A, bode plots for gain spectra (FIG. 18C), and phase spectra for the input-output relationship (FIG. 18D), for three different groups of test subjects. FIGS. 18A-18D demonstrate the ability of EVS testing to quantitatively distinguish between healthy individuals, individuals with mild vestibular balance impairment, and individuals with severe vestibular balance impairments. FIGS. 19A-19D are plots of correlations for the timing of peak short and medium latency responses (SLR and MLR) (FIGS. 19A and 19B) and amplitude (FIGS.

19C and 19D). FIGS. 19A-19D demonstrate the correlation between the severity of vestibular balance impairments and the number of RHIs.

The results collected from the phybrata sensors described herein suggest that EVS-evoked responses may change in a continuous manner with increasing exposure to RHI events, and that this progressive vestibular impairment in combat sports athletes likely results from blows to the head accumulated in sparring practice and competitive bouts throughout their careers. Taken together, EVS-based vestibular assessments may provide a valuable clinical diagnostic tool and help better inform 'return-to-play' and career length decisions for not only combat sports athletes, but potentially other populations at risk of repetitive head impacts. The above EVS coherence delays and amplitude declines also correlate with various phybrata biomarkers for vestibular impairment, enabling the construction of multimodal biomarkers.

Figures 20A, 20B, 20C:
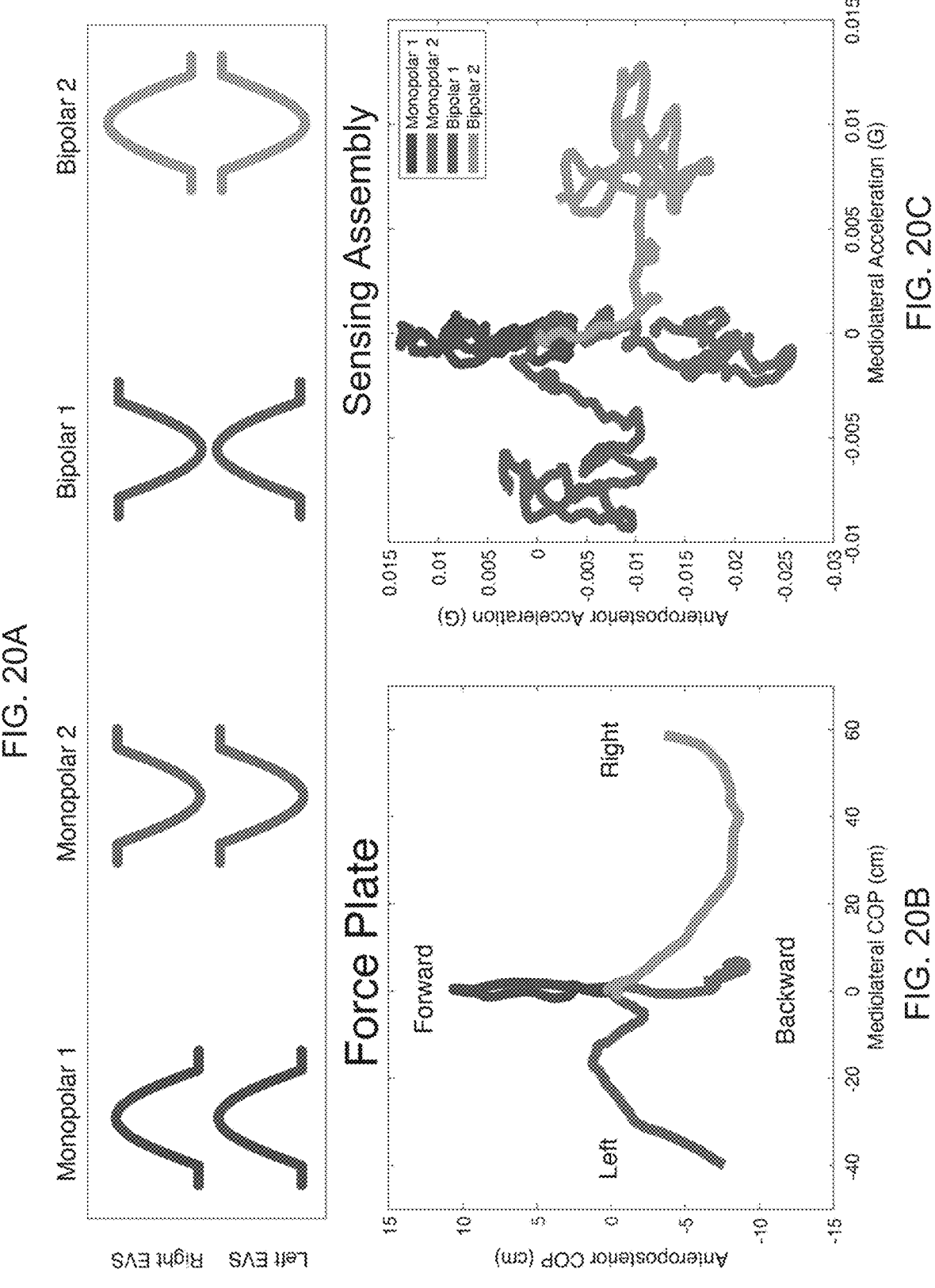
FIGS. 20A-20C are plots of averaged force plate center of pressure (COP) (FIG. 20B) and a mastoid mounted sensing assembly (FIG. 20C) head acceleration in the anterolateral and mediolateral planes evoked by bipolar and monopolar sinusoidal EVS pulses of different polarities (FIG. 20A).

The utility of EVS movement correction disclosed here is illustrated in FIGS. 20A-20C. FIGS. 20A-20C are plots of averaged force plate center of pressure (COP) (FIG. 20B) and a mastoid mounted sensing assembly (FIG. 20C) head acceleration in the anterolateral and mediolateral planes evoked by bipolar and monopolar sinusoidal EVS pulses of different polarities (FIG. 20A). FIGS. 20A-20C demonstrate the feasibility of the phybrata stimulation assemblies and sensing assemblies described herein to generate and control an arbitrary corrective movement response in a user U by applying the four combinations of binaural, bipolar, and monopolar EVS stimulation signals illustrated in FIG. 20A. FIGS. 20B and 20C show the average force plate COP and phybrata sensing assembly head acceleration traces for the different stimulus polarities and electrode configurations.

The averages in FIGS. 20A-20C were computed for each electrode polarity and configuration over 20 repetitive exposures to sinusoidal pulses (duration=5 s; peak=4 mA). The order of sinusoidal pulses was randomly intermixed (20 reps×4 configurations=80 pulses total), such that the participant was unable to predict the direction of the evoked perturbation on each trial. Two isolated bipolar constant current stimulators are integrated into the phybrata sensing assembly to form a sensing and stimulation assembly, so that the electrode configuration can be rapidly switched between binaural bipolar and binaural monopolar modes. With the head facing forward, the bipolar configuration evokes a mediolateral balance perturbation, and the monopolar configuration evokes an anterolateral balance perturbation.

Custom phybrata detection algorithms detect when the participant's motion exceeds a threshold in either the mediolateral or anterolateral planes, and then trigger a sinusoidal EVS pulse that directs the participant back into a neutral position. Pilot testing with patients spanning a wide age range have been used to determine appropriate threshold-level deviations for motion in the mediolateral and anterolateral planes, as well as to calibrate EVS pulses of varying amplitudes and frequencies to the postural responses they evoke. The average vector of postural sway measured from the phybrata sensing assembly is extracted from multiple repeated pulses of the same frequency/amplitude to develop a computational model for how supra-threshold EVS pulses can be applied to enhance standing balance stability.

In some embodiments, phybrata and EVS features may be combined to generate multimodal biomarkers that can further refine diagnoses of physiological impairments caused by head impacts, other injuries, aging, or disease, as well as to quantify recovery from neurological, vestibular, or visual impairments during therapeutic treatment of the impairments using CES, EVS, or ESE. In the case of head impact injuries, for example, research and clinical evidence have revealed that damage accrued to the vestibular system may underlie a significant proportion of the symptomology observed after blunt-force head trauma. Head tilts, rotations, and translations are detected by the vestibular system, which supports a wide variety of important functions, including the stabilization of the eyes/head, the perception of head movement and orientation relative to gravity, the autonomic regulation of heart rate with body tilt, and most importantly, the control of standing balance. Blunt- and blast-force head trauma may cause widespread damage to delicate peripheral and central neuroanatomical structures, including but not limited to, structures involved in vestibular balance processing. Shearing forces acting on the fine stereocilia of vestibular hair cell receptors and their afferents, as well as torsional forces acting on the vestibular nuclear complex (VNc) within the brainstem make the vestibular system particularly vulnerable to impact forces delivered to the head.

As described above, EVS has become an important tool to assess vestibular function. Non-human primate recordings have revealed that EVS bypasses natural vestibular hair cell activation (caused by deflection of kinocillium/stereocillia) and evokes neural responses in vestibular afferents and the vestibular nucleus similar to those evoked by real head rotation. Converging lines of evidence now suggest that EVS evokes net signals of angular velocity and inferred linear acceleration when delivered in a binaural bipolar configuration. Vestibular contributions to balance control can be probed by applying EVS while monitoring the evoked lower-limb muscle activity, ground reaction forces, and/or kinematics of the body. EVS has been used to explore the effect of high vs low annual exposure to soccer headers on upright standing balance. Within the high header exposure group, force plate measurements have revealed a lagging sway response to EVS in a high-exposure group when compared to a low-exposure group, consistent with the phybrata sensor results shown here in FIGS. 16-20C. EVS responses measured using force plates have also revealed a significant decrease in trunk angle, leg angle, and center of mass gain after exposure to headers.

In some embodiments, alternative electrode configurations are utilized on the patient's head to deliver integrated phybrata diagnostic/CES therapeutic treatment modalities for anxiety, depression, insomnia, addiction, chronic pain, epilepsy, obsessive-compulsive disorder, spinal cord injuries, neuropathic pain, ADHD, and MS-related myelin disruption in the brain or spinal cord. Electrical nerve stimulation is a promising approach to counteract multiple sclerosis related neurodegeneration by enhancing myelin regeneration, which can restore nerve conduction and metabolic support to the axon. Immunotherapies are available that can reduce disease activity and related clinical relapses during the relapsing-remitting phase of the disease, but the prevention of disability progression, which is due to axonal and neuronal damage and loss, has yet to be achieved and is therapeutically challenging, particularly during the progressive phase of the disease. In some embodiments, alternative electrode configurations are utilized on the patient's head to deliver integrated phybrata diagnostic/ESE therapeutic treatment modalities for glaucoma, age-related macular degeneration, diabetic retinopathy, and MS-related optical neuritis.

FIG. 21 is a schematic block diagram of a method of generating predictive data indicative of predictive changes in at least one user physiological parameter based on phybrata signatures of a user determined using a sensing assembly, synthetic phybrata data generated using machine learning, and simulated phybrata data developed using a biomechanical model of a user via a neurophysiological sensing system, according to an embodiment. Phybrata and EVS features, feature ensembles, and patterns are utilized in combination with statistical analysis models and machine learning models to derive one or more clinically intuitive quantitative phybrata metrics, predictive models, and synthetic phybrata data that independently and uniquely classify, quantify, and track the time evolution of physiological system impairments resulting from a specific medical condition.

The phybrata and EVS features, feature ensembles, and patterns may also be utilized to adjust quantitative model parameters in biomechanical phybrata models that include a full range of neurosensory input, neuromotor output, and control behaviors in order to replicate experimentally observed normal and impaired physiological system performance and corresponding simulated phybrata data and data metrics derived from a human patient, and age, gender, physiological performance, and impairment-matched patient cohorts. Model parameters are adjusted in a single or multi-step iterative process to achieve a target level of statistical match between digital twin data and patient data.

Phybrata data measured directly from a healthy individual or from an impaired patient is compared with synthetic phybrata data generated by machine learning models and simulated phybrata data generated by biomechanical models of the same individual or patient and age, gender, physiological performance, and impairment-matched cohorts of individuals. The absolute values and changes in differences between the measured and modelled phybrata data and metrics overtime are used to generate a predictive analysis of projected quantitative changes in physiological performance, impairments, disease state, injury state, physiological disruption state, and responses to treatment, medications, therapies, and rehabilitation. In some embodiments, the disease or injury state may include, but is not limited to, concussion, stroke, Parkinsons's disease, multiple sclerosis, elderly frailty, peripheral neuropathies due to diabetes, peripheral arterial disease, spinal stenosis, chronic pain, invasive neurosurgery, and the results of the predictive analysis may be utilized to modify and to monitor and document a patient's response to the course of a treatment, medication, therapy, or rehabilitation.

FIG. 22 is a is a schematic block diagram of a method of generating predictive data indicative of predictive changes in at least one user physiological parameter based on phybrata signatures of a user determined using a sensing assembly, synthetic phybrata data generated using machine learning, and simulated phybrata data developed using a biomechanical model of a user via a neurophysiological sensing system, and generating stimulating signals to treat head motion impairments in the user, according to an embodiment. The method of FIG. 22 is similar to the method of FIG. 21, with the difference that the absolute values and changes in differences between the measured and modelled phybrata data and metrics over time are used to generate EVS signals in real time to reduce, correct, offset, or counteract pathological patient motions such as head tremors or pending falls, or impairments to neurophysiological systems in the body.

Embodiments described herein illustrate the ability of the sensing assemblies described herein to detect normal and pathological features and patterns in phybrata signals that are inherent to human balance and movement stabilization and arise from cerebellar and cortical integration and processing of multiple afferent feedback inputs (visual, vestibular, somatosensory), efferent feedforward motor signals, and musculoskeletal responses. The tiny mass, high sensitivity, and head-mounted design of the sensing assemblies described herein allow removable mounting of the sensing assemblies near the vestibular balance organs enabling the assemblies to detect spatial-domain, time-domain, and frequency-domain features and patterns with a level of detail not previously possible.

Moreover, phybrata time series data and spatial scatter plots, eyes open (Eo) and eyes closed (Ec) phybrata powers, receiver operating characteristic (ROC) curves, phybrata spectral density (PSD) distributions, and time-resolved phybrata spectral density (TRPSD) analyses enable the derivation of simple and clinically intuitive quantitative metrics to classify, quantify, and track the time evolution of vestibular and neurological impairments resulting from concussions or other injuries, aging, or disease. The direct measurements and time-resolved spectral analyses of phybrata signals using the mastoid-mounted sensing assemblies described herein address key limitations of alternative measurement tools used to assess physiological impairments and sensory reweighting following concussions, including computerized dynamic posturography (CDP), video motion capture systems, body-worn sensors, robotic assessments, electrodiagnostic testing such as quantitative electroencephalography (qEEG), motor evoked potentials (MEP), EMG, EVS, electrovestibulography, functional MRI (fMRI), and functional near-infrared spectroscopy (fNIRS).

With reference to FIGS. 23A-34, data was collected from several hundred patients over a 12-month period at multiple clinical sites, including healthy patient assessments and assessments for a variety of neurological conditions. Concussion patients presented with a wide range of injury causes, including automotive accidents, home and workplace falls, and sports-related injuries. Data is from a total of 175 patients (94 female, 81 male, ages 18.1±10.9 yrs, min 7 yrs, max 74 yrs), including those diagnosed with concussion symptoms within 60 days of injury (92 patients: 51 female, 41 male, ages 18.8±13.2 yrs, min 7 yrs, max 74 yrs) and individuals with no diagnosed impairments (83 patients: 43 female, 40 male, ages 17.2±7.7 yrs, min 8 yrs, max 59 yrs). Patients with diagnoses other than concussion were excluded from the analysis. Informed consent was obtained for all participants.

Concussion diagnoses for the patients described herein utilized Sport Concussion Assessment Tool (SCAT5) assessments, computerized neuropsychological testing, vestibular/ocular motor screening (VOMS), and comprehensive neurological clinical exams, including mental/psychiatric status, cranial nerves, and motor, sensory, reflexes, coordination, balance, and gait testing. Patients also underwent autonomic nervous system assessment and assessment of sensory, motor, and cognitive function, visual gaze, and postural stability using robotic assessments of normal and altered reaching movements with the Kinarm End-Point Robotic Device. Assessments were completed with some concussion patients at initial presentation and to trend recovery throughout rehabilitation. Assessments were completed with some athletes at baseline, acutely post-concussion for diagnostic utility, and at follow-up to ascertain clinical and physiological recovery to aid with return-to sport decision making. Patients diagnosed with concussion based on the above physical examination and specific symptom assessments were further divided into those presenting with vestibular impairments, other neurological impairments, or both vestibular and other neurological impairments, in order to develop the most appropriate plan of care.

Patients were tested using the sensing assembly 610*a* described herein, attached to the patient's mastoid using a disposable medical adhesive, as shown in FIG. 6A, while patients stand still for 20 sec with their eyes open (Eo) and then again for 20 sec with their eyes closed (Ec). During testing, participants were instructed to stand upright in a relaxed position with their feet together and their arms at their side while maintaining their gaze in a straight-ahead direction. No talking or arm movements were allowed during the trial. The test administrator always stood by the subjects: (1) to monitor subjects' postural sway throughout the trial; and (2) so that the subjects had no fear of falling during eyes-closed testing. Test data was excluded from the analysis if anomalous patient movement was observed during phybrata testing. A data collection system that included a smartphone app connects to the phybrata sensing assembly via a Bluetooth low-energy (BLE) wireless link to configure and run tests, collect data, and interface with cloud-based data storage, analytics, and reporting services. The phybrata IMU includes a 3-axis accelerometer to record x (anterior-posterior (AP), or front-back), y (vertical), and z (medial-lateral (ML), or left-right) acceleration time series data in units of g. During each 20 sec test, data is recorded at a sampling rate of 100 Hz, generating a total of 2000 samples for each of the 3 axes (x, y, z). The sensing assembly signals are filtered to remove drift.

For each pair of tests (20 sec Eo followed by 20 sec Ec), four phybrata metrics were calculated from the time series data as previously described: Eo and Ec powers (in watts), (Eo+Ec)/2 average power, and Ec/Eo power ratio. Data analyses and plotting were carried out using the commercially licensed statistical analysis software packages NCSS (https://www.ncss.com/) and SigView (https://www.sigview.com/). Data analysis included descriptive statistics, analysis of variance (ANOVA, MANOVA), and receiver operating characteristic (ROC) curves for the 4 phybrata metrics and sub-populations of interest (female vs. male, Eo vs. Ec, no concussion vs. concussion, vestibular impairment vs. neurological impairment). Eo and Ec distributions generally failed 2 or more of 3 normality tests (Shapiro-Wilk, skewness, kurtosis) and were log transformed prior to ANOVA/MANOVA.

Means and 95% confidence intervals (CI) were calculated using the bootstrap method. PSD and TRPSD analyses of phybrata time series data were carried out for individual patients and for ensembles of patients sharing common characteristics (e.g., no concussion vs. concussion, vestibular impairment vs. neurological impairment). Additional benefits of the direct measurement of acceleration and the use of power-based and frequency-based metrics in the present study include greater sensitivity to differences in Eo vs. Ec performance and less sensitivity to sampling duration.

Figures 23A, 23B, 23C, 23D:
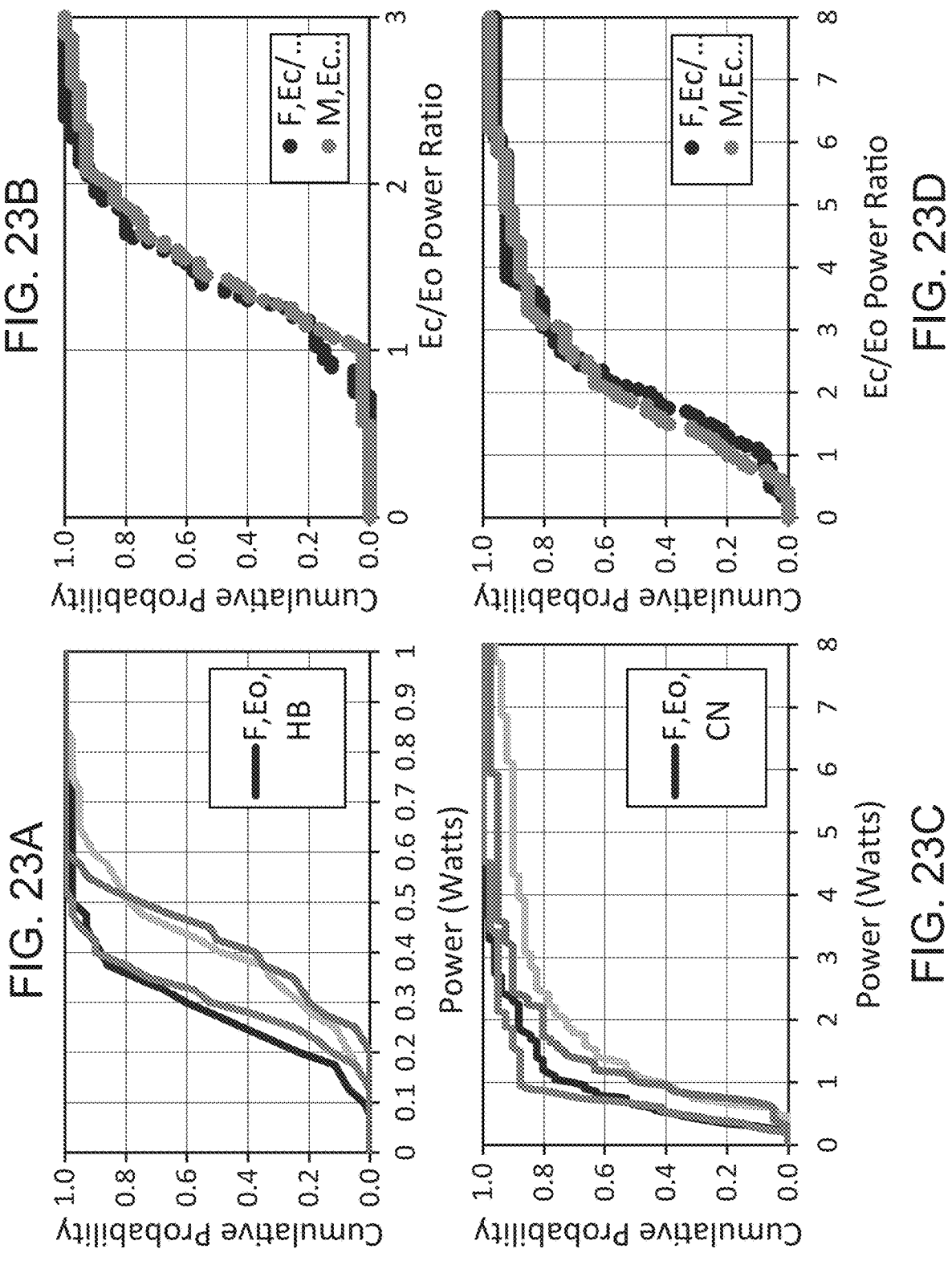
FIGS. 23A-23D are plots of cumulative probability distributions vs. gender and eye state for phybrata metrics for: 83 healthy baseline patients (HB) (FIGS. 23A-23B), and 92 patients with diagnosed concussions (CN) (FIGS. 23C-23D); F=female, M=male, Eo=eyes open, Ec=eyes closed.

FIGS. 23A-23D are plots of cumulative probability distributions vs. gender and eye state for phybrata metrics for 83 healthy baseline patients (HB) (FIGS. 23A-23B), and 92 patients with diagnosed concussions (CN) (FIGS. 23C-23D); F=female, M=male, Eo=eyes open, Ec=eyes closed. FIGS. 23A-23D present cumulative probability distributions (CPDs) for Eo, Ec, and Ec/Eo plotted as a function of gender for the 83 healthy baseline patients (HB) and the 92 patients with diagnosed concussions (CN). Means, 95% CIs, and ANOVA results for these two groups and all 4 phybrata metrics are summarized in Table 4 and Table 5.

TABLE 4

Mean, 95% and ANOVA results for various participants.

| Measure | Condition | Mean | 95% CI | F-ratio | P |
|---|---|---|---|---|---|
| Female: phybrata power | Eyes open | 0.288 | 0.248-0.322 | F (1, 84) = 19.45 | <0.0001 |
| | Eyes closed | 0.413 | 0.370-0.457 | | |
| Male: phybrata power | Eyes open | 0.303 | 0.278-0.328 | F (1, 78) = 28.05 | <0.0001 |
| | Eyes closed | 0.419 | 0.388-0.450 | | |
| Eo power | Female | 0.288 | 0.248-0.322 | F (1, 81) = 1.48 | 0.23 |
| | Male | 0.303 | 0.278-0.328 | | |
| Ec power | Female | 0.413 | 0.370-0.457 | F (1, 81) = 0.41 | 0.53 |
| | Male | 0.419 | 0.388-0.450 | | |
| (Eo + Ec)/2 | Female | 0.351 | 0.312-0.384 | F (1, 81) = 0.95 | 0.33 |
| | Male | 0.361 | 0.338-0.384 | | |
| Ec/Eo ratio | Female | 1.520 | 1.387-1.653 | F (1, 81) = 0.63 | 0.43 |
| | Male | 1.445 | 1.319-1.569 | | |

TABLE 5

Mean, 95% and ANOVA results for various participants.

| Measure | Condition | Mean | 95% CI | F-ratio | P |
|---|---|---|---|---|---|
| Female: phybrata power | Eyes open | 0.936 | 0.703-1.137 | F(1, 100) = 18.65 | <0.0001 |
| | Eyes closed | 2.587 | 0.986-3.609 | | |
| Male: phybrata power | Eyes open | 0.836 | 0.569-1.054 | F(1, 80) = 17.42 | <0.0001 |
| | Eyes closed | 1.600 | 0.945-2.054 | | |
| Eo power | Female | 0.936 | 0.703-1.137 | F(1, 90) = 0.34 | 0.56 |
| | Male | 0.836 | 0.569-1.054 | | |
| Ec power | Female | 2.587 | 0.986-3.609 | F(1, 90) = 1.03 | 0.31 |
| | Male | 1.600 | 0.945-2.054 | | |
| (Eo + Ec)/2 | Female | 1.758 | 0.951-2.350 | F(1, 90) = 0.86 | 0.36 |
| | Male | 1.212 | 0.834-1.528 | | |
| Ec/Eo ratio | Female | 2.516 | 1.916-3.007 | F(1, 90) = 0.38 | 0.54 |
| | Male | 2.286 | 1.801-2.775 | | |

The increase in Ec vs Eo for the healthy population (FIG. 23A) is statistically significant for both females: F(1,84)=19.45, p=0.00003 and males: F(1,78)=28.05, p<0.00001, while the Ec/Eo ratio (FIG. 23B3) does not differ significantly as a function of gender: F(1,81)=0.63, p=0.413. However, the present data does not show a statistically significant difference between females and males for either Eo: F(1,81)=1.48, p=0.23 or Ec: F(1,81)=0.41, p=0.53. This is attributed to any gender difference being masked by larger variations resulting from the significantly wider age range of patients in the present study. Although the CPDs span much wider ranges for the patients with diagnosed concussions, the above trends are maintained in the concussed population: the increase in Ec vs Eo (FIG. 23C) is statistically significant for both females: F(1,100)=18.65, p=0.00004, and males: F(1,80)=17.42, p=0.00008; the Ec/Eo ratio (FIG. 23D) shows no significant difference as a function of gender: F(1,90)=0.38, p=0.54; and no statistically significant difference is observed between females and males for either Eo: F(1,90)=0.34, p=0.56 or Ec: F(1,90)=1.03, p=0.31.

Figure 24:
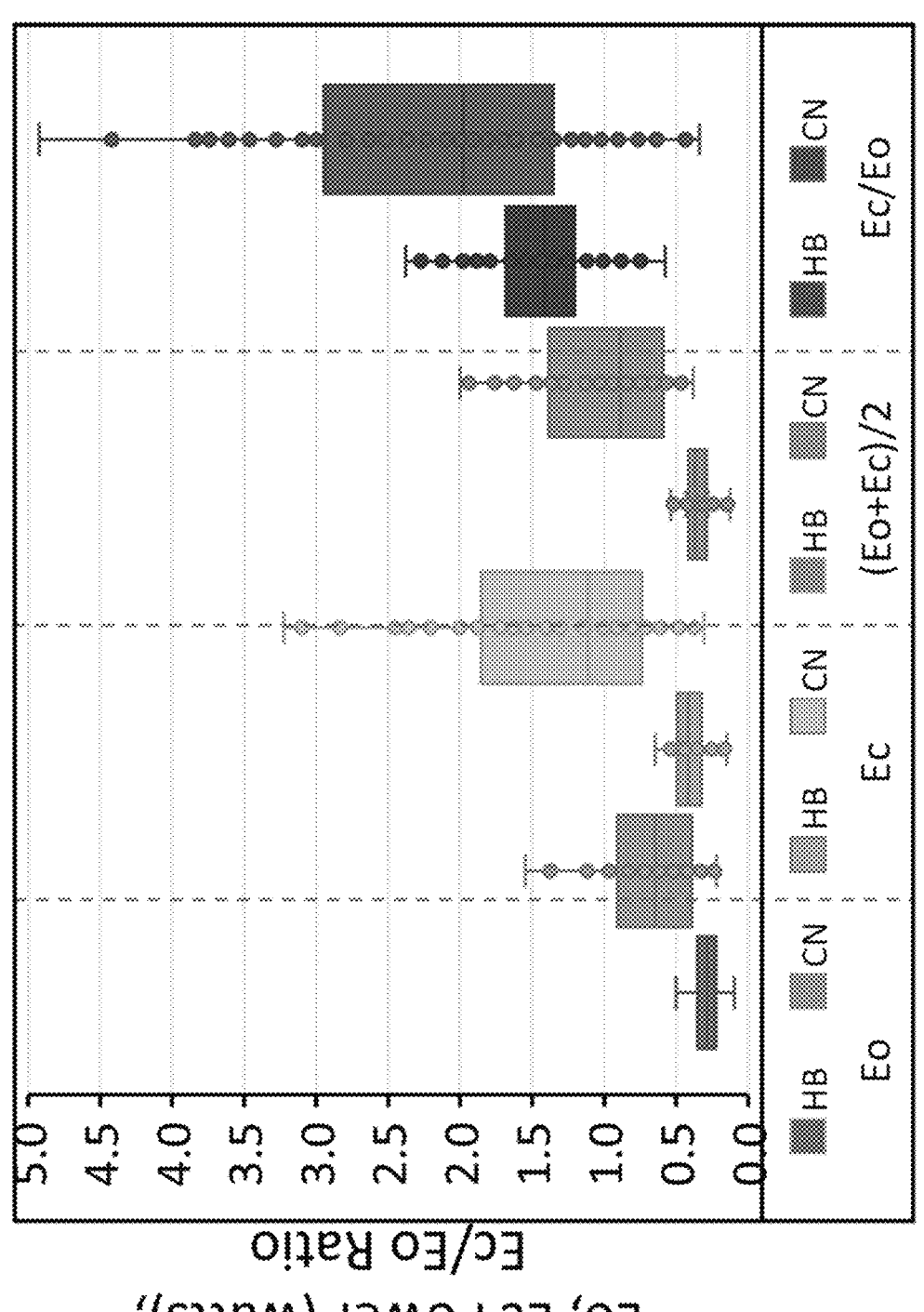
FIG. 24 are box plots showing distributions of 4 phybrata metrics for 83 healthy baseline patients (HB) and 92 patients with diagnosed concussions (CN); Eo=eyes open, Ec=eyes closed.

FIG. 24 are box plots showing distributions of 4 phybrata metrics for 83 healthy baseline patients (HB) and 92 patients with diagnosed concussions (CN); Eo=eyes open, Ec=eyes closed. All 4 phybrata metrics show significant statistical correlations (p<0.0001) with the diagnosis of concussion.

The average power metric (Eo+Ec)/2 shows the strongest correlation: $F(1,171)=164.4$, $p<0.00001$, and may serve as a rapid, simple, and clinically intuitive phybrata-based metric or biomarker to support concussion diagnoses.

Figure 25:
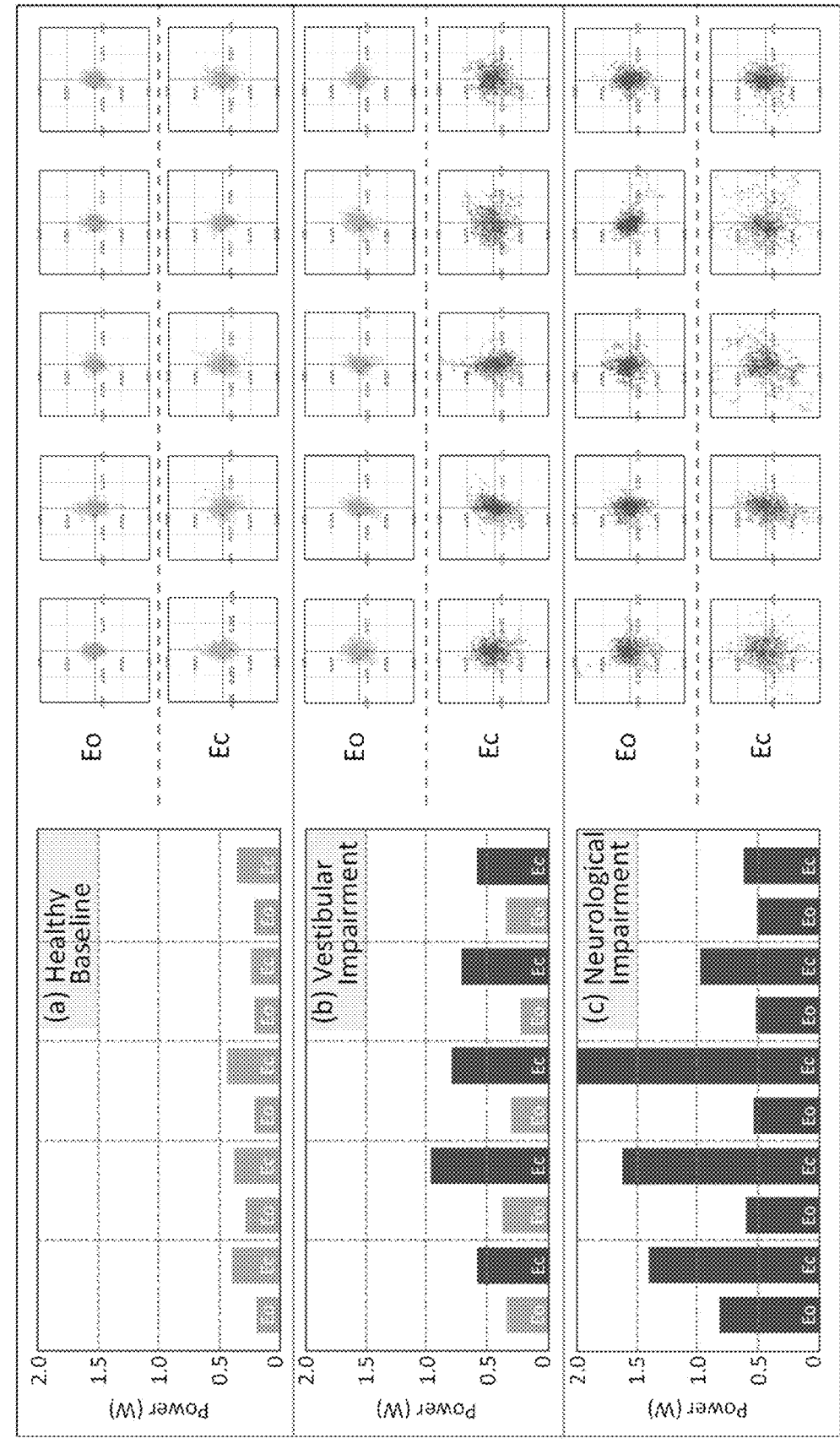
FIG. 25 are bar charts and scatter plots of eyes open (Eo) and eyes closed (Ec) phybrata power histograms (left) and anterior-posterior/medial-lateral (AP/ML) acceleration spatial scatter plots (right) for baseline testing of 5 healthy athletes (FIG. 25, panel (a)), post-concussion testing of 5 athletes with vestibular impairments (FIG. 25, panel (b)), and post-concussion testing of 5 athletes with neurological impairments (FIG. 25, panel (c)).

FIG. 25 illustrates sample Eo and Ec phybrata power histograms and AP/ML acceleration spatial scatter plots for 15 athletes (ages 17-23): 5 healthy athletes during baseline testing (FIG. 25, panel (a)); 5 following a concussion with only vestibular impairments observed during physical examination (FIG. 25, panel (b)); and 5 following a concussion with other neurological impairments observed during physical examination (FIG. 25, panel (c)).

Patients with vestibular impairment only consistently showed Eo phybrata powers that remained below the 95% confidence interval for healthy subjects, but Ec phybrata powers elevated above the 95% confidence interval for healthy subjects (FIG. 25, panel (b)). Patients diagnosed with neurological impairment, on the other hand, typically showed both Eo and Ec phybrata powers significantly elevated above the respective 95% confidence intervals for healthy subjects (FIG. 25, panel (c)). This observation is consistent with vestibular impairments presenting more severely in the absence of visual input, while neurological impairments lead to less efficient integration and/or processing of multiple sensory inputs and degraded postural stabilization regardless of which combination of sensory inputs are available.

Figure 26:
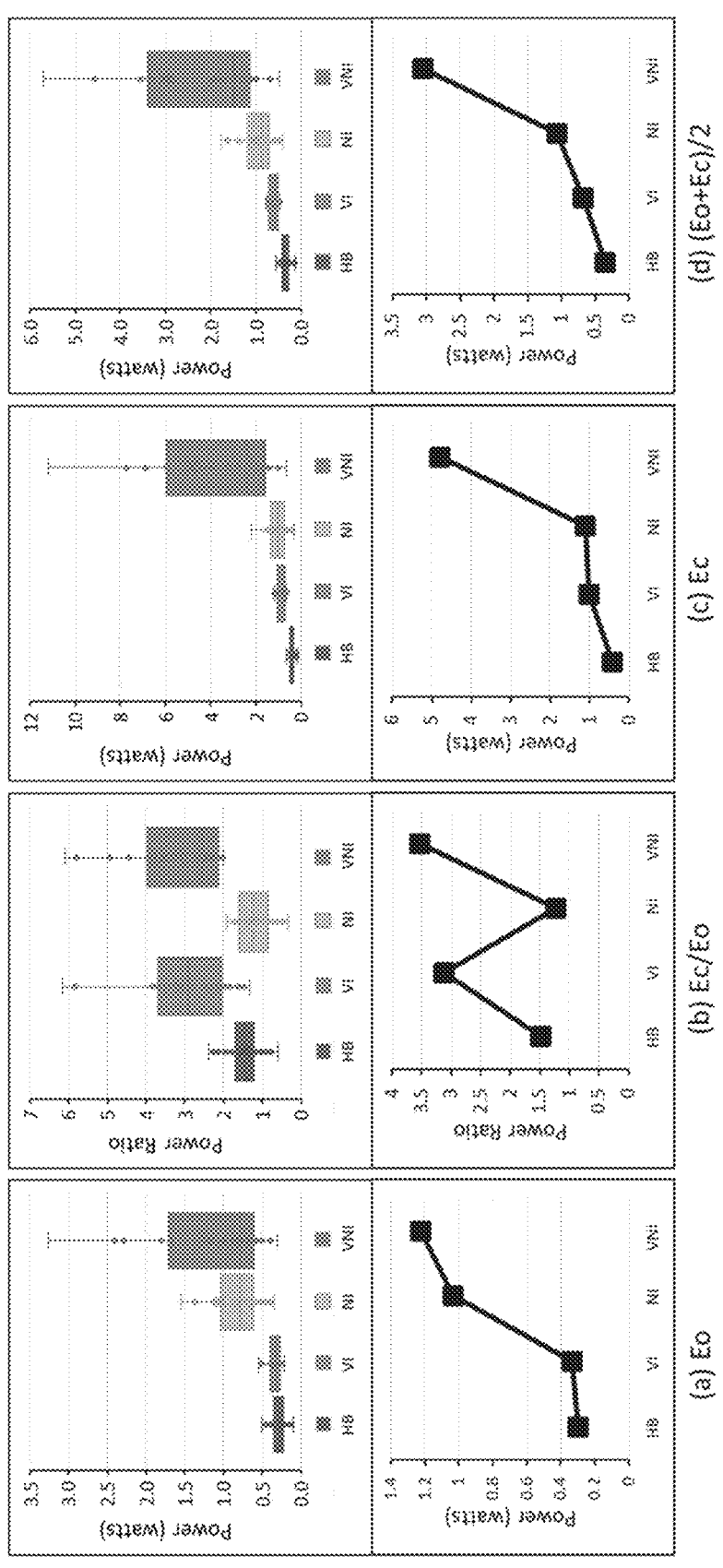
FIG. 26 are box plots and graphs comparing means of 4 phybrata metrics including Eo (FIG. 26, panel (a)), Ec/Eo (FIG. 26, panel (b)), Ec (FIG. 26, panel (c)), and (Eo+Ec)/2 (FIG. 26, panel (d)) for 83 healthy baseline patients (HB); 26 concussion patients with vestibular impairments (VI) only; 40 concussion patients with neurological impairments (NI) only; 26 concussion patients with both vestibular and neurological impairments (VNI); Eo=eyes open, Ec=eyes closed.

FIG. 26 are box plots and graphs comparing means of 4 phybrata metrics including Eo (FIG. 26, panel (a)), Ec/Eo (FIG. 26, panel (b)), Ec (FIG. 26, panel (c)), and (Eo+Ec)/2 (FIG. 26, panel (d)) for 83 healthy baseline patients (HB); 26 concussion patients with vestibular impairments (VI) only; 40 concussion patients with neurological impairments (NI) only; 26 concussion patients with both vestibular and neurological impairments (VNI); Eo=eyes open, Ec=eyes closed. Ec/Eo shows both the strongest correlation with vestibular impairment: $F(1,167)=162.9$, $p<0.00001$, and no statistically significant correlation with neurological impairment: $F(1,167)=1.13$, $p=0.29$. Conversely, Eo shows both the strongest correlation with neurological impairment: $F(1, 167)=191.2$, $p<0.00001$, and no statistically significant correlation with vestibular impairment: $F(1,167)=1.60$, $p=0.21$. This behavior is strikingly evident in the variations of the means of Eo (FIG. 26, panel (a)) and Ec/Eo (FIG. 26, panel (b)) for the 4 sub-populations, and indicates that Eo and Ec/Eo may be utilized as independent measures to support classification of neurological and vestibular impairments, respectively, in patients with diagnosed concussions. The two remaining phybrata metrics, Ec (FIG. 26, panel (c)) and (Eo+Ec)/2 (FIG. 26, panel (d)) show significant correlations to both neurological and vestibular impairments, and thus do not have the same utility as independent measures for impairment classification.

Figure 27:
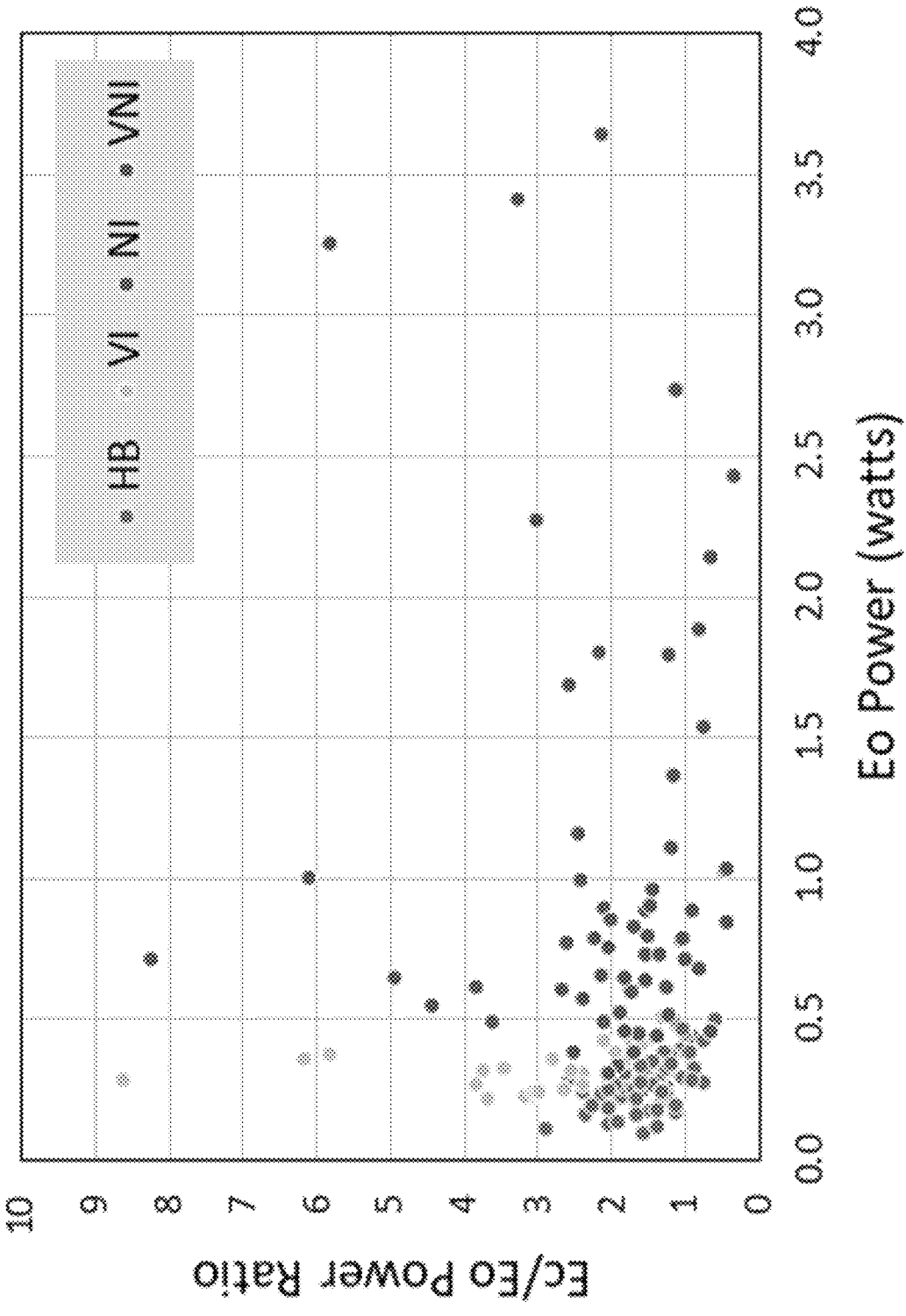
FIG. 27 are scatter plots of Ec/Eo power ratio vs. Eo power for healthy baseline patients (HB) and concussion patients with vestibular impairments (VI), neurological impairments (NI), and both vestibular and neurological impairments (VNI); Eo=eyes open, Ec=eyes closed.

FIG. 27 are scatter plots of Ec/Eo power ratio vs. Eo power for healthy baseline patients (HB) and concussion patients with vestibular impairments (VI), neurological impairments (NI), and both vestibular and neurological impairments (VNI); Eo=eyes open, Ec=eyes closed. The scatter plots of Ec/Eo power ratio vs. Eo power are for all 175 study participants, revealing well-defined data clusters for each of the four subpopulations: HB, VI, NI, and VNI. These results further highlight the ability of a simple and clinically intuitive metrics/biomarkers derived from phybrata test data to distinguish between patients with/without concussion ((Eo+Ec)/2), and to further independently classify accompanying neurological impairments (Eo) and vestibular impairments (Ec/Eo). FIG. 27 also reveals that the data for VNI is split into two sub-clusters in close proximity to the VI-only and NI-only clusters, which may indicate the presence of "predominantly vestibular" vs. "predominantly other neurological" impairments in these patients.

Figure 28:
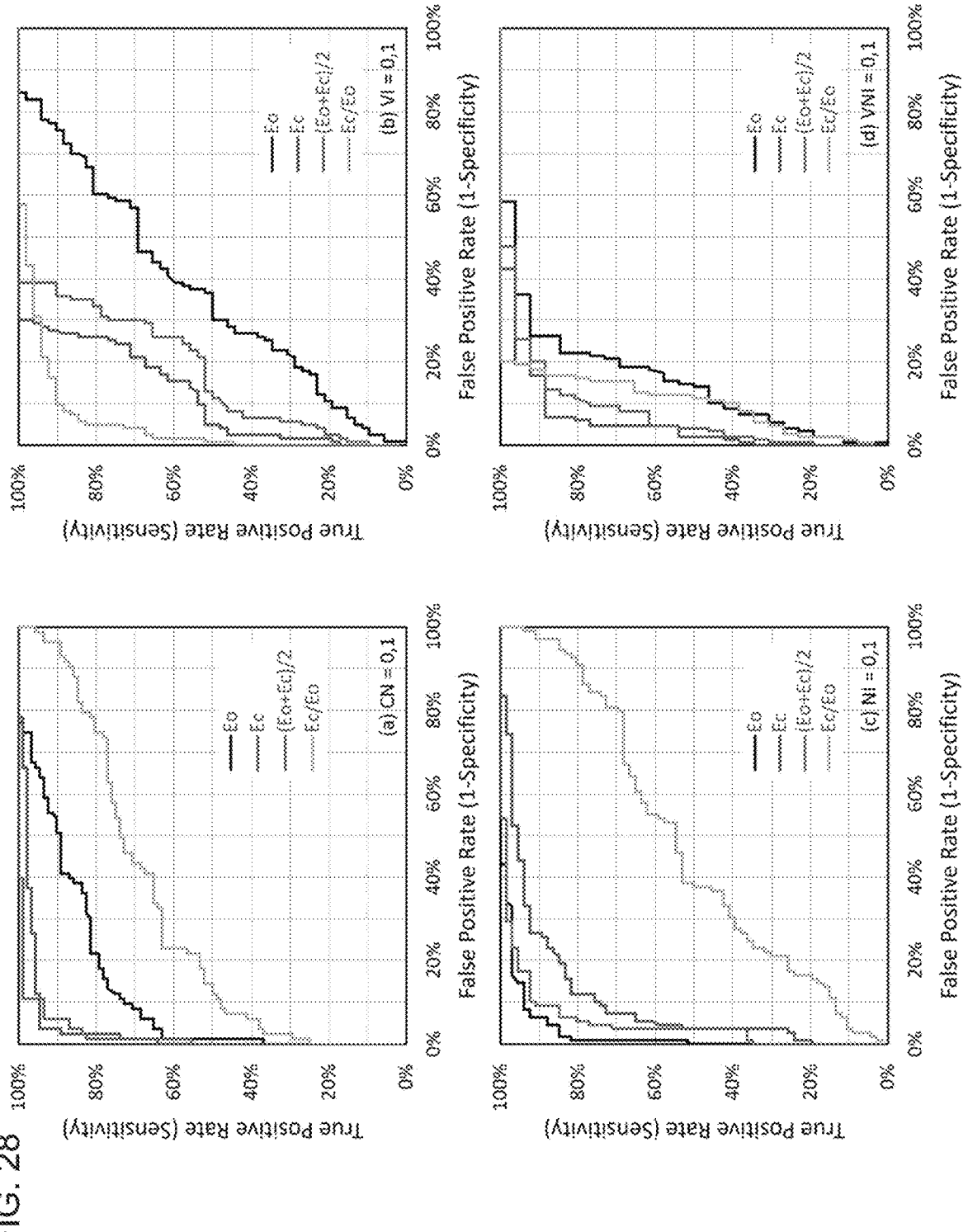
FIG. 28 are plots showing receiver operating characteristic (ROC) curves for 4 clinical diagnostic criteria.

FIG. 28 are plots showing receiver operating characteristic (ROC) curves for 4 clinical diagnostic criteria: (FIG. 28, panel (a)) concussion (CN=0, 1); (FIG. 28, panel (b)) vestibular impairment (VI=0, 1); (FIG. 28, panel (c)) neurological impairment (NI=0, 1); and (FIG. 28, panel (d)) both vestibular and neurological impairments (VNI), for all possible cutoff values of the 4 phybrata metrics Eo, Ec, (Eo+Ec)/2, Ec/Eo; Eo=eyes open, Ec=eyes closed.

As a metric for clinical diagnosis of concussion (FIG. 28, panel (a)), (Eo+Ec)/2 achieves area under the curve (AUC)= 0.981 (95% CI=0.956-0.992), and for a cutoff value of (Eo+Ec)/2=0.49 watts, the corresponding sensitivity and specificity are 0.935 and 0.940, respectively. As a metric for clinical confirmation of the presence of vestibular impairment in patients with diagnosed concussions (FIG. 28, panel (b)), Ec/Eo achieves AUC=0.951 (95% CI=0.904-0.976), and for a cutoff value of Ec/Eo=1.95, the corresponding sensitivity and specificity are 0.904 and 0.902, respectively. As a metric for clinical confirmation of the presence of other neurological impairment in patients with diagnosed concussions (FIG. 28, panel (c)), Eo achieves AUC=0.975 (95% CI=0.944-0.989), and for a cutoff value of Eo=0.45 watts, the corresponding sensitivity and specificity are 0.924 and 0.936, respectively. FIG. 28, panel (d) indicates that none of the 4 phybrata metrics independently classify the presence of both vestibular and neurological impairments.

The above cutoff values for Eo (0.45 watts), (Eo+Ec)/2 (0.49 watts), and Ec/Eo (1.95) agree well with the corresponding 95% CPD values in FIGS. 23A-D, and the box plot distributions in FIG. 24, highlight the utility of these simple and physiologically intuitive phybrata metrics for rapid diagnostic testing. The ROC results further illustrate the utility of the phybrata metrics Eo and Ec/Eo as independent measures: Eo achieves AUC of only 0.63 as a metric to confirm the presence of vestibular impairment (FIG. 28, panel (b)), while Ec/Eo achieves AUC of only 0.52 as a metric to confirm the presence of neurological impairment (FIG. 28, panel (c)). As discussed further below, these ROC results compare favorably with more complex, time consuming, and expensive approaches that combine data from various balance, eye tracking, neurocognitive, and other tests to generate multimodal concussion biomarkers.

To investigate sensory reweighting, FIGS. 29-32 represent normalized ensemble TRPSD plots and spectrograms for the same 15 patients and 3 sub-populations for whom data is presented in FIG. 25.

Figure 29:
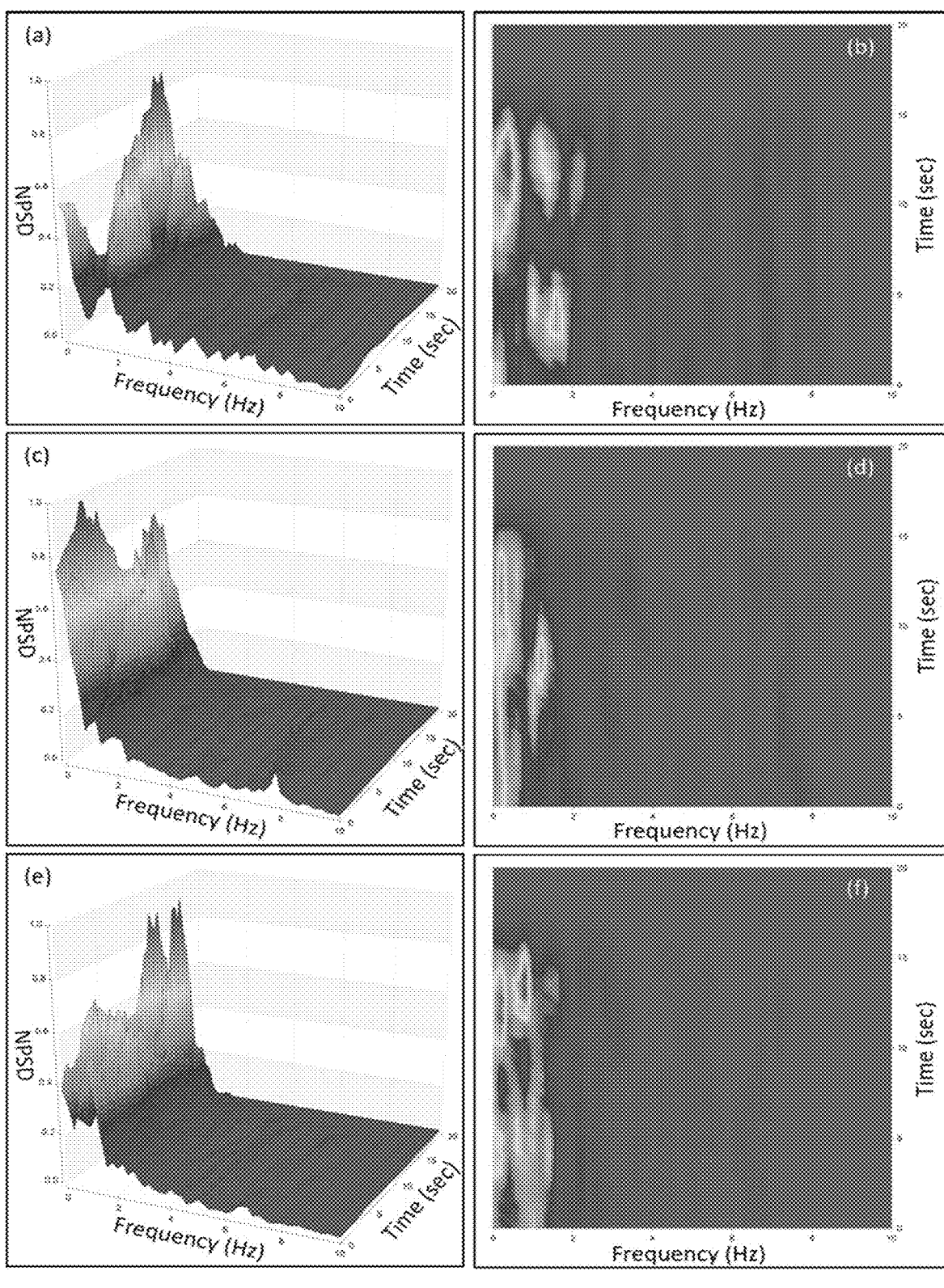
FIG. 29 are normalized ensemble eyes-open (Eo) anterior-posterior (AP) time-resolved phybrata power spectral density (NPSD) plots (left) and spectrograms (right) for baseline testing of 5 healthy patients (FIG. 29, panels (a) and (b)), post-concussion testing of 5 patients with vestibular impairment (FIG. 29, panels (c) and (d)), and post-concussion testing of 5 patients with neurological impairment (FIG. 29, panels (e) and (f)).
Figure 30:
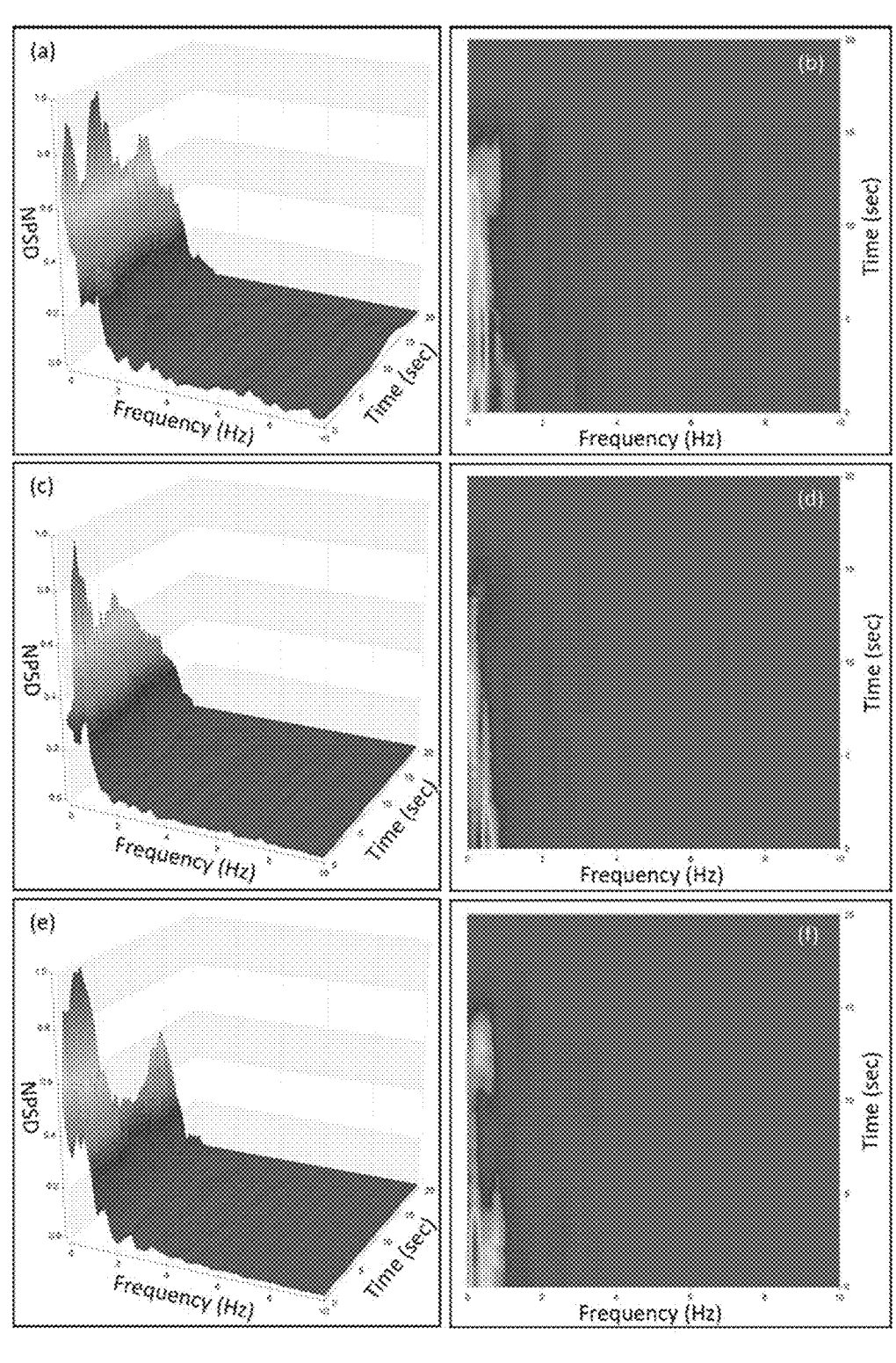
FIG. 30 are normalized ensemble eyes-closed (Ec) anterior-posterior (AP) time-resolved phybrata power spectral density (NPSD) plots (left) and spectrograms (right) for baseline testing of 5 healthy patients (FIG. 30, panels (a) and (b)), post-concussion testing of 5 patients with vestibular impairment (FIG. 30, panels (c) and (d)), and post-concussion testing of 5 patients with neurological impairment (FIG. 30, panels (e) and (f)).
Figure 31:
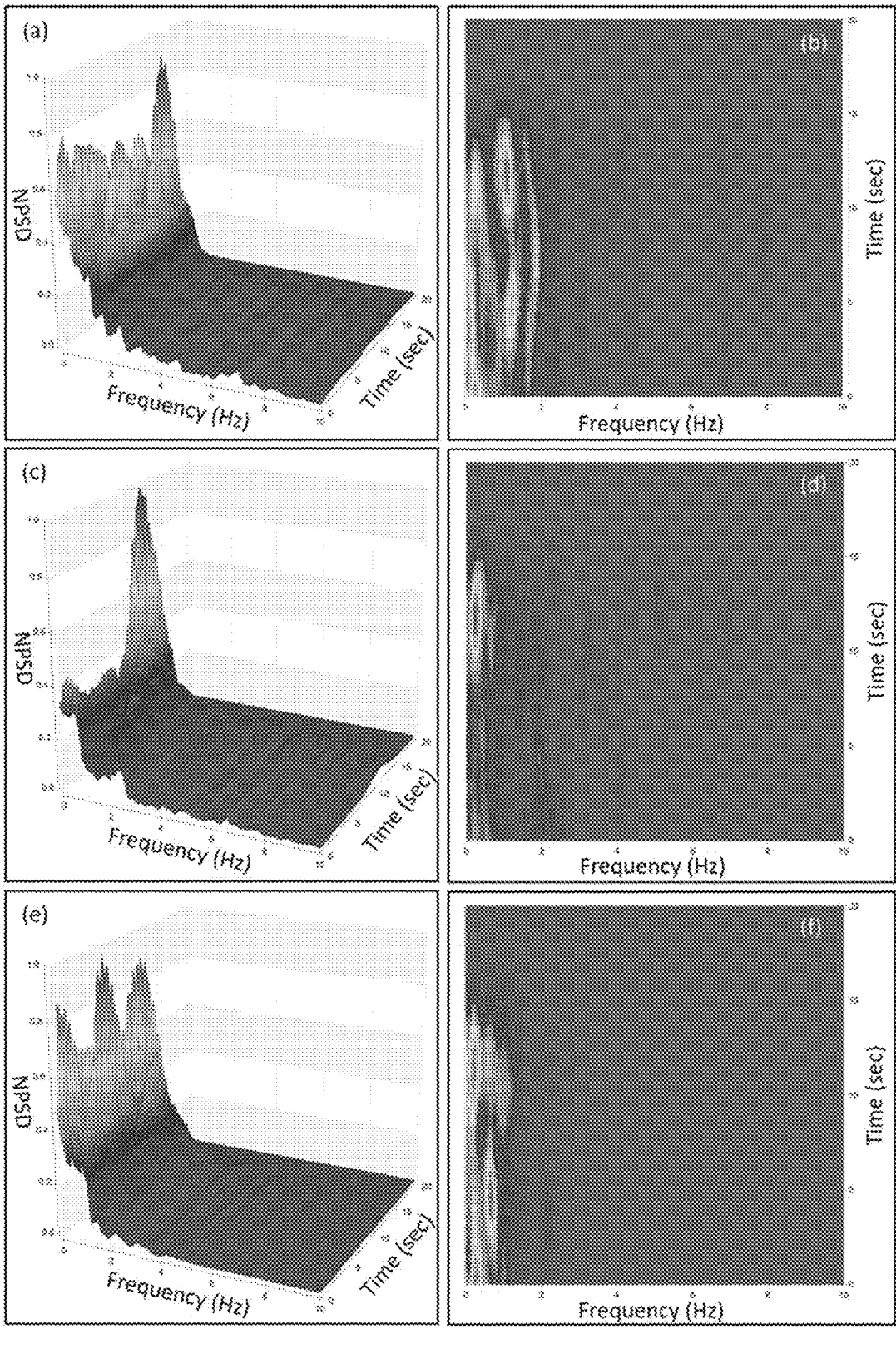
FIG. 31 are normalized ensemble eyes-open (Eo) medial-lateral (ML) time-resolved phybrata power spectral density (NPSD) plots (left) and spectrograms (right) for baseline testing of 5 healthy patients (FIG. 31, panels (a) and (b)), post-concussion testing of 5 patients with vestibular impairment (FIG. 31, panels (c) and (d)), and post-concussion testing of 5 patients with neurological impairment (FIG. 31, panels (e) and (f)).
Figure 32:
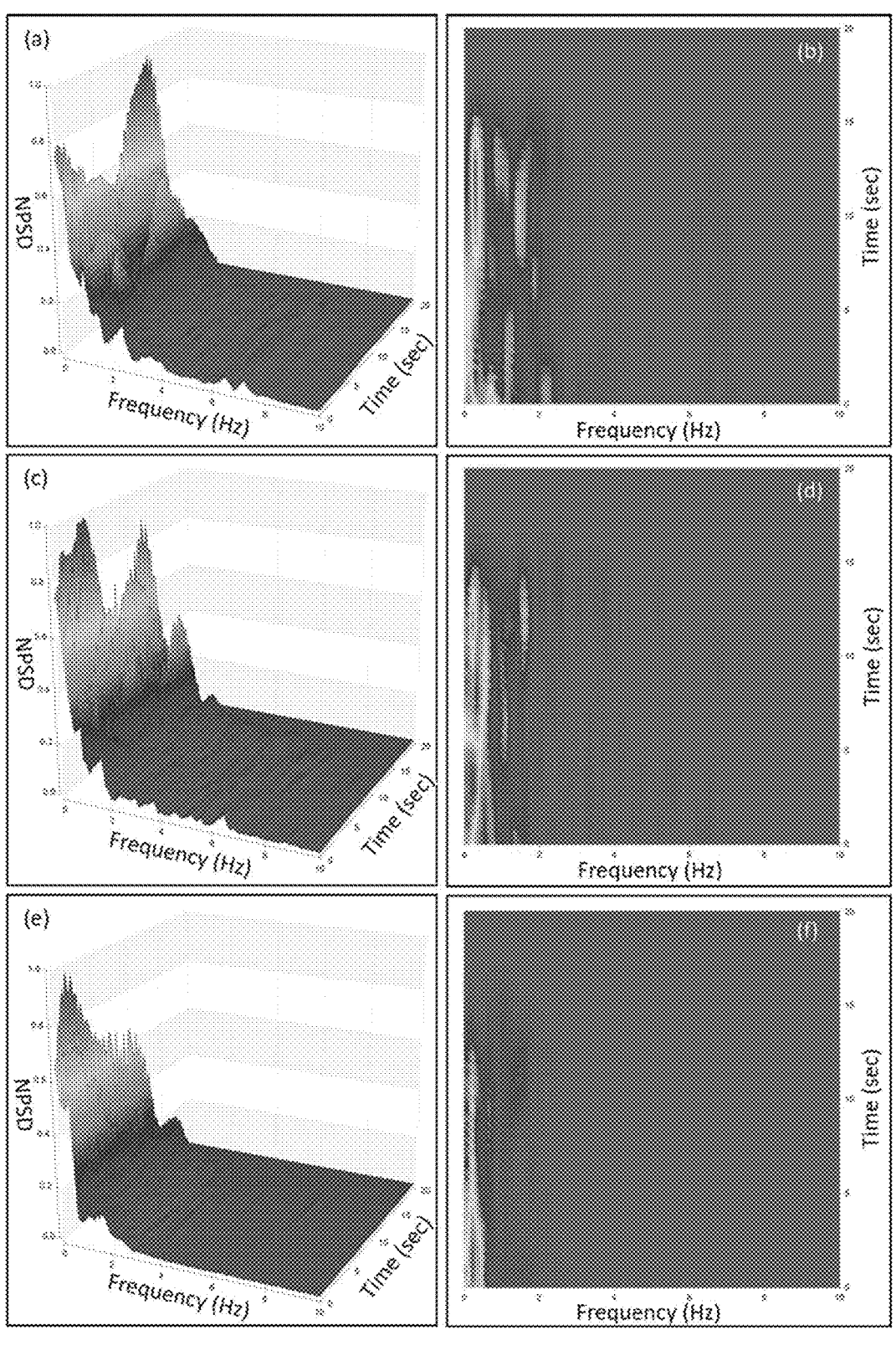
FIG. 32 are normalized ensemble eyes-closed (Ec) medial lateral (ML) time-resolved phybrata power spectral density (NPSD) plots (left) and spectrograms (right) for baseline testing of 5 healthy patients (FIG. 32, panels (a) and (b)), post-concussion testing of 5 patients with vestibular impairment (FIG. 32, panels (c) and (d)), and post-concussion testing of 5 patients with neurological impairment (FIG. 32, panels (e) and (f)).

FIG. 29 presents Eo/AP results, and includes normalized ensemble TRPSD plots (left) for 5 healthy baseline patients (FIG. 29, panel (a)), post-concussion testing of 5 patients with vestibular impairment (FIG. 29, panel (c)), and post-concussion testing of 5 patients with neurological impairment (FIG. 29, panel (e)), along with spectrograms (right) for the same 3 sub-populations (FIG. 29, panels (b), (d), and (f), respectively). FIG. 30 presents Ec/AP results, and includes normalized ensemble TRPSD plots (left) for 5 healthy baseline patients (FIG. 30, panel (a)), post-concussion testing of 5 patients with vestibular impairment (FIG. 30, panel (c)), and post-concussion testing of 5 patients with neurological impairment (FIG. 30, panel (e)), along with spectrograms (right) for the same 3 sub-populations (FIG. 30, panels (b), (d), and (f), respectively). FIG. 31 presents Eo/ML results, and includes normalized ensemble TRPSD plots (left) for 5 healthy baseline patients (FIG. 31, panel (a)), post-concussion testing of 5 patients with vestibular impairment (FIG. 31, panel (b)), and post-concussion testing of 5 patients with neurological impairment (FIG. 31, panel (e)), along with spectrograms (right) for the same 3 sub-populations (FIG. 31, panels (b), (d), and (f), respectively). FIG. 32 presents Ec/IL results, and includes normalized ensemble TRPSD plots (left) for 5 healthy baseline patients (FIG. 32, panel (a)), post-concussion testing of 5 patients with vestibular impairment (FIG. 32, panel (c)), and post-concussion testing of 5 patients with neurological impairment (FIG. 32, panel (e)), along with spectrograms (right) for the same 3 sub-populations (FIG. 32, panels (b), (d), and (f), respectively).

For all 3 sub-populations, a wider range of frequency content is observed for AP motion than for ML motion, consistent with previous studies of healthy young populations, and this relationship is preserved following both vestibular and neurological impairments. For both AP and ML motion and all 3 sub-populations, overall Ec powers are higher than Eo powers, but the normalized high-frequency Ec spectral content is reduced compared to Eo. This relative shift to higher overall postural sway power with lower frequency content is attributed to a shift to a more conservative postural control strategy in the absence of visual input: higher frequency motion resulting from passive, open-loop, continuous, and more complex muscle and joint motion strategies is reduced while lower frequency motion resulting from active, closed-loop, intermittent, and lower complexity activation of musculoskeletal structures increases.

This same overall behavior is observed even more dramatically in FIGS. 29-32 in the sequential differences in both AP and ML TRPSD results proceeding from no impairment to vestibular impairment to neurological impairment, consistent with results using alternative measurement tools to assess physiological impairments following concussion.

Figure 33:
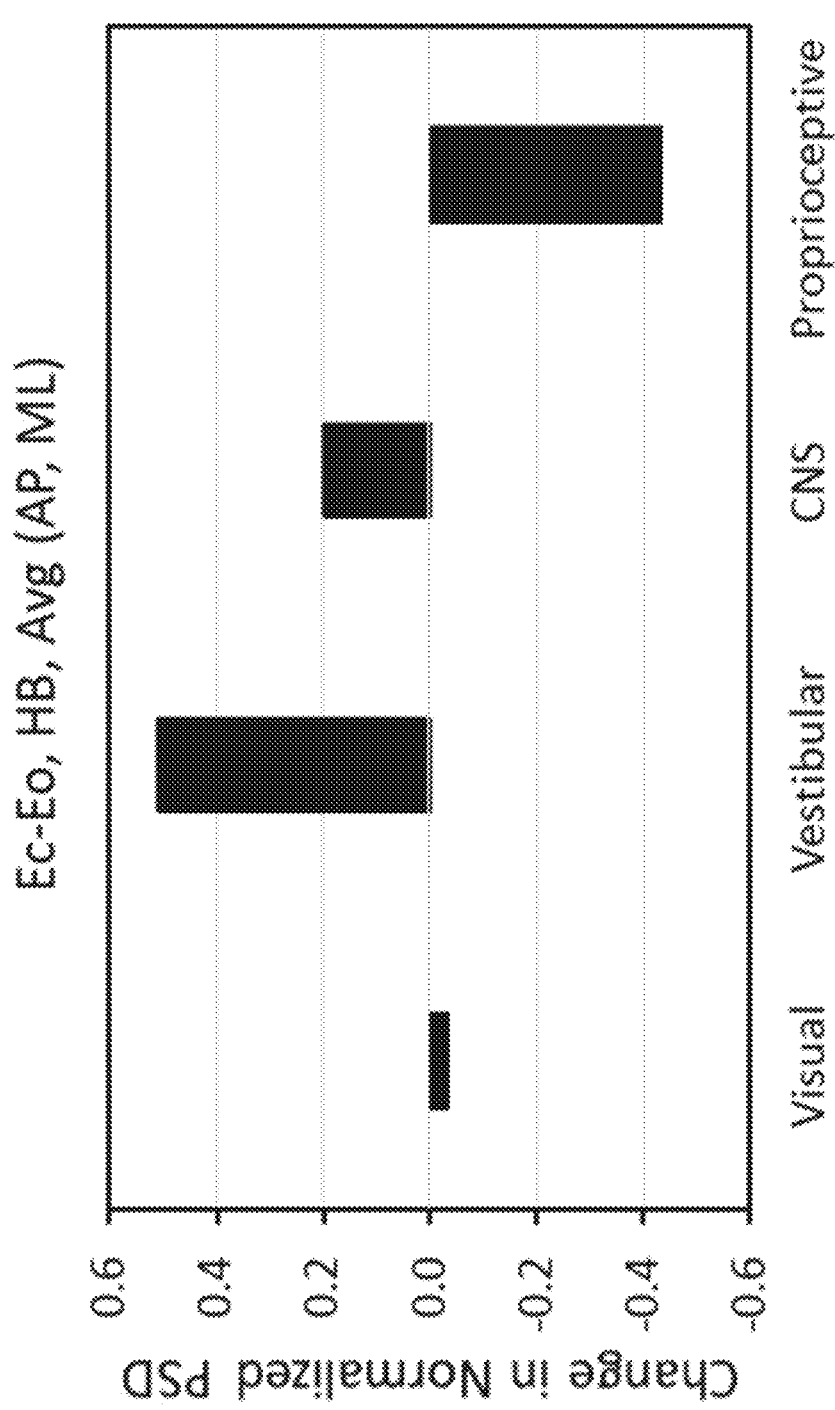
FIG. 33 is a bar chart of changes in normalized ensemble power spectral density (PSD) between eyes-open (Eo) and eyes-closed (Ec) for 5 healthy baseline patients (HB). Ensemble average {AP,ML} PSD changes are summed over phybrata frequency bands corresponding to visual, vestibular, central nervous system (CNS), and proprioceptive control; AP=anterior-posterior, ML=medial-lateral.

Sensory reweighting as a function of specific mechanisms of postural control was investigated by calculating relative changes within 4 frequency bands in the above normalized TRPSD spectra: 1-10 Hz (spinal reflexive loops, proprioception, multi-joint and muscle activity); 0.5-1 Hz (CNS participation, both cerebellar and cortical); 0.1-0.5 Hz (vestibular regulation); 0.02-0.1 Hz (visual regulation). FIG. 33 is a bar chart of changes in normalized ensemble power spectral density (PSD) between eyes-open (Eo) and eyes-closed (Ec) for 5 healthy baseline patients (HB). Ensemble average {AP,ML} PSD changes are summed over phybrata frequency bands corresponding to visual, vestibular, central nervous system (CNS), and proprioceptive control; AP=anterior-posterior, ML=medial-lateral. FIG. 33 plots the change in normalized PSD between Eo and Ec calculated by integrating over time and frequency in each of the 4 frequency bands for the 5 individuals with no diagnosed impairment. For each frequency band, the PSD changes for AP and ML ensembles are averaged.

As in FIGS. 29-32, overall Ec powers are higher than Eo powers, but FIG. 33 reveals the changes in relative redistribution of the normalized power between the 4 spectral bands for Ec vs. Eo. Removing the visual input leads to a small decrease in normalized power in the lowest frequency band, corresponding to the loss of visual regulation, and a large relative decrease in proprioceptive activity (highest frequency band) that is offset by a large relative increase in the vestibular band and a smaller relative increase in the CNS band. This observation is consistent with sensory reweighting to a more conservative postural control strategy in the absence of visual input.

Figure 34:
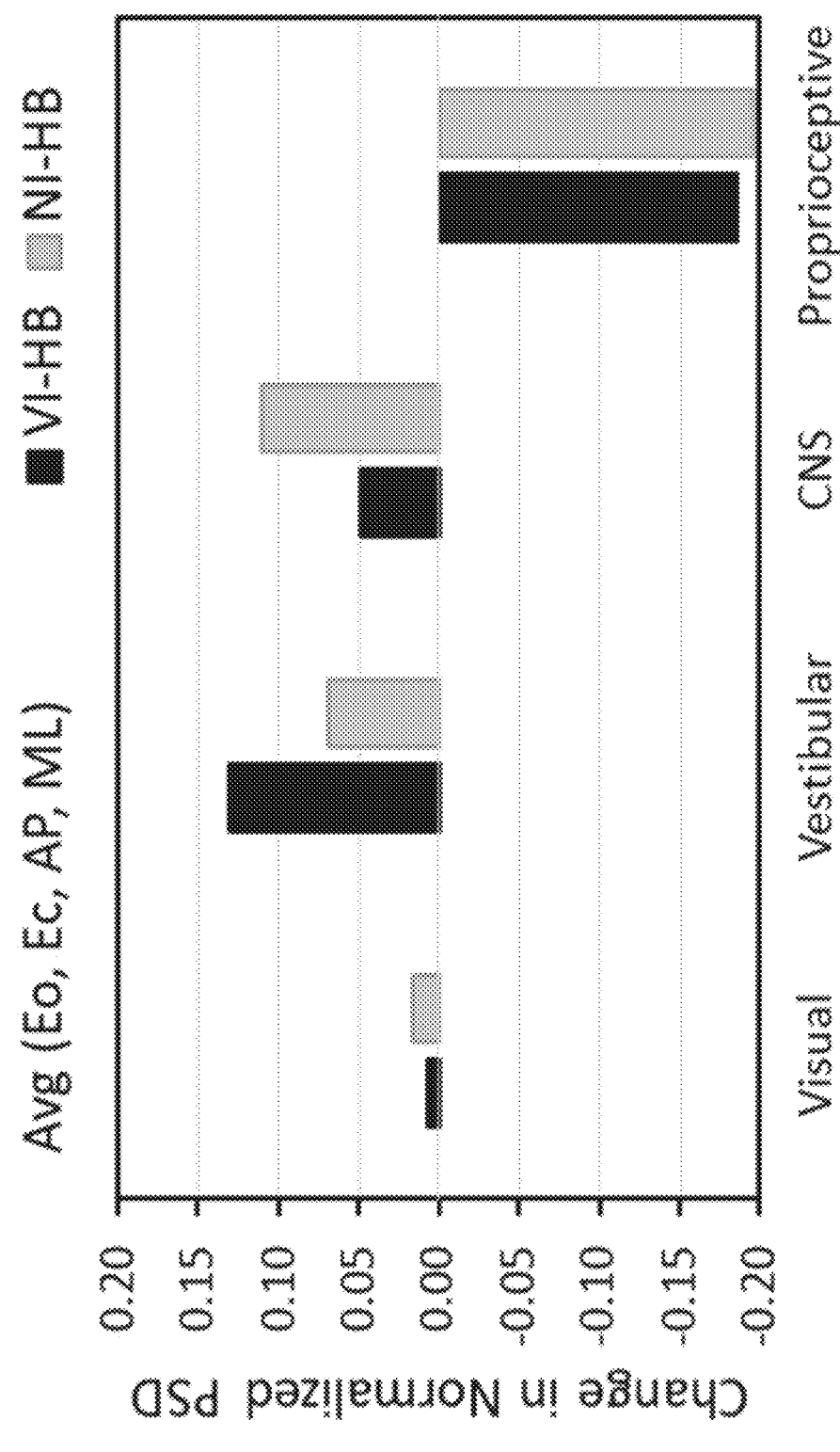
FIG. 34 is a bar chart of changes in normalized ensemble power spectral density (PSD) between 5 healthy baseline patients (HB) and (i) 5 concussion patients with vestibular impairment (VI); and (ii) 5 concussion patients with neurological impairment (NI). For each group, ensemble average {Eo, Ec, AP, ML} PSD changes are summed over phybrata frequency bands corresponding to visual, vestibular, central nervous system (CNS), and proprioceptive control; Eo=eyes open, Ec=eyes closed, AP=anterior-posterior, ML=medial-lateral.

FIG. 34 is a bar chart of changes in normalized ensemble power spectral density (PSD) between 5 healthy baseline patients (HB) and (i) 5 concussion patients with vestibular impairment (VI); and (ii) 5 concussion patients with neurological impairment (NI). For each group, ensemble average {Eo, Ec, AP, ML} PSD changes are summed over phybrata frequency bands corresponding to visual, vestibular, central nervous system (CNS), and proprioceptive control; Eo=eyes open, Ec=eyes closed, AP=anterior-posterior, ML=medial-lateral.

FIG. 34 plots the changes in normalized PSD, over the same 4 frequency bands, between the 5 individuals with no diagnosed impairment (HB) and (i) those with diagnosed vestibular impairment only (VI), (ii) those with diagnosed neurological impairment only (NI). For each frequency band, the normalized PSD changes for Eo/AP, Ec/AP, Eo/ML, and Ec/ML ensembles are averaged. Both vestibular and neurological impairments lead to a large relative decrease in higher frequency proprioceptive activity that is offset primarily by relative increases in both the vestibular and CNS bands. However, vestibular impairment is accompanied by a larger increase in normalized PSD in the vestibular band, while neurological impairment is accompanied by a larger increase in normalized PSD in the CNS band. This observation is consistent with lower efficiencies and higher overall energy dissipations in the postural stabilization contributions from individual physiological systems suffering from impairments.

The results presented above demonstrate the ability of data from a phybrata sensing assembly worn on the mastoid to confirm clinical diagnosis of concussion, provide independent measures that confirm the presence of accompanying neurological and vestibular impairments, and quantify the progression of multi-system physiological impairments and sensory reweighting following concussion.

ROC results have been reported for a variety of concussion diagnostics tools and biomarkers, including symptoms inventories, neurocognitive testing, analyses of head impact kinematics, postural stability assessments, gait analysis, eye movement tracking, vestibular and oculomotor screening, visually evoked potentials, electrovestibulography, robotic assessment of neuromotor performance, blood-based biomarkers, salivary biomarkers, EEG, and MRI assessments of alterations in cerebral blood flow. However, many components of traditional neurocognitive testing have been shown to have limited predictive value, and the use of reduced variable subsets (including balance and eye tracking) has recently been recommended.

Results matching the ROC diagnostic performance of the present phybrata approach have generally required multivariate composite models that combine data from various balance, eye tracking, neurocognitive, and other tests to generate more complex multimodal concussion biomarker. It is expected that the above ROC diagnostic performance of the phybrata sensor may be further enhanced by segmenting patients according to age. CDP-based studies of the age-dependent maturation of sensory systems have revealed that generalized postural stability increases with age but does not reach adult levels until the age of 16 years or later. Somatosensory function has been found to develop earliest, becoming comparable with adult levels by the age of 3-4 years, followed by visual function, which reaches adult levels by the age of 15. The vestibular function requires the longest development period and may not reach adult levels until the age of 16 or older. ANOVA results using 16 years of age as a cutoff to divide the 83 HB individuals in the current study into two groups (40 individuals aged 8-15 years and 43 individuals aged 16-74 years) yielded a statistically significant difference between (Eo+Ec)/2 for the two age groups at the p<0.05 level: $F_{(1,81)}=3.97$, $p=0.0498$. Further age-based segmentation can be incorporated to take account of the degraded postural stability observed in healthy older populations.

ROC results providing independent classification of neurological and vestibular impairments from a single test using a non-invasive wearable sensing assembly are not possible with conventional techniques. The distinction between vestibular organ and brain injury is vital since the appropriate course of treatment and rehabilitation will typically be quite different. However, many concussion patients are still managed uniformly, despite the nature of their injuries, in the hopes that the pertinent physiological impairments will be addressed. Treatment efficiency and patient outcomes can be significantly improved using a tool such as phybrata testing to identify, quantify, and track changes in impairments to specific physiological impairments.

The terms "vestibular impairment" and "neurological impairment" remain broad and include a wide range of potential underlying pathologies. Sensing assemblies described herein include the application of phybrata assessments to provide more detailed classification and tracking of concussion-induced impairments to the CNS (e.g. cortical vs. cerebellar), PNS (e.g. somatic vs. autonomic), vestibular system (e.g. peripheral vs. central, and musculoskeletal system (e.g. impairments to specific muscles and joints), as well as utilizing these additional details as biomarkers to identify different concussion phenotypes and to develop quantitative clinical endpoints to support return-to-activity decisions. In these applications, phybrata data collected from clinical cohorts with a variety of neurogenerative medical conditions and corresponding spatial, time-domain, and frequency-domain features and patterns is used to develop biomarkers with sufficient sensitivity and specificity to diagnose specific medical conditions in addition to their underlying physiological impairments, as well as to support corresponding phenotyping and the development of clinical endpoints for treatment, rehabilitation planning, and pharmacological development and clinical trials. Thus, the phybrata data analysis described herein also offers a clinically intuitive alternative to more complex postural sway data analysis approaches such as approximate entropy stabilogram diffusion analysis, and wavelet analysis.

Unique features and patterns observed in phybrata signatures that may serve as phybrata biomarkers for MS impairments include, but are not limited to: 1) optic nerve demyelination: lack of visual regulation or visual reweighting; 2) spinal demyelination: lack of PSD content above 6 Hz; and 3) neural demyelination: elevated Eo CNS regulation and decrease in CNS regulation between Eo and Ec. FIG. 35, panels A and B are examples of phybrata balance (panel A) and gait parameters (panel B) identified to derive MS-specific phybrata signatures and biomarkers that quantify disease progression and potentially classify lesion location.

Figure 36:
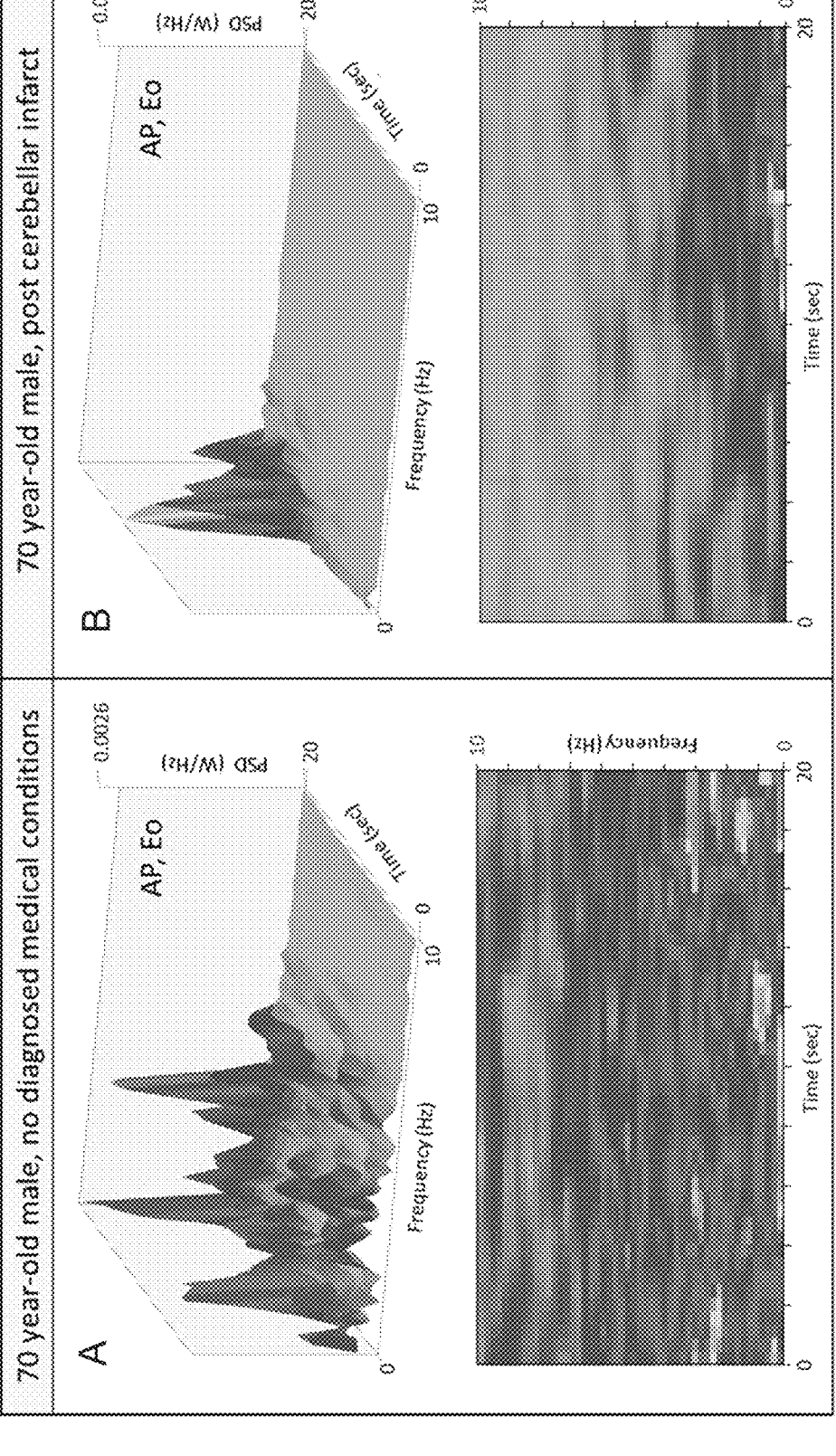
FIG. 36 are normalized eyes-open (Eo) and eyes-closed (Ec) anterior-posterior (AP, x) time-resolved phybrata power spectral density (NPSD) plots (top) and spectrograms (bottom) for a 70 year old male stroke patient (FIG. 35, panel B), and an age/gender-matched control subject with no impairment (FIG. 35, panel A).

FIG. 36 are normalized eyes-open (Eo) and eyes-closed (Ec) anterior-posterior (AP, x) time-resolved phybrata power spectral density (NPSD) plots (top) and spectrograms (bottom) for a 70-year-old male stroke patient (FIG. 36, panel B), and an age/gender-matched control subject with no impairment (FIG. 36, panel A). Unique features and patterns observed in FIG. 36 that serve as phybrata biomarkers for stroke impairments include the suppression of higher frequency cerebellar control and open-loop musculoskeletal postural stabilization following cerebellar infarct.

Figure 37:
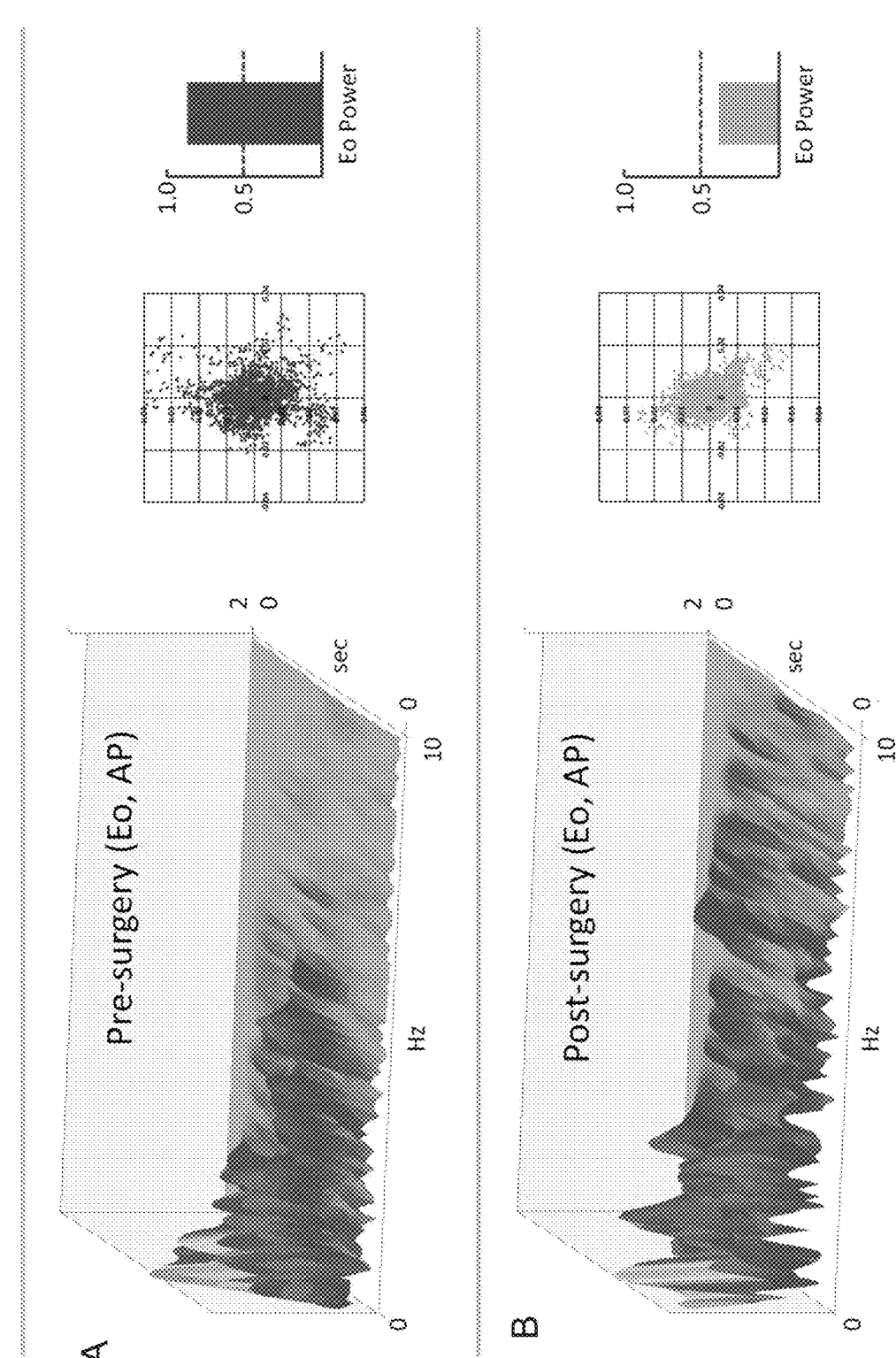
FIG. 37 are normalized eyes-open (Eo) pre-surgery (FIG. 37, panel A), and post-surgery (FIG. 37, panel B) anterior-posterior (AP, x) time-resolved phybrata power spectral density (NPSD) plots, along with AP/MVL acceleration spatial scatter plots and bar graphs of phybrata power, for a Chiari malformation patient.

Phybrata testing also reveals unique features and patterns that serve as phybrata biomarkers for pre-surgical and post-surgical physiological impairments in patients undergoing invasive neurosurgeries for impairments such as Chiari malformation and vestibular schwannoma. For example, FIG. 37 are normalized eyes-open (Eo) pre-surgery (FIG. 37, panel A), and post-surgery (FIG. 37, panel B) anterior-posterior (AP, x) time-resolved phybrata power spectral density (NPSD) plots, along with AP/IL acceleration spatial scatter plots and bar graphs of phybrata power, for a Chiari malformation patient. The pre-surgery test results reveal phybrata power and spatial scatter elevated above the impairment threshold, and suppression of higher frequency musculo-skeletal postural stabilization. The post-surgery test results reveal phybrata power level reduced below impairment threshold, and restoration of higher frequency musculo-skeletal postural stabilization control.

FIG. 38 are scatter plots of Ec/Eo power ratio vs. Eo power for 43 pre-surgery Chiari malformation patients. FIG. 38 reveals well-defined data clusters for four subpopulations: 1) unimpaired: no pre-surgery patients fall lie within this cluster; 2) cerebellar herniation leading predominantly to impaired neural integration of motor afferents involved in postural stability; 3) cerebellar herniation leading predominantly to impaired vestibular control of postural stability; and 4) cerebellar herniation leading to both impaired neural integration of motor afferents and vestibular control. Clinical symptoms from these same patients show similar clustering/phenotyping: cluster 2 shows muscle weakness, dysesthesia in the limbs; cluster 3 shows dizziness and balance problems, and in some cases, also visual problems/nystagmus due to vestibulo-ocular impairment; cluster 4 shows both sets of symptoms.

Figure 39:
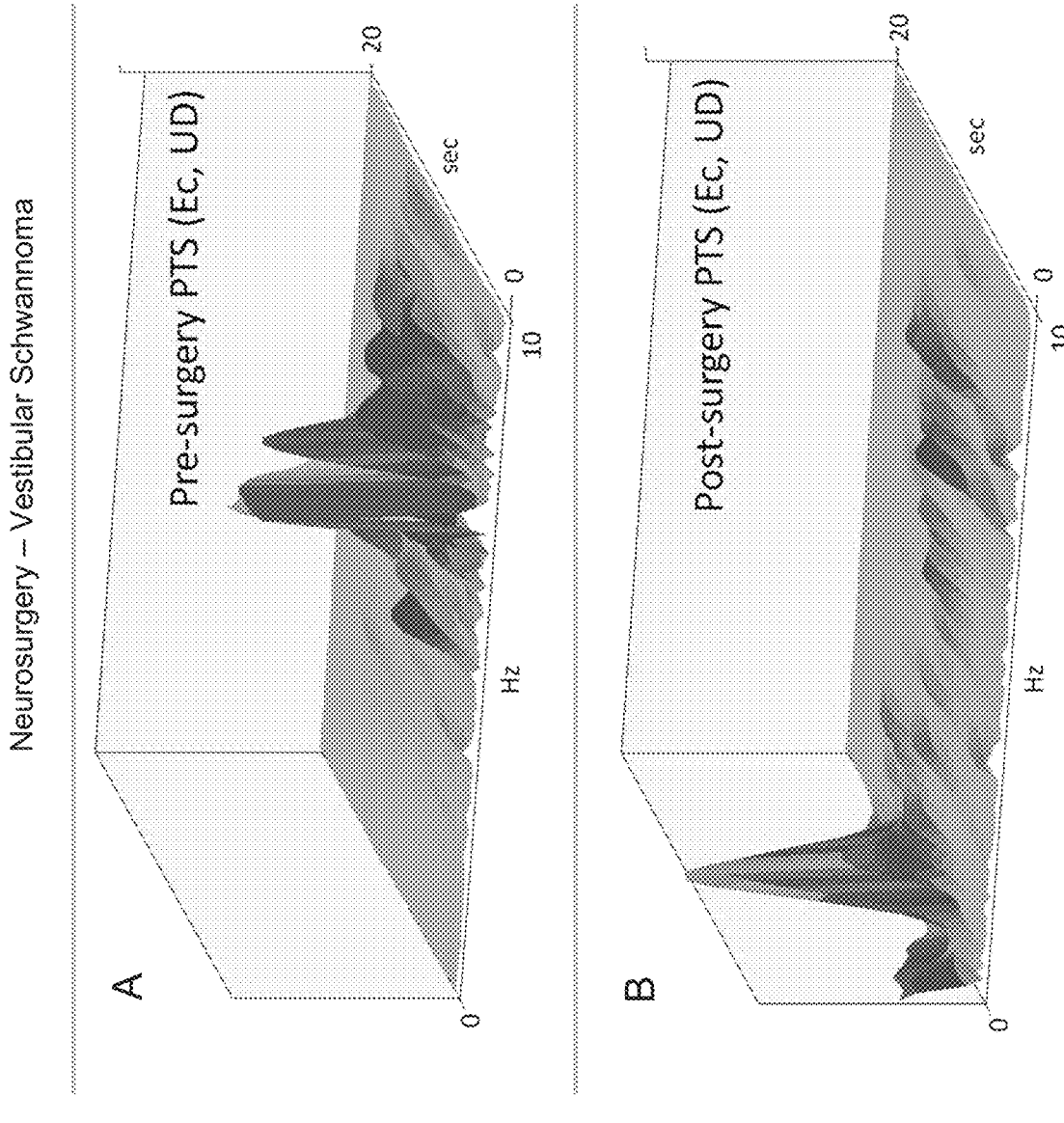
FIG. 39 are normalized eyes-open (Eo) pre-surgery (FIG. 39, panel A) and post-surgery (FIG. 39, panel B) anterior-posterior (AP, x) time-resolved phybrata power spectral density (NPSD) plots for a vestibular schwannoma patient.

FIG. 39 are normalized eyes-open (Eo) pre-surgery (FIG. 39, panel A) and post-surgery (FIG. 39, panel B) anterior-posterior (AP, x) time-resolved phybrata power spectral density (NPSD) plots for a vestibular schwannoma patient. The pre-surgery results reveal pronounced tremor and suppression of normal sensory weighing due to the vestibular schwannoma. The post-surgery results reveal suppression of the tremor and restoration of a more normal sensory weighing profile following gamma knife surgery.

Figure 40A:
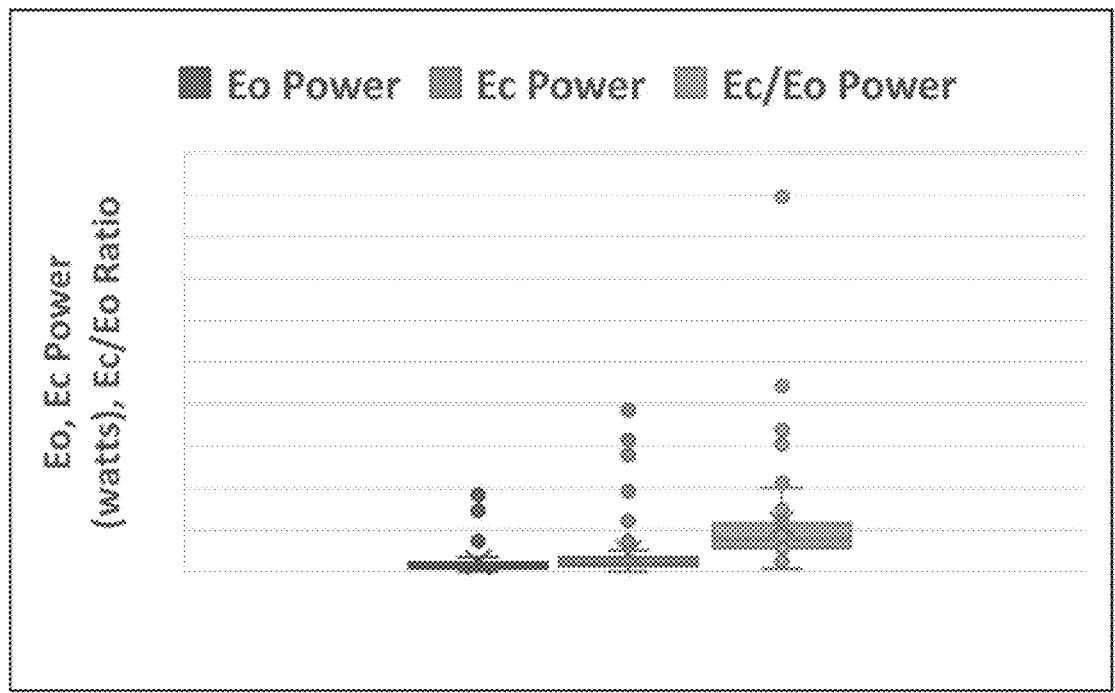
FIG. 40A are box plots for Eo, Ec, and Ec/Eo, and FIG. 40B are scatter plots of Ec/Eo power ratio vs. Eo power (right) for 62 patient tests, both impaired and unimpaired, tested in a chronic pain clinic.
Figure 40B:
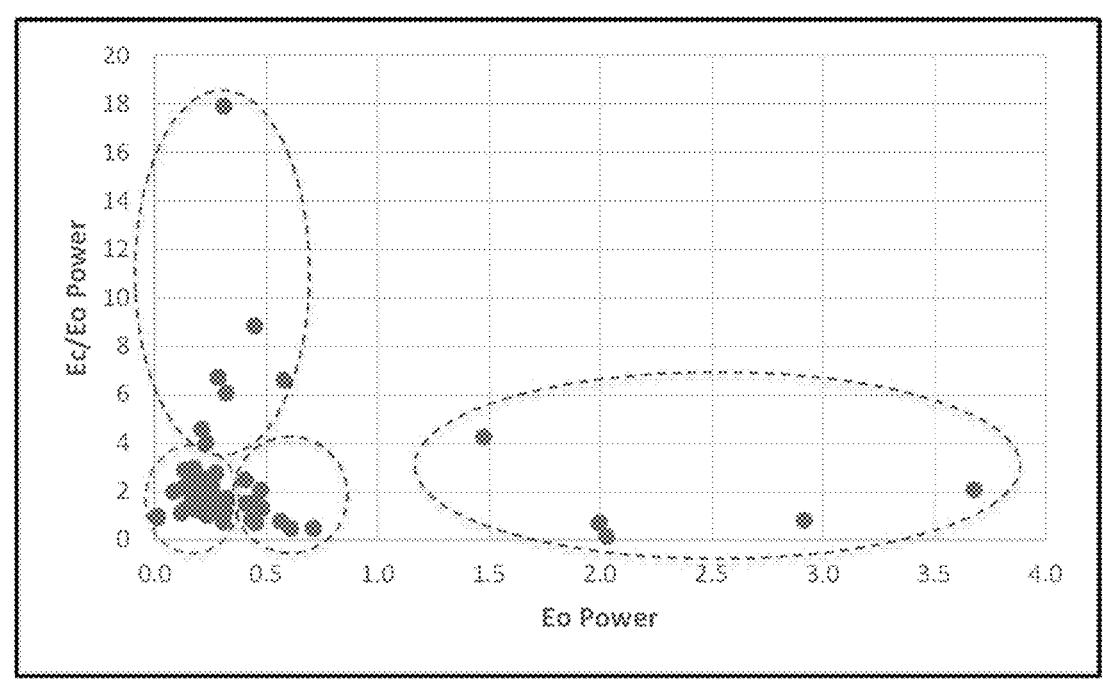

In addition, phybrata testing also reveals unique features and patterns that serve as phybrata biomarkers in patients suffering from chronic pain. FIG. 40A are box plots for Eo, Ec, and Ec/Eo, and FIG. 40B are scatter plots of Ec/Eo power ratio vs. Eo power (right) for 62 patient tests, both impaired and unimpaired, tested in a chronic pain clinic. The outliers in the box plots correspond to patients with diagnosed chronic pain impairments, and the scatter plots reveal well-defined data clusters for healthy and impaired subpopulations that correlate with clinical diagnoses and underlying physiological impairments.

Figure 41:
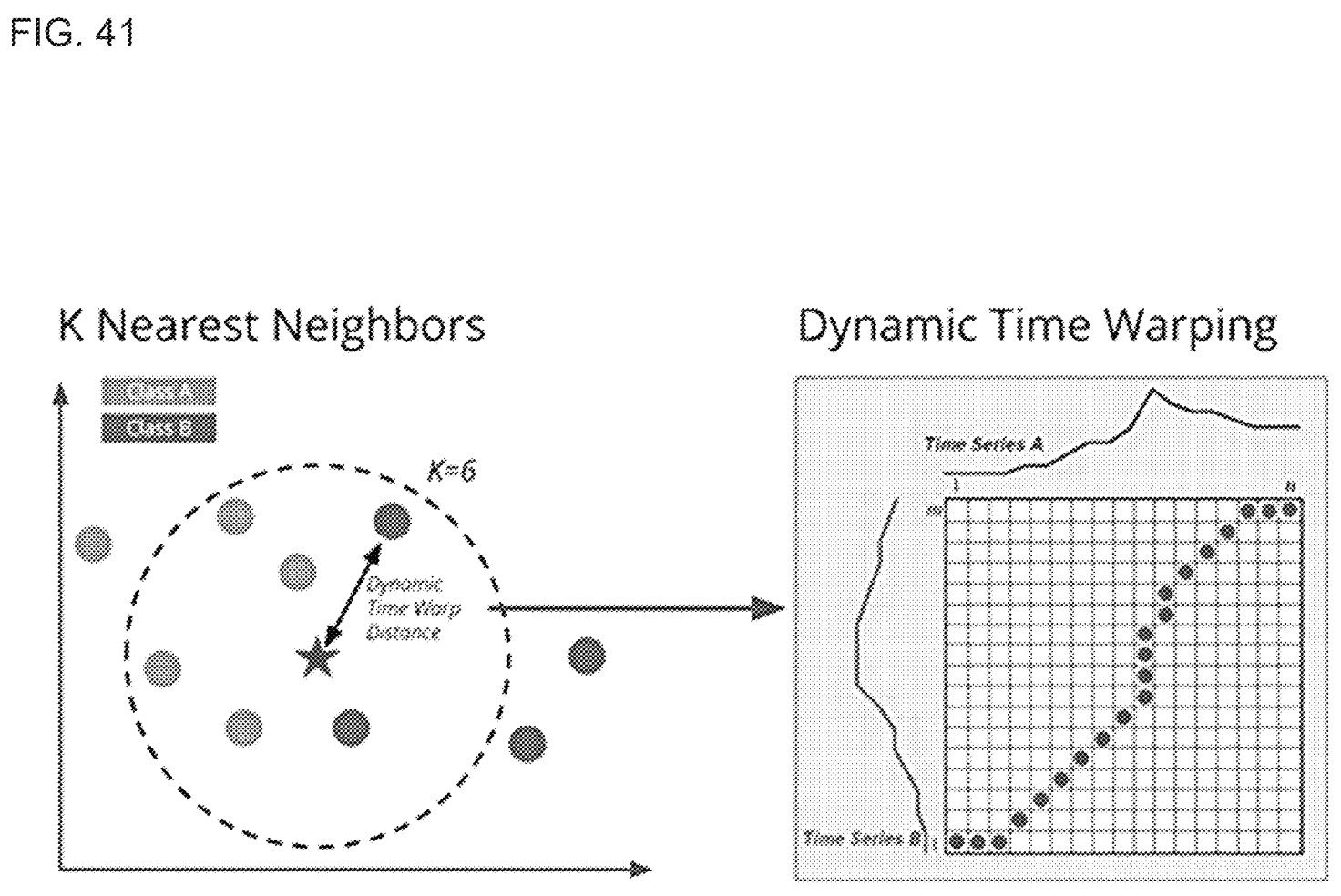

FIG. 41 are plots depicting a method of generating synthetic phybrata data, according to an embodiment. Synthetic phybrata time-series data is generated from experimental phybrata time-series data by applying a Dynamic Time Warping K-Nearest Neighbors (DTW-KNN) technique to the multivariate phybrata time-series signals of each patient test. DTW-KNN quantifies similarity between different time series and generates synthetic versions of data by assigning cumulative weights to a particular patient and their surrounding "K" neighbors. The synthetic time-series are then aligned with their respective features (x, y, and z accelerations and power), weighted, and averaged using Barymetric Averaging (BA) to create synthetically averaged points for each step in the time-series. Averages are computed at each step to generate samples that are representative of the original data, where each original patient is examined at least once in relation to its surrounding neighbors.

For determining DTW, a dissimilarity matrix containing Euclidean distances between every pair of patients and their time-series is calculated. With this dissimilarity matrix, distances between all the patients can be compared and grouped using K Nearest Neighbors (KNN). Selecting the "K" parameter will adjust the nearest neighbors considered in the grouping around a particular patient and represents a flexible hyperparameter chosen beforehand. Once K is selected, weights are normalized (summate to 1), and distributed hierarchically beginning with the randomly chosen patient time-series in the center (w=0.5), each K nearest neighbor (w=0.3/K) and all the remaining non-neighboring time-series (w=0.1/n–k). The weights are then multiplied to each patient's time-step with the values at each step added and subtracted together at random creating new values for a synthetic patient.

In essence, this synthetic patient is largely comprised of the time-series of a subset of patients along with mixing randomness inserted to provide some variation from the original data. Once the synthetic data is created, the similarity between original and synthetic distributions and the predictive utility of the synthetic data are first assessed by visual inspection of global data trends and analyses of statistical distributions, both for time-series data corresponding to individual patients and for data aggregated across specific patient cohorts. A more quantitative assessment is then carried out using paired t-tests at each sequential step in the time-series and then aggregating across the time-series of each patient and quantifying clinical group differences. The utility of synthetic data is further assessed in terms of its contribution to model performance when combined with data from real patients in machine learning (ML) training and test datasets. Similar or increased performance can indicate that relevant differences captured in the synthetic data series during ML model training maintain or bolster the ability to classify real distributions. If the synthetic data differs significantly from the original patient data, then the ML model performance is impaired when evaluated on real patients.

Figures 42A, 42B:
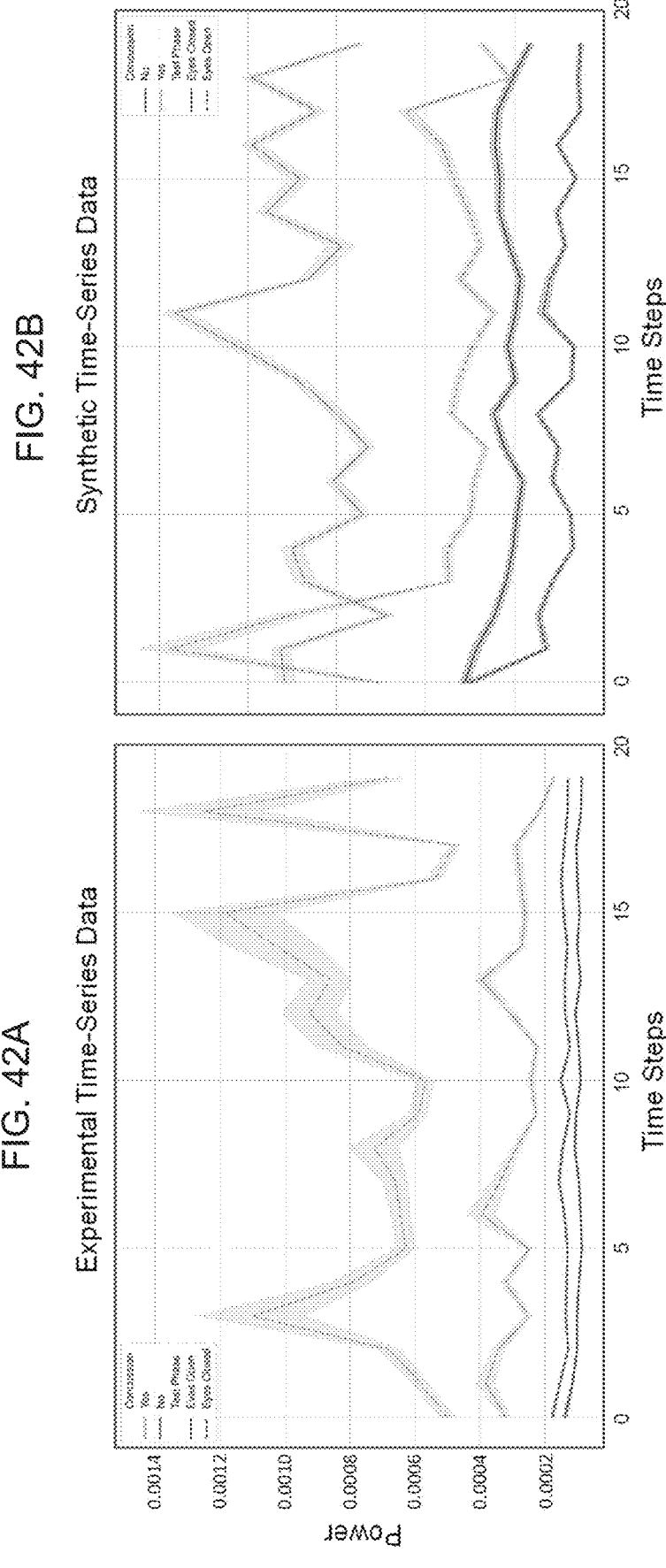
FIGS. 42A-42C are plots comparing experimental concussion patient phybrata data with synthetic phybrata data that replicates the Eo vs Ec and HB vs CN behavior and diagnostic signatures.
Figure 42C:
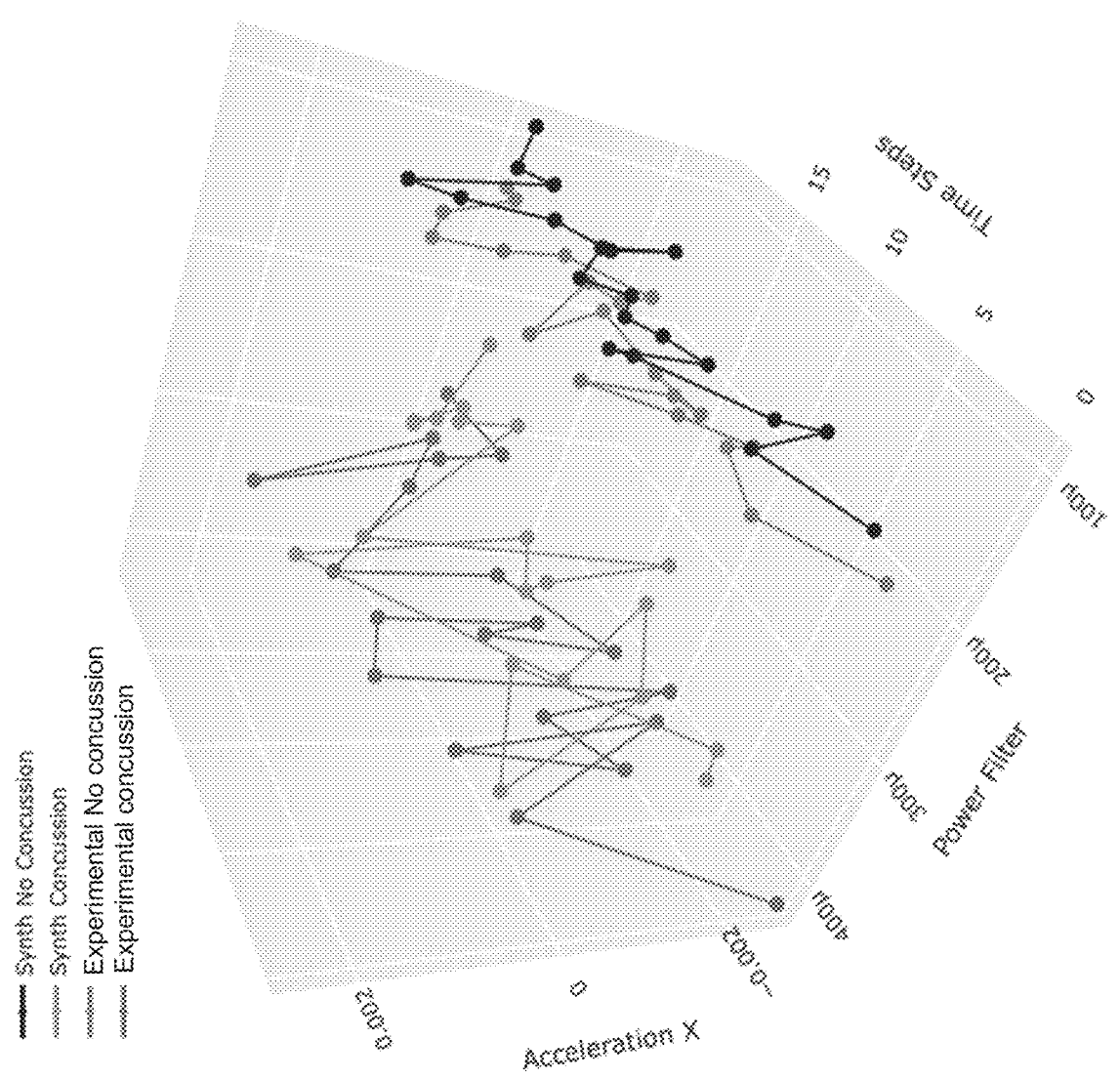

FIGS. 42A-42C are plots of synthetic phybrata data that replicates the Eo vs Ec and HB vs CN behavior and diagnostic signatures of clinical concussion patient data. FIGS. 42A-42C illustrate the ability of synthetic phybrata data to replicate the Eo vs Ec and HB vs CN behavior and diagnostic signatures of clinical concussion patient data. FIGS. 42A-42C compare average Eo and Ec phybrata powers for synthetic (n=120) and actual (n=169) patients separated by clinical group (healthy and concussion). To generate these results, the raw 20-second phybrata acceleration signals (2,000 samples for each of x, y, z accelerations) are first processed to calculate 20-second phybrata power time series (2,000 sample). Each real and synthetic patient's 20-second power time-series is then averaged across successive 1-second intervals to generate 20-sample averaged phybrata power time series. The time-series of all patients in each group (concussed or healthy) are then averaged to generate the group level comparisons shown in FIGS. 42A-42C. The most significant preservation of group differences is observed in the relationship between the Eo and Ec phybrata powers. Higher signal power values plotted across time are visibly associated with individuals diagnosed with concussions whereas lower power values are associated with healthy individuals. Synthetic data samples were then added to a ML model training dataset and the model was used to classify the same clinical test group (healthy and concussion). The performance of the ML model was identical with and without the added synthetic data for all metrics.

Thus, embodiments described herein demonstrate application of phybrata data for the development, refinement, and testing of biomechanical postural sway models that include the full range of active vs. passive, open-loop vs. closed-loop, intermittent vs. continuous, and high-complexity vs. low-complexity control behaviors that have been proposed to account for normal and impaired balance and gait stability and sensory reweighting. For example, in FIGS. 29-32 and FIGS. 9A-9D, higher frequency spinal reflexive loops, proprioception, and more complex multi-joint and muscle activity contributions >4 Hz appear to continuously regulate postural sway, corresponding to open-loop, automatic, "learned" balance strategies, as opposed to lower frequency CNS, vestibular, and visual contributions that clearly reflect the intermittent feedback control arising from CNS integration and processing of multiple sensory afferent and efferent signals.

In the case of concussion injuries, the observed loss of higher frequency coordination, whether due to musculoskeletal/proprioceptive impairment or a shift to a more conservative closed-loop control and ankles-only strategy, may contribute to increased risk of subsequent musculoskeletal injury if not fully rehabilitated before returned to play. Even relatively simple inverted pendulum and feedback control models of the human postural control system can generate COP/COM spatial scatter plots and time-series traces whose gross features closely resemble physiologically measured postural sway data. Variations in the values of parameters such as joint stiffness, damping, feedback time delays, and noise levels are sufficient, for example, to account for typical differences between measured data for healthy elderly vs. young subjects.

FIGS. 43A-43F are plots of simulated phybrata data of a user having no impairment (FIGS. 43A-43B), having central nervous system (CNS) impairment (FIGS. 43C-43D), and peripheral nervous system (PNS) impairment, generated by a biomechanical model that serves as a digital twin of the user, according to an embodiment. For example phybrata sensor data, machine learning models, and biomechanical models may be utilized to build and deploy: "population digital twins" that serve as normative baselines for "healthy" patients; "individual digital twins" that quantify an individual's unique physiological state vs. their own normative population baseline; "backup digital twins" that capture an individual's physiological state before a surgical procedure, prescription drug treatment, rehabilitation, or participation in a clinical trial; "predictive digital twins" that generate predictive analyses of projected quantitative changes in physiological performance, impairments, disease state, physiological disruption state, and responses to treatment, medications, therapies, and rehabilitation; and/or "therapeutic digital twins" that are utilized to monitor patient responses and adjust treatments, medications, therapies, and rehabilitation.

Figure 44:
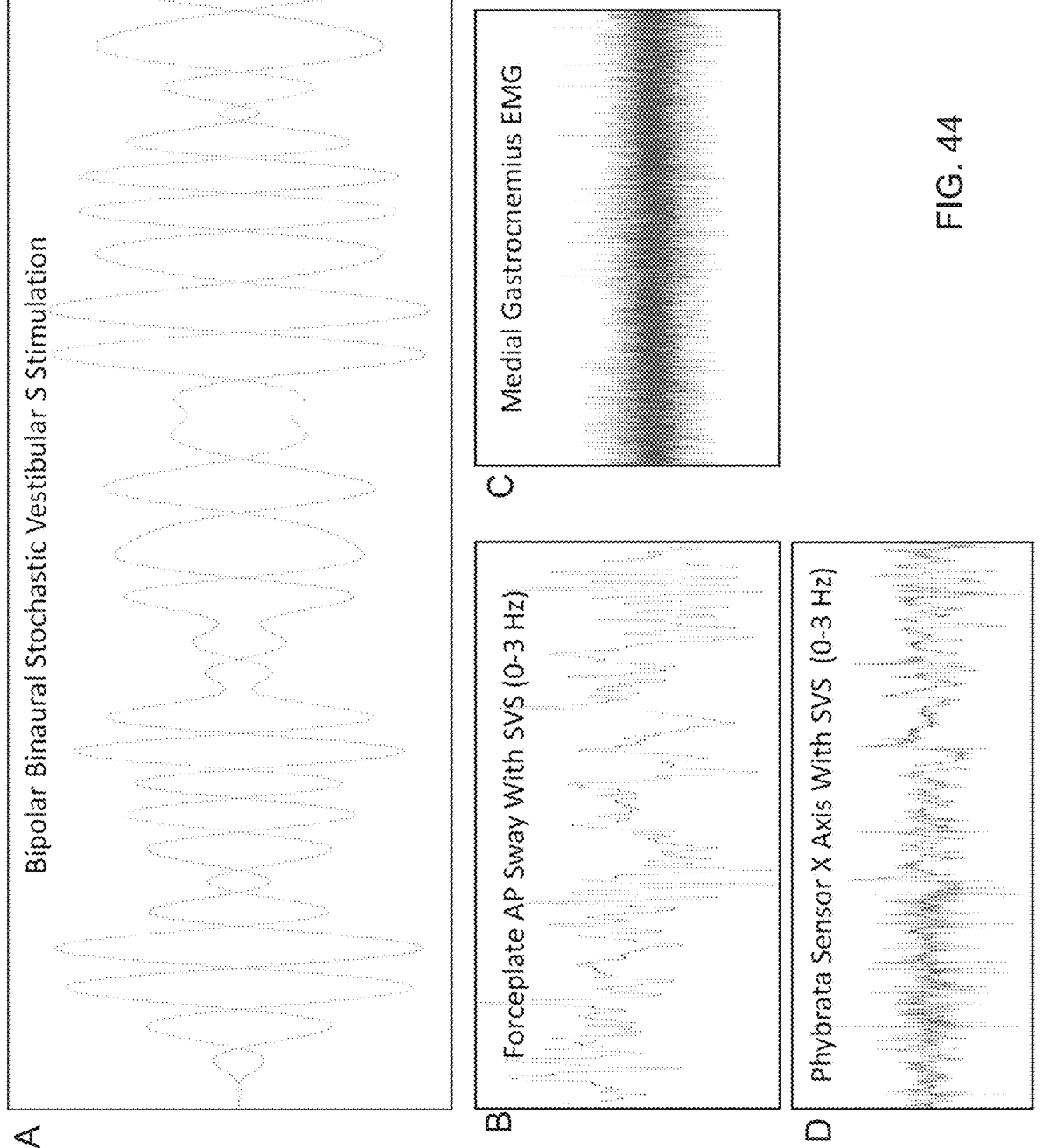
FIG. 44, panels A to D are plots of postural stability data collected simultaneously from a mastoid-mounted phybrata sensor (panel D), electromyography electrodes attached to the calf muscle (panel C), and a force plate (panel B), while vestibular stimulation is applied to the user (panel A).

The execution of a movement such as standing up, sitting down, or walking provokes a perturbation of posture (internal perturbation), which is compensated for by a postural reaction. This occurs with a delay that is comprised of the time for the perturbation to be detected plus the time for transmission through the corrective pathway(s). In contrast, anticipatory postural adjustments correct in advance for the forthcoming perturbation. In some embodiments, an adaptive neural network may be used to control this anticipatory process. For example, FIG. 44, panels A to D are plots of postural stability data collected simultaneously from a mastoid-mounted phybrata sensor (panel D), electromyography electrodes attached to the calf muscle (panel C), and a force plate (panel B), while vestibular stimulation is applied to the user (panel A). As illustrated in FIG. 44, panels A-D, the adaptive neural network described herein learns to differentiate between normal and pathological posture and to calculate the advance timing of postural corrections through a training process in which postural stability data is collected simultaneously from a mastoid-mounted phybrata sensing assembly (FIG. 44, panel D), electromyography electrodes attached to various locations on the body such as the calf muscle (FIG. 44 panel C), a force plate (FIG. 44, panel B), and other assessment tools such as, but not limited to, computerized dynamic posturography or video motion capture systems.

Figure 45:
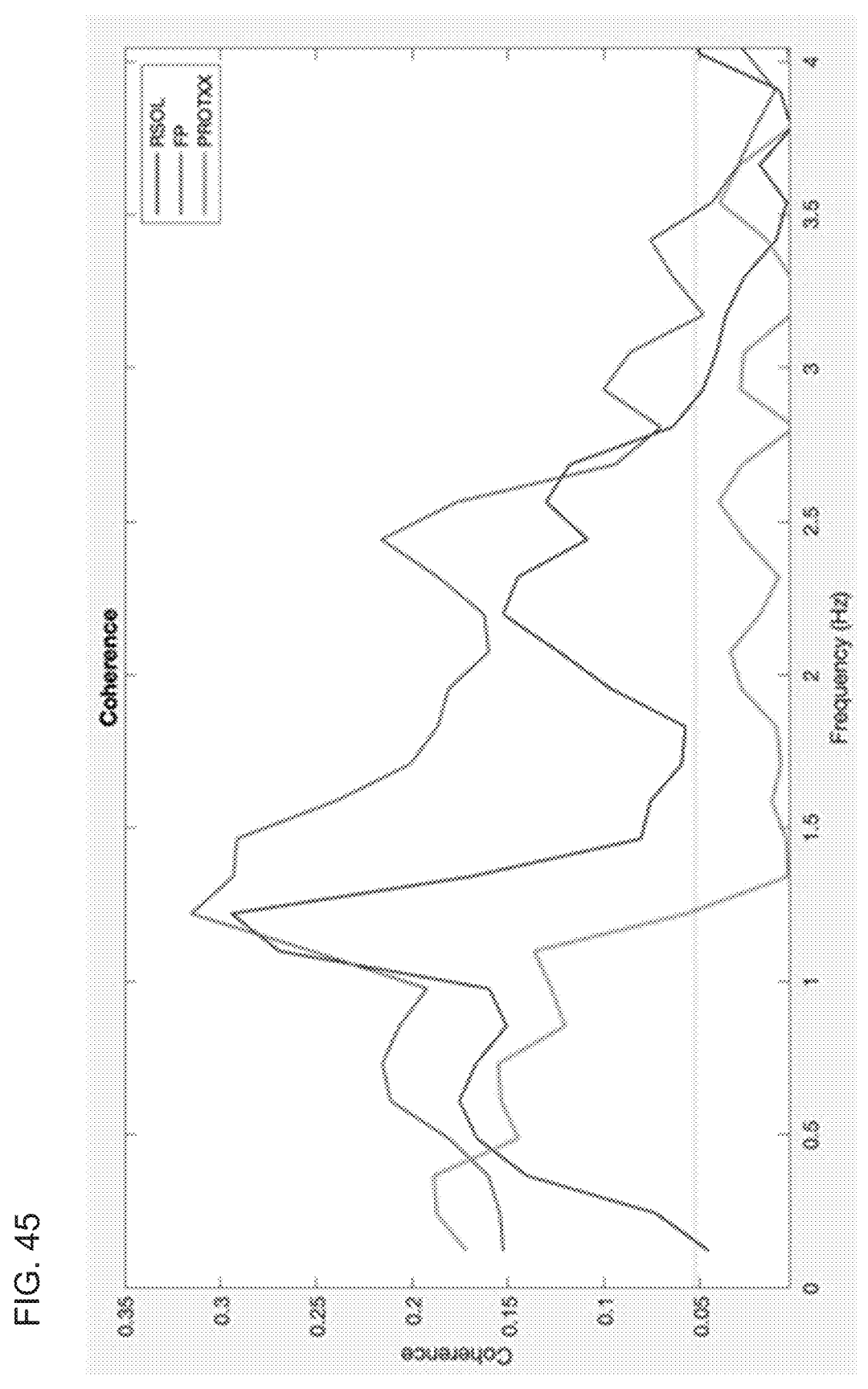
Figure 46:
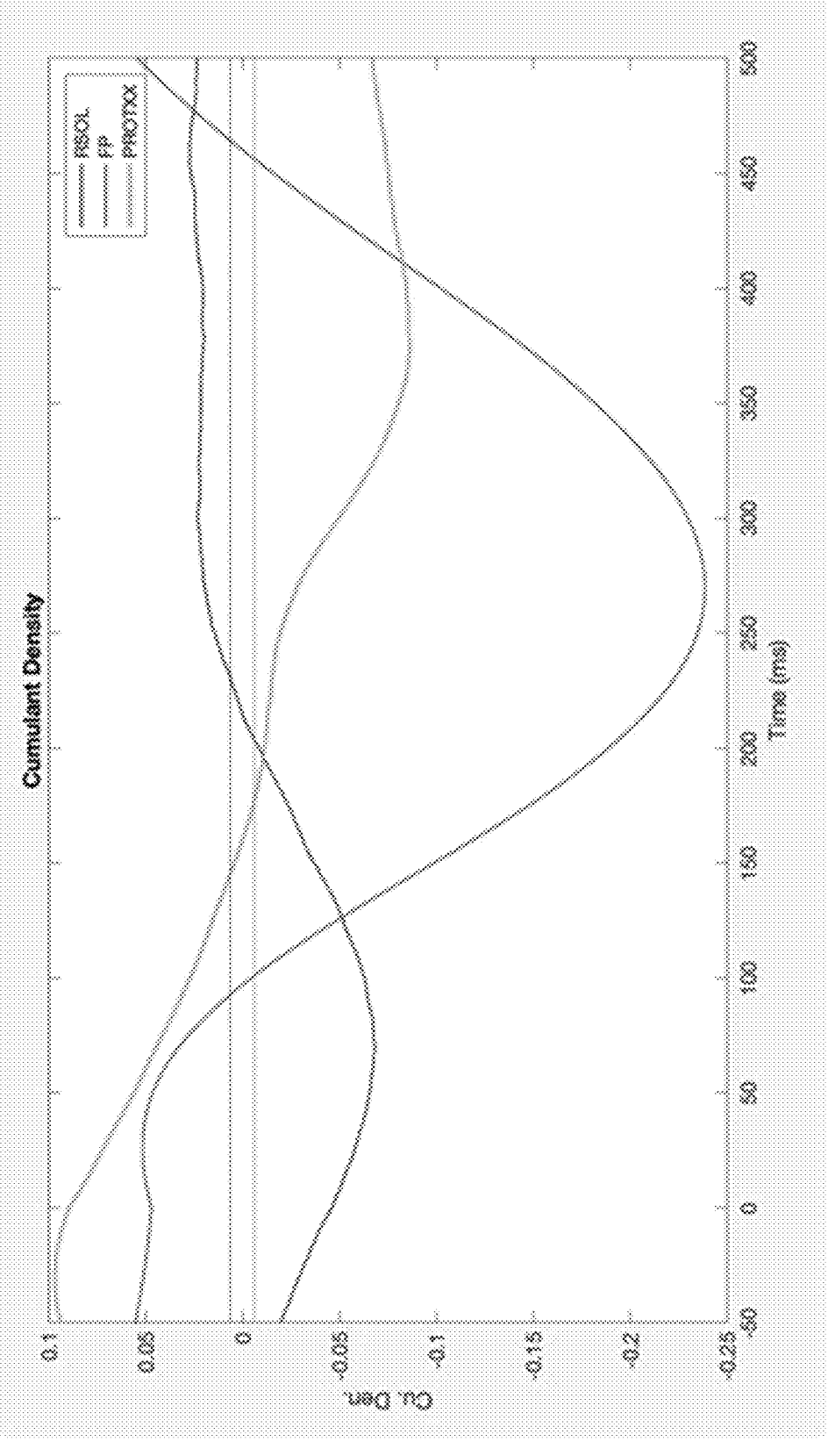
FIG. 46 are plots of calculated time-domain cumulant density between motion signals collected simultaneously from a mastoid-mounted phybrata sensor (PROTXX), electromyography electrodes attached to the calf muscle (RSOL), and a force plate (FP).

FIG. 45 are plots of calculated frequency-domain coherence between motion signals collected simultaneously from a mastoid-mounted phybrata sensor (PROTXX), electromyography electrodes attached to the calf muscle (RSOL), and a force plate (FP) while vestibular stimulation is applied to the user. FIG. 46 are plots of calculated time-domain cumulant density between motion signals collected simultaneously from a mastoid-mounted phybrata sensor (PROTXX), electromyography electrodes attached to the calf muscle (RSOL), and a force plate (FP) while vestibular stimulation is applied to the user. Calculations of the frequency-domain coherence, as illustrated in FIG. 45, and time-domain cumulant density, as illustrated in FIG. 46, between motion signals from different parts of the body may be utilized to determine the magnitudes, phases, and delays between motions of different body segments in order to calculate and adapt EVS waveforms and waveform parameters to achieve the desired reduction, correction, or compensation for degraded balance or gait. The adaptive neural network learns to differentiate between normal and pathological movement through a training process such as a balance and gait analysis test, as described previously with respect to FIGS. 11A-11B.

Figure 47:
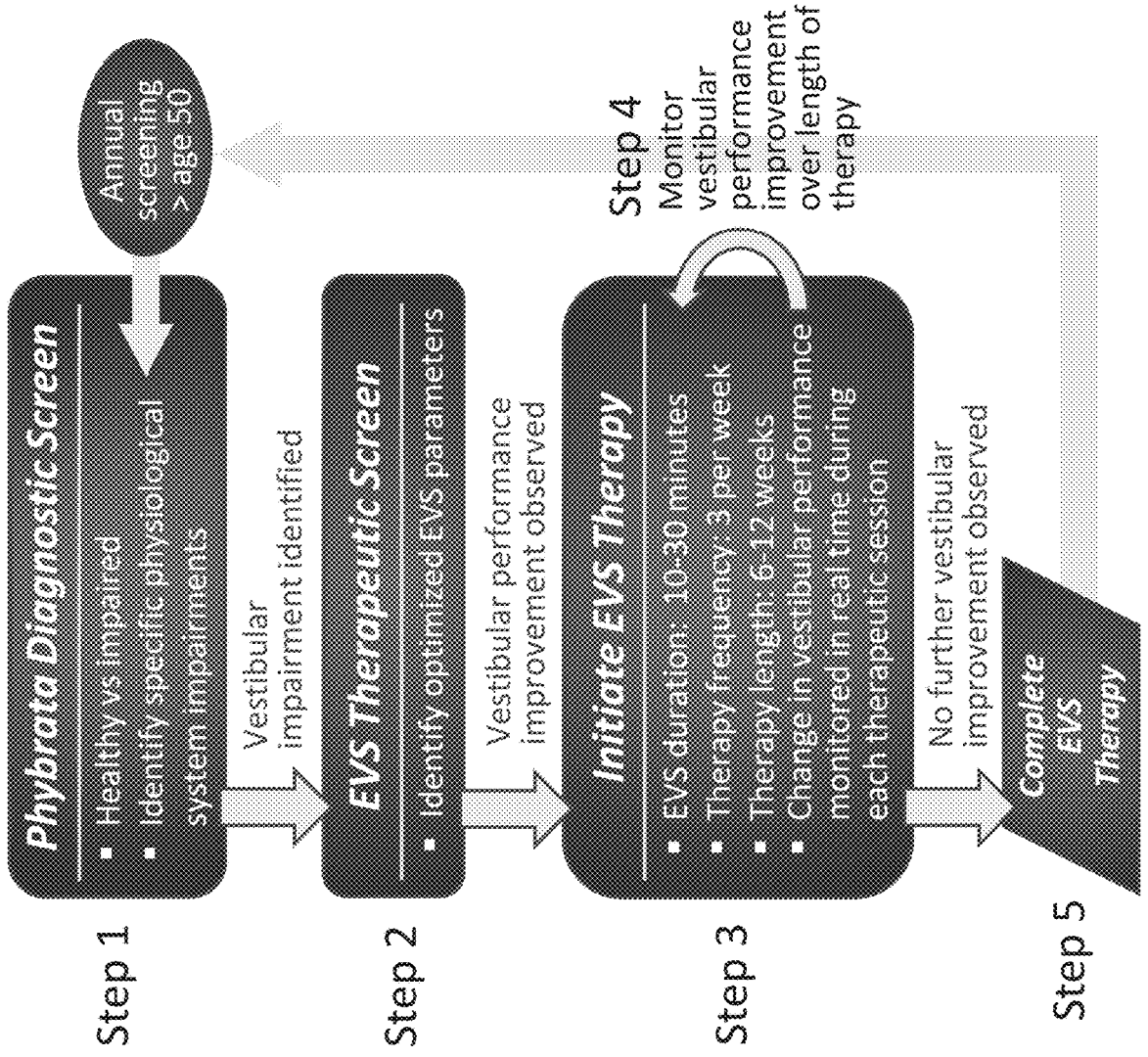
FIG. 47 is a schematic flow diagram of a method for detecting and correcting vestibular balance impairments using a sensing and stimulation assembly, according to an embodiment.
Figure 48A:
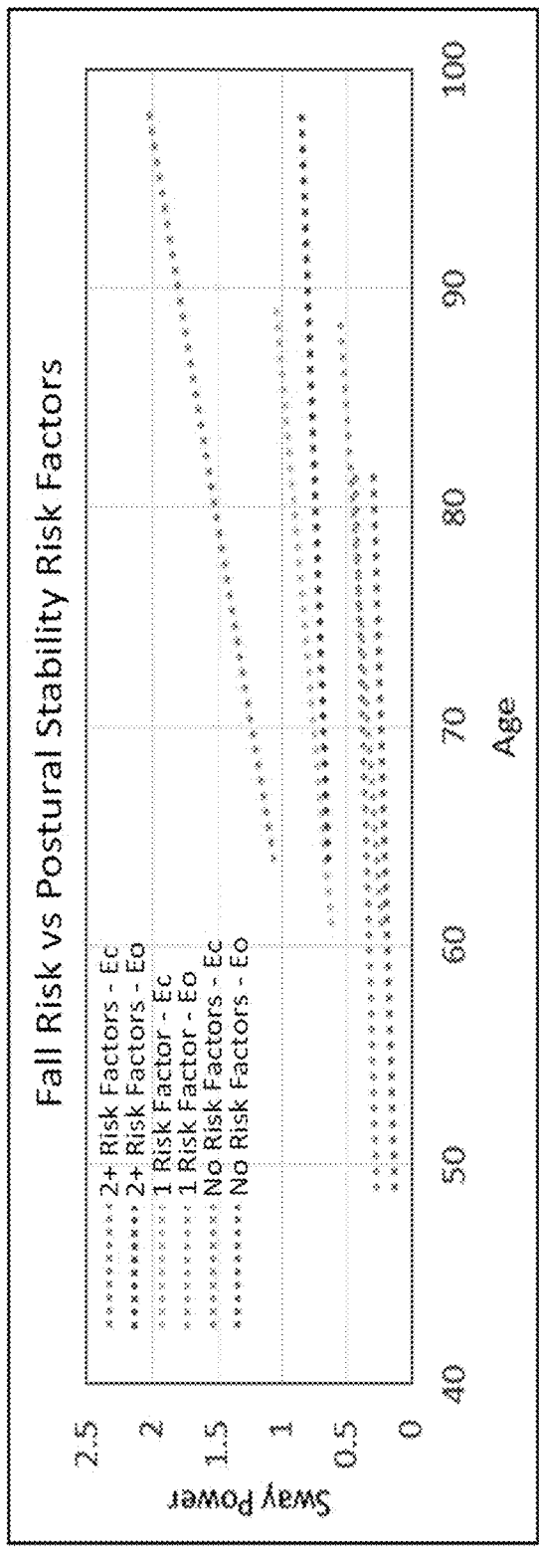
FIGS. 48A and 48B are plots of age-related impairment parameters, and Eo and Ec phybrata data measured from a set of patients collected using a neurophysiological sensing assembly mounted on a mastoid of the patients.
Figure 48B:
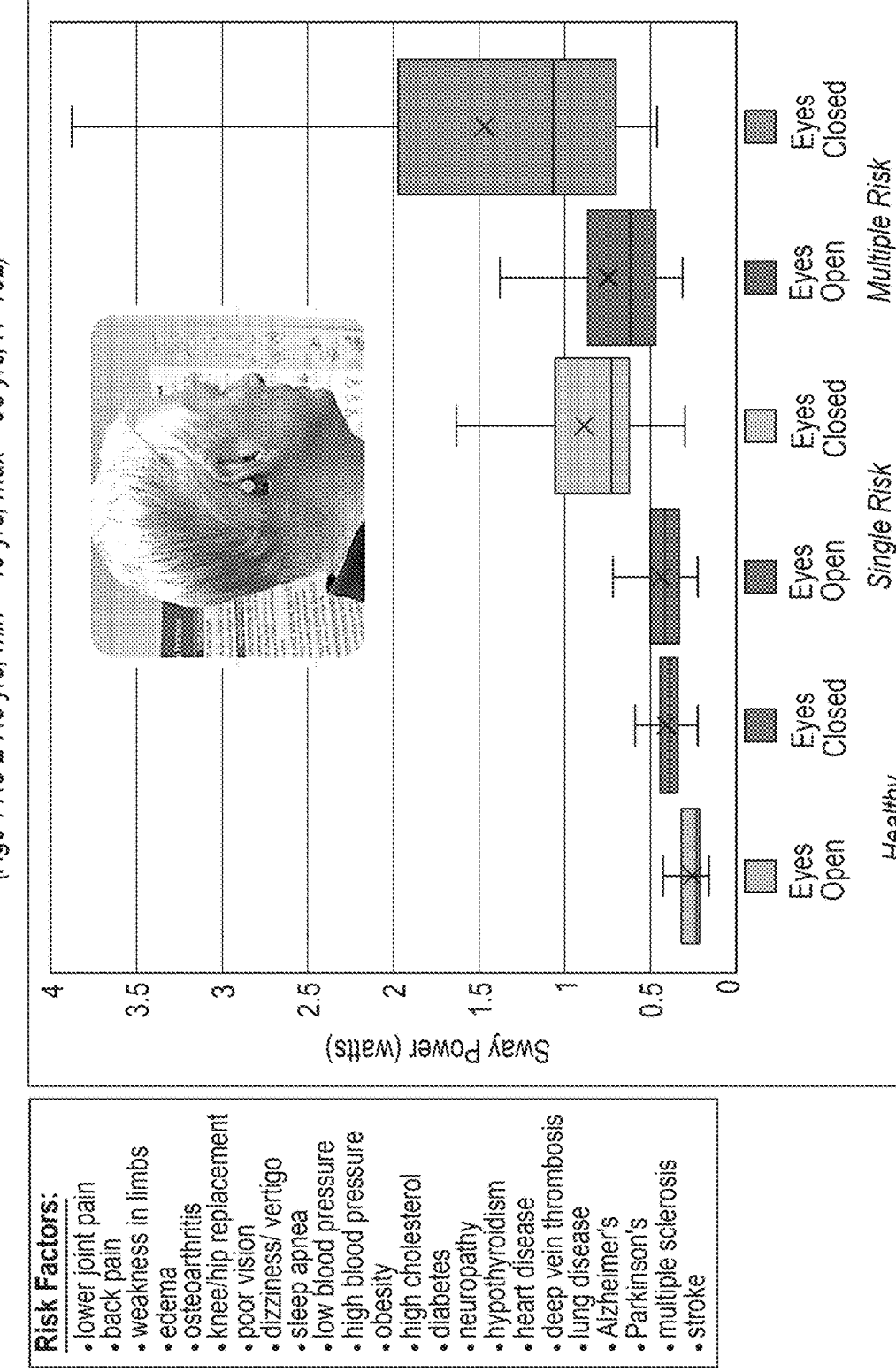

FIG. 47 is a schematic flow diagram of a method for detecting and correcting vestibular balance impairments using a sensing and stimulation assembly, according to an embodiment. At step 1, the sensing and stimulation assembly is used to screen for multiple physiological system impairments, including impairments to the vestibular balance system. The screening may be carried out by mounting the sensing and stimulation assembly on the mastoid of the user, and the phybrata sensors sensed for a time period in a range of 0.5 minutes to 5 minutes, inclusive (e.g., 0.5, 0.6, 0.7, 0.8, 0.9, 1.0, 1.5, 2.0, 2.5, 3.0, 3.5, 4.0, 4.5, or 5.0 mins, inclusive). These may allow determination of healthy vs. impaired patients, and/or identification of specific neurophysiological impairments. For example, the sensing and stimulation assembly may be used to determine balance impairments and related fall risks, as illustrated in FIGS. 48A and 48B, which are plots of age-related impairment parameters, and Eo and Ec phybrata data measured from a set of patients collected using a sensing and stimulation assembly mounted on a mastoid of the patients.

At step 2, if a vestibular impairment is identified, the caregiver (e.g., a doctor, clinician, rehabilitator) may administer a stimulation signal therapeutic screen (e.g., an EVS, a CES, and/or an ESE stimulation signal) for a time period in a range of 2 mins to 20 mins, inclusive (e.g., 2, 3, 4, 5, 6, 7, 8, 9, 10, 12, 14, 16, 18, or 20 mins, inclusive), to identify subthreshold stochastic stimulation parameters that optimize balance improvement. For example, the sensing and stimulation assemblies described herein may allow caregivers to identify the EVS stimulation parameters that optimize balance improvement. Optimal EVS current levels and frequencies are different for each patient. In some embodiments, identification of the EVS stimulation parameters that optimize balance improvement, including EVS current levels and frequencies, utilize one or more phybrata biomarkers. These phybrata biomarkers may be derived from spatial-domain phybrata data, time-domain phybrata data, frequency-domain phybrata data, and phybrata sensory reweighting data.

Figures 49, 50:
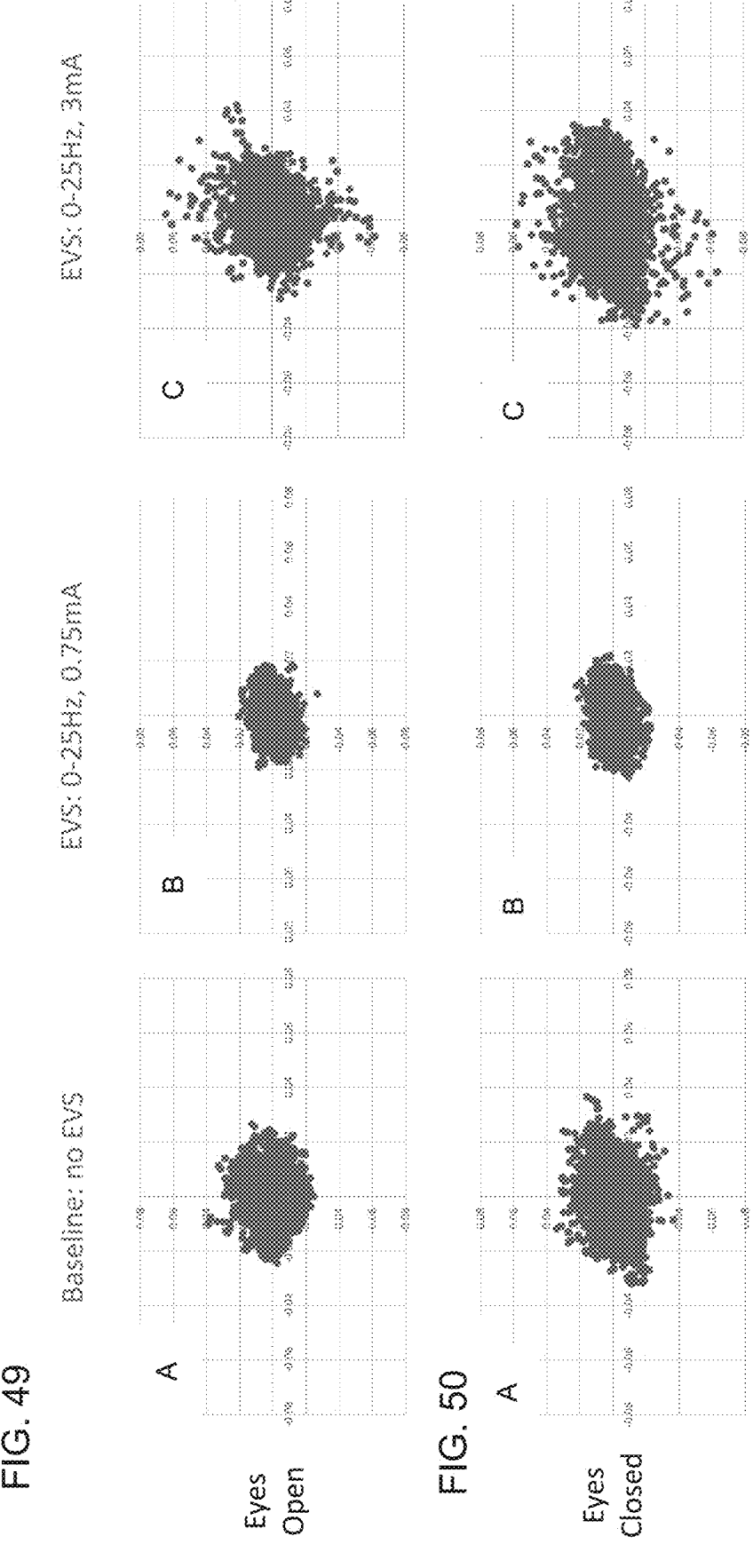
FIG. 49, panels A-C are spatial scatter plots of phybrata acceleration data collected using a neurophysiological sensing system with a user's eyes open.
FIG. 50, panels A-C are scatter plots of time domain data collected using a neurophysiological monitoring system with the user's eyes closed, and that are used to derive phybrata signatures for optimizing electro vestibular stimulation (EVS) signals applied to the user via a stimulation assembly that may be included in the neurophysiological sensing system.

For example, FIG. 49, panels A-C are scatter plots of time domain data collected using a neurophysiological sensing system with a user's eyes open, and FIG. 50 are scatter plots of time domain data collected using a neurophysiological monitoring system with the user's eyes closed, and that are used to derive phybrata signatures for optimizing electro vestibular stimulation (EVS) signals applied to the user via a stimulation assembly that may be included in the neurophysiological sensing system. The scatter plots shown in FIGS. 49 and 50 illustrate spatial-domain phybrata acceleration data.

Figure 51:
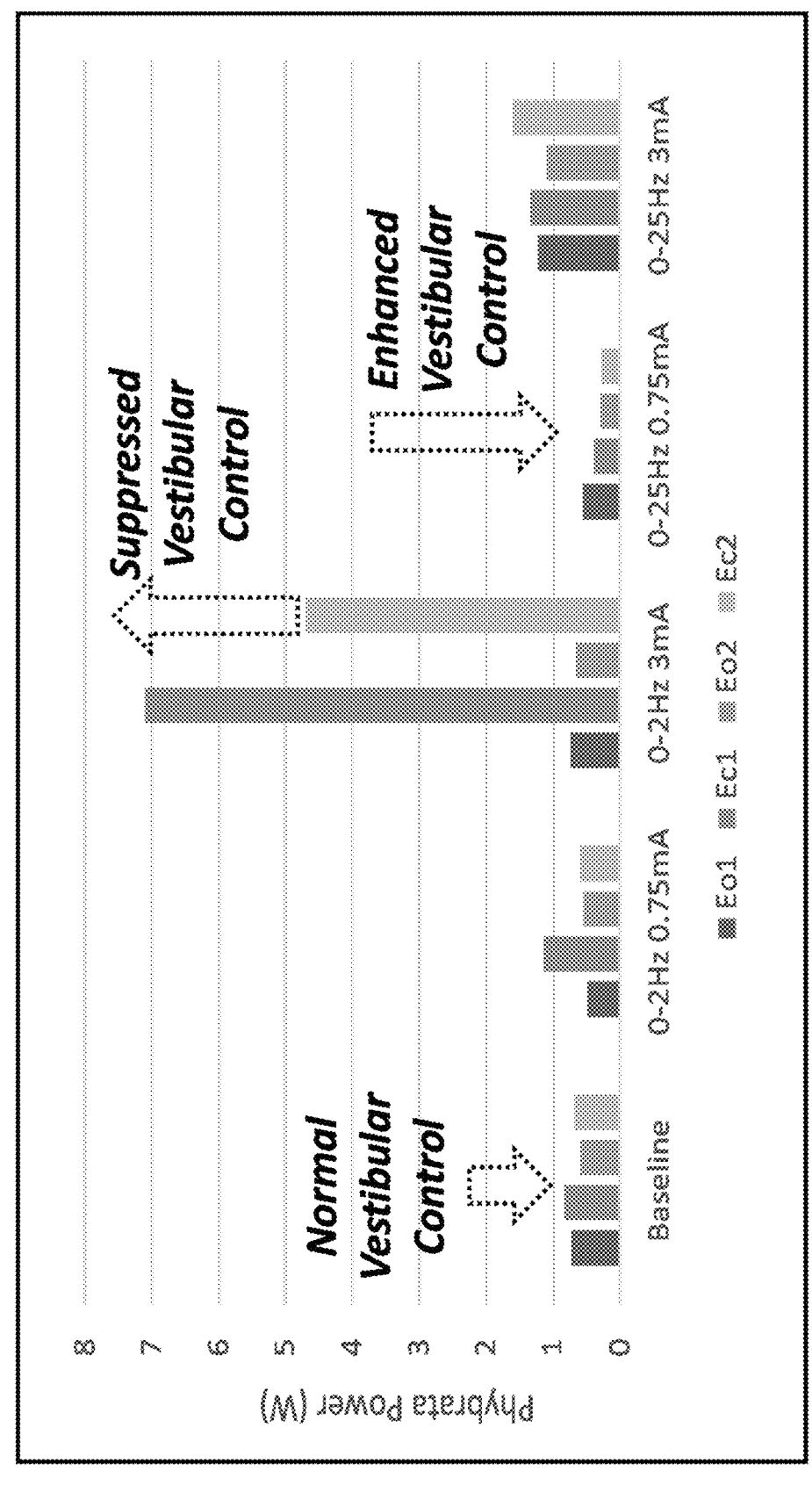
FIG. 51 is a bar chart of phybrata power histograms derived from a neurophysiological sensing system with users' eyes open (Eo1 and Eo2) and eyes closes (Ec1 and Ec2) collected using a sensing assembly included in a neurophysiological sensing system, which are used to derive phybrata signatures for optimizing EVS signals applied to the user via a stimulation assembly that may be included in the neurophysiological sensing system.

FIG. 51 is a bar chart of time domain data collected using a neurophysiological sensing system with users' eyes open (Eo1 and Eo2) and eyes closes (Ec1 and Ec2) collected using the neurophysiological monitoring system, which are used to derive phybrata signatures for optimizing EVS signals applied to the user via a stimulation assembly that may be included in the neurophysiological sensing system. The bar chart in FIG. 51 illustrates time-domain phybrata acceleration and power data.

Figure 52:
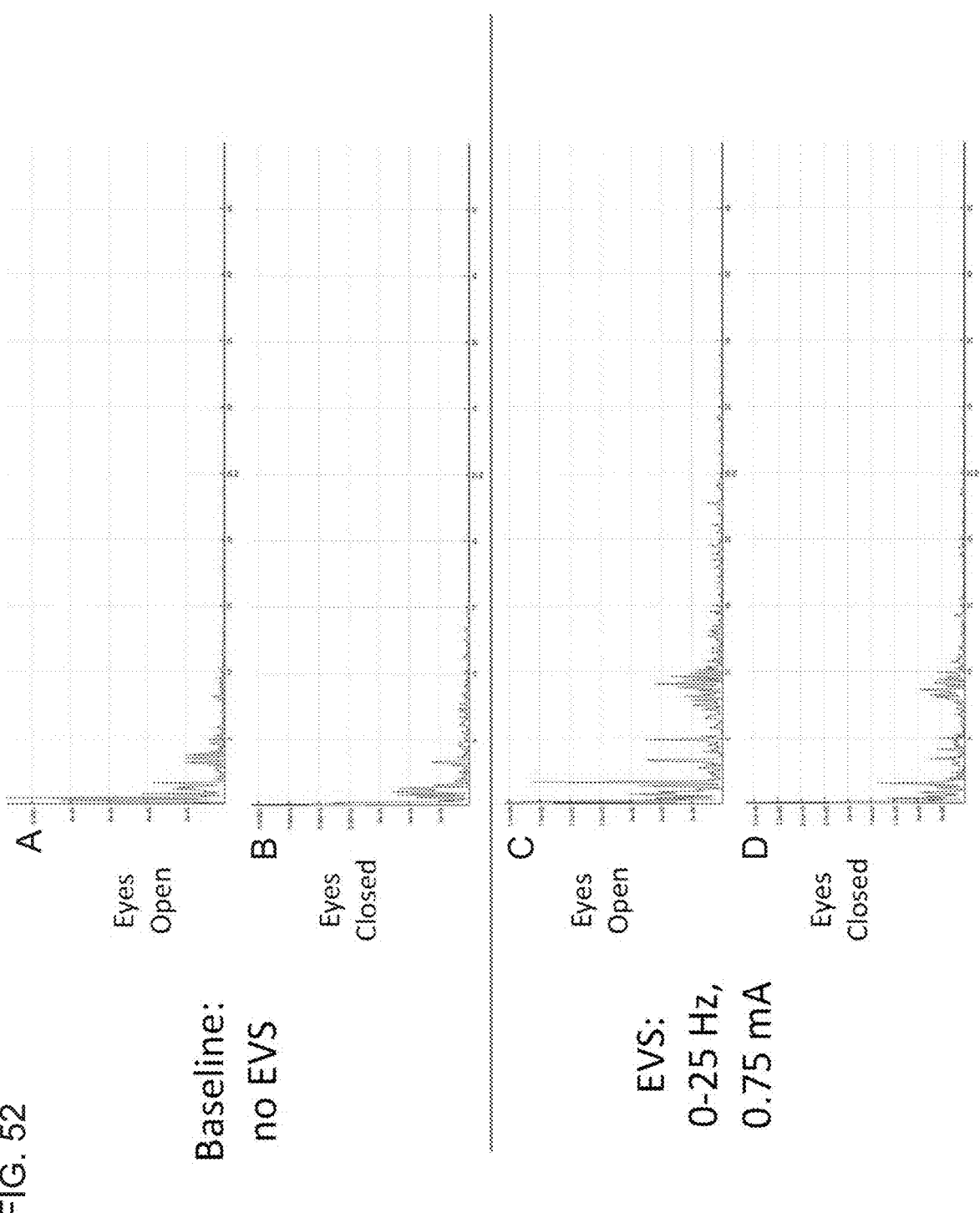
FIG. 52, panels A-B are plots of baseline phybrata frequency-domain data collected using a neurophysiological sensing system with a user's eye open (Eo, panel A), and eyes closed (Eo, panel B), and FIG. 52 panels, C-D are plots of phybrata frequency-domain data collected while applying a EVS stimulation with the user's eye open (Eo, panel C) and eyes closed (Ec, panel D), and which can be used to derive phybrata signatures for optimizing EVS signals applied to the user via a stimulation assembly that may be included in the neurophysiological sensing system.

FIG. 52, panels A-B are plots of baseline frequency domain data collected using a neurophysiological sensing system with a user's eye open (Eo, panel A), and eyes closed (Eo, panel B), and FIG. 52 panels, C-D are plots of frequency domain data collected while applying a EVS stimulation with the user's eye open (Eo, panel C) and eyes closed (Ec, panel D), and which can be used to derive phybrata signatures for optimizing EVS signals applied to the user via a stimulation assembly that may be included in the neurophysiological sensing system. FIG. 52 illustrates frequency-domain phybrata data.

Figure 53:
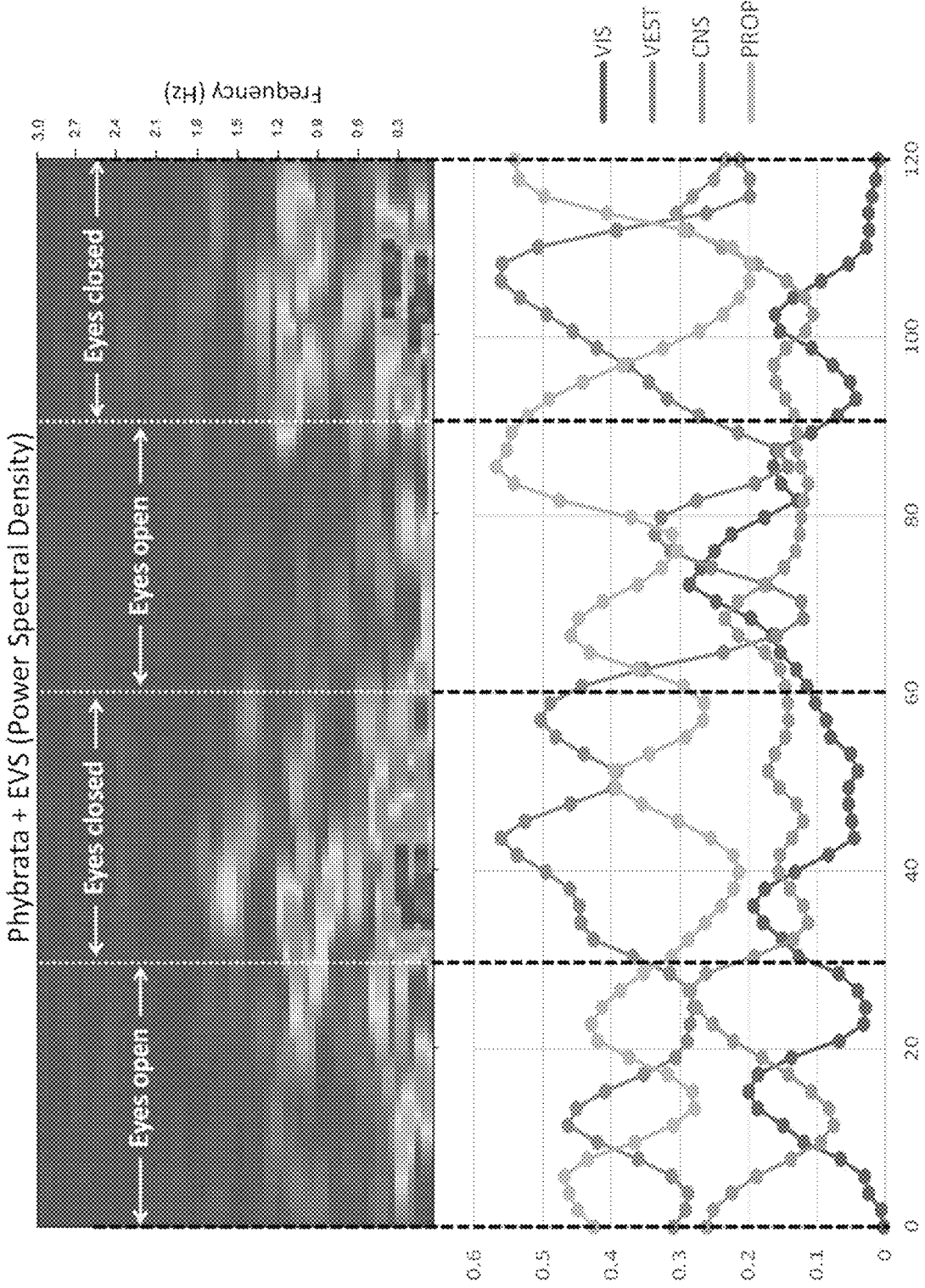
FIG. 53 are plots of sensory reweighting data collected using a neurophysiological sensing system with a user's eye open (Eo), and eyes closed (Ec), which can be used to derive phybrata signatures for optimizing EVS signals applied to the user via a stimulation assembly that may be included in the neurophysiological sensing system.

FIG. 53 are plots of time-resolved frequency-domain phybrata data (top trace) and phybrata sensory reweighting data (bottom trace) collected using a neurophysiological sensing system with a user's eye open (Eo) and eyes closed (Ec), which can be used to derive phybrata signatures for optimizing EVS signals applied to the user via a stimulation assembly that may be included in the neurophysiological sensing system.

Figure 54A:
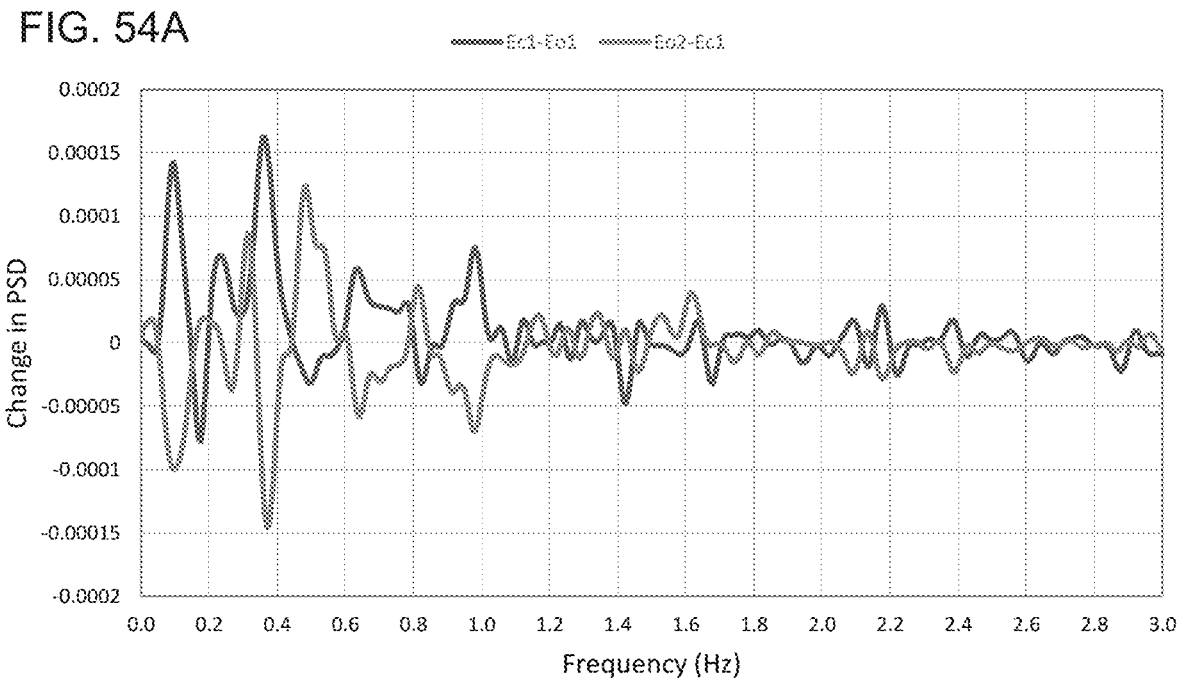
FIG. 54A-54B are plots of sensory reweighting data collected using a neurophysiological sensing system with a user's eye open (Eo), and eyes closed (Ec), which can be used to derive phybrata signatures for optimizing EVS signals applied to the user via a stimulation assembly that may be included in the neurophysiological sensing system.
Figure 54B:
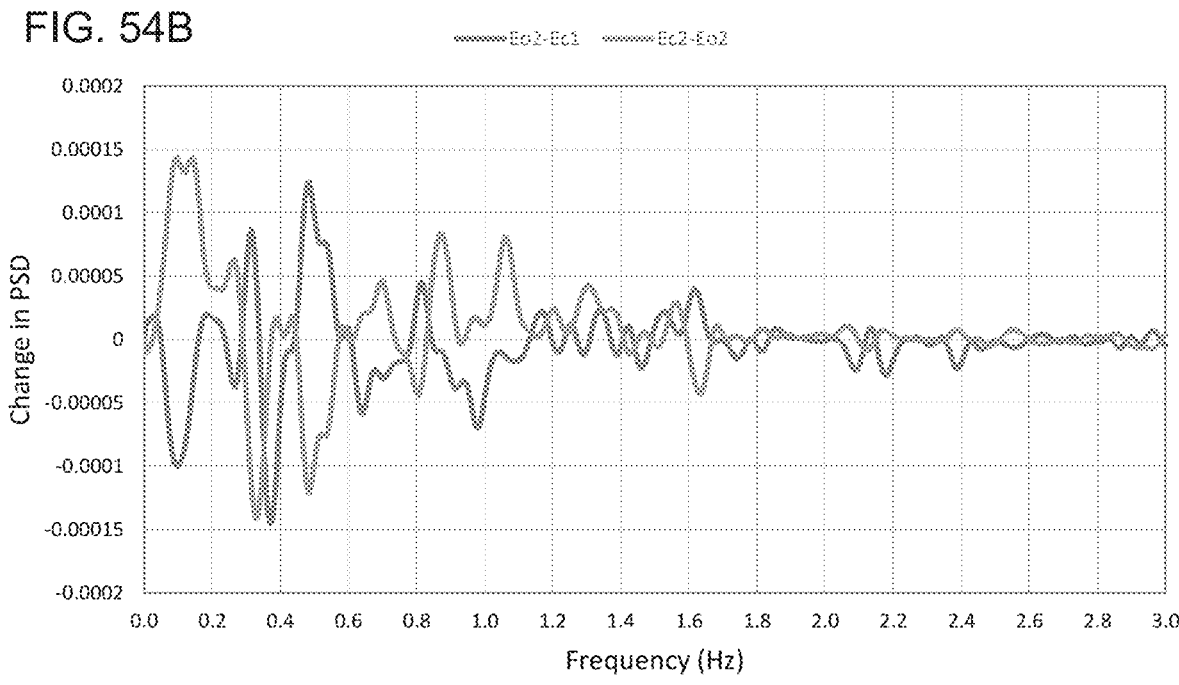
Figure 55:
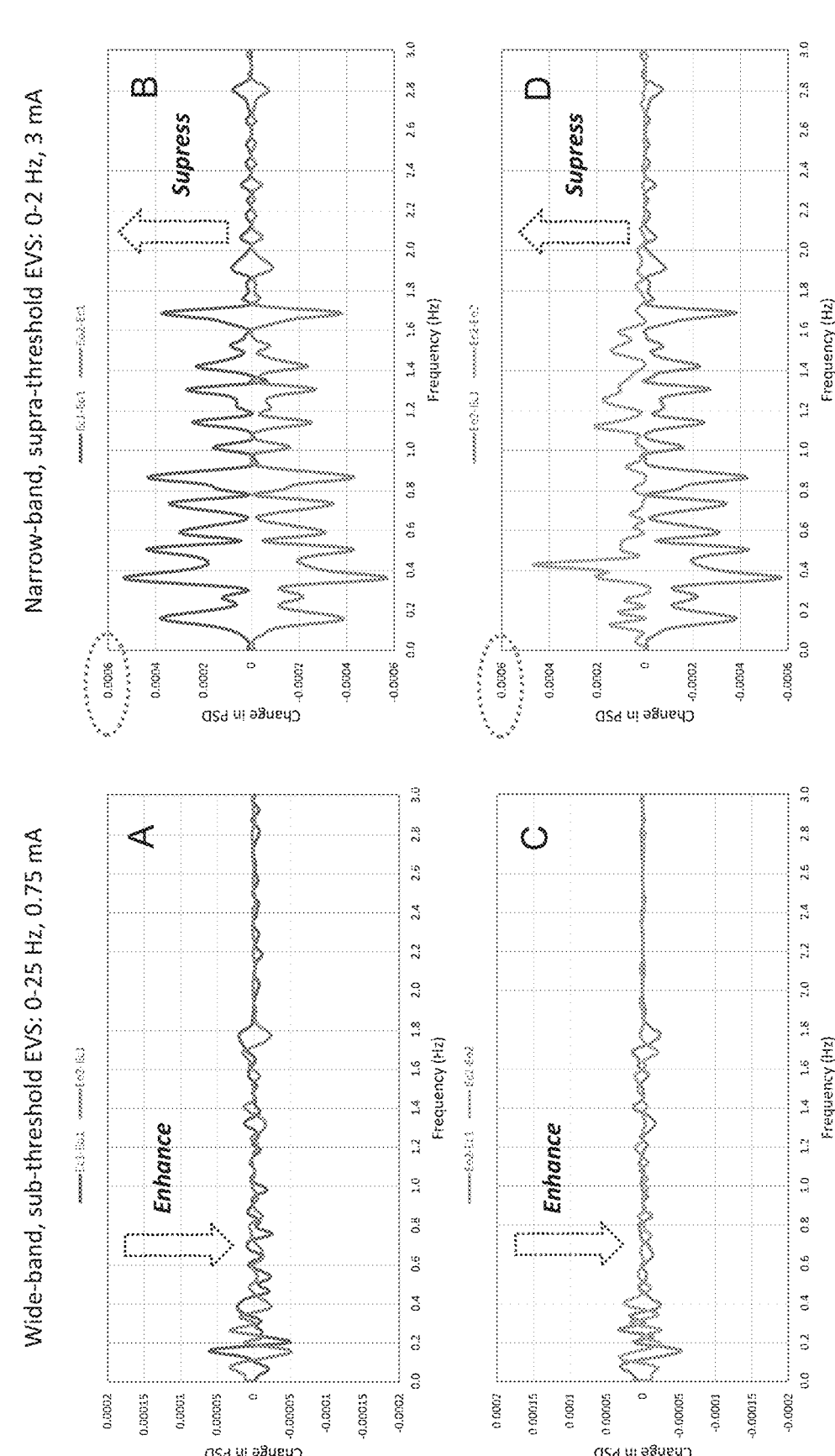
FIG. 55, panels A-D are enhanced (panels A and C), and suppressed (panels B and D) of sensory reweighting data collected using a neurophysiological sensing system with a user's eye open (Eo), and eyes closed (Ec), which can be used to derive phybrata signatures for optimizing EVS signals applied to the user via a stimulation assembly that may be included in the neurophysiological sensing system.

FIG. 54A-54B are plots of sensory reweighting data collected using a neurophysiological sensing system with a user's eye open (Eo), and eyes closed (Ec), which can be used to derive phybrata signatures for optimizing EVS signals applied to the user via a stimulation assembly that may be included in the neurophysiological sensing system. FIG. 55, panels A-D are EVS-enhanced balance control (panels A and C), and EVS-suppressed balance control (panels C and D) quantified using sensory reweighting data collected using a neurophysiological sensing system with a user's eye open (Eo) and eyes closed (Ec), which can be used to derive phybrata signatures for optimizing EVS signals applied to the user via a stimulation assembly that may be included in the neurophysiological sensing system. FIGS. 54A-54B, and FIG. 55, panels A-D illustrate phybrata sensor reweighting data.

At step 3 in FIG. 47, once vestibular performance improvement is observed, multisession stimulation signal therapy using the sensing and stimulation assembly described herein is initiated. For example, clinicians can then prescribe the appropriate 6-12 weeks, inclusive, EVS therapy, with the patient typically wearing the device 1-5 times a week, inclusive, for 10-30 minutes, inclusive, during each session, during which the optimized EVS signal from step 2 is applied. Single-session EVS therapeutic improvement can persist for 24-72 hours, inclusive. Multi-session (12 weeks) therapeutic improvements can persist up to 6 months. The ability to monitor the patient's response as the EVS is being applied and progress over time enables adaptive therapeutic treatment that's personalized to each patient's unique balance impairment and recovery trajectory. FIG. 56, panels A-D are phybrata spatial scatter plots (panels A-C) and Ec/Eo phybrata power ratio histograms (panel D) from a sequence of pre-EVS therapy baseline tests and post-EVS therapy treatments demonstrating cumulative and persistent EVS-induced improvements in the balance performance of a user with a head-impact-induced vestibular balance impairment.

At step 4 in FIG. 47, the patient's response is monitored during each stimulation signal therapeutic session, enabling adaptive therapeutic treatment personalized to each patient's unique balance impairment and recovery trajectory. Monitoring vestibular performance improvement over the length of the stimulation therapy treatment allows the clinician to continuously assess the patient's response to the EVS or any other stimulation signal therapy. In some embodiments, the clinician may adjust the EVS stimulation parameters prior to or following each therapeutic session to achieve continuing improvement or to increase the level of improvement. In some embodiments, the target level of vestibular performance improvement to be achieved over the multi-week duration of the EVS treatment is the level observed when the optimized EVS signal is applied in the initial diagnostic session in step 2.

At step 5 in FIG. 47, if and when no further vestibular performance improvement is observed, the EVS or any other stimulation signal therapy treatment can be ended. In some embodiments, the patient may then undergo follow-up assessments as in step 1 and step 2, and the stimulation signal (e.g., EVS) therapy treatment can be repeated using the sensing and stimulation assembly. In some embodiments, steps 1-5 are carried out by a clinician. In some embodiments, steps 1 and 2 are carried out by a clinician, who then prescribes at-home use of the sensing and stimulation assembly, and the patient then carries out steps 3-5 at home. In some embodiments, steps 1-5 are all fully automated by the system (e.g., the system 100, 200, 400) including the sensing and stimulation assembly, allowing the patient to obtain the sensing and stimulation assembly from a clinical provider or a pharmacy and carry out steps 1-5 at home. In some embodiments, the sensing and stimulation assembly is worn continuously to provide continuous assessment and adaptive correction of vestibular balance impairments and related fall risks, similar to the manner in which a hearing aid is worn continuously to provide continuous assessment and adaptive correction of hearing impairments.

The assessment of postural instabilities and impaired balance, which are related to changes in cortical, sensory, and motor functions, is recognized as an important non-invasive tool in the treatment of a wide range of medical conditions, including as a component of pre-hospital and clinical stroke scales. Studies comparing the outcome of instrumented posturography and the most commonly used clinical functional balance tests indicate that instrumented posturography provides more reliable feedback on stroke patients' balance impairments and should be recommended for use in clinical practice in addition to clinical functional tests. Instrumented balance testing can reveal patient-specific balance control problems following stroke, can direct treatment, and can monitor rehabilitation of post-acute stroke patients.

Theoretical and experimental studies have revealed a combination of passive, intermittent, and continuous control of human balance in order to minimize energy consumption while maximizing stability. Measurements of human postural sway in quiet stance reveal a motion spectrum with frequencies in the range 0-20 Hz, which is the physiologically relevant range of joint oscillations, and amplitudes on the order of mm to cm, reflecting both natural and pathological involuntary motion caused by delays and gains inherent to the above biological feedback and control systems. Time-resolved postural sway data reveal the combination of passive, intermittent, and continuous control of human balance, and can discriminate four distinct frequency bands that correspond to the following mechanisms of postural control: 2-20 Hz (spinal reflexive loops, proprioception, multi-joint and muscle activity); 1-2 Hz (cerebellar); 0.2-1 Hz (vestibular); and 0.02-0.2 Hz (visual).

Changes in this motion spectrum can quantify cerebellar, proprioceptive, vestibular, and oculomotor ataxia's due to stroke, MS, brain tumor, head injury, and other causes of damage to different motor or sensory regions of the central nervous system, as well as from peripheral nerve pathology. Features extracted from quantitative posturography have been shown to enable localization of cerebellar lesions and quantitative studies of cerebellar diseases. As described herein, the lightweight, mastoid-mounted sensing assemblies can capture the richest set of motion signals. Since the sensing assembly described herein specifically measure physiological vibration accelerations, these motions are therefore referred to as "phybrata". The head serves both as an egocentric reference for balance, walking, and most other voluntary motor activities, and is also the recipient of significant blood flow directed toward the brain. Since phybrata signals are non-stationary, time-frequency analysis and other non-linear spectral analysis tools must be applied in order to capture the significant time varying spectral changes that result from intermittent control using multiple physiological system inputs and outputs. In the present disclosure, ensemble-average time-frequency phybrata distributions may be utilized to identify statistically significant spectral features that can distinguish patients vs. control groups.

In some embodiments, the sensing assemblies described herein may also record ballistocardiographic (BCG) head movements (predominantly vertical), which enable lead-free heart rate monitoring, as well as intercranial pulsatility-induced motion of the head (predominantly left-right) due to pulsatile cerebral blood flow (PCBF). PCBF motion can be utilized to quantify hypertension, a key risk factor for stroke associated with diffuse brain tissue atrophy and white matter degeneration. In some embodiments, the sensing assemblies described herein may also include a photoplethysmographic optical blood flow sensor (PPG) that simultaneously captures the subject's heart-rate information, providing a gating signal for phase locked detection to increase the signal-to-noise ratio (SNR) of the BCG and PCBF signals.

The study of cardiovascular function with galvanic vestibular stimulation has shown that changes in neural structures involved in the vestibulo-autonomic reflex can lead to changes in heart rate that persist following EVS, and that this response differs when using unilateral or transmastoid (bilateral) stimulation. In some embodiments, the sensing and stimulation assembly described herein can be used to reduce heart rate and heart rate variability associated with postural orthostatic tachycardia syndrome (POTS), a condition that affects circulation and blood flow. Heart rate and blood pressure work together to keep the blood flowing at a healthy pace, which requires constant adaptation to changes in the body's orientation. This process involves the autonomic nervous system, which automatically controls and regulates vital bodily functions, and which has a significant reliance on proper functioning of the vestibular system to provide information on the orientation of the body. Improper functioning can lead to orthostatic intolerance, in which symptoms such as lightheadedness, fainting and an uncomfortable, rapid increase in heartbeat develop when standing up from a reclining position.

People with POTS cannot coordinate the balancing act of blood vessel squeeze and heart rate response. This means the blood pressure cannot be kept steady and stable. In some embodiments, the sensing systems described herein may be configured to detect changes in body orientation, the photoplethysmographic optical blood flow sensor (PPG) captures related changes in the subject's heart-rate information, and the stimulation system applies transmastoid EVS stimulation to prevent POTS-related increases in heart rate.

The rich set of phybrata features detected by the sensing assemblies described herein may allow quantitative metrics to be constructed and used with high levels of sensitivity and specificity to classify medical conditions such as stroke type and severity for patients with stroke. Data collected using the sensing assemblies described herein in longitudinal observational clinical studies, along with additional patient tests and assessments during a wide range of regular clinical assessments, research studies, and clinical trials support the assessment of new therapies and treatments targeting improved care and rehabilitation of complex medical conditions. A wide range of parameters can be derived from the raw phybrata data to characterize the spatial, temporal, and frequency-domain characteristics of the patient's phybrata data, including postural, mechanocardiographic, and intercranial pulsatility features that can be used as predictive variables. Frequency domain features are particularly promising candidates as predictive variables that may show significant statistical correlation with, for example, specific stroke types due to the unique impairments they trigger in specific physiological systems. Clinical assessments and diagnoses can be used to classify ischemic strokes, for example, as follows: 1) stroke cause: thrombotic or embolic, LVO or non-LVO; 2) stroke severity: TIA, mild stroke (NIHSS<8), moderate stroke (NIHSS 8-16), severe stroke (NIHSS>16); 3) brain region: brainstem, cerebrum, cerebellum; and 4) cerebral circulation (anterior, posterior), hemisphere (left, right), lobe (parietal, frontal, temporal, occipital).

Combining phybrata data from stroke patients and age-matched healthy patients allows quantification of both absolute values of various potential predictive variables and differences with respect to healthy population normative values. Statistical analyses can include cumulative probability distributions (CPDs), univariate and multivariate regression analyses, and the training of machine learning models. Univariate logistic regression models can first be constructed to assess the strength of the association between each of the potentially predictive variables and diagnosed outcomes. Multivariate logistic regression models can then be constructed to predict the same outcomes in the same cohort. Variables found to be associated with p values <0.20, for example, in the univariate models can be included in the multivariate models. A backward model selection procedure can then be applied to eliminate the variables with higher p values and construct multivariate logistic regression models using variables with p values <0.05, for example, for the target outcomes.

Figure 57:
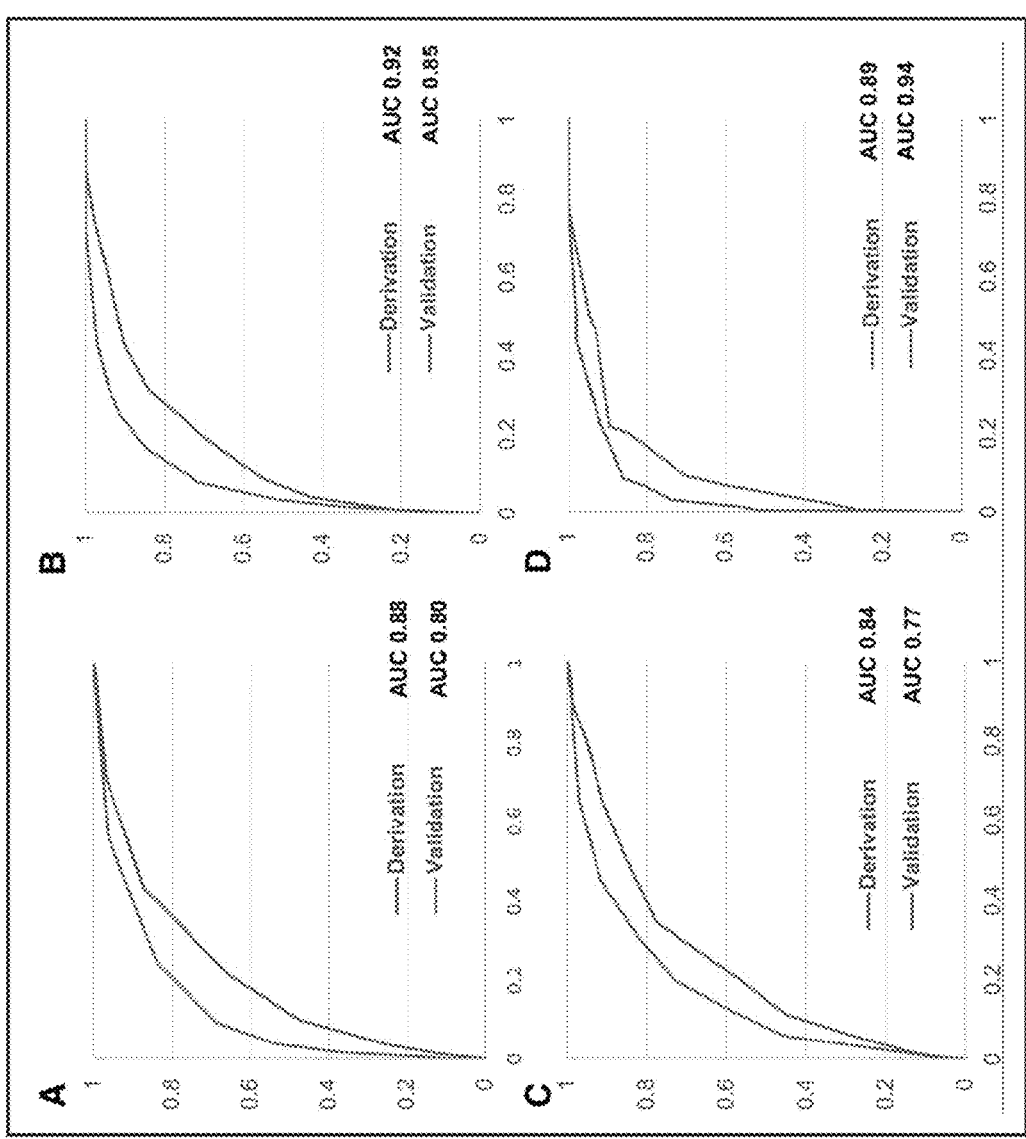
FIG. 57, panels A-D show example receiver operating characteristic (ROC) curves for the machine learning classification of different stroke types.

Correlations can be quantified between these models and, for example, pre-hospital stroke assessment scales, baseline NIHSS scores, and 30/60/90-day outcomes using conventional stroke severity scores. Changes in the values of candidate predictive variables can also be analyzed over extended periods of time to identify trends observed between intake, treatment, discharge, and rehabilitation. Multivariate regression models can be constructed as above using phybrata data and demonstrating statistically significant correlation (for example, p<0.05) with target diagnostic outcomes. These multivariate logistic regression models are then used to develop clinical prediction rules, and the discriminatory performances of the rules is assessed by analyzing the receiver-operating characteristic curves when these rules are applied to larger validation cohorts and a wider range of target stroke outcomes, as illustrated in FIG. 57, panels A-D, which show example receiver operating characteristic (ROC) curves for the classification of different stroke types.

FIG. 58A is a schematic block diagram illustrating a design process for a catalog of health impairment models that can be used to classify specific medical conditions, according to an embodiment. Data collected from stroke populations or other populations of clinical interest is further utilized for machine learning model training and optimization to maximize diagnostic sensitivity and specificity, track changes in patient phybrata signals during treatment and rehabilitation, and enhance the physical interpretation of classification results by visualizing data features that contribute to classification of specific disorders. The above data analyses determine the additional enhancements in sensitivity and specificity with which the machine learning models included in the neurophysiological sensing and stimulation systems (e.g., the system 100, 200, 400) described herein can classify strokes or other clinically relevant medical conditions based upon feature sets present in the phybrata data compared to logistical regression models. Applications of the phybrata data also include quantifying the efficacy of rehabilitation practices and therapeutics within clinical healthcare and rehabilitation organizations.

In some embodiments, the phybrata data may be further utilized to develop and train machine learning models that automate a variety of data inspection and analysis tasks. Machine learning tools are already used to help clinicians translate complex biomedical data sets such as brain images, patient biopsy images, and electrocardiogram (ECG) waveforms into accurate and quantitative diagnostics. Deep learning approaches using a convolutional neural network (CNN) can identify features automatically, enabling end-to-end classification of time series data generated by devices such as the phybrata sensor described here without any upfront feature engineering or data preprocessing.

The systems and methods described herein may adapt a deep learning signal classification model using a low-complexity CNN designed specifically for time series classification. A catalog of machine learning models may be developed, as shown in FIG. 57 to classify specific medical conditions based upon unique patterns of spatial, time domain, and frequency features detected in phybrata data. Specific medical conditions include those identified as high priorities by clinical partners, all of which have all been shown in the medical literature to provoke symptoms that include balance impairments observable via postural stability testing.

Figure 58B:
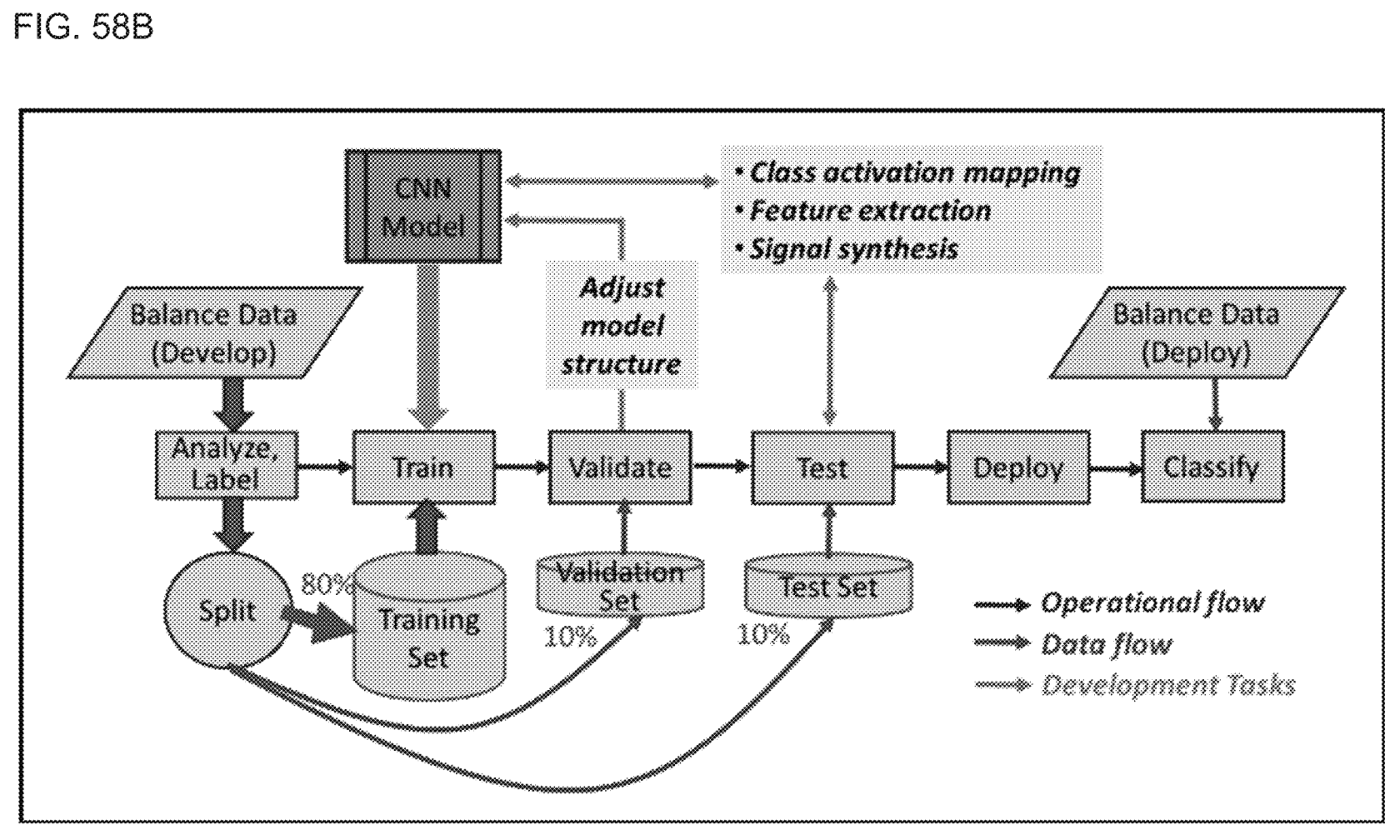
Figure 59:
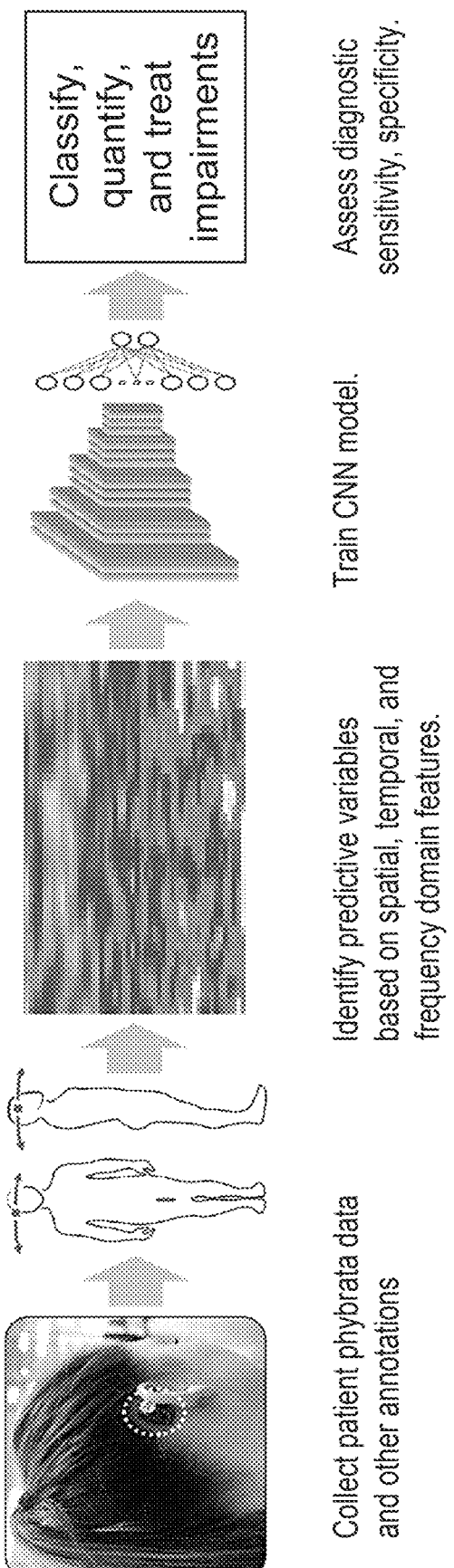
FIG. 59 is an illustration of a method for detection of patterns in phybrata data and their use as digital biomarkers to classify, quantify, and treat specific impairments, according to an embodiment.

Phybrata data may be further utilized for: CNN machine learning model training, as illustrated in FIG. 58B, which is a schematic block diagram of a process of CNN model training, performance testing, and balance signal synthesis, according to some embodiments. The ability to extract patterns from phybrata data and use these patterns as digital biomarkers to classify, quantify, treat specific impairments, as shown in FIG. 59, enables earlier detection; better quantification of treatment/rehab outcomes; tracking of changes in patient phybrata signals as a result of disease progression, treatment, or rehabilitation; enhancing the physical interpretation of classification results by visualizing data features that contribute to CNN classification of specific disorders (FIG. 58B); and comparative analyses with synthetic phybrata signals generated from predictive human phybrata models to identify quantitative signatures that distinguish different physiological impairments and health risks.

The classification performance of any trained machine learning model is ultimately limited by the accuracy with which the data collector labels training data sets. As described herein, the observed statistical correlations between specific disorders and elevated phybrata levels are utilized as a tool to refine and improve the accuracy of training data classification. The physical interpretation of CNN classification results is a challenge that has received a great deal of attention in image processing, due to the impressive classification performance but limited understanding of why they perform so well.

In contrast, systems and methods described herein use Class Activation Mapping to identify contributing spatial, temporal, and frequency regions/features in the raw data that activate specific filters within the CNN during signal classification. Time series data are then synthesized with specific features and statistical behaviors that model the CNN neural activation process, analogous to recent approaches in image processing. These synthesized signals then serve as the basis for the development of a biomechanical model as previously described, leveraging the extensive bodies of literature related to modeling human postural sway and developing bipedal robots capable of mimicking human motor functions. This model can be used to generate comparative phybrata signatures to support the identification of quantitative signatures that distinguish different physiological impairments and health risks. Such phybrata signatures may include: 1) the intermittent timing, durations, and delays, and gains in CNS integration of afferent inputs and generation of efferent outputs, calculated from time and frequency spectral analyses of the phybrata signals; 2) the specific gain reductions and delays introduced into each of the afferent neural input signals that are processed and integrated to maintain postural stability (such gain reductions and delays result from impairments in the patient's sensory, musculoskeletal, cardiovascular, and central nervous systems, and are calculated from time and frequency spectral analyses of the phybrata signals); and 3) the reductions in the accuracy and timing coherence of the efferent neural output signals that carry neural impulses away from the central nervous system (cortical and cerebellar) and toward muscles to initiate the motor movements required to maintain postural stability (such reductions in accuracy and timing are calculated via fitting of measured phybrata signals to synthetic phybrata signals predicted by the biomechanical model).

Having identified phybrata signal features that correspond to target disorders, the synthesis of postural sway signals is then exploited in the present invention to mimic specific disorders by maximizing classification activations, as illustrated in FIG. 58B. For example, training data is scanned to find those signals that maximize certain filter activations. Those input signals that give the strongest output for the "healthy" class and each disorder class are then reverse engineered in order to generate synthetic time series data with specific features and statistical behavior that model those classes. One example target is to maximize internal unit activation with these reverse engineered inputs, by observing which internal filters fire most for each class, and then reverse engineer an input signal that maximizes the output of that filter. Thus, machine learning models are trained to classify a wide range of specific impairments, allowing the development, evaluation, and release of an expanding catalog of impairment/risk models that can be used to flag many different potential health risks across many different populations using wearable sensor data gathered in a non-invasive one-minute phybrata test using a sensor small enough to be worn behind the ear by users of any age.

FIGS. 60-63 describe results from a machine learning impairment classification study in which phybrata data were analyzed from 175 patients at three clinical sites. Phybrata testing using the sensing assemblies described herein was included in regularly scheduled clinical patient assessments, the study was conducted in accordance with the Declaration of Helsinki under Western IRB Study Number 1,188,786, and informed consent was obtained for all participants in the study. Study participants included 94 females and 81 males (ages 18.1±10.9 years, min 7 years, max 66 years), including 92 patients diagnosed with concussion (51 female, 41 male, ages 18.8±13.2 years, min 7 years, max 74 years) and 83 healthy participants (43 female, 40 male, ages 17.2±7.7 years, min 8 years, max 74 years). Comprehensive clinical concussion assessments were first completed for all patients, followed by testing with the phybrata sensing assembly. Of the 92 patients diagnosed with concussion, 26 were diagnosed with vestibular impairments via clinical assessment, 40 with neurological impairments, and 26 with both vestibular and neurological impairments. A total of six patients with incomplete phybrata signal datasets were excluded from the ML analyses, leaving a sample size of 169 patients.

Patients were tested using phybrata sensing assembly described herein attached to the patient's mastoid using a disposable medical adhesive while patients stood still for 20 seconds with Eo and then again for 20 seconds with Ec. During testing, participants were instructed to stand upright in a relaxed position with their feet together and their arms at their sides while maintaining their gaze in a straight-ahead direction. The phybrata sensing assembly that was used for collecting the data included a 3-axis accelerometer to record x (anterior-posterior (A-P), or front-back), y (vertical), and z (medial-lateral (M-L), or left-right) acceleration time series data in units of g. During each 20 second test data are recorded at a sampling rate of 100 Hz, generating a total of 2,000 samples for each of the 3 axes (x, y, z). The accelerometer signals are filtered to remove drift. Phybrata time-series data and spatial scatter plots, Eo and Ec phybrata powers, average power (Eo+Ec)/2, Ec/Eo phybrata power ratio, time-resolved phybrata signal power spectral density (PSD) distributions, sensory reweighting profiles, and ROC curves were compared for individuals with no objective impairments and those clinically diagnosed with concussions and accompanying vestibular impairment, neurological impairment, or both vestibular and neurological impairments. Manual feature extraction and ROC analyses indicated that the average power (Eo+Ec)/2 may be utilized to support clinical diagnosis of concussion, while Eo and Ec/Eo may be utilized as independent measures to confirm accompanying neurological and vestibular impairments, respectively. All three measures demonstrated AUC, sensitivity, specificity, and accuracy above 90% for their respective diagnoses.

The following two preprocessing pipelines were utilized to prepare the phybrata time series data for the ML analyses for both binary classification of study population into "healthy" vs. "concussion" groups (Use Case 1) and, for the above "concussion" group, multiclass prediction of specific physiological impairments as "vestibular" vs. "neurological" vs. "both" (Use Case 2):

1. Time-Series Averaging (TSA): For each Eo and Ec patient test phase, the three phybrata time-series signals (x, y, z) and the phybrata power (calculated using the vector sum of the three acceleration components) were averaged over one-second timesteps (100 samples per step), reducing the dimensionality of each time series from 2000 samples to 20 samples. Once averaged, the data were either used in their existing form for CNNs or converted such that each time-step represents a column instead of a row for classical ML models. There are two reasons for using this averaging approach as an alternative to using the raw signal. First, the raw data contains 6,000 measurements per patient test (100 Hz sampling over 20 s for each of the x, y, and z axes), which presents challenges for training classical ML models, since the number of data features greatly exceeds the number of patients. This excessive number of features can lead to models that overfit and generalize poorly to data from new patients. Second, the computational advantages in using an averaged timeseries instead of a full time-series signal recording can enable much faster and lower computational complexity training and classification, allowing the use of remote sensor devices that do not require cloud connectivity for computational support. No frequency features were extracted from the TSA preprocessed data.

2. Non-Time-Series (NTS) Feature Extraction: Standard statistical measures (variance, mean, standard deviation, min, max and median) were calculated for each of the three phybrata time-series signals (x, y, and z accelerations) and several additional power and frequency features extracted for both Eo and Ec test phases, including phybrata powers within the physiological-system-specific frequency bands discussed above. To extract the power features, the phybrata power was first calculated at each value in the accelerometer time-series data. The power values were then summed for each respective test phase (e.g., Eo Power and Ec Power) and the powers for the two phases were averaged (e.g., (Ec+Eo)/2). Phybrata signal PSD curves were also calculated using Welch's method and these PSD curves were then used to calculate phybrata powers within specific frequency bands. PSD variations within specific spectral bands, as well as correlated PSD variations across multiple spectral bands, were shown to help quantify the sensory reweighting that often accompanies many neurophysiological impairments and may thus also serve as useful ML classification features.

Figure 60:
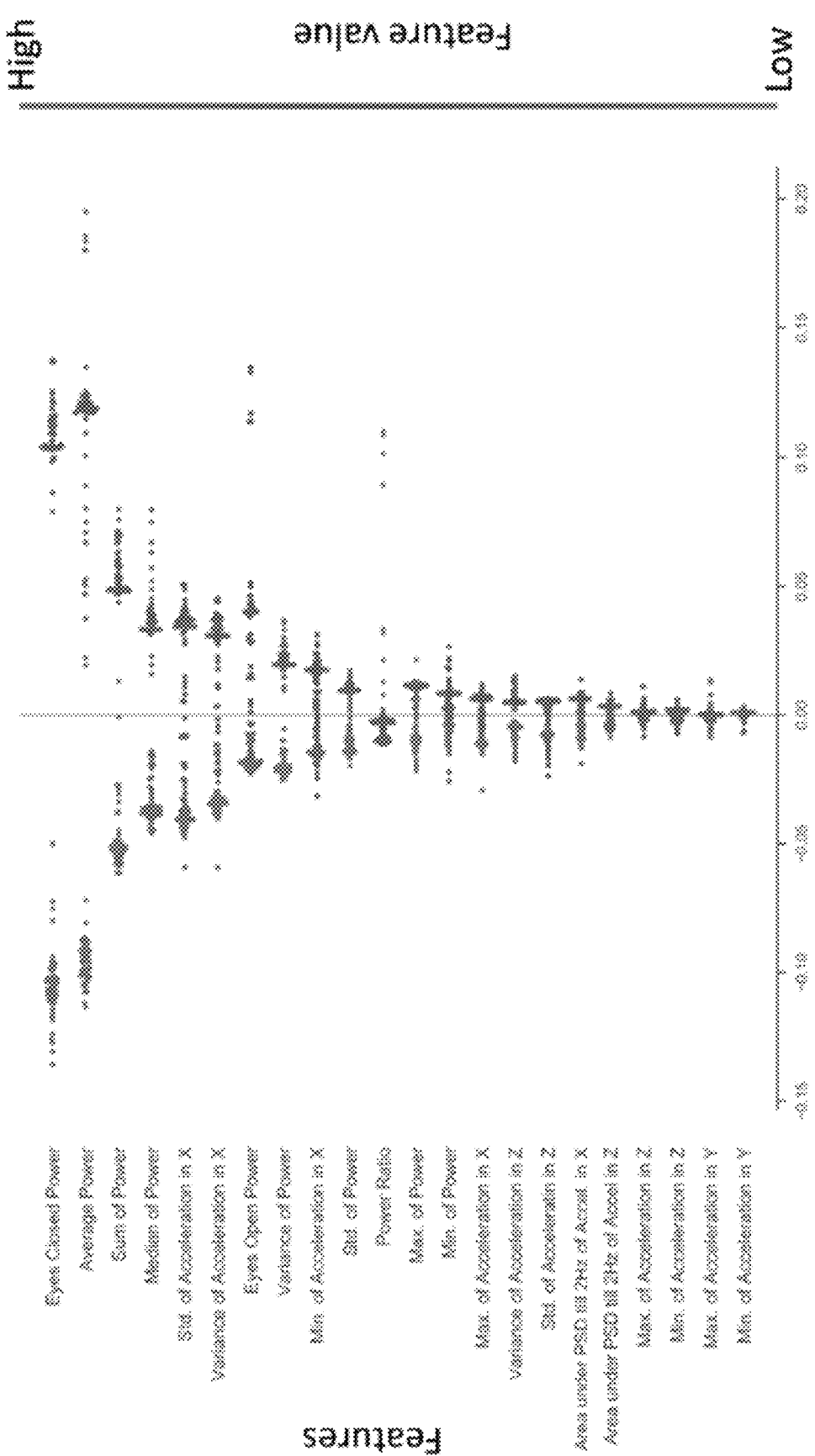
FIG. 60 are plots of Random Forest SHAP values for all patients in the training set (n=108). Features are ranked top to bottom (top being the largest contributor). A single point represents a patient's SHAP value for a given feature. Along the x-axis, a positive (negative) SHAP value indicates the features' impact toward classifying a patient as concussed (healthy control).

Shapley additive explanations (SHAP) is a method for explaining how complex machine learning models make decisions with the data they receive by computing the magnitudes of the contributions from each individual feature to a model's output. FIG. 60 presents the SHAP values for features derived from the x-axis phybrata signals of training set patients for the best performing RF model. Feature importance is ranked from top to bottom (left y-axis). The two most robust features in terms of their contributions to classification are the Ec power and average power, consistent with previous results. The third and fourth most robust predictors were the sum and median power, which showed a similar pattern of values in relation to outcome. These power features are followed by the x acceleration features, particularly standard deviation and variance in the global x (A-P) signal. Notable features that were considered reasonably useful for RF training and prediction were eyes-open power, the variance of power, and the Ec/Eo power ratio. The y (vertical) and z (M-L) features were found to be less robust in prediction for RF. The actual values of the features (right y-axis) are suggestive that higher x (A-P) accelerations and phybrata powers (red) are linked with a prediction of concussion, while lower accelerations and powers (blue) and smaller x feature values are linked with a prediction of healthy, with the exception of the global minimum for x (Min. of Accel X) and z (Min. of Accel Z). Less significant z and y features for RF also appear clustered around the center axis at the bottom of the plot, indicating minimal predictive impact on model output.

Figure 61:
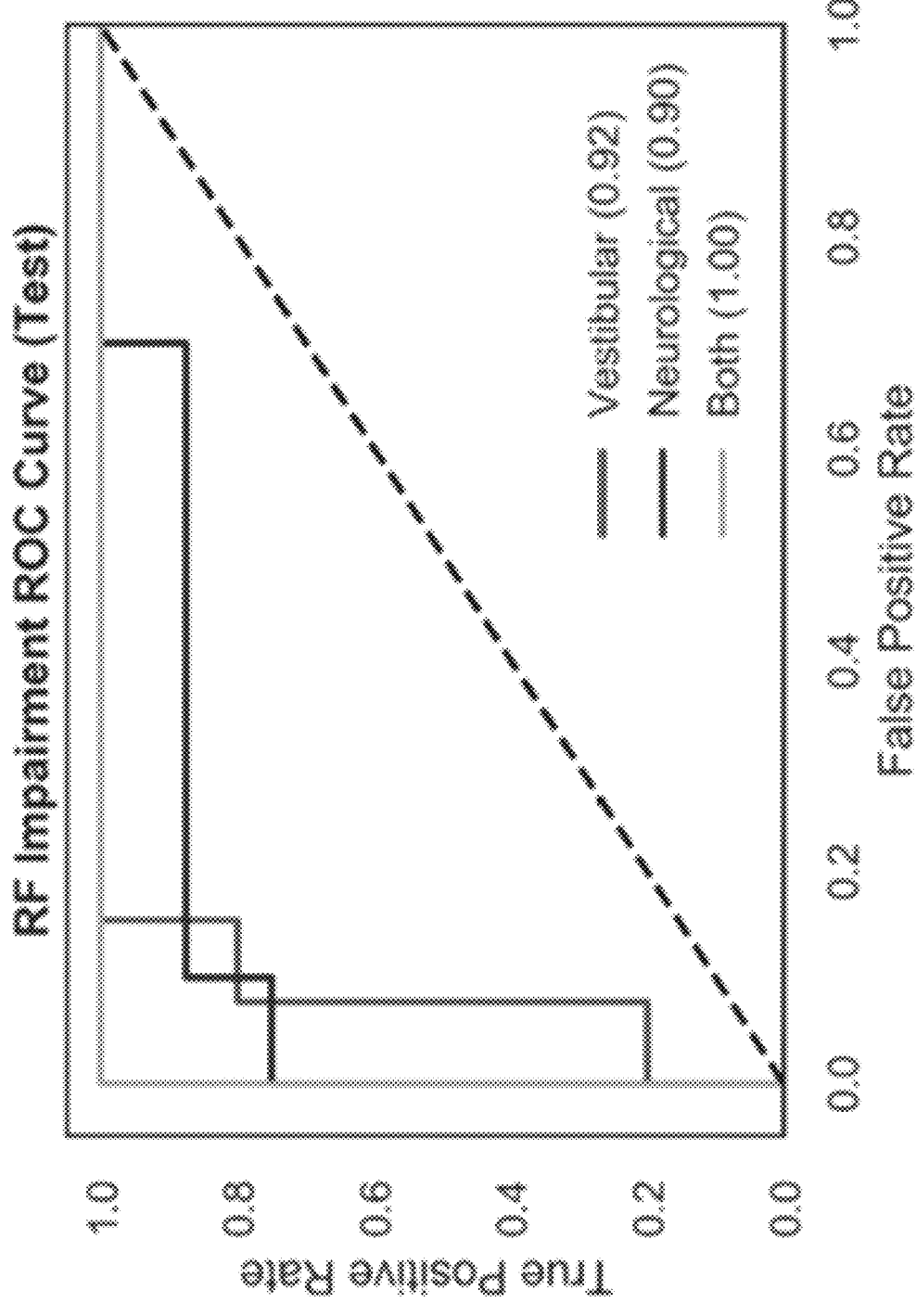
FIG. 61 are ROC curves for multiclass impairment prediction using the RF model and NTS preprocessing pipeline. Each curve represents the specific impairment vs. the rest of the classes (one vs. rest) and depicts the trade-off between True Positive Rates (TPR) and False Positive Rates (FPR) for each physiological impairment condition. The ROC performance is based upon the optimal threshold selected by the model for the testing set. The three colored curves correspond to vestibular impairment=green, neurological impairment=blue, both=yellow. The dotted black line represents random performance.

FIG. 61 presents RF test ROC curves for the multiclass impairment prediction, with each curve representing the specific impairment vs. the other two diagnoses (vestibular vs. rest; neurological vs. rest; both vs. rest). ROC curves represent the tradeoff between the True Positive Rate (TPR) and False Positive Rate (FPR) for an optimized decision threshold. This decision threshold is learned during model training and translated to the testing set used to generate the curves in FIG. 61. The area underneath each curve (AUC) in FIG. 61 quantifies model performance in relation to TPR and FPR. Vestibular and neurological ROC curves showed AUC scores of 0.92, and 0.90 respectively, while the ROC curve for patients with both impairments exhibits an AUC of 1.00.

Figure 62:
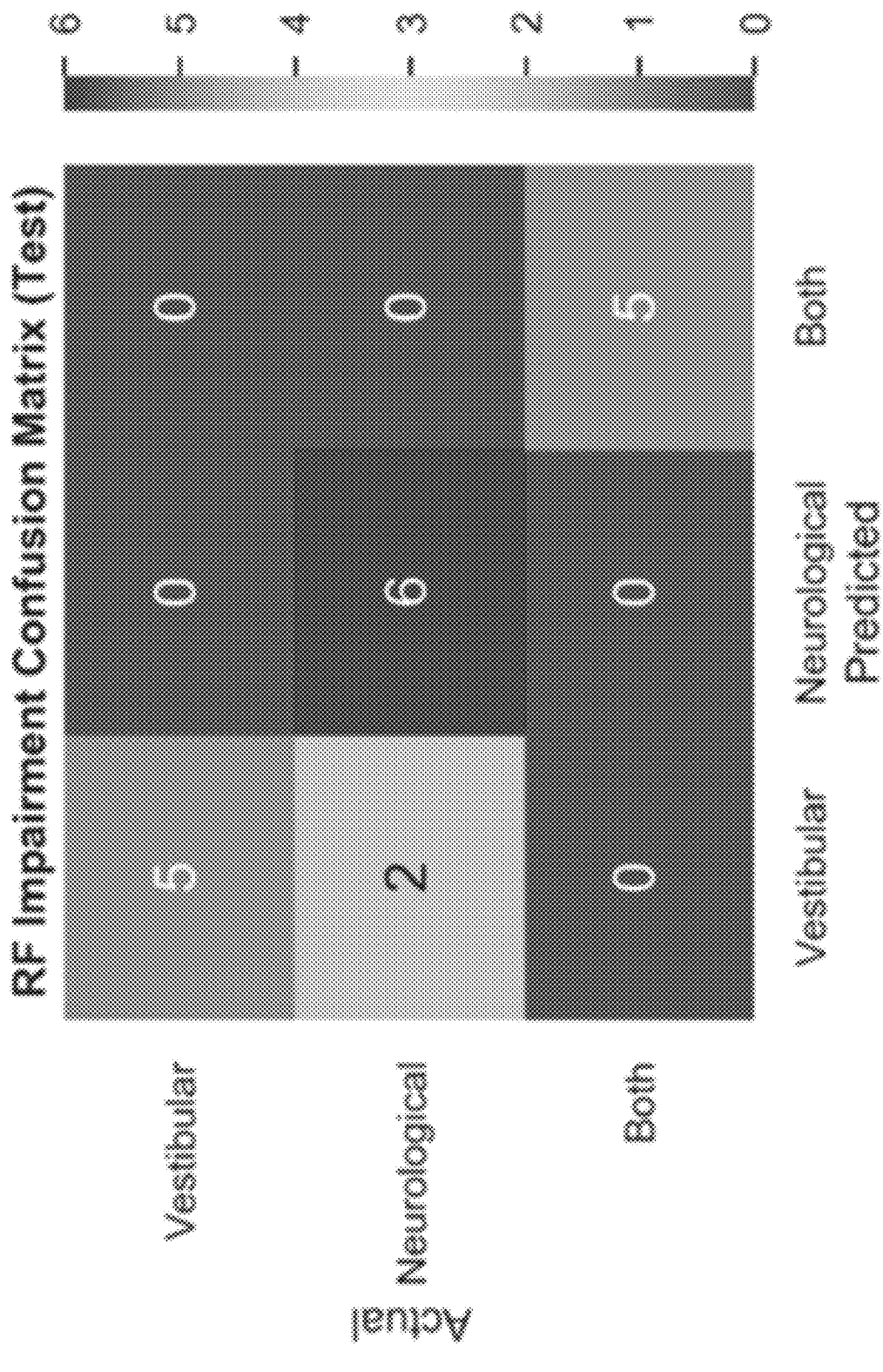
FIG. 62 is a testing set confusion matrix for the RF machine learning model. Model predictions for each impairment (x-axis) are contrasted with actual impairment outcomes (y-axis) to categorize the correct and incorrect predictions made.

FIG. 62 depicts the RF testing set confusion matrix (n=18) for the three impairment classes. RF correctly classified all vestibular (1.0, 5/5) patients, most neurological (0.75, 6/8) patients, and all patients with both (1.0, 5/5) impairments. The two mistakes in the test set both relate to model predictions of vestibular impairments for patients who had been clinically diagnosed with neurological impairments.

Figure 63:
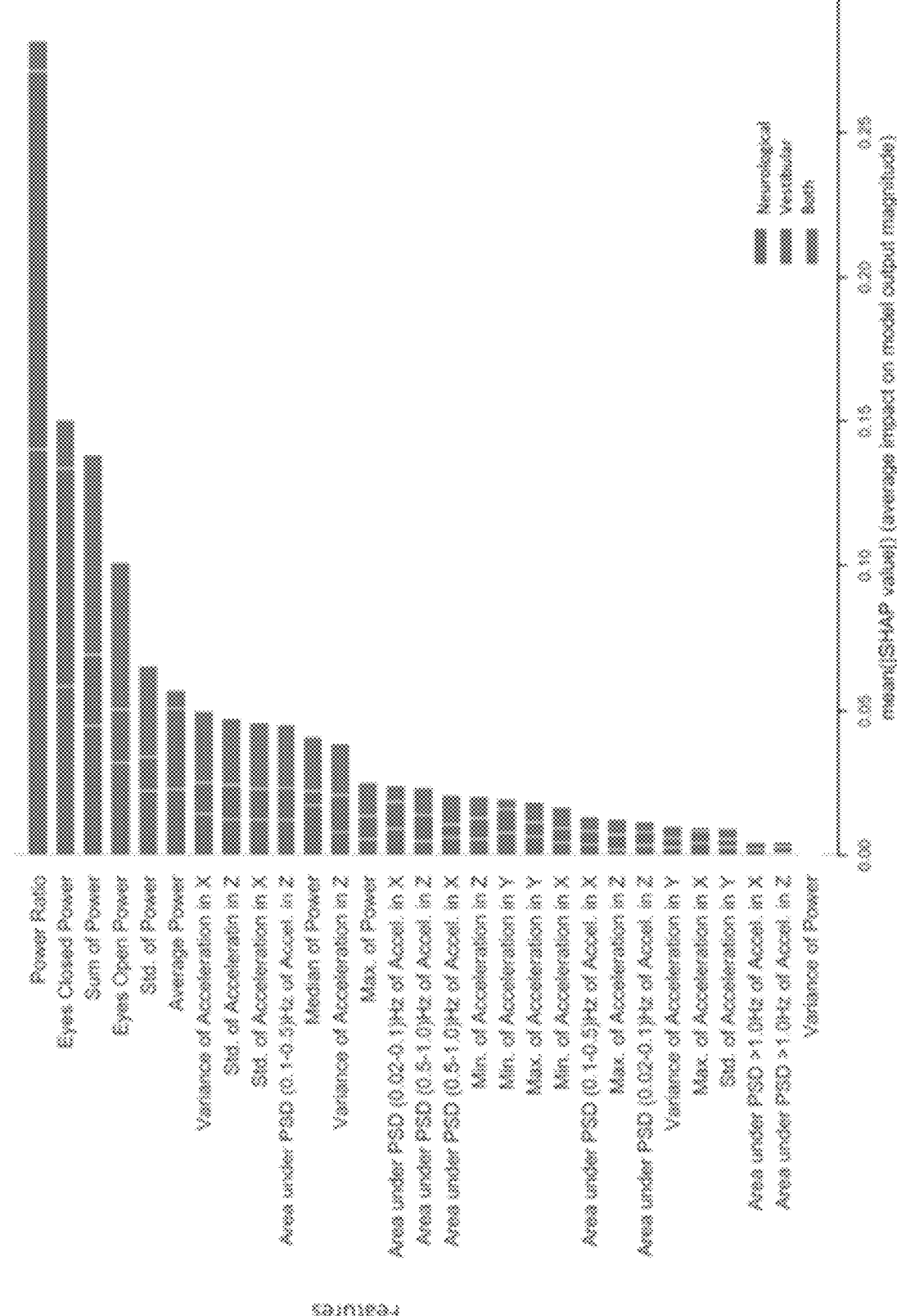
FIG. 63 are bar charts of mean SHAP value contribution (x-axis) of each feature (y-axis) for every impairment condition ranked from top to bottom in terms of importance.

FIG. 63 presents SHAP value rankings of feature importance for the multiclass application of the RF model using the NTS preprocessing pipeline. The Ec/Eo power ratio was clearly the most robust predictor overall in the NTS RF model, contributing significantly to the classification of neurological (SHAP=0.14) and vestibular (SHAP=0.13) impairments as opposed to both (SHAP=0.01). Ec and Eo power features made the second and fourth largest contributions, and also captured unique aspects of variation in each impairment that differ from the Ec/Eo power ratio. In particular, Ec power contributed to neurological (SHAP=0.05) and vestibular (SHAP=0.08) impairment classifications, but very little for individuals with both (SHAP=0.02). Conversely, Eo power and Sum Power account for individuals with both (Eo SHAP=0.05; Sum power SHAP=0.06) significantly better than Ec power, slightly less for neurological (Eo SHAP=0.03; Sum power SHAP=0.05) and significantly less for vestibular (Eo=0.02; Sum power SHAP=0.02) impairments.

Finally, standard deviation of power and Average Power (Ec+Eo)/two rounded out the top six features for predicting neurological impairment (Std. power SHAP=0.02; Average power SHAP=0.02), vestibular impairment (Std. power SHAP=0.01; Average power SHAP=0.03) and both impairments (Std. power SHAP=0.03; Average power SHAP=0.01). The highest-ranking phybrata frequency band feature is the "Area under PSD (0.1-0.5) Hz of Accel. in z", which is the frequency band corresponding to vestibular regulation of postural control. It is important to note here that the relative contribution of various phybrata features to specific impairments may be related to the ML model as well as the data consumed by the model, so that the SHAP value rankings shown in FIG. 63 may change for different ML models.

As used herein, the singular forms "a", "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "example" as used herein to describe various embodiments or arrangements is intended to indicate that such embodiments or arrangements are possible examples, representations, and/or illustrations of possible embodiments or arrangements (and such term is not intended to connote that such embodiments or arrangements are necessarily crucial, extraordinary, or superlative examples).

The arrangements described herein have been described with reference to drawings. The drawings illustrate certain details of specific arrangements that implement the systems, methods and programs described herein. However, describing the arrangements with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As used herein, the term "circuit" may include hardware structured to execute the functions described herein. In some arrangements, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some arrangements, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicatively coupled to one or more memory or memory devices. In this regard, the one or more processors may execute instructions stored in the memory or may execute instructions otherwise accessible to the one or more processors. In some arrangements, the one or more processors may be embodied in various ways. The one or more processors may be constructed in a manner sufficient to perform at least the operations described herein. In some arrangements, the one or more processors may be shared by multiple circuits (e.g., circuit A and circuit B may comprise or otherwise share the same processor which, in some example arrangements, may execute instructions stored, or otherwise accessed, via different areas of memory). Alternatively or additionally, the one or more processors may be structured to perform or otherwise execute certain operations independent of one or more co-processors. In other example arrangements, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory.

The one or more processors may take the form of a single core processor, multi-core processor (e.g., a dual core processor, triple core processor, quad core processor, etc.), microprocessor, etc. In some arrangements, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations.

An exemplary system for implementing the overall system or portions of the arrangements might include a general purpose computing computers in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other arrangements, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example arrangements described herein.

It should also be noted that the term "input devices," as described herein, may include any type of input device including, but not limited to, a keyboard, a keypad, a mouse, joystick, touch sensitive screen or other input devices performing a similar function. Comparatively, the term "output device," as described herein, may include any type of output device including, but not limited to, a computer monitor, printer, facsimile machine, or other output devices performing a similar function.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative arrangements. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule based logic and other logic to accomplish the various database searching steps, correlation steps, comparison steps and While this specification contains many specific implementation details, these should not be construed as limitations on the scope of any arrangement or of what may be claimed, but rather as descriptions of features specific to particular implementations of particular arrangements. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A system, comprising:
a sensing assembly configured to be disposed on a mastoid of a user, the sensing assembly including:
a housing,
a first sensor disposed in the housing and configured to measure a first physiological acceleration (phybrata) signal from the user, and
a second sensor disposed in the housing and configured to measure a second phybrata signal from the user, the second phybrata signal being different from the first phybrata signal; and
a controller in communication with the sensing assembly, the controller configured to:
receive a first phybrata data from the sensing assembly, the first phybrata data including information obtained from the first phybrata signal and the second phybrata signal,
determine a phybrata parameter associated with the user based on the first phybrata data,
determine a phybrata signature associated with the user based on the phybrata parameter;

determine a corrective electrical vestibular stimulation (EVS) parameter based on the phybrata signature, the corrective EVS parameter configured to reduce a head tremor; and
generate a corrective EVS signal indicative of the corrective EVS parameter, the generated corrective EVS signal configured to cause an electrode to apply the corrective EVS signal to the user.

2. The system of claim 1, wherein the first phybrata signal includes a linear acceleration measured over a period of time.

3. The system of claim 1, wherein the phybrata parameter includes spatial-domain parameters, time-domain parameters, or frequency-domain parameters, each of the spatial-domain parameters, time-domain parameters, or frequency-domain parameters including at least one of temporal acceleration plots, spatial scatter plots, eyes open (Eo) powers, eyes closed (Ec) powers, receiver operating characteristic (ROC) curves, phybrata power spectral density (PSD) plots, time-resolved phybrata power spectral density (TRPSD) plots, or sensory reweighting responses.

4. The system of claim 1, wherein the phybrata signature includes at least one of spatial-domain phybrata features, time-domain phybrata features, or frequency-domain phybrata features.

5. The system of claim 1, wherein the controller is further configured to:
determine a quantitative phybrata metric based on the phybrata signature, the quantitative phybrata metric configured to independently classify, quantify, and/or track a magnitude and time evolution of at least one of a balance performance, a postural stability performance, a movement performance, a physiological disruption, or a physiological impairment associated with the user.

6. The system of claim 1, wherein the controller is further configured to:
generate synthetic phybrata data associated with the user based on the first phybrata data;
determine synthetic phybrata parameters associated with the user based on the phybrata parameter;
determine a synthetic phybrata signature associated with the user based on the phybrata signature; and
determine a synthetic quantitative phybrata metric based on the synthetic phybrata signature, the synthetic quantitative phybrata metric configured to classify, quantify, and/or track a magnitude and time evolution of at least one of a balance performance, a postural stability performance, a movement performance, a physiological disruption, or a physiological impairment associated with the user.

7. The system of claim 1, wherein the controller is further configured to:
generate a biomechanical model of the user;
generate simulated phybrata data associated with the biomechanical model of the user based on the first phybrata data;
determine simulated phybrata parameters associated with the biomechanical model of the user based on the phybrata parameter;
determine a simulated phybrata signature associated with the biomechanical model of the user based on the phybrata signature; and
determine a simulated quantitative phybrata metric based on the simulated phybrata signature, the simulated quantitative phybrata metric configured to classify, quantify, and/or track a magnitude and time evolution of at least one of a balance performance, a postural stability performance, a movement performance, a physiological disruption, or a physiological impairment associated with the user.

8. The system of claim 7, wherein the biomechanical model is configured to include a range of neurosensory inputs and neuromotor outputs associated with the user.

9. The system of claim 7, wherein the controller is further configured to:

generate adjusted phybrata data based on the first phybrata data, synthetic phybrata data, and the simulated phybrata data; and determine an adjusted phybrata signature indicative of the adjusted phybrata data associated with the user.

10. The system of claim 9, wherein the controller is further configured to:

receive a second phybrata data from the sensing assembly;

compare the second phybrata data with the adjusted phybrata data;

generate predictive data based on the comparing the second phybrata data with the adjusted phybrata data, the predictive data being indicative of projected physiological changes in the user; and generate a predictive phybrata signature indicative of the predictive data.

11. The system of claim 10, wherein the projected physiological changes include changes in at least one of the balance performance, the postural stability performance, or the movement performance of the user.

12. The system of claim 10, wherein the projected physiological changes include changes in a disease state of the user.

13. The system of claim 12, wherein the disease state includes at least one of a concussion, a stroke, Parkinson's diseases, multiple sclerosis, elderly frailty, peripheral neuropathy, peripheral arterial disease, spinal stenosis, chronic pain, or invasive surgery.

14. The system of claim 10, wherein the projected physiological changes include changes in a response to a treatment, a medication, a therapy, or rehabilitation.

15. A system, comprising:

a stimulation assembly, including:

a housing configured to be worn on a body of a user, and a set of electrodes coupled to the housing, at least a portion of the set of electrodes configured to be disposed on a mastoid of the user, the set of electrodes including electrical vestibular stimulation (EVS) electrodes; and a controller in communication with the stimulation assembly, the controller configured to:

receive a phybrata signature that is associated with the user and indicative of at least one of a vestibular impairment, an involuntary physical motion, a head tremor, or a fall, determine stimulation signal parameters based on the phybrata signature, and selectively generate a signal based on the stimulation signal parameters, the signal configured to activate at least one pair of the set of electrodes to apply an EVS waveform to the user corresponding to the stimulation signal parameters, the EVS waveform including a therapeutic EVS signal or a corrective EVS signal, the therapeutic EVS signal or the corrective EVS signal configured to reduce a head tremor.

16. The system of claim 15, wherein the stimulation assembly is configured to be worn around a neck of the user.

17. The system of claim 15, wherein the portion of the set of electrodes is a first portion of the set of electrodes, and a second portion of the set of electrodes is configured to be disposed on a neck of the user.

18. The system of claim 15, wherein:

the controller is further configured to:

determine, based on the phybrata signature, relative timings for a postural reaction and anticipatory adjustment of the user, calculate a predicted physiological signature associated with the user, the predicted physiological signature including at least one of a predicted magnitude of motion, a predicted phase of the motion, and a predicted delay between motions of the body of the user, and generate and selectively adjust parameters of the EVS waveform applied to the user based on the predicted physiological signature so as to adjust a balance performance, postural stability performance, or movement performance of the user.

19. The system of claim 18, wherein:

the phybrata signature is indicative of the vestibular impairment in the user due to age, injury, or disease; and the EVS waveform is configured to correct the vestibular impairment.

20. The system of claim 18, wherein the therapeutic EVS signal is configured to improve disrupted balance performance, the postural stability performance, or the movement performance.

21. The system of claim 18, wherein the corrective EVS signal is configured to induce a postural response in the user back towards a neutral position to reduce a risk of the fall.

22. The system of claim 18, wherein the corrective EVS signal is configured to reduce heart rate variability associated with postural orthostatic tachycardia syndrome (POTS).

23. The system of claim 15, wherein the set of electrodes further include cranial electrical stimulation (CES) electrodes.

24. The system of claim 23, wherein:

the at least one pair of the set of electrodes is configured to further apply a CES waveform to the user; and the controller is further configured to:

determine, based on the phybrata signature, relative timings for a postural reaction and anticipatory adjustment of the user, calculate a predicted signature associated with the user, the predicted signature including at least one of a predicted magnitude of a motion, a predicted phase of the motion, and a predicted delay between motions of the body of the user, and generate and selectively adjust parameters of the CES waveform applied to the user based on the predicted signature to adjust a neuromotor, neurosensory, neurocognitive, or neuropsychological impairment of the user.

25. The system of claim 15, wherein the set of electrodes further include electrical stimulation of the eye (ESE) electrodes.

26. The system of claim 25, wherein:

the at least one pair of the set of electrodes is configured to further apply an ESE waveform; and the controller is further configured to:

determine, based on the phybrata signature, relative timings for a postural reaction and anticipatory adjustment of the user, calculate a predicted signature associated with the user, the predicted signature including at least one of a predicted magnitude of a motion, a predicted phase of the motion, and a predicted delay between motions of the body of the user, and generate and selectively adjust parameters of the ESE waveform applied to the user based on the predicted signature to adjust a neuromotor or neurosensory impairment of the user.

27. The system of claim 26, wherein:

the neurosensory impairment is optical neuritis caused by one or more multiple sclerosis lesions on an optic nerve.

28. A system, comprising:

a sensing and stimulation assembly, including:

a housing, a first sensor disposed in the housing and configured to measure a first phybrata signal from a user, a second sensor disposed in the housing and configured to measure a second phybrata signal from the user, the second phybrata signal being different from the first phybrata signal, and a set of electrodes coupled to the housing, at least a portion of the set of electrodes configured to be disposed on a mastoid of the user, the set of electrodes including electrical vestibular stimulation (EVS) electrodes; and a controller communicatively coupled to the sensing and stimulation assembly, the controller configured to:

receive phybrata data from the sensing and stimulation assembly, the phybrata data including information obtained from the first phybrata signal and the second phybrata signal, determine a phybrata parameter associated with the user based on the phybrata data, determine a phybrata signature that is associated with the user based on the phybrata parameter and indicative of at least one of a vestibular impairment, an involuntary physical motion, a head tremor, or a fall, determine stimulation signal parameters based on the phybrata signature, and selectively generate a signal based on the stimulation signal parameters, the signal configured to activate at least one pair of the set of electrodes to apply an EVS waveform to the user corresponding to the stimulation signal parameters, the EVS waveform including a therapeutic EVS signal or a corrective EVS signal, the corrective EVS signal configured to reduce the head tremor.

29. The system of claim 28, wherein the controller is further configured to:

determine, based on the phybrata signature, relative timing for a postural reaction and anticipatory adjustment of the user.

30. The system of claim 28, wherein the controller is further configured to:

determine, based on the phybrata signature, relative timing for a postural reaction and anticipatory adjustment of the user; and calculate a predicted physiological signature associated with the user.

31. The system of claim 28, wherein the controller is further configured to:

determine, based on the phybrata signature, relative timing for a postural reaction and anticipatory adjustment of the user;

calculate a predicted physiological signature associated with the user; and generate and selectively adjust parameters of the EVS waveform applied to the user based on the predicted physiological signature.

32. A system, comprising:

a sensing assembly configured to be disposed on a mastoid of a user, the sensing assembly including:

a housing, a first sensor disposed in the housing and configured to measure a first phybrata signal from the user, and a second sensor disposed in the housing and configured to measure a second phybrata signal from the user, the second phybrata signal different from the first phybrata signal; and a controller in communication with the sensing assembly, the controller configured to:

receive a first phybrata data from the sensing assembly, the first phybrata data including information obtained from the first phybrata signal and the second phybrata signal, determine a phybrata parameter associated with the user based on the first phybrata data, determine a phybrata signature associated with the user based on the phybrata parameter;

generate a corrective signal indicative of a corrective parameter determined based on the phybrata signature, the generated corrective signal configured to cause an electrode to apply the corrective signal to the user;

generate a biomechanical model of the user;

generate simulated phybrata data associated with the biomechanical model of the user based on the first phybrata data;

determine simulated phybrata parameters associated with the biomechanical model of the user based on the phybrata parameter;

determine a simulated phybrata signature associated with the biomechanical model of the user based on the phybrata signature;

determine a simulated quantitative phybrata metric based on the simulated phybrata signature, the simulated quantitative phybrata metric configured to classify, quantify, and/or track a magnitude and time evolution of at least one of a balance performance, a postural stability performance, a movement performance, a physiological disruption, or a physiological impairment associated with the user;

generate adjusted phybrata data based on the first phybrata data, synthetic phybrata data, and the simulated phybrata data;

determine an adjusted phybrata signature indicative of the adjusted phybrata data associated with the user;

receive a second phybrata data from the sensing assembly;

compare the second phybrata data with the adjusted phybrata data;

generate predictive data based on the comparing between the second phybrata data with the adjusted phybrata data, the predictive data indicative of projected physiological changes in the user; and generate a predictive phybrata signature indicative of the predictive data.

* * * * *